(12) United States Patent
Borthwick et al.

(10) Patent No.: US 11,401,265 B2
(45) Date of Patent: *Aug. 2, 2022

(54) BICYCLOHETEROARYL-HETEROARYL-BENZOIC ACID COMPOUNDS AS RETINOIC ACID RECEPTOR BETA (RARβ) AGONISTS

(71) Applicant: King's College London, London (GB)

(72) Inventors: Alan David Borthwick, London (GB); Mark Trevor Mills, Nottingham (GB); Jane Theresa Brown, Nottingham (GB); Jonathan Patrick Thomas Corcoran, London (GB); Maria Beatriz De Castro Vasconcelos Goncalves, London (GB); Sarkis Barret Kalindjian, Surrey (GB)

(73) Assignee: King's College London

( * ) Notice: Subject to any disclaimer, the term of this patent is extended or adjusted under 35 U.S.C. 154(b) by 0 days.

This patent is subject to a terminal disclaimer.

(21) Appl. No.: 16/997,855

(22) Filed: Aug. 19, 2020

(65) Prior Publication Data

US 2021/0130337 A1    May 6, 2021

Related U.S. Application Data

(63) Continuation of application No. 16/536,441, filed on Aug. 9, 2019, now Pat. No. 10,752,616, which is a continuation of application No. 15/997,796, filed on Jun. 5, 2018, now Pat. No. 10,385,044, which is a continuation of application No. 15/533,492, filed as application No. PCT/EP2015/080029 on Dec. 16, 2016, now Pat. No. 9,994,559.

(30) Foreign Application Priority Data

Dec. 17, 2014    (GB) .................................... 1422472

(51) Int. Cl.
*A61P 25/02* (2006.01)
*A61P 25/14* (2006.01)
*A61P 25/16* (2006.01)
*C07D 413/04* (2006.01)
*C07D 417/04* (2006.01)
*A61K 31/41* (2006.01)

(52) U.S. Cl.
CPC ............ *C07D 413/04* (2013.01); *A61K 31/41* (2013.01); *A61P 25/02* (2018.01); *A61P 25/14* (2018.01); *A61P 25/16* (2018.01); *C07D 417/04* (2013.01)

(58) Field of Classification Search
CPC ..... C07D 413/04; C07D 417/04; A61P 25/14; A61P 25/02; A61P 25/16; A61P 43/00; A61P 25/28; A61P 25/00; A61P 15/10; A61K 31/41; A61K 31/4245
See application file for complete search history.

(56) References Cited

U.S. PATENT DOCUMENTS

| | | | |
|---|---|---|---|
| 5,998,459 A | 12/1999 | Tsuda et al. | |
| 6,110,959 A | 8/2000 | Tagami et al. | |
| 6,121,309 A | 9/2000 | Tagami et al. | |
| 6,258,811 B1 | 6/2001 | Yamauchi et al. | |
| 6,329,402 B1 | 12/2001 | Kikuchi et al. | |
| 6,355,669 B1 | 3/2002 | Yamauchi et al. | |
| 6,358,995 B1 * | 3/2002 | Tagami .................. A61P 19/00 562/490 |

(Continued)

FOREIGN PATENT DOCUMENTS

| | | |
|---|---|---|
| EP | 0889032 A1 | 1/1999 |
| EP | 0930075 A1 | 7/1999 |

(Continued)

OTHER PUBLICATIONS

Great Britain Search Report dated Oct. 5, 2015 in GB 1422472.9.
International Search Report dated Mar. 16, 2016 in PCT/EP2015/080029.
Written Opinion dated Mar. 16, 2016 in PCT/EP2015/080029.
IPRP issued Jun. 20, 2017 in PCT/EP2015/080029.
Agudo et al. (2010) "A retinoic acid receptor beta agonist (CD2019) overcomes inhibition of axonal outgrowth via phosphoinositide 3-kinase signalling in the injured adult spinal cord", Neurobiol Dis 37:147-155.

(Continued)

*Primary Examiner* — Amanda L. Aguirre
(74) *Attorney, Agent, or Firm* — Adsero IP

(57) ABSTRACT

The present invention pertains generally to the field of therapeutic compounds, and more specifically to certain bicycloheteroaryl-heteroaryl-benzoic acid compounds of the following formula (for convenience, collectively referred to herein as "BHBA compounds"), which, inter alia, are (selective) retinoic acid receptor beta (RARβ) (e.g., RARβ2) agonists. The present invention also pertains to pharmaceutical compositions comprising such compounds, and the use of such compounds and compositions, both in vitro and in vivo, to (selectively) activate RARβ (e.g., RARβ2), to cause or promote neurite development, neurite outgrowth, and/or neurite regeneration, and in the treatment of diseases and conditions that are mediated by RARβ (e.g., RARβ2), that are ameliorated by the activation of RARβ (e.g., RARβ2), etc., including, e.g., neurological injuries such as spinal cord injuries.

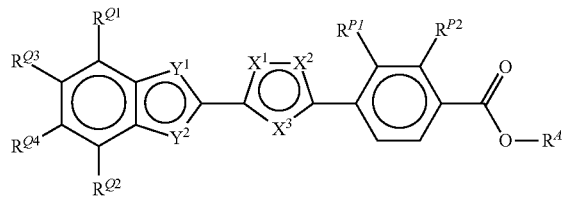

26 Claims, 3 Drawing Sheets

(56) References Cited

U.S. PATENT DOCUMENTS

| | | | |
|---|---|---|---|
| 6,992,096 B2* | 1/2006 | Karp | C07D 413/04 |
| | | | 548/131 |
| 9,994,559 B2* | 6/2018 | Borthwick | A61P 25/28 |
| 10,385,044 B2* | 8/2019 | Borthwick | A61P 25/00 |
| 10,752,616 B2* | 8/2020 | Borthwick | C07D 417/04 |
| 2003/0045546 A1 | 3/2003 | Cai et al. | |
| 2004/0152699 A1 | 8/2004 | Arora et al. | |
| 2004/0204461 A1 | 10/2004 | Karp et al. | |
| 2005/0154012 A1 | 7/2005 | Cai et al. | |
| 2009/0176837 A1 | 7/2009 | Olsson et al. | |
| 2009/0253699 A1* | 10/2009 | Almstead | C07D 277/30 |
| | | | 514/363 |
| 2011/0081297 A1 | 4/2011 | Barrow et al. | |
| 2017/0327489 A1 | 11/2017 | Bothwick et al. | |
| 2019/0010146 A1 | 1/2019 | Borthwick et al. | |
| 2020/0055862 A1 | 2/2020 | Borthwick et al. | |

FOREIGN PATENT DOCUMENTS

| | | |
|---|---|---|
| EP | 1025857 A1 | 8/2000 |
| JP | 2003 081832 | 3/2003 |
| WO | WO 00/57900 A2 | 10/2000 |
| WO | WO 03/062230 A1 | 7/2003 |
| WO | WO 2005/077373 A2 | 8/2005 |
| WO | WO 2009/146343 A1 | 12/2009 |
| WO | WO 2011/072281 A1 | 6/2011 |

OTHER PUBLICATIONS

Bastien et al. (2004) Nuclear retinoid receptors and the transcription of retinoid-target genes. Gene 328:1-16.

Bernard et al. (1992) "Identification of synthetic retinoids with selectivity for human nuclear retinoic acid receptor gamma", *Biochem. Biophys. Res. Commun.*, vol. 186(2), pp. 977-983.

Bradbury et al. (2002) Chondroitinase ABC promotes functional recovery after spinal cord injury. Nature 416:636-640.

Cho et al. (2010) "The palladium-catalyzed trifluoromethylation of aryl chlorides", Science, vol. 328, No. 5986, pp. 1679-1681.

Corcoran et al. (1999) "Nerve growth factor acts via retinoic acid synthesis to stimulate neurite outgrowth" [letter]. Nat Neurosci 2(4):307-308.

Corcoran et al. (2000) "The role of retinoic acid receptors in neurite outgrowth from different populations of embryonic mouse dorsal root ganglia" [In Process Citation]. J Cell Sci 113 (Pt 14):2567-2574.

Corcoran et al. (2002) "Retinoic acid receptor beta2 and neurite outgrowth in the adult mouse spinal cord in vitro", J Cell Sci 115:3779-3786.

Delescluse et al. (1991) "Selective high affinity retinoic acid receptor alpha or beta-gamma ligands," Mol. Pharmacol., vol. 40, pp. 556-562.

Goncalves et al. (2009) "Sequential RARbeta and alpha signalling in vivo can induce adult forebrain neural progenitor cells to differentiate into neurons through Shh and FGF signalling pathways", Dev. Biol., vol. 326, pp. 305-313.

He et al. (2004) "The nogo signaling pathway for regeneration block", Annu Rev Neurosci 27:341-368.

Imazaki et al. (2012) "Ruthenium-Catalyzed Transformation of Aryl and Alkenyl Triflates to Halides", Journal of the American Chemical Society, vol. 134, No. 36, pp. 14760-14763.

Kikuchi et al. (2000) "Synthesis and structure-activity relationships of 5,6,7,8-tetrahydro-5,5,8,8-tetramethyl-2-quinoxaline derivatives with retinoic acid receptor α activity", J. Med. Chem., vol. 43, pp. 409-419.

Kwon et al. (2001) "Spinal cord regeneration: from gene to transplants", Spine 26(24S):S13-S22.

Leid et al. (1992) "Multiplicity generates diversity in the retinoic acid signalling pathways" Trends Biochem Sci 17:427-433.

Lu et al. (2004) "Combinatorial therapy with neurotrophins and cAMP promotes axonal regeneration beyond sites of spinal cord injury", J Neurosci 24(28):6402-6409.

Lund et al. (2005) "Discovery of a potent, orally available, and isoform-selected retinoica acid β2 receptor agonist", J. Med. Chem., vol. 48, pp. 7517-7519.

Maden et al. (1996) "Vitamin A-deficient quail embryos have half a hindbrain and other neural defects", Curr. Biol., vol. 6. No. 4, pp. 417-426.

McOmie et al. (1968) "Demethylation of aryl methyl ethers by boron tribromide", Tetrahedron, vol. 24, No. 5, pp. 2289-2292.

Pan et al. (2011) "An Improved Palladium-Catalyzed Conversion of Aryl and Vinyl Triflates to Bromides and Chlorides", Organic Letters, vol. 13, No. 18, pp. 4974-4976.

Quinn et al. (1991) "Enhanced neuronal regeneration by retinoic acid of murine dorsal root ganglia and of fetal murine and human spinal cord in vitro" In Vitro Cell Dev Biol 27A:55-62.

Ritter (1993) "Synthetic transformations of vinyl and aryl triflates", Synthesis, vol. 8, pp. 735-762.

Schnell et al. (1994) "Neurotrophin-3 enhances sprouting of corticospinal tract during development and after adult spinal cord lesion" [see comments]. Nature 367:170-173.

Seino et al. 2004, "Prevention of acute and chronic allograft rejection by a novel retinoic acid receptor-α-selective agonist", Inter. Immunology, vol. 16, No. 5, pp. 665-673.

So et al. (2006) "Interactions between retinoic acid, nerve growth factor and sonic hedgehog signalling pathways in neurite outgrowth" Dev Biol 298:167-175.

Watson et al. (2009) "Formation of ArF from LPdAr(F): Catalytic conversion of aryl triflates to aryl fluorides", Science, vol. 325, pp. 1661-1664.

White et al. (1998) "Defects in embryonic hindbrain development and fetal resorption resulting from vitamin A deficiency in the rat are prevented by feeding pharmacological levels of all-trans-retinoic acid", Proc. Natl. Acad. Sci. USA, vol. 95, pp. 13459-13464.

Williams et al. (2005) "A complementary peptide approach applied to the design of novel semaphorin/neuropilin antagonists" J Neurochem 92:1180-1190.

Wong et al. (2006) "Retinoic acid receptor beta2 promotes functional regeneration of sensory axons in the spinal cord" Nat Neurosci 9:243-250.

Yip et al. (2006) "Lentiviral vector expressing retinoic acid receptor beta2 promotes recovery of function after corticospinal tract injury in the adult rat spinal cord. Hum Mol Genet" 15(21):3107-3118.

Yoshimura et al. (2000) "Discovery of novel and potent retinoic acid receptor α agonists: synthesis and evaluation of benzofuranyl-pyrrole and benzothiophenyl-pyrrole derivatives", J. Med. Chem., vol. 43, pp. 2929-2937.

* cited by examiner

ABSTRACT BICYCLOHETEROARYL-HETEROARYL-BENZOIC ACID COMPOUNDS AS RETINOIC ACID RECEPTOR BETA (RARβ) AGONISTS

BICYCLOHETEROARYL-HETEROARYL-BENZOIC ACID COMPOUNDS AS RETINOIC ACID RECEPTOR BETA (RARβ) AGONISTS

RELATED APPLICATIONS

This application is a continuation of U.S. application Ser. No. 15/997,796, filed Jun. 5, 2018, entitled "Bicycloheteroaryl-Heteroaryl-Benzoic Acid Compounds as Retinoic Acid Receptor Beta (RARβ) Agonists", now U.S. Pat. No. 10,385,044, which is a continuation of U.S. application Ser. No. 15/533,492, filed Jun. 6, 2017, now U.S. Pat. No. 9,994,559. U.S. application Ser. No. 15/533,492 is a 35 U.S.C. § 371 national phase application of International application serial no. PCT/EP2015/080029 (WO 2016/097004), filed on Dec. 16, 2015. International application serial no PCT/EP2015/080029 claims priority to United Kingdom patent application number 1422472.9 filed Dec. 17, 2014. The contents of each of the referenced applications are incorporated herein by reference in their entirety.

TECHNICAL FIELD

The present invention pertains generally to the field of therapeutic compounds, and more specifically to certain bicycloheteroaryl-heteroaryl-benzoic acid compounds (for convenience, collectively referred to herein as "BHBA compounds"), which, inter alia, are (selective) retinoic acid receptor beta (RARβ) (e.g., RARβ2) agonists. The present invention also pertains to pharmaceutical compositions comprising such compounds, and the use of such compounds and compositions, both in vitro and in vivo, to (selectively) activate RARβ (e.g., RARβ2), to cause or promote neurite development, neurite outgrowth, and/or neurite regeneration, and in the treatment of diseases and conditions that are mediated by RARβ (e.g., RARβ2), that are ameliorated by the activation of RARβ (e.g., RARβ2), etc., including, e.g., neurological injuries such as spinal cord injuries.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Nerve Injury

As yet, there are no effective treatments for nerve injuries including spinal cord injuries (SCI), stroke, and peripheral nerve injuries. The inventors have identified a novel signalling mechanism—the retinoid signalling pathway—that can be stimulated in models of nerve injury leading to axonal outgrowth and functional recovery. See, for example, Maden and Corcoran, 2000. This pathway is activated by retinoic acid (RA) binding to the retinoic acid receptor (RAR) that acts in the nucleus to drive the synthesis of RNA and hence produces proteins for axonal outgrowth. The inventors have shown that the RARβ2 subtype is specifically involved in this process.

Retinoid Signalling and Neurite Outgrowth

There are at least three causes for the lack of axonal outgrowth of central nervous system (CNS) neurons after spinal cord injury. First: the presence of growth inhibiting molecules, including Nogo-A, myelin-associated glycoprotein (MAG) and oligodendrocyte myelin glycoprotein (Omgp) (see, e.g., He and Koprivica, 2004). Second: insufficiency of growth-promoting factors, which are well-known for their ability to promote neurite outgrowth in vitro and to induce some axonal outgrowth when administered to injured cord (see, e.g., Schnell et al., 1994; Lu et al., 2004). Third: the lack of an appropriate 'growth programme' by damaged neurones (see, e.g., Kwon and Tetzlaff, 2001). One factor that can induce such a growth programme is RA signalling (see, e.g., Quinn and De Boni, 1991). This is mediated by RARs and retinoid X receptors (RXRs), both of which have three subtypes (α, β, and γ and various isoforms) (see, e.g., Bastien and Rochette-Egly, 2004). Transcription occurs when RA binds to an RAR/RXR heterodimer which then binds to retinoic acid response elements (RAREs) located in the regulatory regions of target genes (see, e.g., Bastien and Rochette-Egly, 2004).

RARβ2 Signalling Mediates Neurite Outgrowth

Retinoid signalling is important for the development of the embryo. When the nervous system is deprived of RA during development, neurite outgrowth fails, for example, in the RA deficient embryo (see, e.g., Maden et al., 1996; White et al., 1998). By using a panel of RARβ agonists, the inventors have shown that RARβ signalling is required for retinoid mediated neurite outgrowth of neurons, whereas RARα or RARγ signalling has no effect (see, e.g., Corcoran et al., 2000). More specifically it is the activation of RARβ2 that mediates this effect (see, e.g., Corcoran et al., 2000) and this is auto-regulated by its ligand (see, e.g., Leid et al., 1992). Activation of RARβ2 by retinoids results in neurite outgrowth of cultured embryonic dorsal root ganglia (DRG), spinal cord, and adult DRG (see, e.g., Corcoran et al., 2000; Corcoran and Maden, 1999; So et al., 2006; Corcoran et al., 2002). When RARβ2 is transduced into cultured adult rodent spinal cord explants, which do not normally express this receptor, neurite outgrowth occurs (see, e.g., Corcoran et al., 2002).

RARβ2 Signalling Mediates Axonal Outgrowth

A test of the importance of RARβ signalling in axonal outgrowth comes from gene-deleted RARβ null mice. In a peripheral nerve crush model, axonal outgrowth is impeded compared to normal mice which express RARβ2 in their DRG neurons (see, e.g., Corcoran and Maden, 1999; So et al., 2006).

Furthermore, it can be demonstrated that RARβ2 expression is essential for axonal outgrowth in vivo by overexpressing it in models of spinal cord injury. In rodents, models of avulsion (where the axons of the peripheral sensory axons are damaged leading to forelimb paralysis), the overexpression of RARβ2 into the neurons of the injured DRG leads to axonal outgrowth across the dorsal root entry zone (DREZ) and back into the spinal cord leading to functional recovery (see, e.g., Wong et al., 2006).

Another model of spinal cord lesion is one that severs the corticospinal tract (CST). The cell bodies of these CST neurons are located in the brain. The CST forms the major descending pathway in the dorsal columns of the spinal cord and their damage results in functional impairments of some motor tasks. The CST lesion can be achieved by the crush of the spinal cord at the level of C4 in rodents. This results in loss of function of the forelimbs. Recently, it has been demonstrated that overexpression of RARβ2 by lentiviral vectors in adult CST neurons results in outgrowth of CST axons and functional recovery of the forelimb (see, e.g., Yip et al., 2006).

The inventors have now shown that RARβ agonists are likely to be useful in the treatment of nerve injury. RARβ agonists initiate axonal outgrowth in models of nerve injury and functional recovery occurs. Studies demonstrating these findings are described in more detail in the Examples below.

Lund et al., 2005, describes certain 4,4'-biphenylcarboxlyic acid compounds that allegedly have RARβ2 agonist activity.

Kikuchi et al., 2000, describes certain tetrahydro-tetramethyl-2-quinoxaoline compounds that allegedly have RARα agonist activity.

Yoshimura et al., 2000, describes certain benzofuranyl-pyrrole and benzothiophenyl-pyrrole compounds that allegedly have RARα agonist activity.

Seino et al., 2004, describes the use of an RARα agonist, ER-38925, in the prevention of actute and chronic allograft rejection.

Tagami et al., 2000a, Tagami et al., 2000b, and Tagami et al., 2002 all describe certain compounds allegedly exhibiting retinoic acid receptor agonism.

Kikuchi et al., 2001 describes certain compound allegeldly having the activity of retinoic acid.

Tsuda et al., 1999, describes certain compounds which allegedly are useful in the treatment of pollakiuria and urinary incontinence.

Cai et al., 2003 and Cai et al., 2005 describe certain compounds which allegedly are activators of caspases and inducers of apoptosis.

Olsson et al., 2009, describes certain compounds that allegedly have activity at RARβ2 receptors.

SUMMARY OF THE INVENTION

One aspect of the invention pertains to certain bicyclo-heteroaryl-heteroaryl-benzoic acid compounds (for convenience, collectively referred to herein as "BHBA compounds"), as described herein.

Another aspect of the invention pertains to a composition (e.g., a pharmaceutical composition) comprising a BHBA compound, as described herein, and a pharmaceutically acceptable carrier or diluent.

Another aspect of the invention pertains to method of preparing a composition (e.g., a pharmaceutical composition) comprising the step of mixing a BHBA compound, as described herein, and a pharmaceutically acceptable carrier or diluent.

Another aspect of the present invention pertains to a method of activating retinoic acid receptor β (RARβ) (for example, RARβ2) in vitro or in vivo, comprising contacting RARβ (for example, RARβ2) with an effective amount of a BHBA compound, as described herein.

Another aspect of the present invention pertains to a method of selectively activating retinoic acid receptor β (RARβ) (for example, RARβ2) (e.g., with respect to RARα and/or RARγ), in vitro or in vivo, comprising contacting RARβ (for example, RARβ2) with an effective amount of a BHBA compound, as described herein.

One aspect of the present invention pertains to a method of causing or promoting neurite development, neurite outgrowth, and/or neurite regeneration, comprising contacting a neuron, in vitro or in vivo, with an effective amount of a BHBA compound, as described herein.

Another aspect of the present invention pertains to a BHBA compound as described herein for use in a method of treatment of the human or animal body by therapy.

Another aspect of the present invention pertains to use of a BHBA compound, as described herein, in the manufacture of a medicament for use in treatment.

Another aspect of the present invention pertains to a method of treatment comprising administering to a subject in need of treatment a therapeutically-effective amount of a BHBA compound, as described herein, preferably in the form of a pharmaceutical composition.

In one embodiment, the treatment is treatment of a neurological injury.

In one embodiment, the treatment is treatment of an injury of the central nervous system (CNS).

In one embodiment, the treatment is treatment of an injury of the peripheral nervous system (PNS).

In one embodiment, the treatment is treatment of a nerve injury.

In one embodiment, the treatment is treatment of a PNS nerve injury.

In one embodiment, the treatment is treatment of a CNS nerve injury.

In one embodiment, the treatment is treatment of a spinal cord injury.

In one embodiment, the treatment is treatment of a spinal cord injury caused by trauma.

In one embodiment, the treatment is treatment of an optic nerve injury.

In one embodiment, the treatment is treatment of an optic nerve injury caused by glaucoma.

In one embodiment, the treatment is treatment of a neuropathy.

In one embodiment, the treatment is treatment of a PNS neuropathy.

In one embodiment, the treatment is treatment of a CNS neuropathy.

In one embodiment, the treatment is treatment of a spinal cord neuropathy.

In one embodiment, the treatment is treatment of an optic nerve neuropathy.

In one embodiment, the treatment is treatment of diabetic neuropathy (i.e., neuropathy associated with diabetes mellitus).

In one embodiment, the treatment is treatment of AIDS neuropathy (i.e., neuropathy associated with AIDS).

In one embodiment, the treatment is treatment of leprotic neuropathy (i.e., neuropathy associated with leprosy).

In one embodiment, the treatment is treatment of peripheral neuropathy (for example, polyneuropathy, mononeuropathy, mononeuritis multiplex, or autonomic neuropathy).

In one embodiment, the treatment is treatment of a neurodegenerative disorder.

In one embodiment, the treatment is treatment of a cognitive disorder, memory impairment, memory deficit, senile dementia, Alzheimer's disease, early stage Alzheimer's disease, intermediate stage Alzheimer's disease, late stage Alzheimer's disease, cognitive impairment, or mild cognitive impairment.

In one embodiment, the treatment is treatment of Huntington's disease.

In one embodiment, the treatment is treatment of Parkinson's disease.

In one embodiment, the treatment is treatment of motor neurone disease.

In one embodiment, the treatment is treatment of localised paralysis.

In one embodiment, the treatment is treatment of Bell's palsy.

In one embodiment, the treatment is treatment of neurally-based impotence.

In one embodiment, the treatment is treatment of neurally-based impotence caused by nerve trauma following radical prostatectomy.

In one embodiment, the treatment is treatment of paralysis, for example, monoplegia, quadriplegia, or paraplegia.

In one embodiment, the treatment is treatment of a neurological disorder caused by a neurological injury.

In one embodiment, the treatment is treatment of a neurological disorder caused by a neuropathy, for example, as described above.

In one embodiment, the treatment is treatment of a neurological injury caused by a neuropathy, for example, as described above.

Another aspect of the present invention pertains to a kit comprising (a) a BHBA compound, as described herein, preferably provided as a pharmaceutical composition and in a suitable container and/or with suitable packaging; and (b) instructions for use, for example, written instructions on how to administer the compound.

Another aspect of the present invention pertains to a BHBA compound obtainable by a method of synthesis as described herein, or a method comprising a method of synthesis as described herein.

Another aspect of the present invention pertains to a BHBA compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

Figure 1A:
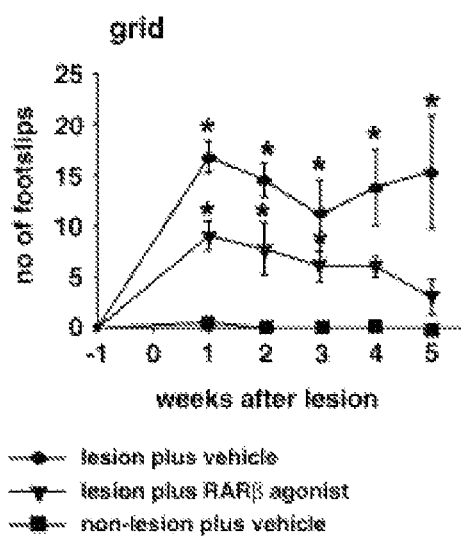
FIGS. 1A and 1B show two graphs of the number of rat footslips as a function of the number of weeks after lesion, for grid task (FIG. 1A) and beam task (FIG. 1B), as described in the biological modeling study below.

One aspect of the present invention relates to certain compounds that are generally related to benzoic acid.

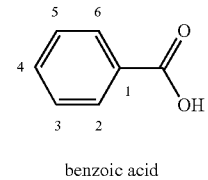

benzoic acid

All of the compounds are further characterised by a 4-oxadiazolyl or 4-thiadiazolyl substituent.

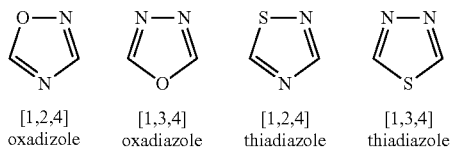

[1,2,4] oxadizole   [1,3,4] oxadiazole   [1,2,4] thiadiazole   [1,3,4] thiadiazole Additionally, all of the compounds are further characterized by a benzofuranyl, benzooxazolyl, benzothiofuranyl, or benzothiazolyl substituent on the 4-oxadiazolyl or 4-thiadiazolyl group.

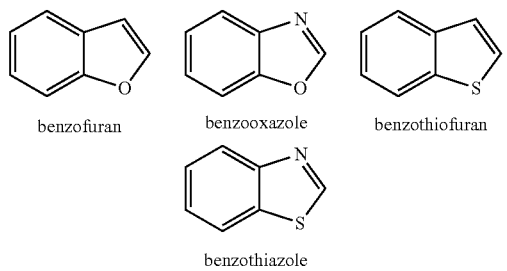

benzofuran   benzooxazole   benzothiofuran benzothiazole

Thus, one aspect of the present invention pertains to compounds of the following formula, and pharmaceutically acceptable salts, hydrates, and solvates thereof, wherein $X^1$, $X^2$, $X^3$, $Y^1$, $Y^2$, $-R^{Q1}$, $-R^{Q2}$, $-R^{Q3}$, $-R^{Q4}$, $-R^{P1}$, $-R^{P2}$, and $-R^4$ are as defined herein (for convenience, collectively referred to herein as "bicycloheteroaryl-heteroaryl-benzoic acid compounds" or "BHBA compounds"):

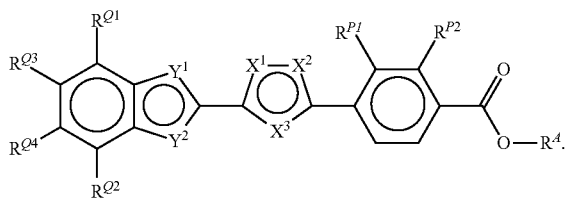

Some embodiments of the invention include the following:

(1) A compound of the following formula, or a pharmaceutically acceptable salt, hydrate, or solvate thereof:

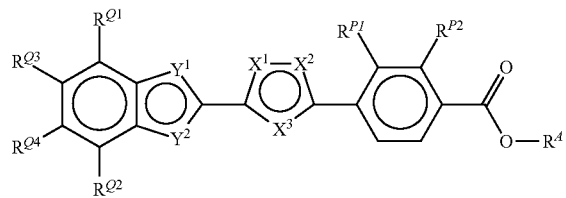

wherein:
one of $X^1$, $X^2$, and $X^3$ is independently O or S;
each of the other two of $X^1$, $X^2$, and $X^3$ is N;
$Y^1$ is independently O or S;
$Y^2$ is independently CH, $CR^Y$ or N;
—$R^Y$ is saturated linear or branched $C_{1-3}$alkyl;
—$R^{Q1}$ is independently —$R^{Q1A}$, —$R^{Q1B}$, or —$R^{Q1C}$;
—$R^{Q1A}$ is saturated linear or branched $C_{1-3}$alkyl;
—$R^{Q1B}$ is —F, —Cl, —Br, or —I; —$R^{Q1C}$ is —$CF_3$;
—$R^{Q2}$ is independently —$R^{Q2A}$, —$R^{Q2B}$, or —$R^{Q2C}$;
—$R^{Q2A}$ is saturated linear or branched $C_{1-3}$alkyl;
—$R^{Q2B}$ is independently —F, —Cl, —Br, or —I;
—$R^{Q2C}$ is —$CF_3$;
—$R^{Q3}$ is independently —H or —$R^{Q3X}$;
—$R^{Q3X}$ is independently —$R^{Q3A}$, —$R^{Q3B}$—$R^{Q3C}$, or —$R^{Q3D}$;
—$R^{Q3A}$ is saturated linear or branched $C_{1-3}$alkyl;
—$R^{Q3B}$ is saturated linear or branched $C_{1-3}$alkoxy;
—$R^{Q3C}$ is independently —F, —Cl, —Br, or —I;
—$R^{Q3D}$ is —$CF_3$;
—$R^{Q4}$ is independently —H or —$R^{Q4X}$;
—$R^{Q4X}$ is independently —$R^{Q4A}$, —$R^{Q4B}$, —$R^{Q4C}$, or —$R^{Q4D}$;
—$R^{Q4A}$ is saturated linear or branched $C_{1-3}$alkyl;
—$R^{Q4B}$ is saturated linear or branched $C_{1-3}$alkoxy;
—$R^{Q4C}$ is independently —F, —Cl, —Br, or —I;
—$R^{Q4D}$ is —$CF_3$;
one of —$R^{P1}$ and —$R^{P2}$ is —H or —$R^P$;
the other of —$R^{P1}$ and —$R^{P2}$ is —H;
—$R^P$ is independently —$R^{PA}$, —$R^{PB}$, —$R^{PC}$, or —$R^{PD}$;
—$R^{PA}$ is saturated linear or branched $C_{1-3}$alkyl;
—$R^{PB}$ is independently —F, —Cl, —Br, or —I;
—$R^{PC}$ is —$CF_3$;
—$R^{PD}$ is independently —$NH_2$ or —$NHR^{PDD}$;
—$R^{PDD}$ is saturated linear or branched $C_{1-3}$alkyl;
—$R^A$ is independently —H or —$R^{AA}$; and
—$R^{AA}$ is independently saturated linear or branched $C_{1-4}$alkyl, phenyl, or benzyl.

For the avoidance of doubt, it is not intended that any two or more of —$R^{Q1}$, —$R^{Q2}$, —$R^{Q3}$, —$R^{Q4}$, —$R^{P1}$, —$R^{P2}$, and —$R^Y$ together form a ring fused to the ring (or rings) to which they are attached. For example, it is not intended that —$R^{P1}$ and —$R^{P2}$ together form a ring fused to the ring to which they are attached. Similarly, it is not intended that —$R^{Q1}$ and —$R^Y$ together form a ring fused to the rings to which they are attached.

The Groups $X^1$, $X^2$, and $X^3$ (2) A compound according to (1), wherein:
one of $X^1$, $X^2$, and $X^3$ is O; and
the other two of $X^1$, $X^2$, and $X^3$ is N;

(3) A compound according to (1), wherein:
one of $X^1$, $X^2$, and $X^3$ is S; and
the other two of $X^1$, $X^2$, and $X^3$ is N;

(4) A compound according to (1), wherein:
$X^1$ is independently O or S; $X^2$ is N; and $X^3$ is N.

(5) A compound according to (1), wherein:
$X^1$ is N; $X^2$ is independently O or S; and $X^3$ is N.

(6) A compound according to (1), wherein:
$X^1$ is N; $X^2$ is N; and $X^3$ is independently O or S.

(7) A compound according to (1), wherein:
$X^1$ is O; $X^2$ is N; and $X^3$ is N.

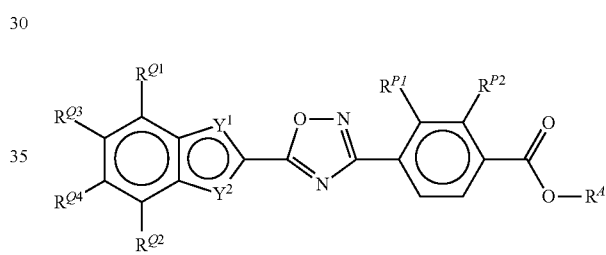

(8) A compound according to (1), wherein:
$X^1$ is N; $X^2$ is O; and $X^3$ is N.

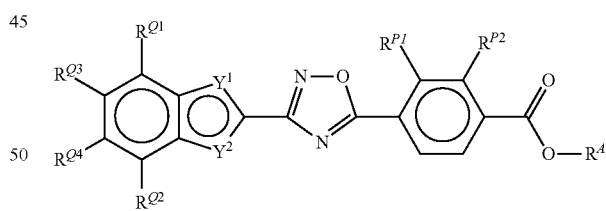

(9) A compound according to (1), wherein:
$X^1$ is N; $X^2$ is N; and $X^3$ is O.

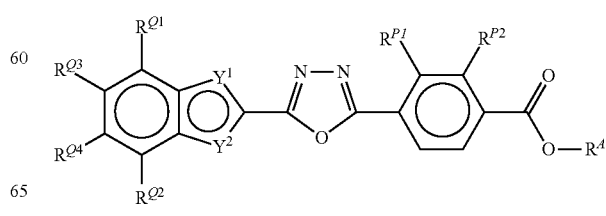

(10) A compound according to (1), wherein:
$X^1$ is S; $X^2$ is N; and $X^3$ is N.

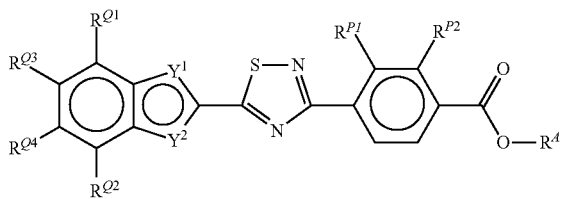

(11) A compound according to (1), wherein:
$X^1$ is N; $X^2$ is S; and $X^3$ is N.

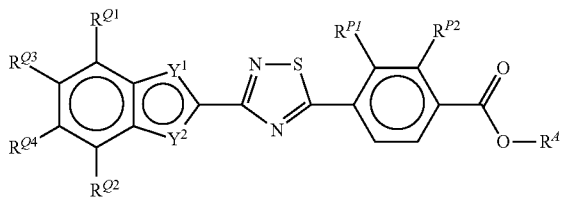

(12) A compound according to (1), wherein:
$X^1$ is N; $X^2$ is N; and $X^3$ is S.

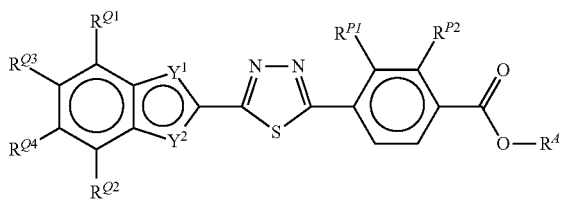

The Groups $Y^1$ and $Y^2$

(13) A compound according to any one of (1) to (12), wherein:
$Y^1$ is O; and
$Y^2$ is independently CH, $CR^Y$ or N.

(14) A compound according to any one of (1) to (12), wherein:
$Y^1$ is O; and
$Y^2$ is independently CH or $CR^Y$.

(15) A compound according to any one of (1) to (12), wherein:
$Y^1$ is S; and
$Y^2$ is independently CH, $CR^Y$ or N.

(16) A compound according to any one of (1) to (12), wherein:
$Y^1$ is S; and
$Y^2$ is independently CH or $CR^Y$.

(17) A compound according to any one of (1) to (12), wherein:
$Y^1$ is independently O or S; and
$Y^2$ is independently CH or $CR^Y$.

(18) A compound according to any one of (1) to (12), wherein:
$Y^1$ is independently O or S; and
$Y^2$ is CH.

(19) A compound according to any one of (1) to (12), wherein:
$Y^1$ is independently O or S; and
$Y^2$ is $CR^Y$.

(20) A compound according to any one of (1) to (12), wherein:
$Y^1$ is independently O or S; and
$Y^2$ is N.

(21) A compound according to any one of (1) to (12), wherein:
$Y^1$ is O; and
$Y^2$ is CH.

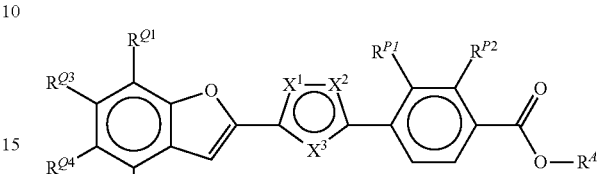

(22) A compound according to any one of (1) to (12), wherein:
$Y^1$ is O; and
$Y^2$ is $CR^Y$.

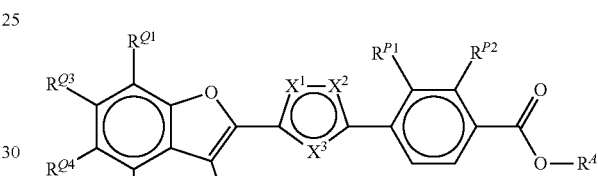

(23) A compound according to any one of (1) to (12), wherein:
$Y^1$ is O; and
$Y^2$ is N.

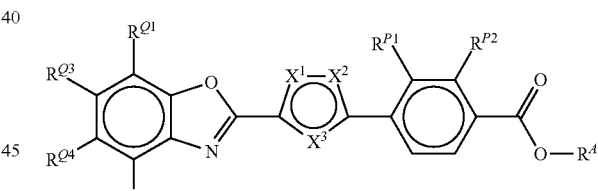

(24) A compound according to any one of (1) to (12), wherein:
$Y^1$ is S; and
$Y^2$ is CH.

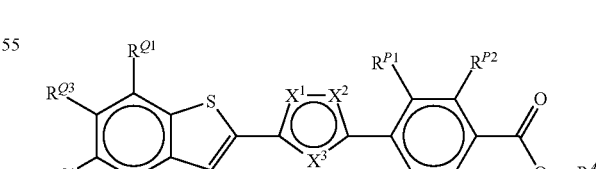

(25) A compound according to any one of (1) to (12), wherein:
$Y^1$ is S; and
$Y^2$ is $CR^Y$.

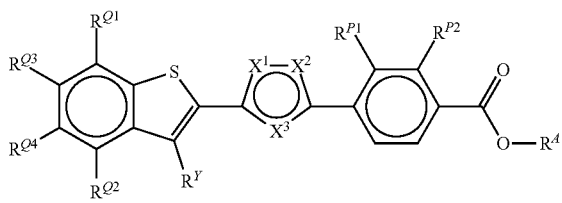

(26) A compound according to any one of (1) to (12), wherein:
Y$^1$ is S; and
Y$^2$ is N.

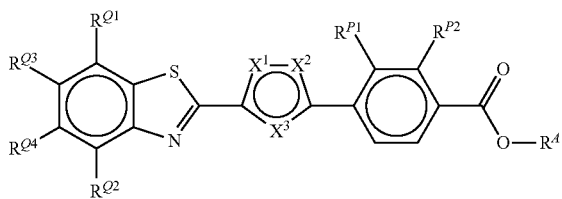

The Group —R$^Y$

(27) A compound according to any one of (1) to (26), wherein —RY, if present, is independently -Me, -Et, -nPr, or -iPr.

(28) A compound according to any one of (1) to (26), wherein —RY, if present, is independently -Me or -Et.

(29) A compound according to any one of (1) to (26), wherein —RY, if present, is -Me.

The Group —R$^{Q1}$

(30) A compound according to any one of (1) to (29), wherein —R$^{Q1}$ is independently —R$^{Q1A}$ or —R$^{Q1B}$.

(31) A compound according to any one of (1) to (29), wherein —R$^{Q1}$ is independently —R$^{Q1B}$ or —R$^{Q1C}$.

(32) A compound according to any one of (1) to (29), wherein —R$^{Q1}$ is —R$^{Q1A}$.

(33) A compound according to any one of (1) to (29), wherein —R$^{Q1}$ is —R$^{Q1B}$.

(34) A compound according to any one of (1) to (29), wherein —R$^{Q1}$ is —R$^{Q1C}$.

The Group —R$^{Q1A}$

(35) A compound according to any one of (1) to (34), wherein —R$^{Q1A}$, if present, is independently -Me, -Et, -nPr, or -iPr.

(36) A compound according to any one of (1) to (34), wherein —R$^{Q1A}$, if present, is independently -Me or -Et.

(37) A compound according to any one of (1) to (34), wherein —R$^{Q1A}$, if present, is -Me.

The Group —R$^{Q1B}$

(38) A compound according to any one of (1) to (37), wherein —R$^{Q1B}$, if present, is independently —F, —Cl, or —Br.

(39) A compound according to any one of (1) to (37), wherein —R$^{Q1B}$, if present, is independently —F or —Cl.

(40) A compound according to any one of (1) to (37), wherein —R$^{Q1B}$, if present, is —F.

(41) A compound according to any one of (1) to (37), wherein —R$^{Q1B}$, if present, is —Cl.

(42) A compound according to any one of (1) to (37), wherein —R$^{Q1B}$, if present, is —Br.

The Group —R$^{Q2}$

(43) A compound according to any one of (1) to (42), wherein —R$^{Q2}$ is independently —R$^{Q2A}$ or —R$^{Q2B}$.

(44) A compound according to any one of (1) to (42), wherein —R$^{Q2}$ is independently —R$^{Q2B}$ or —R$^{Q2C}$.

(45) A compound according to any one of (1) to (42), wherein —R$^{Q2}$ is —R$^{Q2A}$.

(46) A compound according to any one of (1) to (42), wherein —R$^{Q2}$ is —R$^{Q2B}$.

(47) A compound according to any one of (1) to (42), wherein —R$^{Q2}$ is —R$^{Q2C}$.

The Group —R$^{Q2A}$

(48) A compound according to any one of (1) to (47), wherein —R$^{Q2A}$, if present, is independently -Me, -Et, -nPr, or -iPr.

(49) A compound according to any one of (1) to (47), wherein —R$^{Q2A}$, if present, is independently -Me or -Et.

(50) A compound according to any one of (1) to (47), wherein —R$^{Q2A}$, if present, is -Me.

The Group —R$^{Q2B}$

(51) A compound according to any one of (1) to (50), wherein —R$^{Q2B}$, if present, is independently —F, —Cl, or —Br.

(52) A compound according to any one of (1) to (50), wherein —R$^{Q2B}$, if present, is independently —F or —Cl.

(53) A compound according to any one of (1) to (50), wherein —R$^{Q2B}$, if present, is —F.

(54) A compound according to any one of (1) to (50), wherein —R$^{Q2B}$, if present, is —Cl.

(55) A compound according to any one of (1) to (50), wherein —R$^{Q2B}$, if present, is —Br.

The Groups —R$^{Q1}$ and —R$^{Q2}$

(56) A compound according to any one of (1) to (55), wherein —R$^{Q1}$ and —R$^{Q2}$ are the same.

(57) A compound according to any one of (1) to (55), wherein —R$^{Q1}$ and —R$^{Q2}$ are different.

The Group —R$^{Q3}$

(58) A compound according to any one of (1) to (57), wherein —R$^{Q3}$ is —H.

(59) A compound according to any one of (1) to (57), wherein —R$^{Q3}$ is —R$^{Q3X}$.

The Group —R$^{Q3X}$

(60) A compound according to any one of (1) to (59), wherein —R$^{Q3X}$, if present, is —R$^{Q3A}$.

(61) A compound according to any one of (1) to (59), wherein —R$^{Q3X}$, if present, is —R$^{Q3B}$.

(62) A compound according to any one of (1) to (59), wherein —R$^{Q3X}$, if present, is —R$^{Q3C}$.

(63) A compound according to any one of (1) to (59), wherein —R$^{Q3X}$, if present, is —R$^{Q3D}$.

The Group —R$^{Q3A}$

(64) A compound according to any one of (1) to (63), wherein —R$^{Q3A}$, if present, is independently -Me, -Et, -nPr, or -iPr.

(65) A compound according to any one of (1) to (63), wherein —R$^{Q3A}$, if present, is independently -Me or -Et.

(66) A compound according to any one of (1) to (63), wherein —R$^{Q3A}$, if present, is -Me.

The Group —R$^{Q3B}$

(67) A compound according to any one of (1) to (66), wherein —R$^{Q3B}$, if present, is independently —OMe, —OEt, —O-nPr, or —O-iPr.

(68) A compound according to any one of (1) to (66), wherein —R$^{Q3B}$, if present, is independently —OMe or -OEt.

(69) A compound according to any one of (1) to (66), wherein —$R^{Q3B}$, if present, is —OMe.

The Group —$R^{Q3C}$

(70) A compound according to any one of (1) to (69), wherein —$R^{Q3C}$, if present, is independently —F, —Cl, or —Br.

(71) A compound according to any one of (1) to (69), wherein —$R^{Q3C}$, if present, is independently —F or —Cl.

(72) A compound according to any one of (1) to (69), wherein —$R^{Q3C}$, if present, is —F.

(73) A compound according to any one of (1) to (69), wherein —$R^{Q3C}$, if present, is —Cl.

(74) A compound according to any one of (1) to (69), wherein —$R^{Q3C}$, if present, is —Br.

The Group —$R^{Q4}$

(75) A compound according to any one of (1) to (74), wherein —$R^{Q4}$ is —H.

(76) A compound according to any one of (1) to (74), wherein —$R^{Q4}$ is —$R^{Q4X}$.

The Group —$R^{Q4X}$

(77) A compound according to any one of (1) to (76), wherein —$R^{Q4X}$, if present, is —$R^{Q4A}$.

(78) A compound according to any one of (1) to (76), wherein —$R^{Q4X}$, if present, is —$R^{Q4B}$.

(79) A compound according to any one of (1) to (76), wherein —$R^{Q4X}$, if present, is —$R^{Q4C}$.

(80) A compound according to any one of (1) to (76), wherein —$R^{Q4X}$, if present, is —$R^{Q4D}$.

The Group —$R^{Q4A}$

(81) A compound according to any one of (1) to (80), wherein —$R^{Q4A}$, if present, is independently -Me, -Et, -nPr, or -iPr.

(82) A compound according to any one of (1) to (80), wherein —$R^{Q4A}$, if present, is independently -Me or -Et.

(83) A compound according to any one of (1) to (80), wherein —$R^{Q4A}$, if present, is -Me.

The Group —$R^{Q4B}$

(84) A compound according to any one of (1) to (83), wherein —$R^{Q4B}$, if present, is independently —OMe, —OEt, —O-nPr, or —O-iPr.

(85) A compound according to any one of (1) to (83), wherein —$R^{Q4B}$, if present, is independently —OMe or -OEt.

(86) A compound according to any one of (1) to (83), wherein —$R^{Q4B}$, if present, is —OMe.

The Group —$R^{Q4C}$

(87) A compound according to any one of (1) to (86), wherein —$R^{Q4C}$, if present, is independently —F, —Cl, or —Br.

(88) A compound according to any one of (1) to (86), wherein —$R^{Q4C}$, if present, is independently —F or —Cl.

(89) A compound according to any one of (1) to (86), wherein —$R^{Q4C}$, if present, is —F.

(90) A compound according to any one of (1) to (86), wherein —$R^{Q4C}$, if present, is —Cl.

(91) A compound according to any one of (1) to (86), wherein —$R^{Q4C}$, if present, is —Br.

The Groups —$R^{P1}$ and —$R^{P2}$

(92) A compound according to any one of (1) to (91), wherein:
—$R^{P1}$ is independently —H or —$R^P$; and —$R^{P2}$ is —H.

(93) A compound according to any one of (1) to (91), wherein:
—$R^{P1}$ is —H; and —$R^{P2}$ is independently —H or —$R^P$.

(94) A compound according to any one of (1) to (91), wherein:
—$R^{P1}$ is —H; and —$R^{P2}$ is —H.

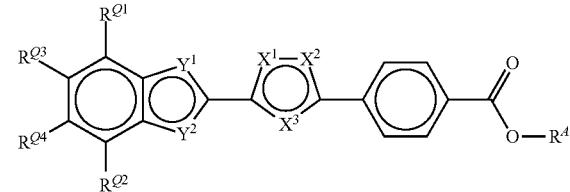

(95) A compound according to any one of (1) to (91), wherein:
—$R^{P1}$ is —$R^P$; and —$R^{P2}$ is —H.

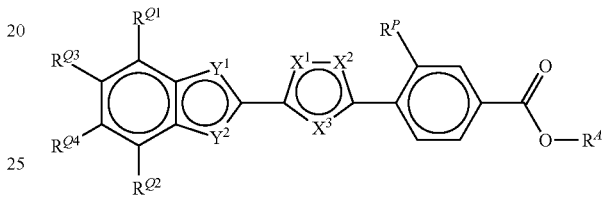

(96) A compound according to any one of (1) to (91), wherein:
—$R^{P1}$ is —H; and —$R^{P2}$ is —$R^P$.

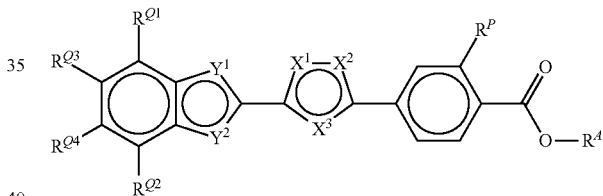

The Group —$R^P$

(97) A compound according to any one of (1) to (96), wherein —$R^P$, if present, is independently —$R^{PA}$, —$R^{PB}$, or —$R^{PC}$.

(98) A compound according to any one of (1) to (96), wherein —$R^P$, if present, is independently —$R^{PA}$, —$R^{PB}$, or —$R^{PD}$.

(99) A compound according to any one of (1) to (96), wherein —$R^P$, if present, is independently —$R^{PA}$ or —$R^{PB}$.

(100) A compound according to any one of (1) to (96), wherein —$R^P$, if present, is —$R^{PA}$.

(101) A compound according to any one of (1) to (96), wherein —$R^P$, if present, is —$R^{PB}$.

(102) A compound according to any one of (1) to (96), wherein —$R^P$, if present, is —$R^{PC}$.

(103) A compound according to any one of (1) to (96), wherein —$R^P$, if present, is —$R^{PD}$.

The Group —$R^{PA}$ (104) A compound according to any one of (1) to (103), wherein —$R^{PA}$, if present, is independently -Me or -Et.

(105) A compound according to any one of (1) to (103), wherein —$R^{PA}$, if present, is -Me.

The Group —$R^{PB}$ (106) A compound according to any one of (1) to (105), wherein —$R^{PB}$, if present, is independently —F, —Cl, or —Br.

(107) A compound according to any one of (1) to (105), wherein —$R^{PB}$, if present, is independently —F or —Cl.

(108) A compound according to any one of (1) to (105), wherein —$R^{PB}$, if present, is —F.

(109) A compound according to any one of (1) to (105), wherein —$R^{PB}$, if present, is —Cl.

(110) A compound according to any one of (1) to (105), wherein —$R^{PB}$, if present, is —Br.

The Group —$R^{PD}$ (111) A compound according to any one of (1) to (110), wherein —$R^{PD}$, if present, is —$NH_2$.

(112) A compound according to any one of (1) to (110), wherein —$R^{PD}$, if present, is —$NHR^{PDD}$.

The Group —$R^{PDD}$ (113) A compound according to any one of (1) to (112), wherein —$R^{PDD}$ if present, is independently -Me or -Et.

(114) A compound according to any one of (1) to (112), wherein —$R^{PDD}$, if present, is -Me.

The Group —$R^A$ (115) A compound according to any one of (1) to (114), wherein —$R^A$ is —H.

(116) A compound according to any one of (1) to (114), wherein —$R^A$ is —$R^{AA}$.

The Group —$R^{AA}$ (117) A compound according to any one of (1) to (116), wherein —$R^{AA}$, if present, is independently saturated linear or branched $C_{1-4}$alkyl.

(118) A compound according to any one of (1) to (116), wherein —$R^{AA}$, if present, is independently -Me, -Et, -nPr, -iPr, -nBu, or -tBu.

(119) A compound according to any one of (1) to (116), wherein —$R^{AA}$, if present, is independently -Me, -Et, -nPr, or -iPr.

(120) A compound according to any one of (1) to (116), wherein —$R^{AA}$, if present, is independently -Me or -Et.

(121) A compound according to any one of (1) to (116), wherein —$R^{AA}$, if present, is -Me.

(122) A compound according to any one of (1) to (116), wherein —$R^{AA}$, if present, is -Et.

Specific Compounds (123) A compound according to (1), which is compound one of the following formulae, or a pharmaceutically acceptable salt, hydrate, or solvate thereof:

| Code No. | Synthesis # | Structure |
|---|---|---|
| BHBA-001 | 1 | 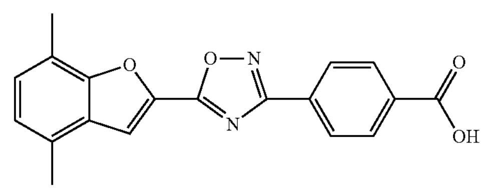 [SMILES: Cc1ccc(C)c2oc(-c3nc(-c4ccc(C(=O)O)cc4)no3)cc12] |
| BHBA-002 | 2 | 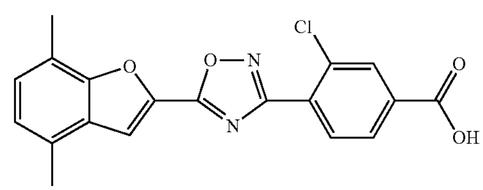 [SMILES: Cc1ccc(C)c2oc(-c3nc(-c4ccc(C(=O)O)cc4Cl)no3)cc12] |
| BHBA-003 | 6 | 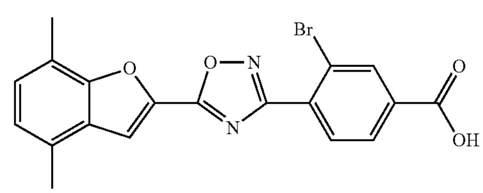 [SMILES: Cc1ccc(C)c2oc(-c3nc(-c4ccc(C(=O)O)cc4Br)no3)cc12] |
| BHBA-004 | 7 | 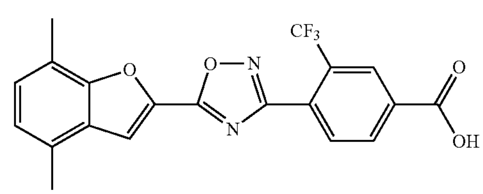 [SMILES: Cc1ccc(C)c2oc(-c3nc(-c4ccc(C(=O)O)cc4C(F)(F)F)no3)cc12] |
| BHBA-005 | 5 | 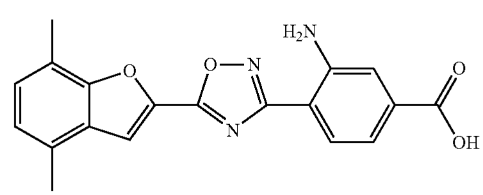 [SMILES: Cc1ccc(C)c2oc(-c3nc(-c4ccc(C(=O)O)cc4N)no3)cc12] |

-continued

| Code No. | Synthesis # | Structure |
|---|---|---|
| BHBA-006 | 3 | 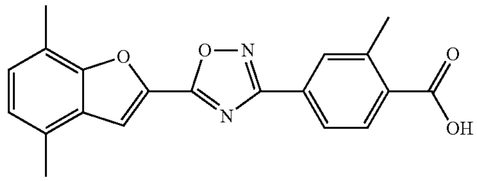 [SMILES: Cc1cc(-c2noc(-c3cc4c(C)ccc(C)c4o3)n2)ccc1C(=O)O] |
| BHBA-007 | 4 | 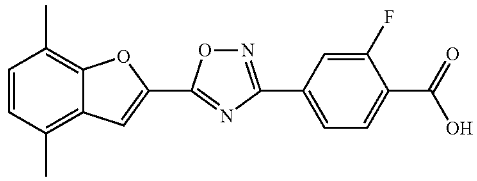 [SMILES: Cc1ccc(C)c2oc(-c3nc(-c4ccc(C(=O)O)c(F)c4)no3)cc12] |
| BHBA-008 | 8 | 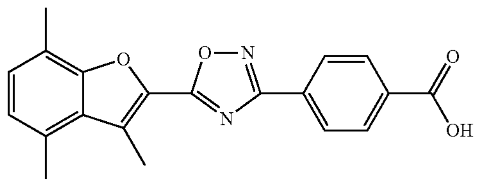 [SMILES: Cc1ccc(C)c2c(C)c(-c3nc(-c4ccc(C(=O)O)cc4)no3)oc12] |
| BHBA-009 | 9 | 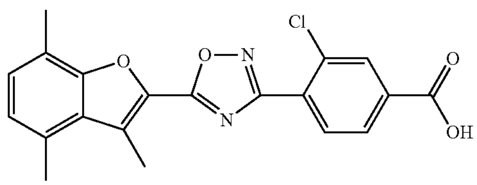 [SMILES: Cc1ccc(C)c2c(C)c(-c3nc(-c4ccc(C(=O)O)cc4Cl)no3)oc12] |
| BHBA-010 | 10 | 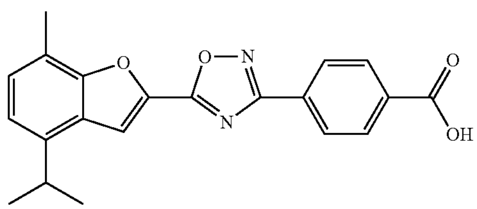 [SMILES: Cc1ccc(C(C)C)c2cc(-c3nc(-c4ccc(C(=O)O)cc4)no3)oc12] |
| BHBA-011 | 15 | 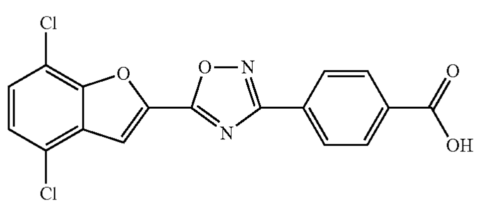 [SMILES: O=C(O)c1ccc(-c2noc(-c3cc4c(Cl)ccc(Cl)c4o3)n2)cc1] |
| BHBA-012 | 18 | 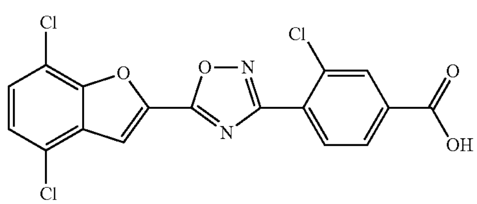 [SMILES: O=C(O)c1ccc(-c2noc(-c3cc4c(Cl)ccc(Cl)c4o3)n2)c(Cl)c1] |
| BHBA-013 | 17 | 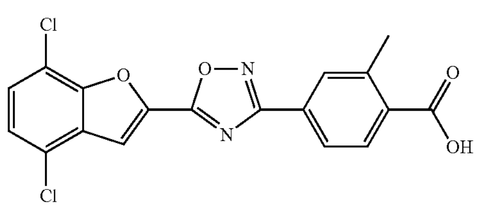 [SMILES: Cc1cc(-c2noc(-c3cc4c(Cl)ccc(Cl)c4o3)n2)ccc1C(=O)O] |

-continued

| Code No. | Synthesis # | Structure |
|---|---|---|
| BHBA-014 | 16 | 4,7-dichlorobenzofuran-2-yl linked via 1,2,4-oxadiazole to 2-fluoro-4-carboxyphenyl |
| BHBA-015 | 11 | 7-chloro-4-methylbenzofuran-2-yl linked via 1,2,4-oxadiazole to 4-carboxyphenyl |
| BHBA-016 | 13 | 4-chloro-7-methylbenzofuran-2-yl linked via 1,2,4-oxadiazole to 4-carboxyphenyl |
| BHBA-017 | 12 | 7-chloro-4-methylbenzofuran-2-yl linked via 1,2,4-oxadiazole to 3-chloro-4-carboxyphenyl |
| BHBA-018 | 14 | 4-chloro-7-methylbenzofuran-2-yl linked via 1,2,4-oxadiazole to 3-chloro-4-carboxyphenyl |
| BHBA-019 | 19 | 7-fluoro-4-(trifluoromethyl)benzofuran-2-yl linked via 1,2,4-oxadiazole to 4-carboxyphenyl |
| BHBA-020 | 20 | 7-fluoro-4-(trifluoromethyl)benzofuran-2-yl linked via 1,2,4-oxadiazole to 3-chloro-4-carboxyphenyl |
| BHBA-021 | 21 | 4,7-dimethylbenzothiophen-2-yl linked via 1,2,4-oxadiazole to 4-carboxyphenyl |

-continued

| Code No. | Synthesis # | Structure |
|---|---|---|
| BHBA-022 | 22 | 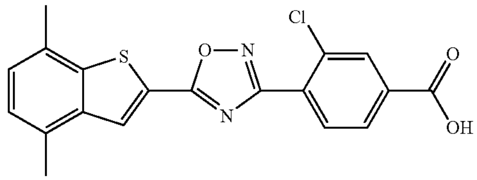 [SMILES: Cc1ccc(C)c2sc(-c3nc(-c4ccc(C(=O)O)cc4Cl)no3)cc12] |
| BHBA-023 | 24 | 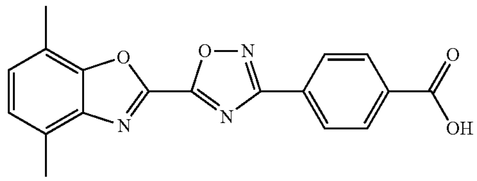 [SMILES: Cc1ccc(C)c2oc(-c3nc(-c4ccc(C(=O)O)cc4)no3)nc12] |
| BHBA-024 | 26 | 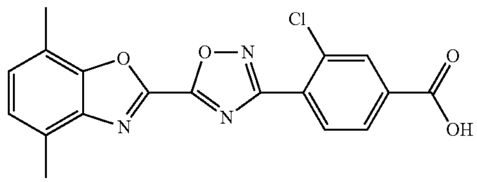 [SMILES: Cc1ccc(C)c2oc(-c3nc(-c4ccc(C(=O)O)cc4Cl)no3)nc12] |
| BHBA-025 | 27 | 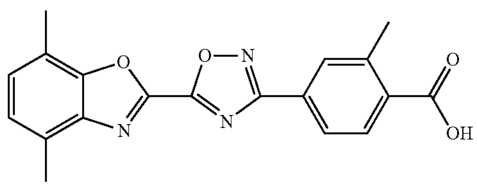 [SMILES: Cc1cc(-c2noc(-c3nc4c(C)ccc(C)c4o3)n2)ccc1C(=O)O] |
| BHBA-026 | 25 | 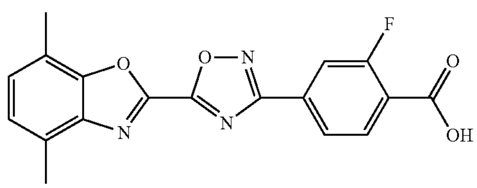 [SMILES: Cc1ccc(C)c2oc(-c3nc(-c4ccc(C(=O)O)c(F)c4)no3)nc12] |
| BHBA-027 | 23 | 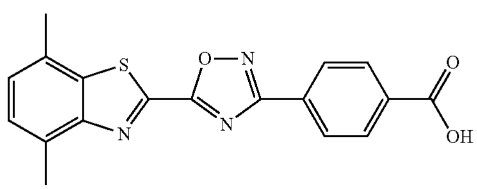 [SMILES: Cc1ccc(C)c2sc(-c3nc(-c4ccc(C(=O)O)cc4)no3)nc12] |
| BHBA-028 | 28 | 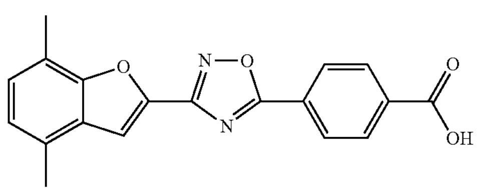 [SMILES: Cc1ccc(C)c2oc(-c3noc(-c4ccc(C(=O)O)cc4)n3)cc12] |
| BHBA-029 | 29 | 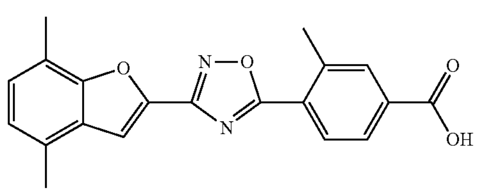 |

-continued

| Code No. | Synthesis # | Structure |
|---|---|---|
| BHBA-030 | 33 | 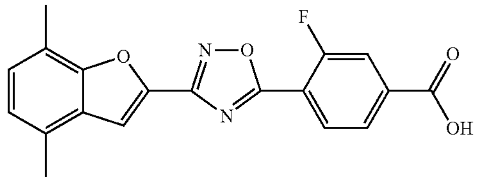 [SMILES: Cc1ccc(C)c2oc(-c3noc(-c4ccc(C(=O)O)cc4F)n3)cc12] |
| BHBA-031 | 32 | 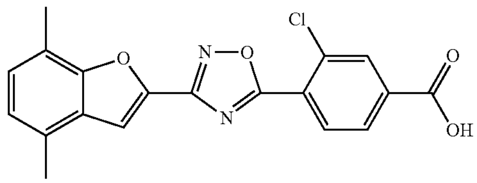 |
| BHBA-032 | 31 | 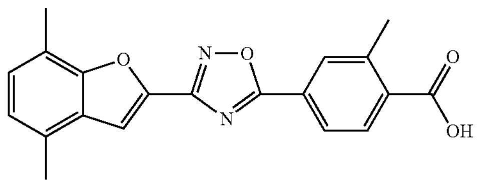 |
| BHBA-033 | 30 | 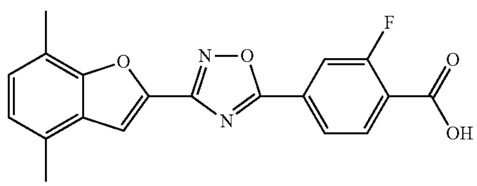 |
| BHBA-034 | 34 | 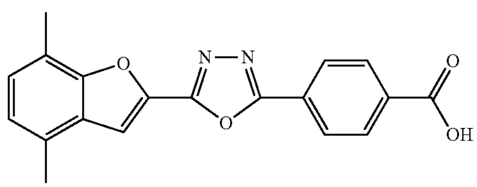 |
| BHBA-035 | 35 | 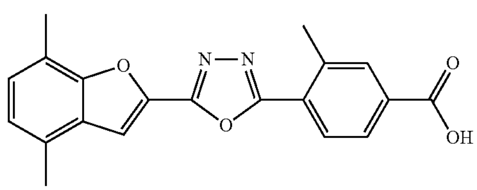 [SMILES: Cc1cc(C(=O)O)ccc1-c1nnc(-c2cc3c(C)ccc(C)c3o2)o1] |
| BHBA-036 | 37 | 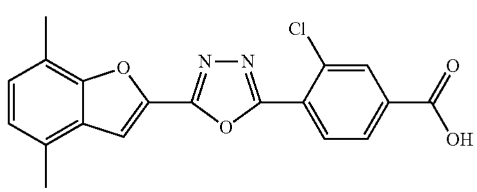 [SMILES: Cc1ccc(C)c2oc(-c3nnc(-c4ccc(C(=O)O)cc4Cl)o3)cc12] |
| BHBA-037 | 36 | 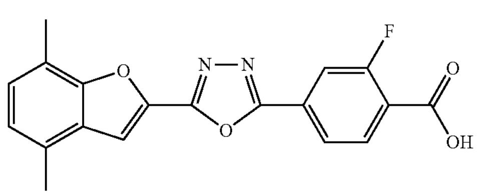 |

-continued

| Code No. | Synthesis # | Structure |
|---|---|---|
| BHBA-038 | 38 | 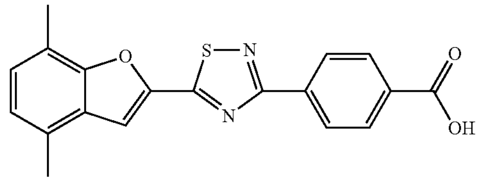 |
| BHBA-039 | 41 | 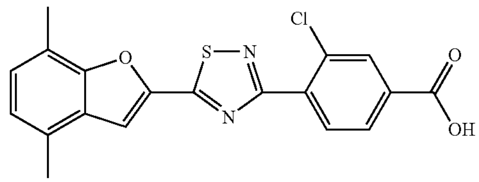 |
| BHBA-040 | 40 | 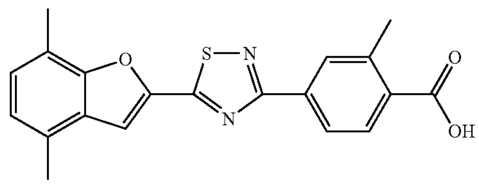 |
| BHBA-041 | 41 | 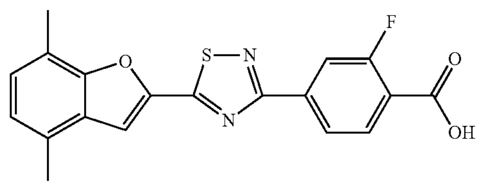 |
| BHBA-042 | 42 | 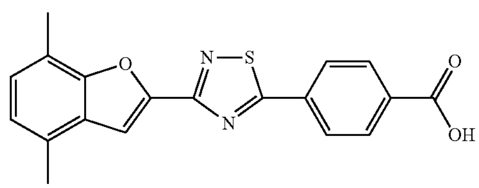 |
| BHBA-043 | 43 | 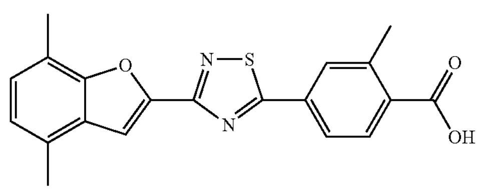 |
| BHBA-044 | 44 | 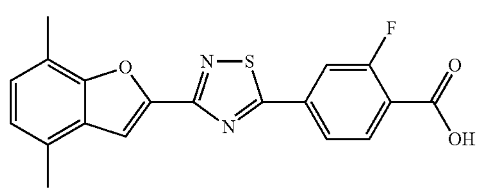 |
| BHBA-045 | 45 | 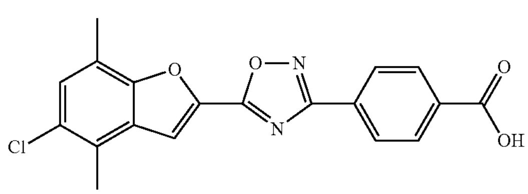 [SMILES: Cc1c(Cl)cc(C)c2oc(-c3nc(-c4ccc(C(=O)O)cc4)no3)cc12] |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., $X^1$, $X^2$, $X^3$, $Y^1$, $Y^2$, —$R^Y$, —$R^{Q1}$, —$R^{Q1A}$, —$R^{Q1B}$, —$R^{Q1C}$, —$R^{Q2}$, —$R^{Q2A}$, —$R^{Q2B}$, —$R^{Q2C}$, —$R^{Q3}$, —$R^{Q3X}$, —$R^{Q3A}$, —$R^{Q3B}$, —$R^{Q3C}$, —$R^{Q3D}$, —$R^{Q3E}$, —$R^{Q4}$, —$R^{Q4X}$, —$R^{Q4A}$, —$R^{Q4B}$, —$R^{Q4C}$, —$R^{Q4D}$, —$R^{P1}$, —$R^{P2}$, —$R^P$, —$R^{PA}$, —$R^{PB}$, —$R^{PC}$, —$R^{PD}$, —$R^{PDD}$, —$R^A$, —$R^{AA}$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to BHBA compounds, as described herein, in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

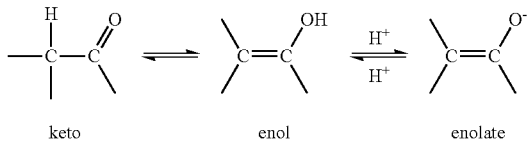

keto  enol  enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures thereof.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH—Teoc), as a 2,2,2-trichloroethyloxy amide (—NH-Troc), as an allyloxy amide (—NH—Alloc), as a 2(-phenylsulfonyl)ethyloxy amide (—NH—Psec); or, in suitable cases (e.g., cyclic amines), as a nitroxide radical (>N—O.).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Several methods for the chemical synthesis of compounds of the present invention are described herein. These and/or other well known methods may be modified and/or adapted in known ways in order to facilitate the synthesis of additional compounds within the scope of the present invention.

In one approach, certain compounds of the invention may conveniently be prepared by oxadiazole formation using a para-hydroxycarbamimidoylbenzoate and a suitably substituted carboxylic acid compound. Subsequent deprotection gives the corresponding benzoic acid compound.

For example, union of a suitably substituted carboxylic acid, e.g., 1(i), with a suitably substituted para-hydroxycarbamimidoylbenzoate compound, e.g., 1(ii), gives the corresponding oxadiazole, e.g., 1(iii). Oxadiazole formation may be carried out using a variety of conditions, for example, under reflux, under dehydrating conditions, e.g., using Dean-Stark or soxhlet apparatus, using an acid or anhydride or a coupling agent, e.g., thionyl chloride, T3P, CDI, or EDC, under the usual conditions. Hydrolysis of the benzoate moiety under the usual conditions gives the corresponding benzoic acid, e.g., 1(iv).

An example of such a method is illustrated in the following scheme.

Scheme 1

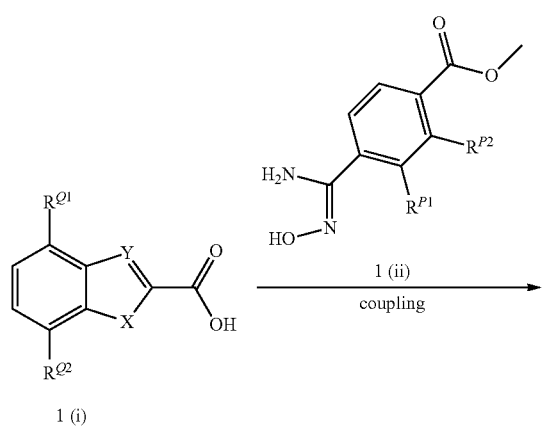

1(i)

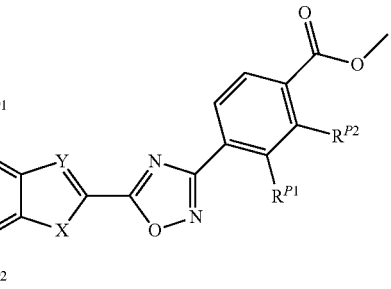

1(iii)

1(iv)

Suitable amidoxime compounds may be prepared, for example, by the addition of hydroxylamine to a suitably substituted para-cyano-benzoate, e.g., 2(i), in methanol and water to give the corresponding para-hydroxycarbamimidoylbenzoate, e.g., 2(ii).

An example of such a method is illustrated in the following scheme.

Scheme 2

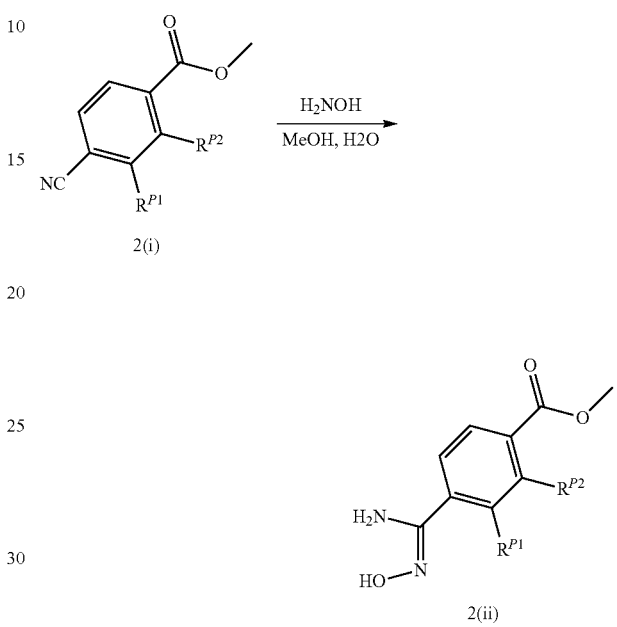

Suitable substituted carboxylic acid compounds, e.g., 3(v), may be prepared, for example, by reacting an α-haloester with a suitably substituted salicylaldehyde (X=O) or thiosalicylaldehyde (X=S), e.g. 3(ii). Hydrolysis of the ester e.g. 3(iii) gives the carboxylic acid e.g., 3(v). The salicylaldehyde may be obtained by formylation of a suitably substituted phenol or thiophenol with formic acid under standard conditions.

Alternatively, the suitably substituted phenol (X=O) or thiophenol (X=S) may be reacted with a protected α-haloaldehyde to give the corresponding benzofuran or benzothiophene e.g. 3(iv). Ortho-lithiation and quenching with carbon dioxide furnishes the carboxylic acid compound, e.g., 3(v).

An example of each method is illustrated in the following scheme.

Scheme 3

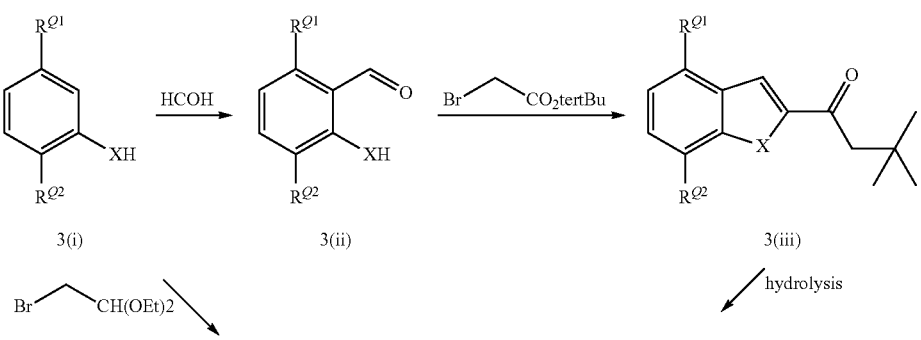

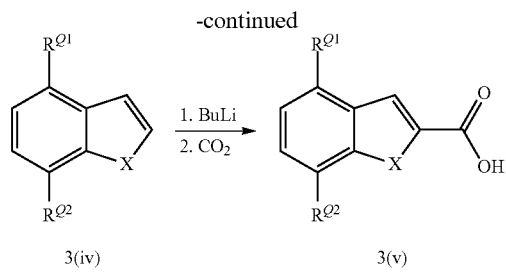

3(iv) → 3(v)

In another approach, certain compounds of the invention may conveniently be prepared by reduction of an arylnitro group. The resulting aniline may be functionalised further by diazotisation and displacement, or the benzoate moiety may be hydrolysed to furnish the corresponding benzoic acid.

For example, reduction of a suitably substituted and protected arylnitro compound, e.g., 4(i), with tin (II) chloride gives an aniline, e.g., 4(ii). This is then reacted further, either to remove protecting groups, e.g., hydrolysis of the ester gives carboxylic acid compound, e.g., 4(iii), or the aniline compound, e.g., 4(ii), undergoes diazotisation to form the diazonium salt which can be displaced to give an aryl halide. Hydrolysis of the benzoate moiety under the usual conditions gives the corresponding benzoic acid, e.g., 4(v).

An example of each method is illustrated in the following schemes.

-continued

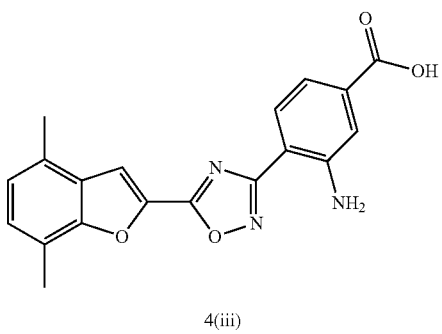

4(iii)

Scheme 4a

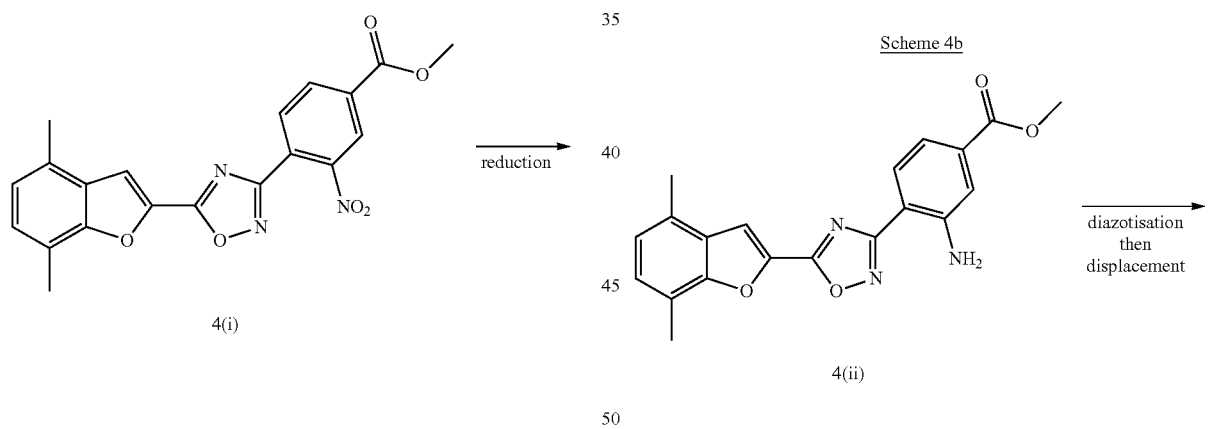

Scheme 4b

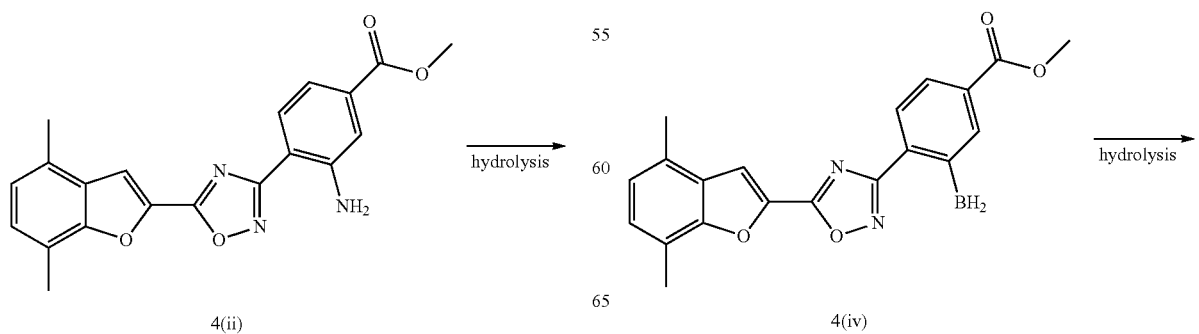

-continued

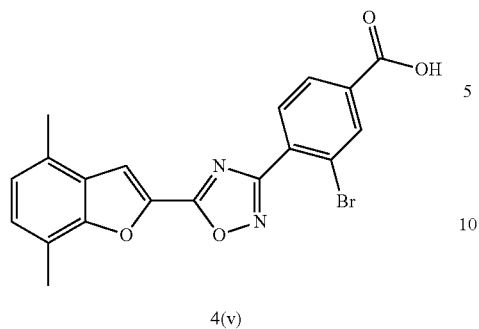

4(v)

In another approach, certain compounds of the invention may conveniently be prepared by oxadiazole formation using a suitably substituted mono-protected dibenzoic acid compound and a suitably substituted para-hydroxycarbamimidoyl compound.

For example, union of a suitably substituted hydroxycarbamimidoyl compound, e.g., 5(i), with the carboxylic acid of a suitably substituted para-hydroxycarbonylbenzoate compound, e.g., 5(ii), gives the corresponding oxadiazole, e.g., 5(iii). Oxadiazole formation may be carried out using a variety of conditions, as described above. Hydrolysis of the benzoate moiety under the usual conditions gives the corresponding benzoic acid, e.g., 5(iv).

An example of such a method is illustrated in the following scheme.

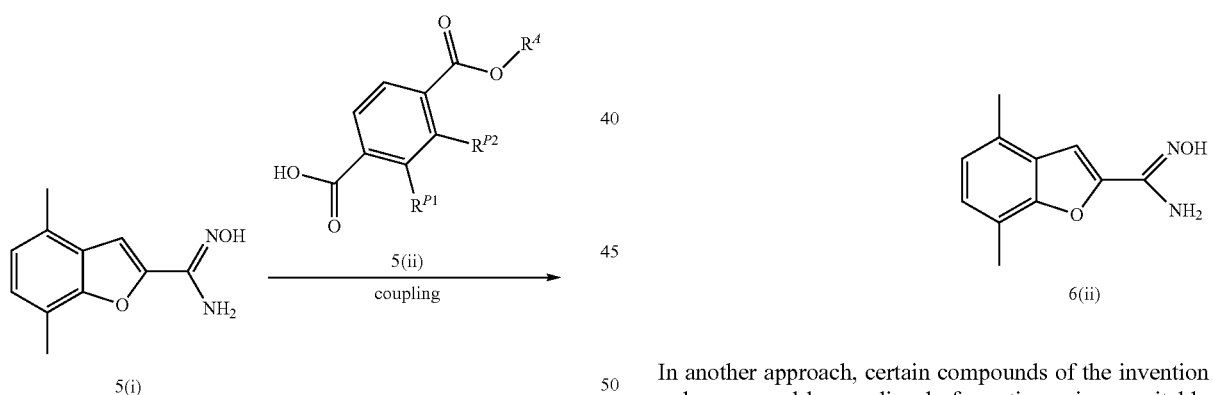

Scheme 5

5(i)

5(ii)
coupling

5(iii)

hydrolysis

-continued

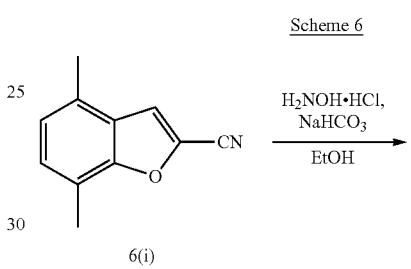

5(iv)

Suitable amidoxime compounds, e.g., 6(ii), may be prepared, for example, by the addition of hydroxylamine to a suitably substituted nitrile, e.g., 6(i).

An example of such a method is illustrated in the following scheme.

Scheme 6

6(i)

$H_2NOH \cdot HCl$, $NaHCO_3$

EtOH

6(ii)

In another approach, certain compounds of the invention may be prepared by oxadiazole formation using a suitably substituted hydrazide compound and a suitably substituted hydroxycarbonylbenzoate compound, followed by ester hydrolysis.

For example, a suitably substituted para-hydroxycarbonylbenzoate, e.g., 7(ii), may be coupled to a suitably substituted hydrazide compound, e.g., 7(i), under standard amide-forming conditions using a coupling agent, e.g., T3P, CDI, EDC, or HOBt. Dehydration and ring closure may be achieved using a variety of conditions, e.g., using Dean-Stark or Soxhlet apparatus or a dehydrating reagent, e.g., phosphoryl chloride. Hydrolysis of the benzoate moiety under the usual conditions gives the corresponding benzoic acid, e.g., 7(v).

An example of such a method is illustrated in the following scheme.

Scheme 7

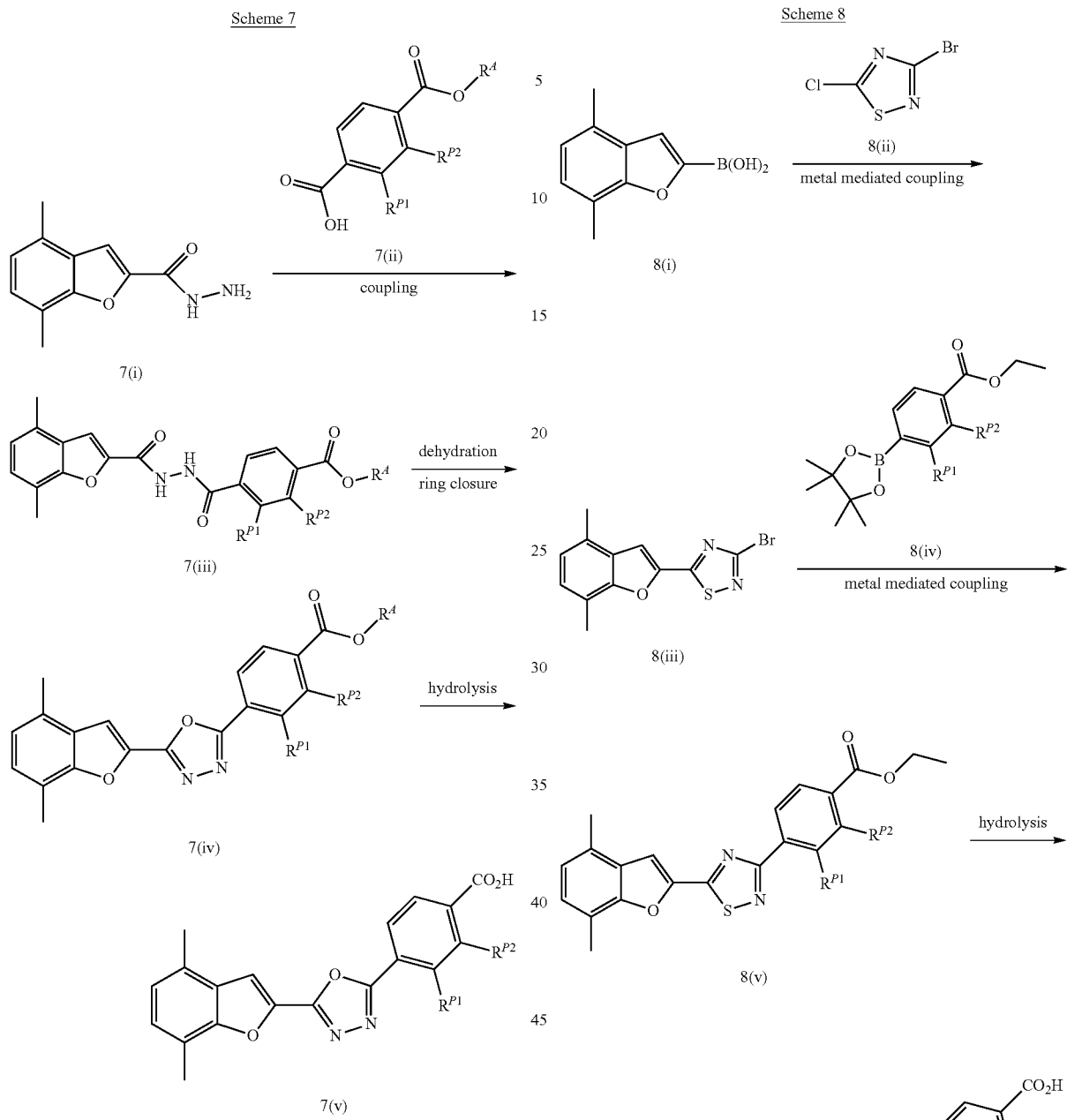

Scheme 8

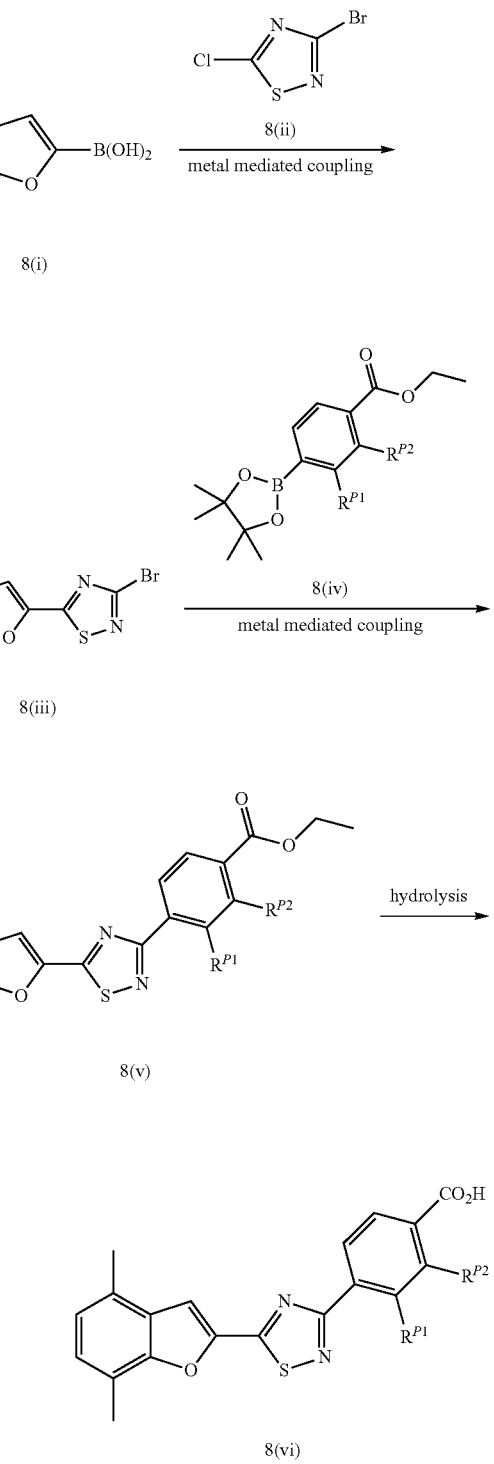

In another approach, certain compounds of the invention may conveniently be prepared using a sequence of catalysed metal-mediated cross-coupling reactions, e.g., Suzuki reactions, Stille reactions, Kumada reactions, etc., to couple suitably substituted suitably protected rings.

For example, a suitably substituted boronic acid, e.g., 8(i), undergoes regio/chemoselective metal-mediated coupling with dihalothiadizaole, e.g., 8(ii), to give bromide, e.g., 8(iii), which then undergoes a second metal-mediated coupling reaction with a suitably substituted suitably protected boronic acid or boronate, e.g., 8(iv). Hydrolysis of the benzoate moiety under the usual conditions gives the corresponding benzoic acid, e.g., 8(vi).

An example of such a method is illustrated in the following scheme.

In another approach, certain compounds of the invention may conveniently be prepared using a different sequence of metal-mediated cross-coupling reactions, e.g. Suzuki reactions, Stille reactions, Kumada reactions, etc., to couple suitably substituted suitably protected rings.

An example of such a method is illustrated in the following scheme.

Scheme 9

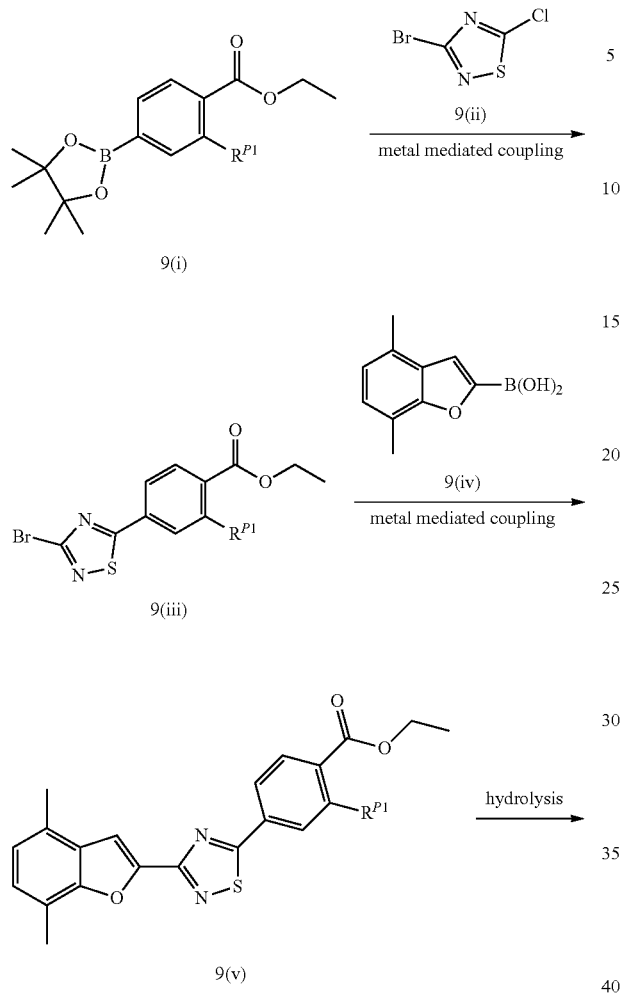

Scheme 10

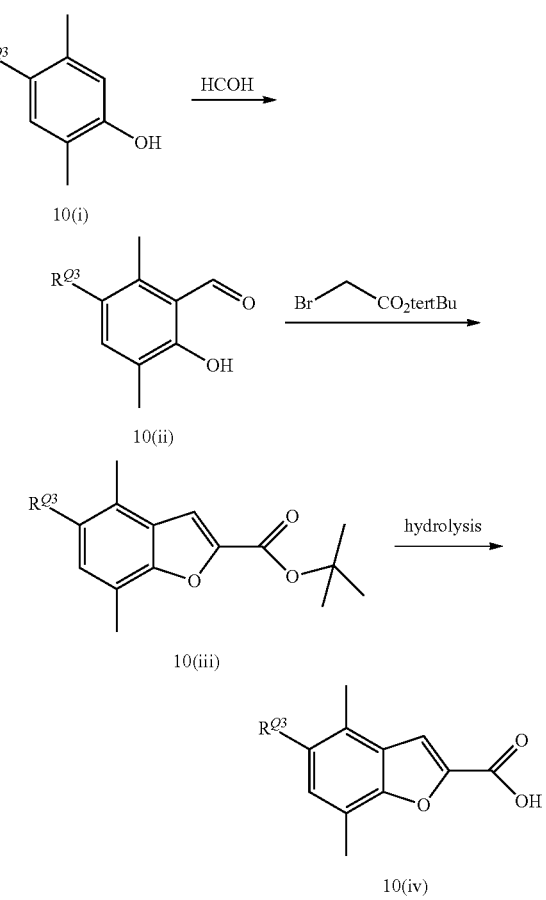

Suitable substituted carboxylic acid compounds, e.g., 10(iv), 11(iv), may be prepared, for example, by reacting a α-haloester with a suitably substituted salicylaldehyde, e.g., 10(ii), 11(ii). Hydrolysis of the ester, e.g., 10(iii), 11(iii), gives the carboxylic acid e.g., 10(iv), 11(iv). The salicylaldehyde may be obtained by formylation of a suitably substituted phenol with formic acid under standard conditions.

Examples of such methods are illustrated in the following schemes.

Scheme 11

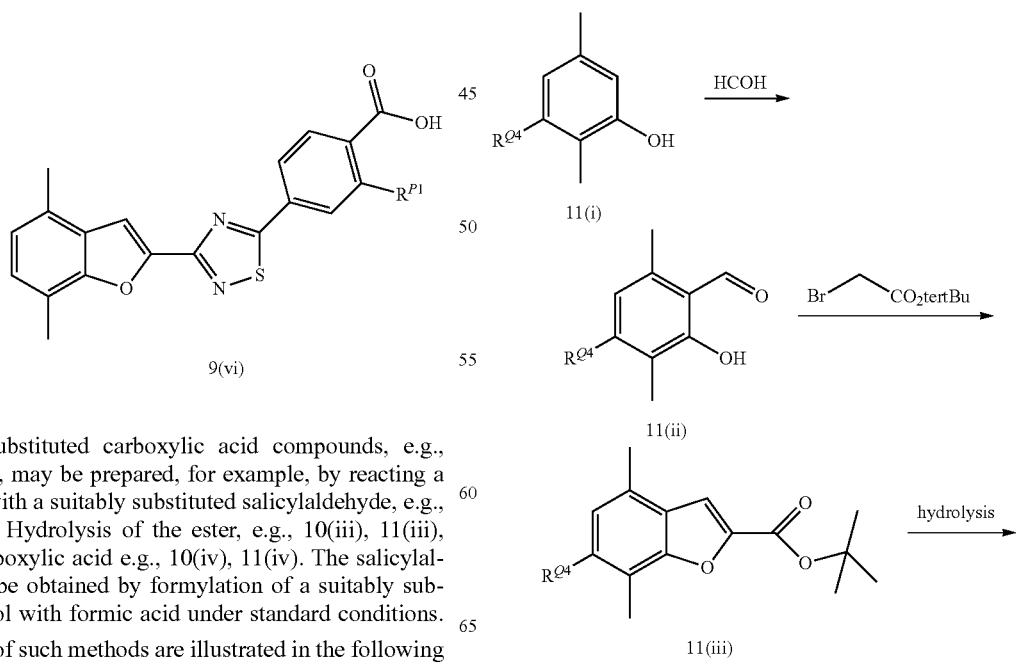

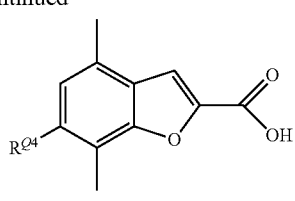

11(iv)

Alternatively, the suitably substituted phenol may be reacted with a protected α-haloaldehyde to give the corresponding benzofuran, e.g., 12 (ii), 13(ii). Ortho-lithiation and quenching with carbon dioxide furnishes the carboxylic acid compound, e.g., 12(iii), 13(iii).

Examples of such methods are illustrated in the following schemes.

Scheme 12

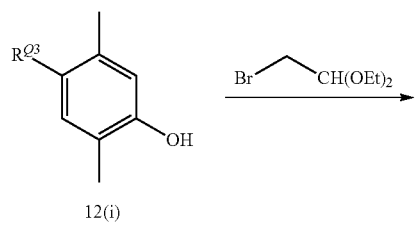

12(i)

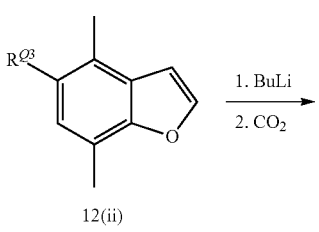

12(ii)

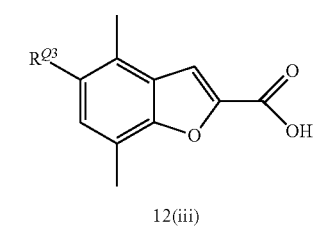

12(iii)

Scheme 13

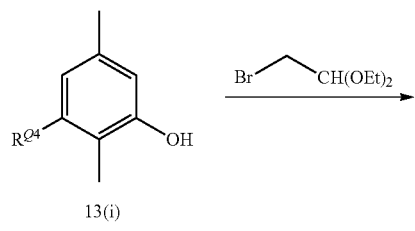

13(i)

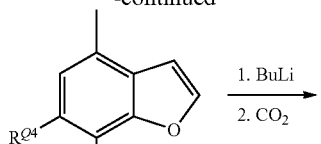

13(ii)

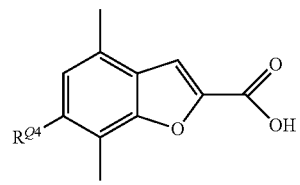

13(iii)

Certain 5-halo substituted carboxylic acid compounds, e.g., 14(ii), may be prepared, for example, by reacting an unsubstituted carboxylic acid compound, e.g., 14(i), with a halogenating agent, e.g., a halo-succinamide in acid (TFA).

An example of such a method is illustrated in the following scheme.

Scheme 14

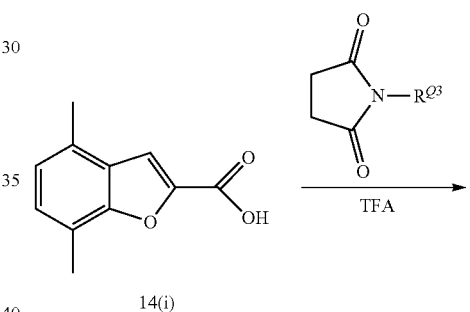

14(i)

14(ii)

Certain 5,6-disubstituted compounds may conveniently be prepared by oxadiazole formation using a para-hydroxycarbamimidoylbenzoate and a suitably substituted carboxylic acid compound. Subsequent deprotection gives the corresponding benzoic acid compound.

For example, union of a suitably substituted carboxylic acid, e.g., 15(i), with para-hydroxycarbamimidoylbenzoate compound, e.g., 15(ii), gives the corresponding oxadiazole, e.g., 15(iii). Oxadiazole formation may be carried out using a variety of conditions, for example, under reflux, under dehydrating conditions, e.g., using Dean-Stark or soxhlet apparatus, using an acid or anhydride or a coupling agent, e.g., thionyl chloride, T3P, CDI, or EDC, under the usual conditions. Hydrolysis of the benzoate moiety under the usual conditions gives the corresponding benzoic acid, e.g., 15(iv).

An example of such a method is illustrated in the following scheme.

Scheme 15

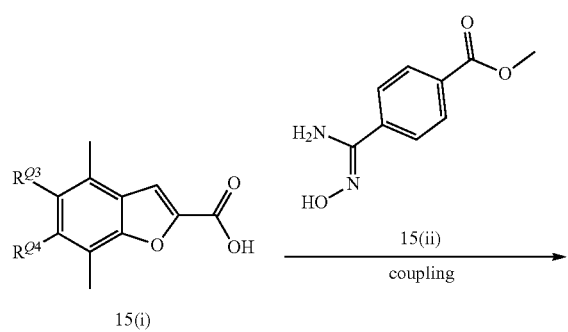

15(i)

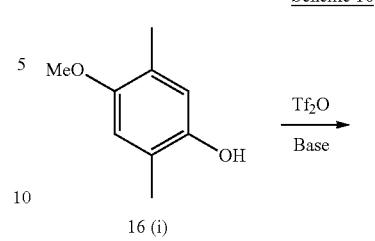

$\xrightarrow[\text{coupling}]{\text{15(ii)}}$

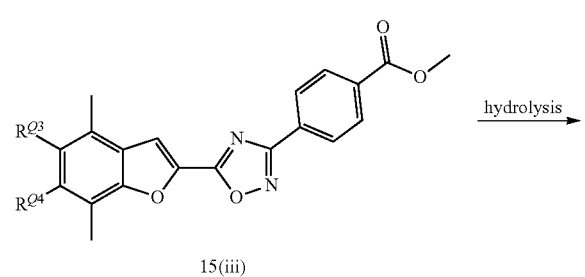

15(iii)

$\xrightarrow{\text{hydrolysis}}$

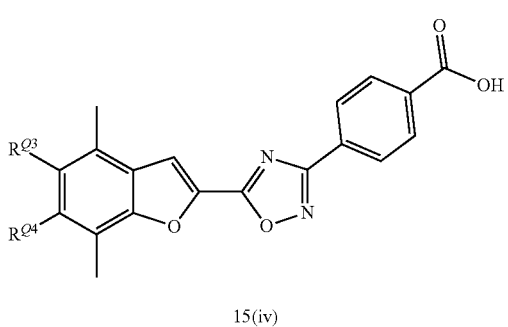

15(iv)

A wide range of 3- and 4-substituted-2,5-dimethyl-phenols are commercially available. Additional 3- and 4-substituted-2,5-dimethyl-phenols, suitable for use in the methods described herein, may be obtained, for example, using methods describes below.

Substituted triflate compounds, e.g., 16(ii), may be prepared, for example, by reacting the phenols, e.g., 16(i), with triflic anhydride in the presence of base for example pyridine or triethylamine. See, e.g., Ritter, 1993. The aryl fluorides, e.g., 16(iii), may be prepared, for example, by reacting the triflates, e.g., 16(ii), with cesium fluoride in the presence of the palladium catalyst [(cinnamyl)PdCl]$_2$ and ligand tBu-BrettPhos. See, e.g., Watson et al., 2009. The phenols, e.g., 16(iv), may be prepared, for example, by reacting the methyl ethers, e.g., 16(iii), with boron tribromide. See, e.g., McOmie et al., 1968.

An example of such a method is illustrated in the following scheme.

Scheme 16

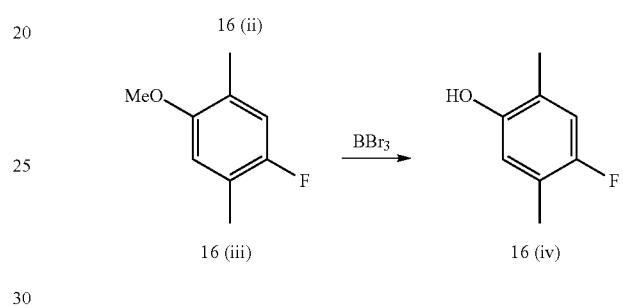

Similarly, the aryl chlorides, e.g., 17(iii), may be prepared, for example, by reacting the triflates, e.g., 17(ii), with potassium chloride in the presence of the palladium catalyst Pd(dba)$_2$, ligand tBuBrettPhos, and potassium fluoride. See, e.g., Pan et al., 2011. The phenols, e.g., 17(iv), may be prepared, for example, by reacting the methyl ethers, e.g., 17(iii), with boron tribromide. See, e.g., McOmie et al., 1968.

An example of such a method is illustrated in the following scheme.

Scheme 17

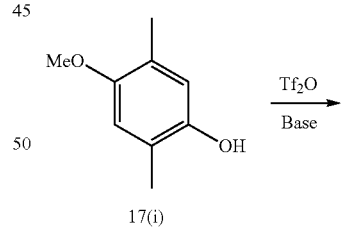

17(i)

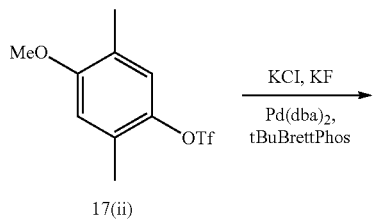

17(ii)

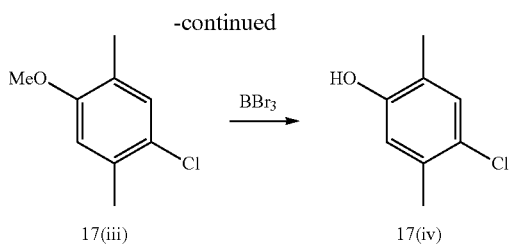

Similarly, the trifluoromethyl compounds, e.g., 18(iv), may be prepared, for example, by reacting the aryl chlorides, e.g., 18(iii), with triethylsilyl $CF_3$ in the presence of the palladium catalyst $Pd(dba)_2$ or $[(allyl)PdCl]_2$, with ligand BrettPhos and potassium fluoride. See, e.g., Cho et al., 2010. The phenols, e.g., 18(v), may be prepared, for example, by reacting the methyl ethers, e.g., 18(iv), with boron tribromide. See, e.g., McOmie et al., 1968.

An example of such a method is illustrated in the following scheme.

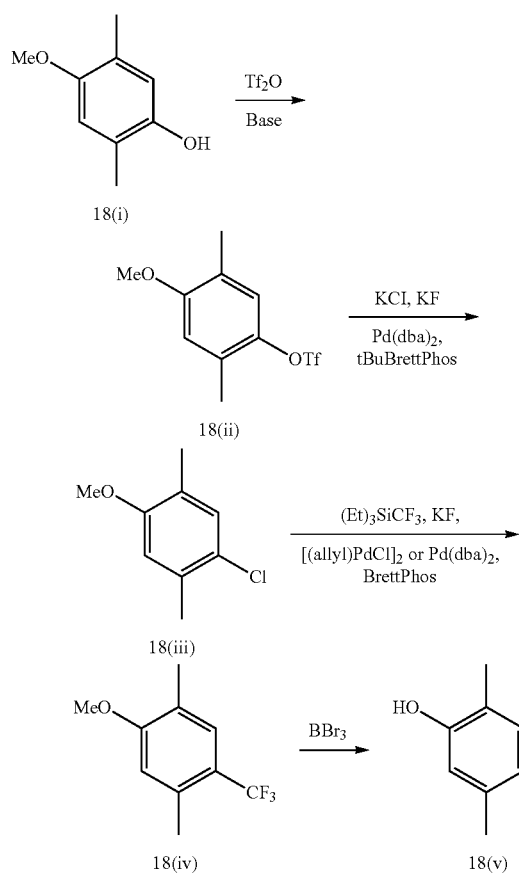

Similarly, substituted triflate compounds, e.g., 19(ii), may be prepared, for example, by reacting the phenols, e.g., 19(i), with triflic anhydride in the presence of base for example pyridine or triethylamine. See, e.g., Ritter, 1993. The aryl fluorides, e.g., 19(iii), may be prepared, for example, by reacting the triflates, e.g., 19(ii), with cesium fluoride in the presence of the palladium catalyst $[(cinnamyl)PdCl]_2$ and ligand tBuBrettPhos. See, e.g., Watson et al., 2009. The phenols, e.g., 19(iv), may be prepared, for example, by reacting the methyl ethers, e.g., 16(iii), with boron tribromide. See, e.g., McOmie et al., 1968.

An example of such a method is illustrated in the following scheme.

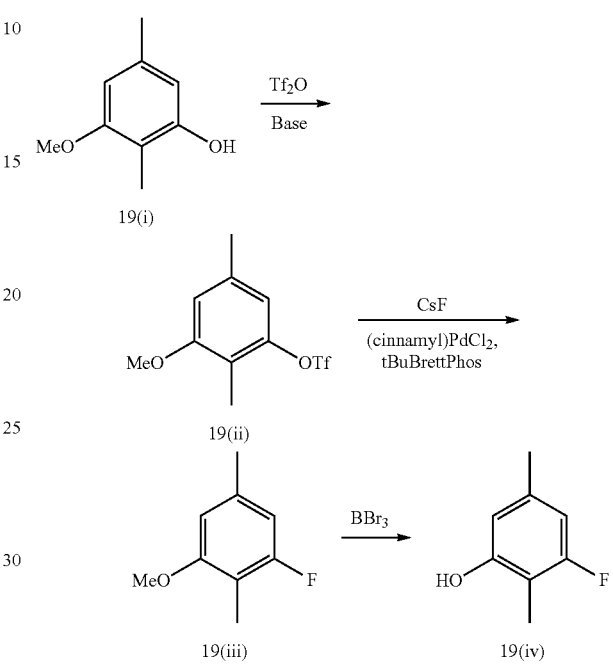

Similarly, the aryl chlorides, e.g., 20 (iii), may be prepared, for example, by reacting the triflates, e.g., 20(ii), with potassium chloride in the presence of the palladium catalyst $Pd(dba)_2$, ligand tBuBrettPhos, and potassium fluoride. See, e.g., Pan et al., 2011. The phenols, e.g., 20(iv), may be prepared, for example, by reacting the methyl ethers, e.g., 20(iii), with boron tribromide. See, e.g., McOmie et al., 1968.

An example of such a method is illustrated in the following scheme.

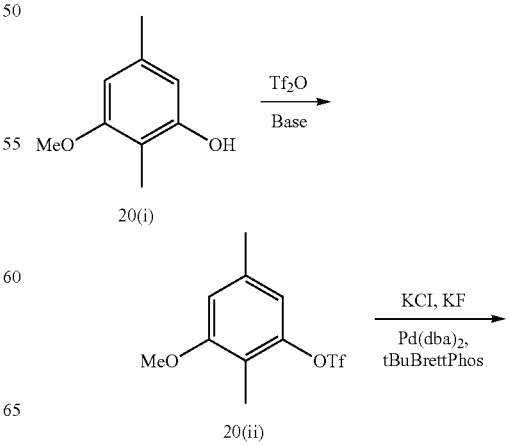

-continued

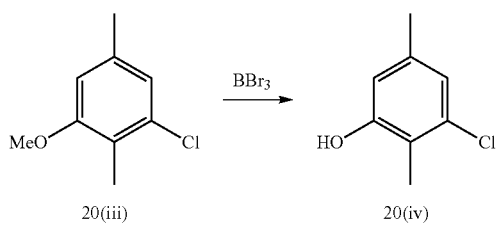

Similarly, the aryl iodides, e.g., 21 (iii), may be prepared, for example, by reacting the triflates, e.g., 21(ii), with sodium iodide in the presence of the ruthenium catalyst [Cp*Ru(MeCN)₃]OTf and 1,3-dimethyl-2-imidazolidinone (DMI). See, e.g., Imazaki et al., 2012. The phenols, e.g., 21(iv), may be prepared, for example, by reacting the methyl ethers, e.g., 21(iii), with boron tribromide. See, e.g., McOmie et al., 1968.

An example of such a method is illustrated in the following scheme.

Scheme 21

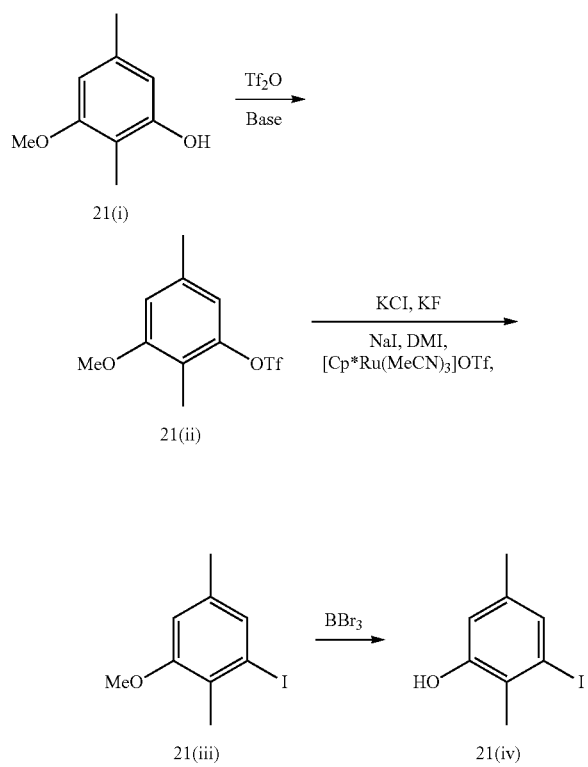

Similarly, the trifluoromethyl compounds, e.g., 22(iv), may be prepared, for example, by reacting the aryl chlorides, e.g., 22(iii), with triethylsilyl CF₃ in the presence of the palladium catalyst Pd(dba)₂ or [(allyl)PdCl]₂, with ligand BrettPhos and potassium fluoride. See, e.g., Cho et al., 2010. The phenols, e.g., 22(v), may be prepared, for example, by reacting the methyl ethers, e.g., 22(iv), with boron tribromide. See, e.g., McOmie et al., 1968.

An example of such a method is illustrated in the following scheme.

Scheme 22

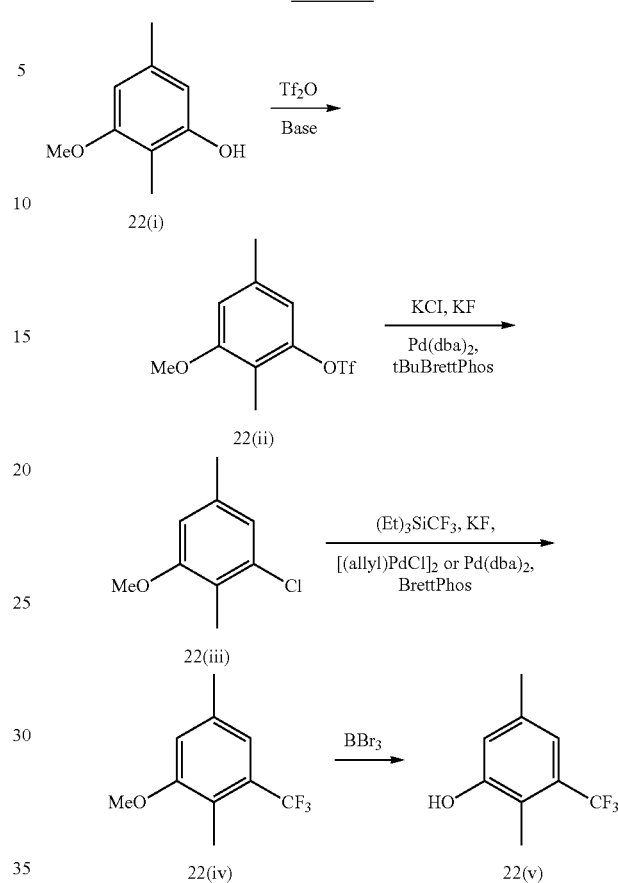

Compositions

One aspect of the present invention pertains to a composition (e.g., a pharmaceutical composition) comprising a BHBA compound, as described herein, and a pharmaceutically acceptable carrier, diluent, or excipient.

Another aspect of the present invention pertains to a method of preparing a composition (e.g., a pharmaceutical composition) comprising mixing a BHBA compound, as described herein, and a pharmaceutically acceptable carrier, diluent, or excipient.

Uses

The compounds described herein are useful, for example, in the treatment of diseases and conditions that are ameliorated by the (selective) activation of RARβ (e.g., RARβ2), such as, for example, neurological injuries such as spinal cord injuries.

Use in Methods of Activating Retinoic Acid Receptor β (RARβ)

One aspect of the present invention pertains to a method of activating retinoic acid receptor β (RARβ) (for example, RARβ2), in vitro or in vivo, comprising contacting RARβ (for example, RARβ2) with an effective amount of a BHBA compound, as described herein.

One aspect of the present invention pertains to a method of selectively activating retinoic acid receptor β (RARβ) (for example, RARβ2) (e.g., with respect to RARα and/or RARγ), in vitro or in vivo, comprising contacting RARβ (for example, RARβ2) with an effective amount of a BHBA compound, as described herein.

In one embodiment, the method is performed in vitro.

In one embodiment, the method is performed in vivo.

One aspect of the present invention pertains to a method of activating retinoic acid receptor β (RARβ) (for example, RARβ2), in a neuronal cell, in vitro or in vivo, comprising contacting the cell with an effective amount of a BHBA compound, as described herein.

One aspect of the present invention pertains to a method of selectively activating retinoic acid receptor β (RARβ) (for example, RARβ2) (e.g., with respect to RARα and/or RARγ) in a neuronal cell, in vitro or in vivo, comprising contacting the cell with an effective amount of a BHBA compound, as described herein.

In one embodiment, the BHBA compound is provided in the form of a pharmaceutically acceptable composition.

Suitable assays for determining RARβ activation (for example, RARβ2 activation) are described herein and/or are known in the art.

Use in Methods of Causing or Promoting Neurite Development, Etc.

The BHBA compounds described herein are useful for causing or promoting neurite development, neurite outgrowth, and/or neurite regeneration.

The term "neurite", as used herein, refers to a projection from the cell body of a neuron, and includes, for example, axons and dendrites.

One aspect of the present invention pertains to a method of causing or promoting neurite development, neurite outgrowth, and/or neurite regeneration, comprising contacting a nueron, in vitro or in vivo, with an effective amount of a BHBA compound, as described herein.

One aspect of the present invention pertains to a method of causing or promoting neurite development, comprising contacting a nueron, in vitro or in vivo, with an effective amount of a BHBA compound, as described herein.

One aspect of the present invention pertains to a method of causing or promoting neurite outgrowth, comprising contacting a nueron, in vitro or in vivo, with an effective amount of a BHBA compound, as described herein.

One aspect of the present invention pertains to a method of causing or promoting neurite regeneration, comprising contacting a nueron, in vitro or in vivo, with an effective amount of a BHBA compound, as described herein.

In one embodiment, the method is performed in vitro.

In one embodiment, the method is performed in vivo.

In one embodiment, the BHBA compound is provided in the form of a pharmaceutically acceptable composition.

Suitable assays for determining or measuring neurite development, neurite outgrowth, and neurite regeneration are described herein and/or are known in the art.

Use in Methods of Therapy

Another aspect of the present invention pertains to a BHBA compound, as described herein, for use in a method of treatment of the human or animal body by therapy.

Use in the Manufacture of Medicaments

Another aspect of the present invention pertains to use of a BHBA compound, as described herein, in the manufacture of a medicament for use in treatment.

In one embodiment, the medicament comprises the BHBA compound.

Methods of Treatment

Another aspect of the present invention pertains to a method of treatment comprising administering to a patient in need of treatment a therapeutically effective amount of a BHBA compound, as described herein, preferably in the form of a pharmaceutical composition.

Conditions Treated—Conditions Mediated by RAR

In one embodiment (e.g., of use in methods of therapy, of use in the manufacture of medicaments, of methods of treatment), the treatment is treatment of a disease or condition that is mediated by RARβ (for example, RARβ2).

Conditions Treated—Conditions Ameliorated by the Activation of RARβ

In one embodiment (e.g., of use in methods of therapy, of use in the manufacture of medicaments, of methods of treatment), the treatment is treatment of: a disease or condition that is ameliorated by the activation of RARβ (for example, RARβ2).

In one embodiment (e.g., of use in methods of therapy, of use in the manufacture of medicaments, of methods of treatment), the treatment is treatment of: a disease or condition that is ameliorated by the selective activation of RARβ (for example, RARβ2) (e.g., with respect to RARα and/or RARγ).

Conditions Treated—Neurological Injuries

In one embodiment (e.g., of use in methods of therapy, of use in the manufacture of medicaments, of methods of treatment), the treatment is treatment of a neurological injury.

The term "neurological injury", as used herein, refers to any injury or damage of the nervous system, including, for example, injury or damage of the nervous system that is mechanically-induced (for example, caused by trauma); chemically-induced (for example, caused by a neurotoxin; or by a treatment regime having an immunosuppressant effect, whether by design or as a side-effect); or disease-related (for example, caused by a microbial, bacterial, fungal, or viral infection; by a neurodegenerative disorder; or by any other nerve tissue-related disorder).

In one embodiment, the treatment is treatment of an injury of the central nervous system (CNS).

In one embodiment, the treatment is treatment of an injury of the peripheral nervous system (PNS).

The term "central nervous system" (CNS), as used herein, refers to the brain and the spinal cord. The term "peripheral nervous system" (PNS), as used herein, refers to neurons, nerves, and ganglia outside of the brain and the spinal cord. The term "nervous system", as used herein, refers to both the CNS and PNS.

In one embodiment, the treatment is treatment of a nerve injury.

In one embodiment, the treatment is treatment of a PNS nerve injury.

In one embodiment, the treatment is treatment of a CNS nerve injury.

In one embodiment, the treatment is treatment of a spinal cord injury.

In one embodiment, the treatment is treatment of a spinal cord injury caused by trauma.

In one embodiment, the treatment is treatment of an optic nerve injury.

In one embodiment, the treatment is treatment of an optic nerve injury caused by glaucoma.

In one embodiment, the treatment is treatment of a neuropathy.

In one embodiment, the treatment is treatment of a PNS neuropathy.

In one embodiment, the treatment is treatment of a CNS neuropathy.

In one embodiment, the treatment is treatment of a spinal cord neuropathy.

In one embodiment, the treatment is treatment of an optic nerve neuropathy.

In one embodiment, the treatment is treatment of diabetic neuropathy (i.e., neuropathy associated with diabetes mellitus).

In one embodiment, the treatment is treatment of AIDS neuropathy (i.e., neuropathy associated with AIDS).

In one embodiment, the treatment is treatment of leprotic neuropathy (i.e., neuropathy associated with leprosy).

In one embodiment, the treatment is treatment of peripheral neuropathy (for example, polyneuropathy, mononeuropathy, mononeuritis multiplex, or autonomic neuropathy).

In one embodiment, the treatment is treatment of a neurodegenerative disorder.

In one embodiment, the treatment is treatment of a cognitive disorder, memory impairment, memory deficit, senile dementia, Alzheimer's disease, early stage Alzheimer's disease, intermediate stage Alzheimer's disease, late stage Alzheimer's disease, cognitive impairment, or mild cognitive impairment.

In one embodiment, the treatment is treatment of Huntington's disease.

In one embodiment, the treatment is treatment of Parkinson's disease.

In one embodiment, the treatment is treatment of motor neurone disease.

In one embodiment, the treatment is treatment of localised paralysis.

In one embodiment, the treatment is treatment of Bell's palsy.

In one embodiment, the treatment is treatment of neurally-based impotence.

In one embodiment, the treatment is treatment of neurally-based impotence caused by nerve trauma following radical prostatectomy.

In one embodiment, the treatment is treatment of paralysis, for example, monoplegia, quadriplegia, or paraplegia.

In one embodiment, the treatment is treatment of a neurological disorder caused by a neurological injury.

In one embodiment, the treatment is treatment of a neurological disorder caused by a neuropathy, for example, as described above.

In one embodiment, the treatment is treatment of a neurological injury caused by a neuropathy, for example, as described above.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment" (that is, treatment of condition encompasses reducing the risk of that condition).

For example, treatment includes the prophylaxis of localised paralysis, reducing the risk of localised paralysis, alleviating the symptoms of localised paralysis, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

For example, it may be beneficial to combine treatment with a compound as described herein with one or more other (e.g., 1, 2, 3, 4) agents or therapies, e.g., that treat a neurological injury.

One aspect of the present invention pertains to a compound as described herein, in combination with one or more additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The BHBA compounds described herein may also be used as cell culture additives to activate RARβ (e.g., RARβ2), e.g., to cause or promote neurite development, neurite outgrowth, and/or neurite regeneration.

The BHBA compounds described herein may also be used, for example, as part of an in vitro assay, for example, in order to determine whether a candidate host is likely to benefit from treatment with the compound in question.

The BHBA compounds described herein may also be used as a standard, for example, in an assay, in order to identify other compounds, other RARβ (e.g., RARβ2) agonists, etc.

Kits

One aspect of the invention pertains to a kit comprising (a) a BHBA compound as described herein, or a composition comprising a BHBA compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The BHBA compound or pharmaceutical composition comprising the BHBA compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the BHBA compound to be administered alone, it is preferable to present it as a pharmaceutical formulation (e.g., composition, preparation, medicament) comprising at least one BHBA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one BHBA compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringers Solution, or Lactated Ringer's Injection. Typically, the concentration of the compound in the liquid is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the BHBA compounds, and compositions comprising the BHBA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular BHBA compound, the route of administration, the time of administration, the rate of excretion of the BHBA compound, the duration of the treatment, other drugs, compounds, and/or materials used in combination, the severity of the condition, and the species, sex, age, weight, condition, general health, and prior medical history of the patient. The amount of BHBA compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the BHBA compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

ABBREVIATIONS

Ac=acetyl
AIBN=azobisisobutyronitrile
aq.=aqueous
Boc=tert-butoxycarbonyl
br=broad
Bu=butyl
conc.=concentrated
CDI=1,1-carbonyldiimidazole
d=doublet
dba=dibenzylideneacetone
DCM=dichloromethane
DIPEA=N,N-diisopropylethylamine
DMAP=4-dimethylaminopyridine
DMF=N,N-dimethylformamide
DMSO=dimethylsulfoxide
DPPF=1,1'-bis(diphenylphosphino)ferrocene
EDC=1-Ethyl-3-(3-dimethylaminopropyl)carbodiimide hydrochloride
eq.=no. of molar equivalents
ES=electrospray
Et=ethyl
h=hour(s)
HATU=2-(7-aza-1H-benzotriazole-1-yl)-1,1,3,3-tetramethyluronium hexafluorophosphate
HOBt=N-hydroxybenzotriazole
HPLC=high performance liquid chromatography
Hz=hertz
L=litre
M=molar
m=multiplet
m-CPBA=meta-chloroperoxybenzoic acid
Me=methyl
min=minute(s)
NBS=N-bromosuccinimide
NMR=nuclear magnetic resonance
Ph=phenyl
PPA=polyphosphoric acid/pyrophosphoric acid
RT=room temperature
s=singlet
satd.=saturated
SAX=solid supported strong anion exchange resin
SCX=solid supported strong cation exchange resin
t=triplet
T3P=2-propanephosphonic acid anhydride
TEA=triethylamine
TFA=trifluoroacetic acid
THF=tetrahydrofuran
TMSCl=trimethylchlorosilane Synthesis 1

4-(5-(4,7-Dimethylbenzofuran-2-yl)-1,2,4-oxadiazol-3-yl)benzoic acid (BHBA-001)

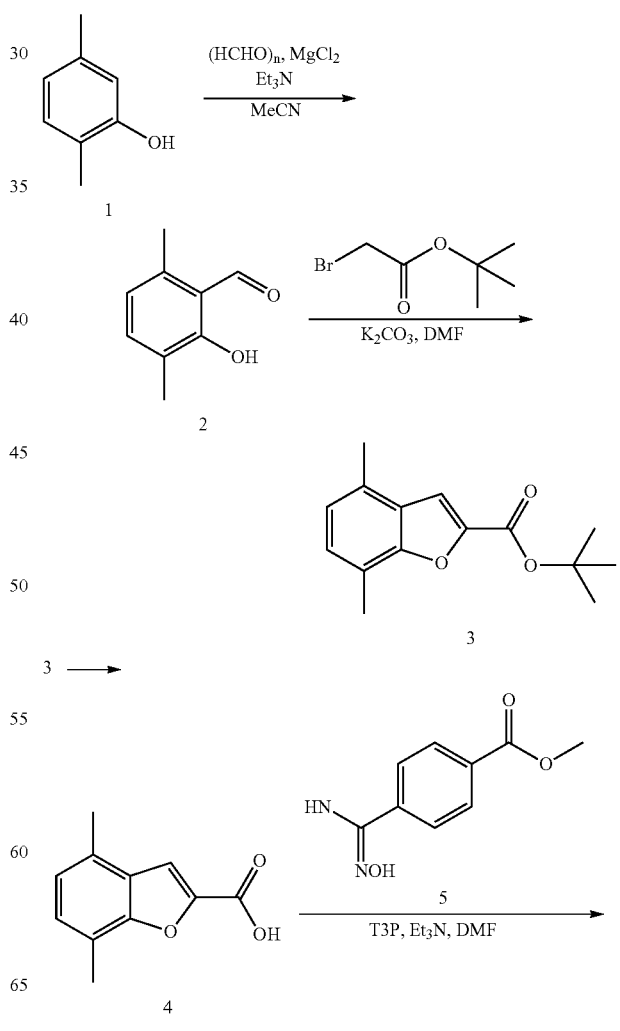

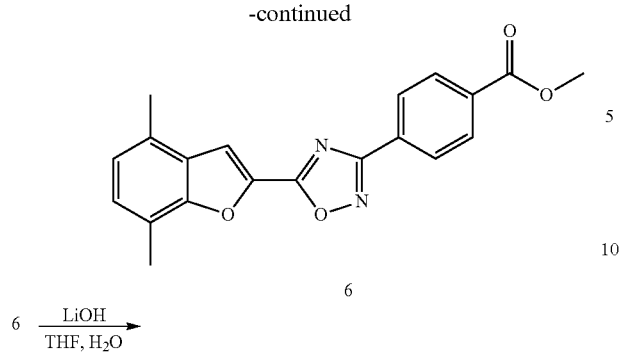

6 $\xrightarrow{\text{LiOH}}$ THF, H$_2$O

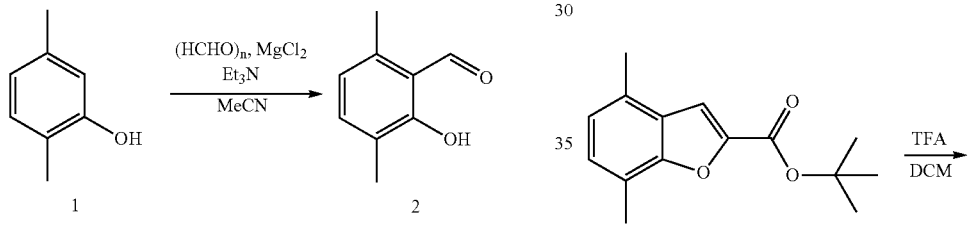

Step (i): 2-Hydroxy-3,6-di methylbenzaldehyde (2)

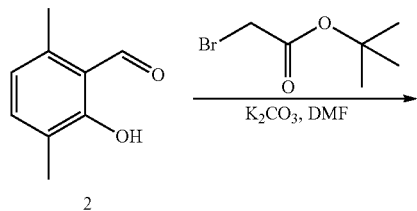

A suspension of 2,5-dimethylphenol (1) (20 g, 160 mmol), paraformaldehyde (34 g, 1.1 mol), MgCl$_2$ (23.4 g, 246 mmol) and Et$_3$N (86 mL, 610 mmol) in anhydrous MeCN (550 mL) was stirred under reflux for 2 h. The reaction mixture was concentrated in vacuo to half the volume and then partitioned between Et$_2$O (200 mL) and 1 M HCl (200 mL). The aqueous phase was further extracted with Et$_2$O (400 mL), then the combined organic extracts were dried over MgSO$_4$ and filtered. The solution was in vacuo and the residue was purified by silica gel chromatography (330 g, 0-20% Et$_2$O in isohexane) to afford the title compound (2) (8.6 g, 35%) as a yellow solid: $^1$H NMR (400 MHz, DMSO-d$_6$) δ: 12.12 (1H, s), 10.29 (1H, s), 7.25 (1H, d), 6.61 (1H, d), 2.56 (3H, s), 2.20 (3H, s).

Step (ii): tert-Butyl 4,7-dimethylbenzofuran-2-carboxylate (3)

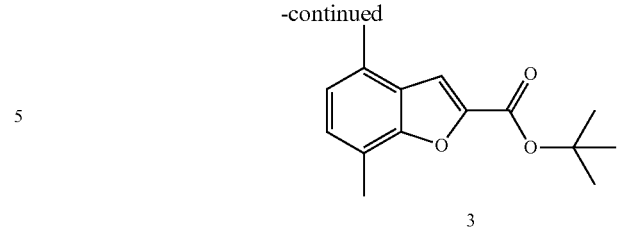

tert-Butyl 2-bromoacetate (10.6 mL, 71.5 mmol) was added dropwise to a stirring suspension of 2-hydroxy-3,6-dimethylbenzaldehyde (2) (8.6 g, 57 mmol) and potassium carbonate (19.8 g, 143 mmol) in anhydrous DMF (40 mL). The reaction mixture stirred under reflux for 20 h. The mixture was partitioned between EtOAc (100 mL) and water (100 mL) and the aqueous phase was further extracted with EtOAc (100 mL). The combined organics were washed with brine (5×100 mL) and concentrated in vacuo. The residue was purified by silica gel chromatography (330 g, 20% MeOH in DCM) to afford the title compound (3) (12.3 g, 87% yield) as a red oil: $^1$H NMR (400 MHz, DMSO-d$_6$) δ: 7.42 (1H, s), 7.04 (2H, dd), 8.33 (1H, d), 2.52 (3H, s), 2.50 (3H, s), 1.63 (9H, s).

Step 4,7-Di methylbenzofuran-2-carboxylic acid (4)

Trifluoroacetic acid (19.2 mL, 249 mmol) was added dropwise to a solution of tert-butyl 4,7-dimethylbenzofuran-2-carboxylate (3) (12.3 g, 49.8 mmol) in DCM (100 mL) at 0° C. After the addition the mixture was allowed to warm to RT and stirred for 20 h. The solvent was removed in vacuo and the residue was partitioned between EtOAc (100 mL) and 1 M HCl (100 mL). The aqueous phase was further extracted with EtOAc (100 mL) and the combined organic solutions were washed with brine (300 mL) and then concentrated in vacuo. The residue was dissolved in EtOAc (100 mL) and then extracted with satd. NaHCO$_3$ solution (200 mL). The aqueous solution was acidified by the addition of conc. HCl and extracted with EtOAc (200 mL). The organic solution was concentrated in vacuo and co-evaporated with toluene to afford the title compound (4) (7.7 g, 81% yield) as a pale brown solid: m/z 190 [M+H]$^+$ (ES$^+$). $^1$H NMR (400 MHz, DMSO-d$_6$) δ: 13.48 (1H, s), 7.72 (1H, s), 7.11 (2H, dd), 2.47 (3H, s), 2.44 (3H, s).

Step (iv): Methyl 4-(5-(4,7-dimethylbenzofuran-2-yl)-1,2,4-oxadiazol-3-yl)benzoate (6)

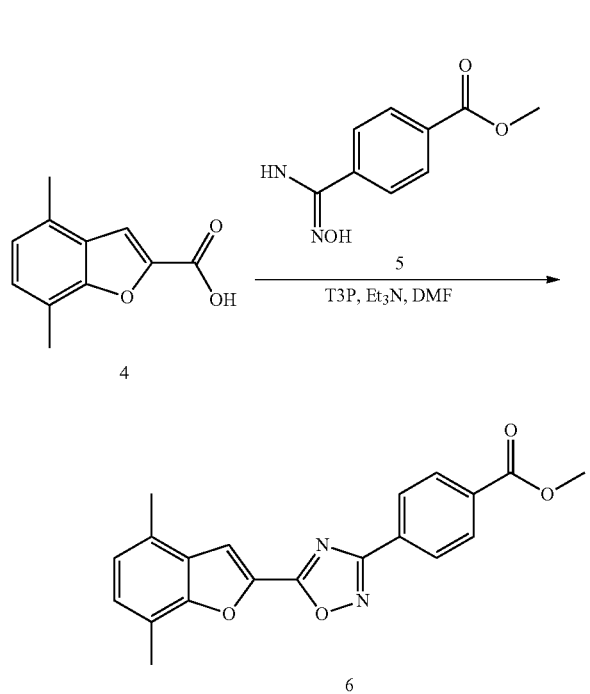

A solution of T3P in EtOAc (50%) (23.2 mL, 39.4 mmol) was added dropwise to a mixture of 4,7-dimethylbenzofuran-2-carboxylic acid (4) (3.0 g, 16 mmol), methyl 4-(N'-hydroxycarbamimidoyl)benzoate (5) (3.1 g, 16 mmol) and Et₃N (11 mL, 79 mmol) in anhydrous DMF (25 mL), stirring at 0° C. The mixture was stirred at 0° C. for 10 min then warmed to 90° C. and stirred for 18 h. The reaction mixture was cooled to RT and poured into iced water (150 mL). The solid was collected, washed with cold EtOAc and dried under suction. The material was purified by trituration with MeOH and dried in vacuo to afford the title compound (6) (3.6 g, 65% yield) as a pink solid: m/z 349 [M+H]⁺ (ES⁺). ¹H NMR (400 MHz, DMSO-d₆) δ: 8.29-8.26 (3H, m), 8.19 (2H, d), 7.29 (1H, d), 7.13 (1H, d), 3.92 (3H, s), 2.56 (3H, s), 2.54 (3H, s).

Step (v): 4-(5-(4,7-Dimethylbenzofuran-2-yl)-1,2,4-oxadiazol-3-yl)benzoic acid (BHBA-001)

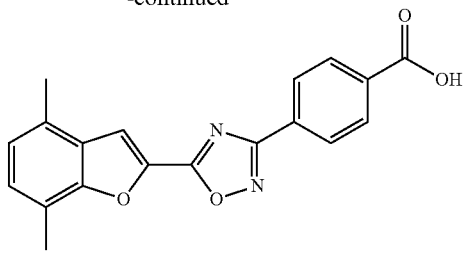

A suspension of methyl 4-(5-(4,7-dimethylbenzofuran-2-yl)-1,2,4-oxadiazol-3-yl)benzoate (6) (100 mg, 0.287 mmol) in THF (1 mL) was treated with LiOH (2 M, aq., 720 μL, 1.4 mmol) and the mixture was stirred at 40° C. for 20 h. The reaction mixture was cooled to RT, then acidified by the dropwise addn of 1 M HCl. The resulting solid was collected by filtration, then dissolved in MeOH and evaporated to dryness to afford the title compound (95 mg, 99% yield) as a white solid: m/z 335 [M+H]⁺ (ES⁺), 333 [M−H]⁻ (ES⁻). ¹H NMR (400 MHz, DMSO-d₆) δ: 13.34 (1H, br. s), 8.25-8.23 (3H, m), 8.16 (2H, d), 7.29 (1H, d), 7.12 (1H, d), 2.56 (3H, s), 2.53 (3H, s).

Synthesis 2

3-Chloro-4-(5-(4,7-dimethylbenzofuran-2-yl)-1,2,4-oxadiazol-3-yl)benzoic acid (BHBA-002)

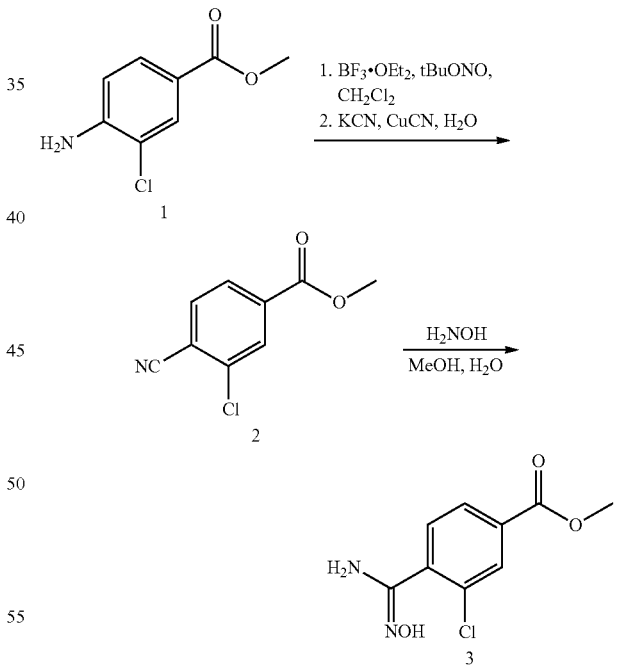

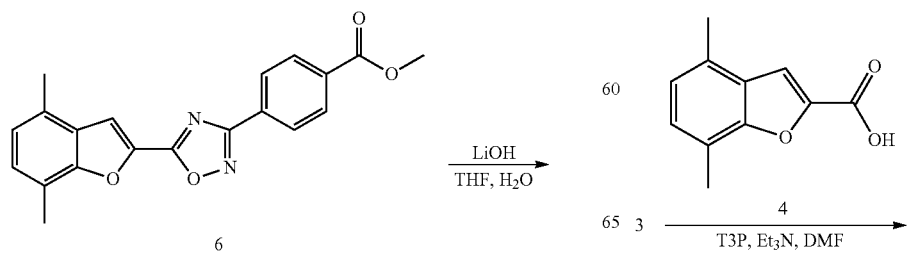

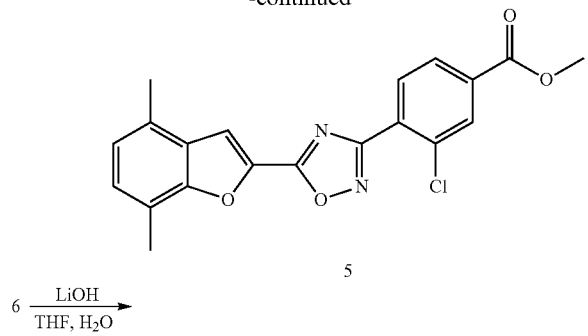

uct was purified by silica gel chromatography (120 g, 0-10% EtOAc in isohexane) to afford the title compound (2) (3.56 g, 68%) as an orange solid: m/z 196 [M+H]$^+$ (ES$^+$); $^1$H NMR (400 MHz, DMSO-d$_6$) δ: 8.17-8.14 (2H, m), 8.04 (1H, dd), 3.91 (3H, s).

Step (ii): Methyl 3-chloro-4-(N'-hydroxycarbamimidoyl)benzoate (3)

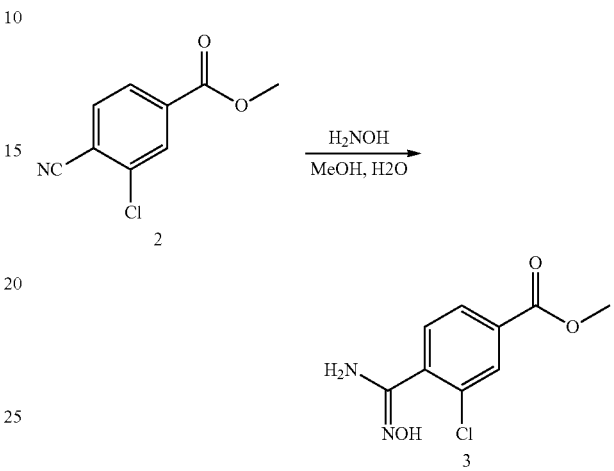

A mixture of methyl 3-chloro-4-cyanobenzoate (2) (2.0 g, 10 mmol) and 50% aq. hydroxylamine solution (1.25 mL, 20.4 mmol) in MeOH (30 mL) was stirred at reflux for 45 min. The reaction mixture was allowed to cool to RT, then diluted with H$_2$O (50 mL) and extracted with EtOAc (150 mL). The organic solution was washed with brine (100 mL), dried over MgSO$_4$ and concentrated in vacuo to give methyl 3-chloro-4-(N'-hydroxycarbamimidoyl)benzoate (3) (1.9 g, 72%) as a yellow solid: m/z 229 [M+H]$^+$ (ES$^+$); $^1$H NMR (400 MHz, DMSO-d$_6$) δ: 9.63 (1H, s), 7.96 (1H, d), 7.94-7.88 (1H, m), 7.58 (1H, d), 5.94 (2H, s), 3.89 (3H, s).

Step (iii): Methyl 3-chloro-4-(5-(4,7-dimethylbenzofuran-2-yl)-1,2,4-oxadiazol-3-yl)benzoate (5)

Step (i): Methyl 3-chloro-4-cyanobenzoate (2)

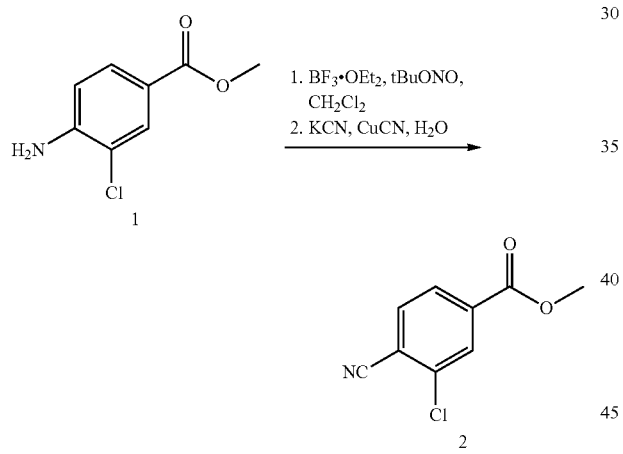

A solution of methyl 4-amino-3-chlorobenzoate (5.0 g, 27 mmol) was stirred at −20° C. in DCM (20 mL) and treated sequentially with a solution of BF$_3$·OEt$_2$ (5.5 mL, 43 mmol) in anhydrous diethyl ether (10 mL) and tert-butyl nitrite (6.0 mL, 46 mmol). The reaction mixture was stirred at −20° C. for 30 min and then allowed to warm slowly to RT and stirred for 72 h. The reaction mixture was filtered and the precipitate was washed sequentially with DCM (50 mL), Et$_2$O (50 mL) and isohexane (50 mL) to afford the intermediate diazonium salt. The salt was dissolved in H$_2$O (200 mL) and slowly added to a stirred mixture of potassium cyanide (1.98 g, 30.4 mmol) and copper (I) cyanide (2.73 g, 30.4 mmol) in H$_2$O (300 mL) at 0-5° C. After the addition the mixture was stirred at 0-5° C. for 0.5 h, then at RT for 18 h. The mixture was treated with 10% aqueous FeCl$_3$ solution (200 mL) and stirred at RT for 30 min. The product was extracted with EtOAc (3×200 mL) and the combined organic extracts were washed with brine (400 mL), dried over MgSO$_4$, filtered and concentrated in vacuo. The prod-

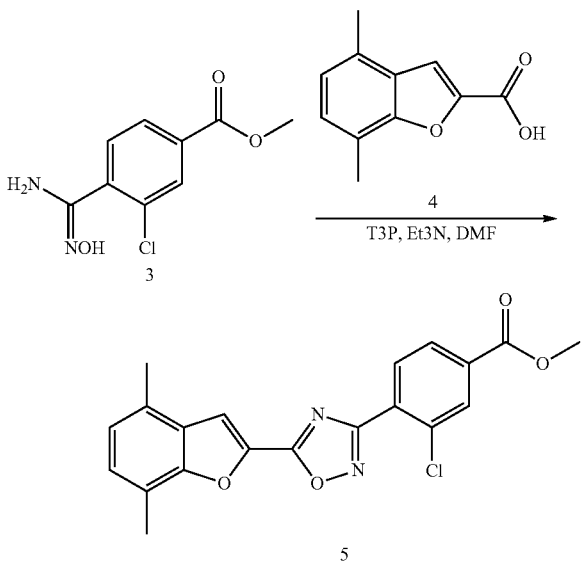

The title compound (68 mg, 20%) was prepared from methyl 3-chloro-4-(N'-hydroxycarbamimidoyl)benzoate (3) using a procedure essentially the same as in step (iv) for (BHBA-001): $^1$H NMR (400 MHz, CDCl$_3$) δ: 8.22 (1H, s), 8.14-8.12 (1H, m), 8.07-8.04 (1H, m), 7.78 (1H, s), 7.17 (1H, d), 7.03 (1H, d), 3.97 (3H, s), 2.58 (3H, s), 2.55 (3H, s).

Step (iv): 3-Chloro-4-(5-(4,7-dimethylbenzofuran-2-yl)-1,2,4-oxadiazol-3-yl)benzoic acid (BHBA-002)

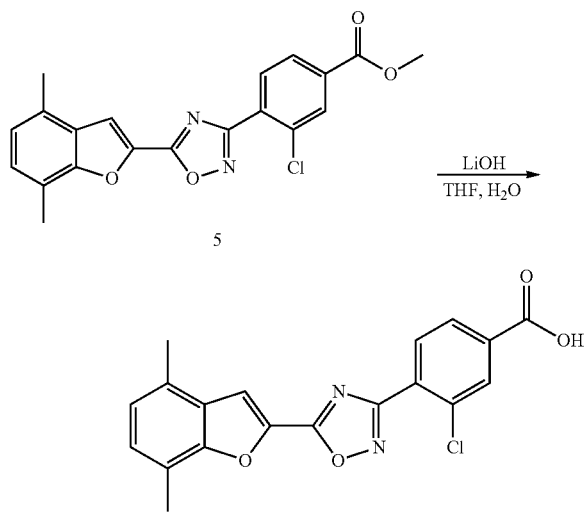 [SMILES: COC(=O)c1ccc(-c2noc(-c3cc4c(C)ccc(C)c4o3)n2)c(Cl)c1 ; "LiOH" ; Cc1ccc(C)c2oc(-c3nc(-c4ccc(C(=O)O)cc4Cl)no3)cc12]

The title compound (68 mg, 20%) was prepared from methyl 3-chloro-4-(5-(4,7-dimethylbenzofuran-2-yl)-1,2,4-oxadiazol-3-yl)benzoate (5) using a procedure essentially the same as in step (v) for (BHBA-001): m/z 367 [M−H]$^-$ (ES$^-$); $^1$H NMR (400 MHz, DMSO-d$_6$) δ: 8.26 (1H, s), 8.16 (1H, d), 8.12 (1H, d), 8.07 (1H, d), 7.29 (1H, d), 7.13 (1H, d), 2.56 (3H, s), 2.53 (3H, s), acid proton not observed.

Synthesis 3

2-Methyl-4-(5-(4,7-dimethylbenzofuran-2-yl)-1,2,4-oxadiazol-3-yl)benzoic acid (BHBA-006)

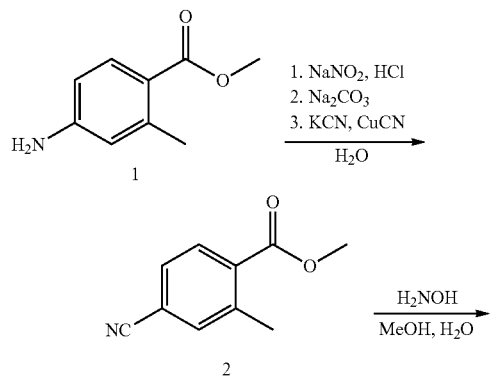

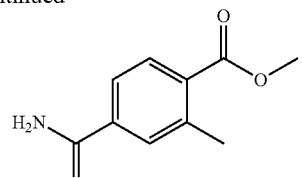

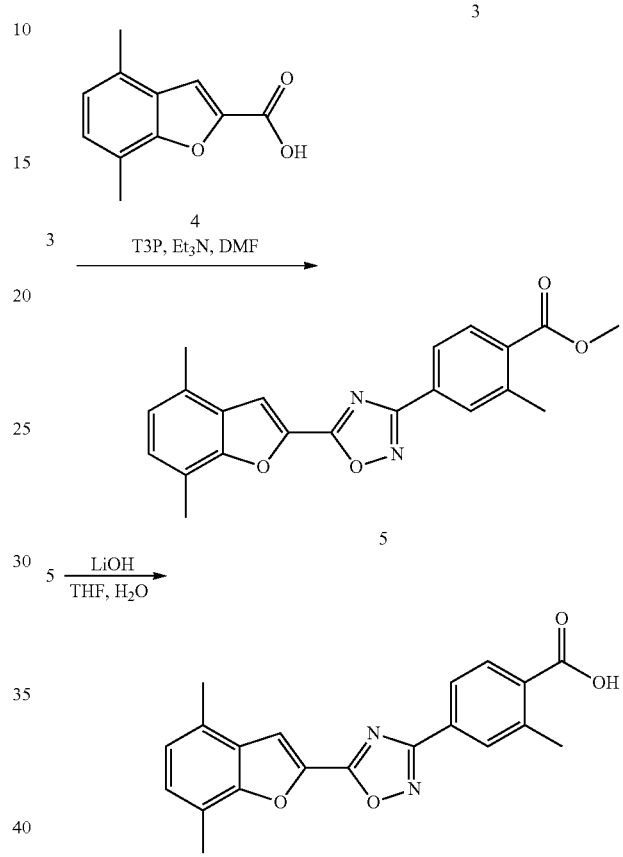

Step (i): Methyl 4-cyano-2-methylbenzoate (2)

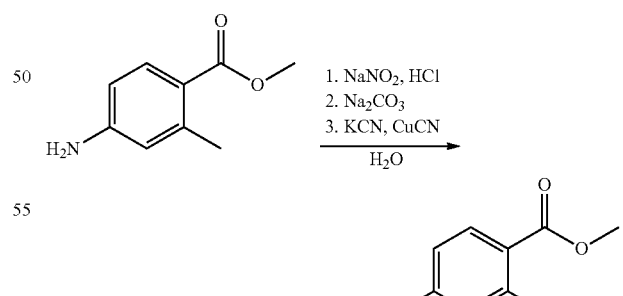

Methyl 4-amino-2-methylbenzoate (1) (4.14 g, 25.1 mmol) was suspended in conc. HCl (20 mL) and H$_2$O (100 mL) and stirred at 0° C. A solution of sodium nitrite (1.73 g, 25.1 mmol) in H$_2$O (50 mL) was slowly added to the suspension such that the temperature was maintained at 0-5°

C. The mixture was made basic by the addition of aq. Na$_2$CO$_3$ and added dropwise to a stirring mixture of potassium cyanide (1.88 g, 28.8 mmol) and copper (I) cyanide (2.58 g, 28.8 mmol) in H$_2$O (200 mL) at 0-5° C. The mixture was stirred at 0-5° C. for 0.5 h, then was warmed to RT and stirred for 18 h. The mixture was stirred at 100° C. for 0.5 h and then cooled to RT and treated with 10% aq. FeCl$_3$ solution (250 mL). The product was extracted with EtOAc (600 mL) and the organic solution was washed with brine (500 mL), dried over Na$_2$SO$_4$, filtered and concentrated in vacuo. The product was purified by silica gel chromatography (120 g cartridge, 0-10% EtOAc in isohexane) to afford a red solid. The product was recrystallised from isohexane/EtOAc to give the title compound (2) (2.58 g, 59%) as an orange solid: $^1$H NMR (400 MHz, CDCl$_3$) δ: 7.97 (1H, dd), 7.58-7.50 (2H, m), 3.93 (3H, s), 2.62 (3H, s).

Step (ii): Methyl 4-(N'-hydroxycarbamimidoyl)-2-methylbenzoate (3)

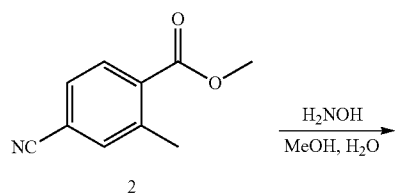

The title compound (3) (1.2 g, 87%) was prepared from methyl 4-cyano-2-methylbenzoate (2) using a procedure essentially the same as in step (iii) for (BHBA-002) except that 20 eq. of hydroxylamine solution was used in EtOH (50 mL) instead of 2 eq. in MeOH and the mixture was heated at reflux for 18 h: m/z 209 [M+H]$^+$ (ES$^+$); $^1$H NMR (400 MHz, DMSO-d$_6$) δ: 9.83 (1H, s), 7.82 (1H, d), 7.67-7.56 (2H, m), 5.90 (2H, s), 3.83 (3H, s), 2.54 (3H, s).

Step (iii): Methyl 4-(5-(4,7-dimethylbenzofuran-2-yl)-1,2,4-oxadiazol-3-yl)-2-methylbenzoate (5)

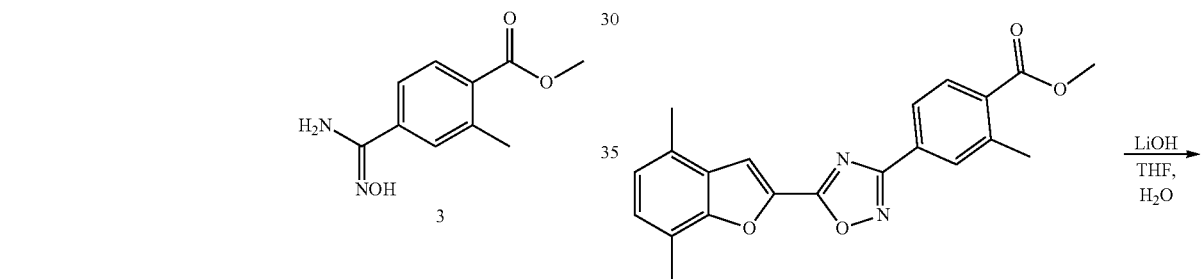

The title compound (5) (56 mg, 16%) was prepared from methyl 4-(N'-hydroxycarbamimidoyl)-2-methylbenzoate (3) using a procedure essentially the same as in step (iv) for (BHBA-001) except that the product was purified by flash chromatography (40 g, 0-5% EtOAc in isohexane), followed by trituration with MeOH: $^1$H NMR (400 MHz, CDCl$_3$) δ: 8.09 (1H, s), 8.04-8.03 (1H, m), 7.77 (1H, s), 7.53-7.50 (1H, m), 7.16 (1H, d), 7.03 (1H, d), 3.92 (3H, s), 2.68 (3H, s), 2.58 (3H, s), 2.55 (3H, s).

Step (iv): 4-(5-(4,7-Dimethylbenzofuran-2-yl)-1,2,4-oxadiazol-3-yl)-2-methylbenzoic acid (BHBA-006)

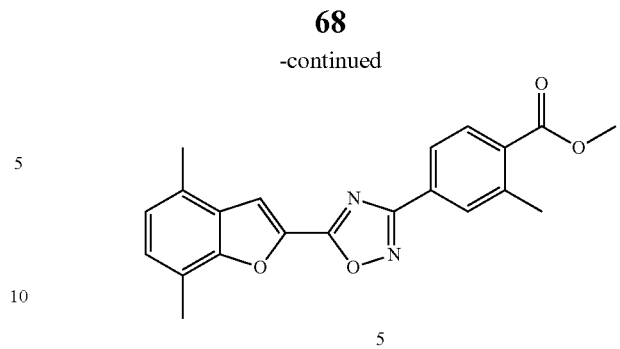

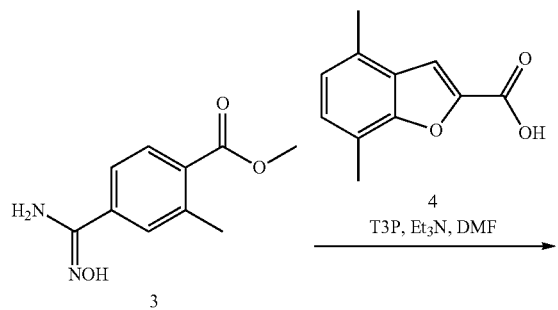

The title compound (54 mg, 100%) was prepared from methyl 4-(5-(4,7-dimethylbenzofuran-2-yl)-1,2,4-oxadiazol-3-yl)-2-methylbenzoate (5) using a procedure essentially the same as in step (v) for (BHBA-001): m/z 347 [M−H]$^−$ (ES$^−$); $^1$H NMR (400 MHz, DMSO-d$_6$) δ: 13.14 (1H, br. s), 8.25 (1H, s), 8.05-8.02 (3H, m), 7.29 (1H, d), 7.13 (1H, d), 2.64 (3H, d), 2.56 (3H, s), 2.53 (3H, s).

Synthesis 4

2-Fluoro-4-(5-(4,7-dimethylbenzofuran-2-yl)-1,2,4-oxadiazol-3-yl)benzoic acid (BHBA-007)

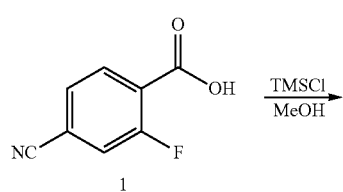

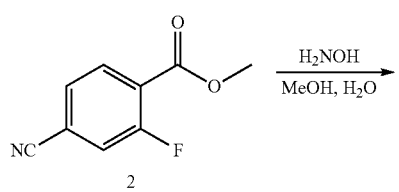

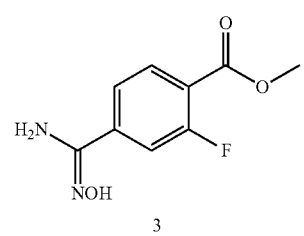

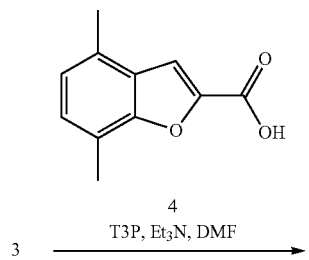

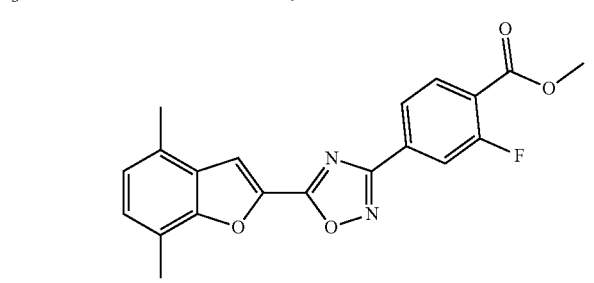

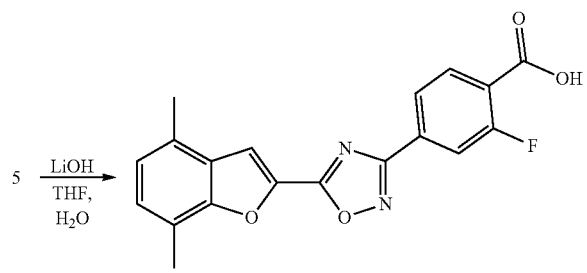

Step (i): Methyl 4-cyano-2-fluorobenzoate (2)

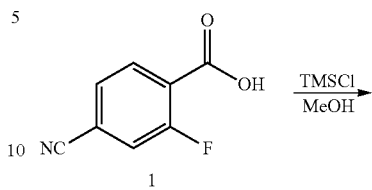

A mixture of 4-cyano-2-fluorobenzoic acid (5.0 g, 30 mmol) (1) and chlorotrimethylsilane (13.5 mL, 106 mmol) in MeOH (100 mL) was stirred at 60° C. for 4 h and then concentrated in vacuo. The residue was dissolved in EtOAc (100 mL), washed with satd. aq. NaHCO$_3$ (200 mL), dried over MgSO$_4$, filtered and concentrated in vacuo to afford the title compound (2) (5.2 g, 97%) as a pale yellow solid: $^1$H NMR (400 MHz, DMSO-d$_6$) δ: 8.07-8.01 (2H, m), 7.83 (1H, dd), 3.90 (3H, s).

Step (ii): Methyl 2-fluoro-4-(N'-hydroxycarbamimidoyl)benzoate (3)

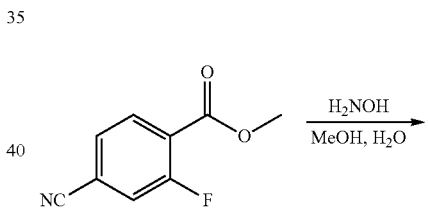

A mixture of methyl 4-cyano-2-fluorobenzoate (2) (1.0 g, 5.6 mmol) and 50% aq. hydroxylamine (6.84 mL, 112 mmol) in EtOH (30 mL) was stirred at reflux for 18 h. The reaction mixture was cooled to RT, diluted with H$_2$O (20 mL) and extracted with EtOAc (60 mL). The organic solution was washed with brine (100 mL), dried over MgSO$_4$, filtered and concentrated in vacuo to give methyl 2-fluoro-4-(N'-hydroxycarbamimidoyl) benzoate (3) (260 mg, 22%) as a 1:1 mixture of methyl and ethyl esters that was progressed without purification: m/z 227, 213 [M+H]$^+$ (ES$^+$).

Step (iii): Methyl/Ethyl 4-(5-(4,7-dimethylbenzo-furan-2-yl)-1,2,4-oxadiazol-3-yl)-2-fluorobenzoate (5)

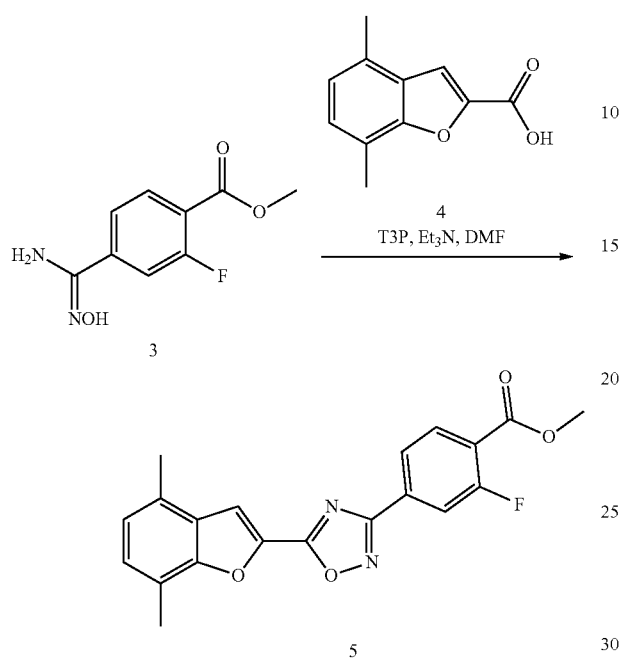

Using a procedure essentially the same as in step (iv) for (BHBA-001), a 1:1 mixture of methyl 4-(5-(4,7-dimethyl-benzofuran-2-yl)-1,2,4-oxadiazol-3-yl)-2-fluorobenzoate and ethyl 4-(5-(4,7-dimethylbenzofuran-2-yl)-1,2,4-oxadi-azol-3-yl)-2-fluorobenzoate (5) (80 mg, 18%) was prepared from the mixture of esters described in step (ii) above. The mixture was progressed without further purification.

Step (iv): 4-(5-(4,7-Dimethylbenzofuran-2-yl)-1,2,4-oxadiazol-3-yl)-2-fluorobenzoic acid (BHBA-007)

The title compound (47 mg, 73%) was prepared from the mixture of esters described in step (iii) above, using a procedure essentially the same as in step (v) for (BHBA-001): m/z 351 [M–H]⁻ (ES⁻); $^1$H NMR (400 MHz, DMSO-$d_6$) δ: 13.61 (1H, br. s), 8.25 (1H, s), 8.16-8.06 (1H, m), 8.06-8.00 (1H, m), 7.94 (1H, dd), 7.33-7.24 (1H, m), 7.17-7.08 (1H, m), 2.56 (3H, s), 2.53 (3H, s).

Synthesis 5

3-Amino-4-(5-(4,7-dimethylbenzofuran-2-yl)-1,2,4-oxadiazol-3-yl)benzoic acid (BHBA-005)

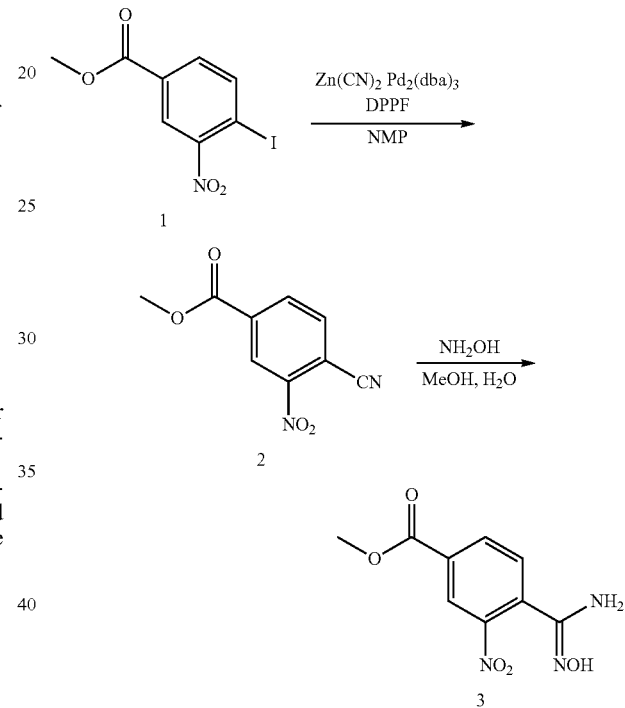

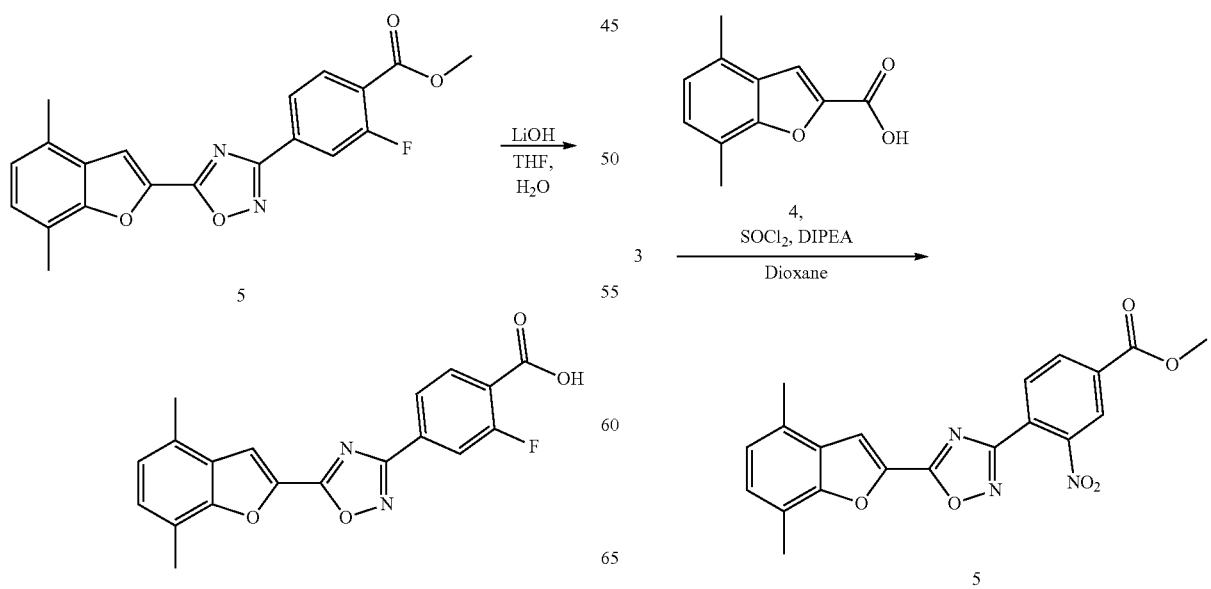

-continued

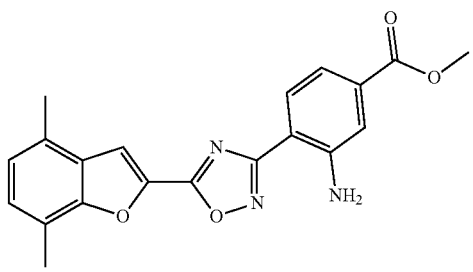

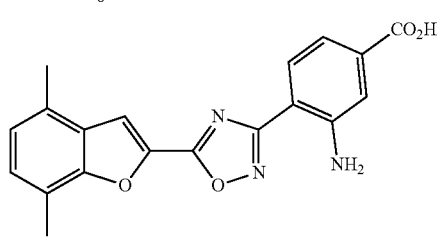

Step (i): Methyl 4-cyano-3-nitrobenzoate (2)

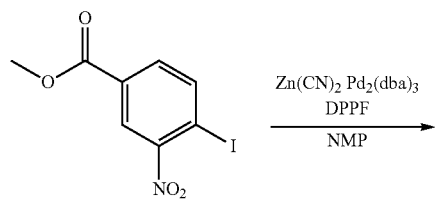

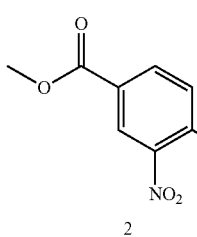

A mixture of methyl 4-iodo-3-nitrobenzoate (1) (25 g, 81 mmol) and dicyanozinc (5.74 g, 48.9 mmol) in NMP (200 mL) and water (0.5 mL) was flushed with nitrogen. Pd$_2$(dba)$_3$ (2.98 g, 3.26 mmol) and 1,1'-bis(diphenylphosphino) ferrocene (5.42 g, 9.77 mmol) were added and the reaction vessel was again flushed with nitrogen and then stirred at 110° C. for 90 mins. The mixture was allowed to cool to RT and then poured into EtOAc (700 mL). The solution was washed with water (400 mL) and brine (100 mL), then dried over MgSO$_4$, filtered and concentrated in vacuo. The material was purified by silica gel chromatography (120 g, 0-80% DCM in isohexane) to afford the title compound (2) (12 g, 72%) as a yellow solid: $^1$H NMR (400 MHz, CDCl$_3$) δ: 8.93 (1H, d), 8.45 (1H, dd), 8.03 (1H, d), 4.03 (3H, s).

Step (ii): Methyl 4-(N-hydroxycarbamimidoyl)-3-nitrobenzoate (3)

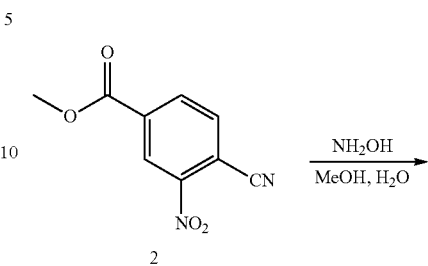

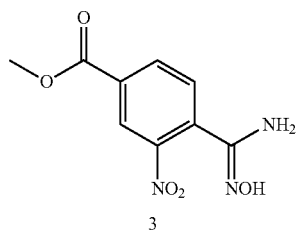

Methyl 4-cyano-3-nitrobenzoate (2) (12 g, 58 mmol) was dissolved in MeOH (125 mL) and cooled to 0° C. before being treated with hydroxylamine (50% in water) (2.1 mL, 70 mmol). The mixture was stirred at RT for 16 h after which a further portion of hydoxylamine solution was added (1.0 mL, 33 mmol), followed by THF (50 mL). The mixture continued to stir at RT for 24 h, then another portion of hydroxylamine solution (1.0 mL, 33 mmol) was added and stirring continued for a further 24 h. The mixture was diluted with toluene (100 mL) and concentrated in vacuo. The residue was suspended in DCM/THF (1:1, 250 mL) and the minimum of MeOH to obtain dissolution was added. The solution was then concentrated in vacuo onto silica and the product was purified by silica gel chromatography (80 g, 40-80% EtOAc in isohexane) to afford the title compound (3) (6.5 g, 47%) as a yellow solid: m/z 240 [M+H]$^+$ (ES$^+$); $^1$H NMR (400 MHz, DMSO-d$_6$) δ: 9.93 (1H, s), 8.28 (1H, d), 8.22 (1H, dd), 7.82 (1H, d), 6.14 (2H, s), 3.91 (3H, s).

Step (iii): Methyl 4-(5-(4,7-dimethylbenzofuran-2-yl)-1,2,4-oxadiazol-3-yl)-3-nitrobenzoate (5)

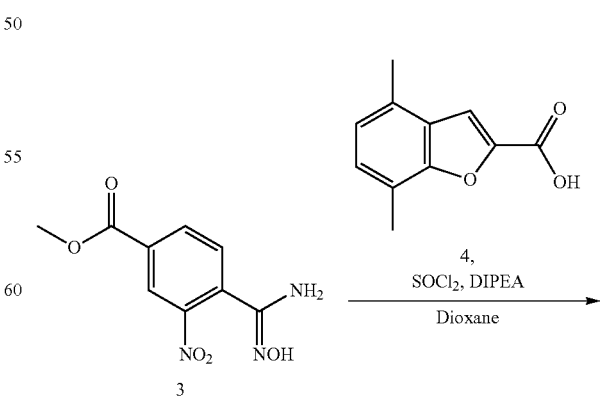

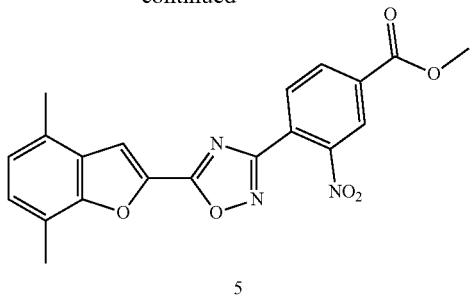

A mixture of 4,7-dimethylbenzofuran-2-carboxylic acid (4) (2.73 g, 14.3 mmol) and thionyl chloride (3.14 mL, 43.1 mmol) in toluene (20 mL) was stirred at 100° C. for 4 h. The mixture was cooled to RT, then concentrated in vacuo and co-evaporated with toluene. The residue was then dissolved in dioxane (30 mL) and treated with a mixture of methyl 4-(N-hydroxycarbamimidoyl)-3-nitrobenzoate (3) (3.43 g, 14.3 mmol) and DIPEA (3.76 mL, 21.5 mmol) in dioxane (40 mL). The mixture was stirred at RT for 2 h, then at 90° C. for 18 h. The mixture was cooled to RT, poured onto iced water (100 mL) and the product was extracted with EtOAc (200 mL). The organic solution was dried over MgSO$_4$, filtered and concentrated in vacuo. The residue was purified by silica gel chromatography (40 g, 0-100% DCM in isohexane) to afford the title compound (5) (2.3 g, 41%) as a pale yellow solid: m/z 394 [M+H]$^+$ (ES$^+$); $^1$H NMR (400 MHz, DMSO-d$_6$) δ: 8.61 (1H, d), 8.45 (1H, dd), 8.27 (1H, s), 8.23 (1H, d), 7.30-7.13 (2H, m), 3.97 (3H, s), 2.55 (3H, s), 2.51 (3H, s).

Step (iv): Methyl 3-amino-4-(5-(4,7-dimethylbenzofuran-2-yl)-1,2,4-oxadiazol-3-yl)benzoate (6)

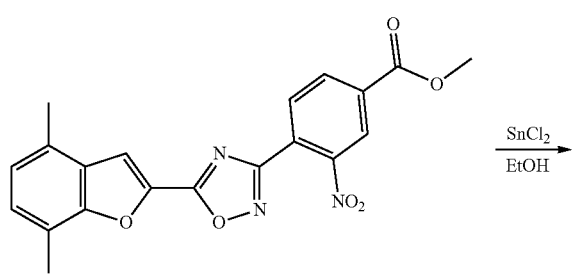

Methyl 4-(5-(4,7-dimethylbenzofuran-2-yl)-1,2,4-oxadiazol-3-yl)-3-nitrobenzoate (5) (2 g, 5 mmol) was dissolved in EtOH (100 mL), treated with tin (II) chloride dihydrate (11.5 g, 50.8 mmol) and the mixture was heated at reflux for 2 h. The mixture was then cooled to RT and concentrated in vacuo. The residue was partitioned between EtOAc (200 mL) and 1 M NaOH (100 mL). The resulting thick biphasic suspension was filtered, and then the phases were separated. The aqueous phase was further extracted with EtOAc (100 mL) and the combined organic extracts were dried over MgSO$_4$, filtered and concentrated in vacuo. The material was purified by silica gel chromatography (12 g, 0-10% EtOAc in isohexane) to afford the title compound (6) (600 mg, 33%) as a pale yellow solid: m/z 364 [M+H]$^+$ (ES$^+$); $^1$H NMR (400 MHz, DMSO-d$_6$) δ: 8.26 (1H, s), 8.11 (1H, d), 7.59 (1H, d), 7.32-7.25 (2H, m), 7.12 (1H, d), 6.66 (2H, s), 3.87 (3H, s), 2.56 (3H, s), 2.53 (3H, s).

Step (v): 3-Amino-4-(5-(4,7-dimethylbenzofuran-2-yl)-1,2,4-oxadiazol-3-yl)benzoic acid (BHBA-005)

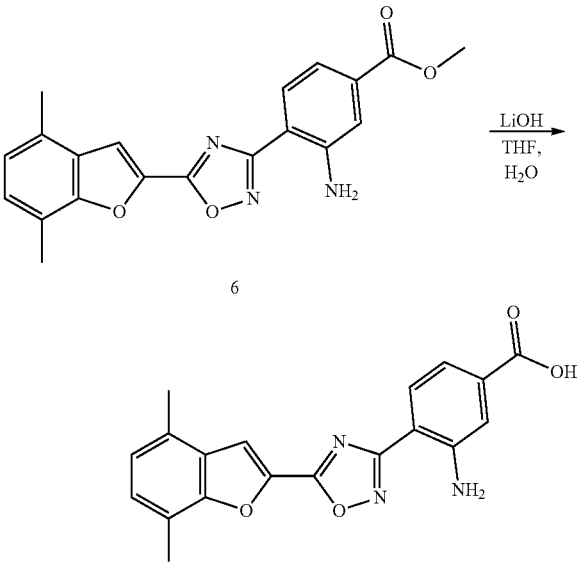

The title compound (1.5 mg, 4%) was prepared from methyl 3-amino-4-(5-(4,7-dimethylbenzofuran-2-yl)-1,2,4-oxadiazol-3-yl)benzoate (6) using a procedure essentially the same as in step (v) for (BHBA-001): m/z 350 [M+H]$^+$ (ES$^+$), 348 [M−H]$^-$ (ES$^-$); $^1$H NMR (400 MHz, DMSO-d$_6$) δ: 8.24 (1H, s), 8.06 (1H, d), 7.56 (1H, d), 7.33-7.21 (2H, m), 7.12 (1H, d), 6.57 (2H, s), 2.55 (3H, s), 2.53 (3H, s), the acid proton was not observed.

Synthesis 6

3-Bromo-4-(5-(4,7-dimethylbenzofuran-2-yl)-1,2,4-oxadiazol-3-yl)benzoic acid (BHBA-003)

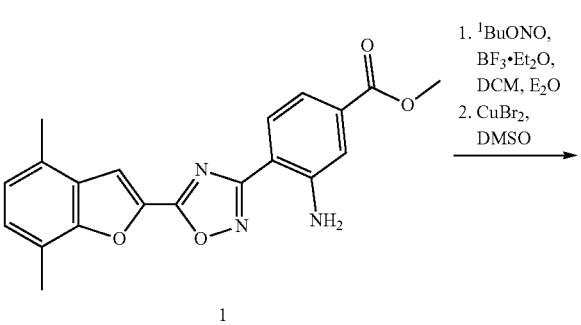

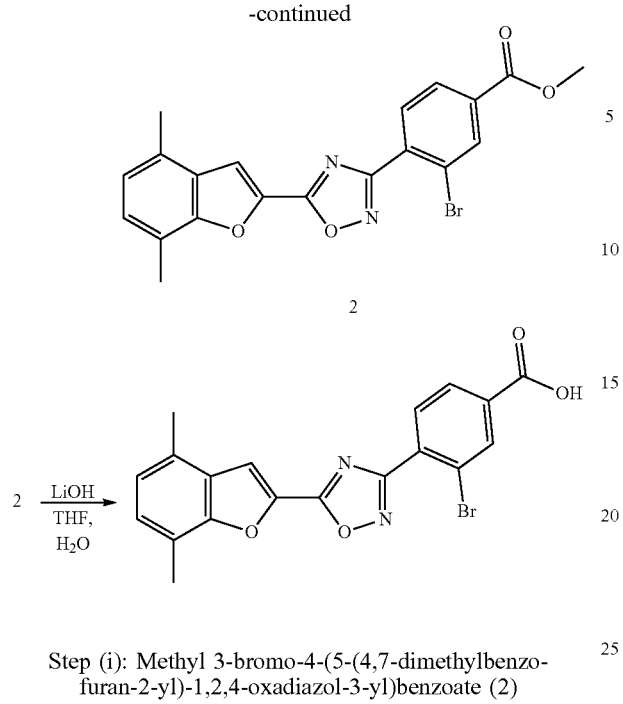

2

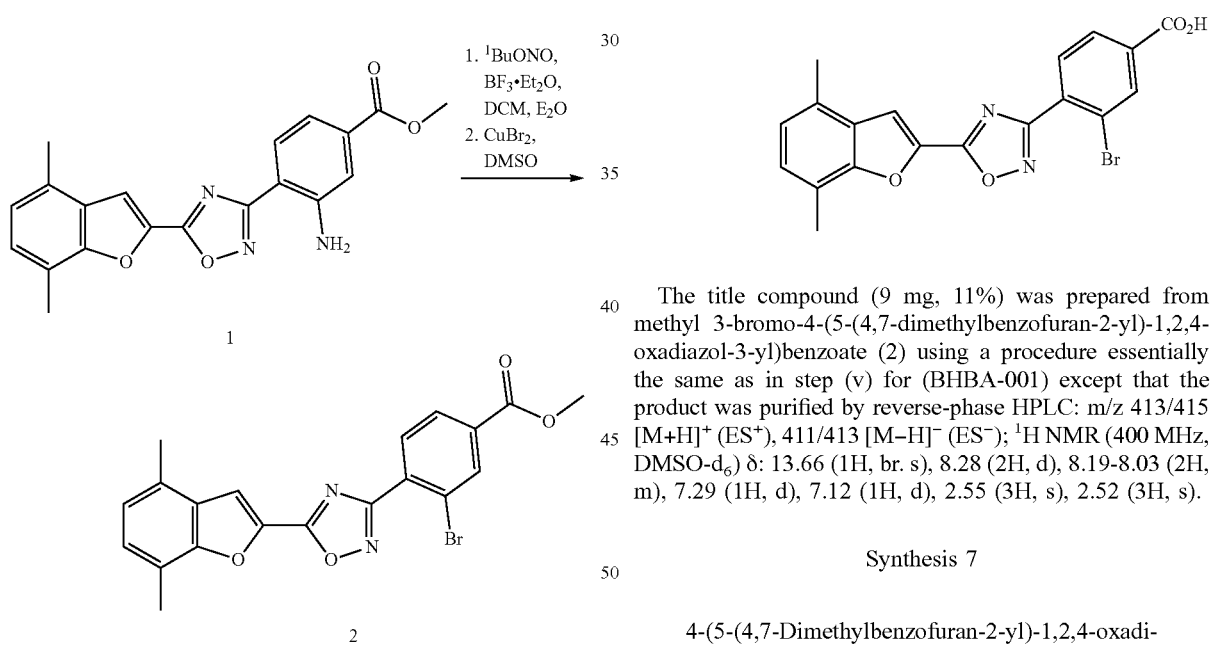

A solution of BF$_3$·OEt$_2$ (55.8 µL, 0.440 mmol) in anhydrous Et$_2$O (2.5 mL) was added to a stirring solution of methyl 3-amino-4-(5-(4,7-dimethylbenzofuran-2-yl)-1,2,4-oxadiazol-3-yl)benzoate (1) (100 mg, 0.275 mmol) in DCM (5 mL) at −20° C. tert-Butyl nitrite (48.2 mg, 0.468 mmol) was then added and the mixture was stirred at −20° C. for 30 min, then allowed to warm slowly to RT and stirred for an additional 2 h. The mixture was concentrated in vacuo and the residue was triturated with isohexane. The intermediate diazonium salt was dissolved in DMSO (1 mL) and copper (II) bromide (157 mg, 0.703 mmol) was added. The mixture was stirred at 100° C. for 30 min. then cooled to RT. The mixture was diluted with ethyl acetate (40 mL) and washed sequentially with water (30 mL) and brine (10 mL). The organic solution was dried over Na$_2$SO$_4$, filtered and concentrated in vacuo. The product was purified by silica gel chromatography (12 g, 0-5% EtOAc in isohexane) to afford the title compound (2) (51 mg, 43%) as a white solid: $^1$H NMR (400 MHz, DMSO-d$_6$) δ: 8.33 (1H, d), 8.26-8.25 (1H, m), 8.20-8.11 (2H, m), 7.29 (1H, d), 7.12 (1H, d), 3.93 (3H, s), 2.55 (3H, s), 2.52 (3H, s).

Step (ii): 3-Bromo-4-(5-(4,7-dimethylbenzofuran-2-yl)-1,2,4-oxadiazol-3-yl)benzoic acid (BHBA-0031

The title compound (9 mg, 11%) was prepared from methyl 3-bromo-4-(5-(4,7-dimethylbenzofuran-2-yl)-1,2,4-oxadiazol-3-yl)benzoate (2) using a procedure essentially the same as in step (v) for (BHBA-001) except that the product was purified by reverse-phase HPLC: m/z 413/415 [M+H]$^+$ (ES$^+$), 411/413 [M−H]$^-$ (ES$^-$); $^1$H NMR (400 MHz, DMSO-d$_6$) δ: 13.66 (1H, br. s), 8.28 (2H, d), 8.19-8.03 (2H, m), 7.29 (1H, d), 7.12 (1H, d), 2.55 (3H, s), 2.52 (3H, s).

Synthesis 7

4-(5-(4,7-Dimethylbenzofuran-2-yl)-1,2,4-oxadiazol-3-yl)-3-(trifluoromethyl)benzoic acid (BHBA-004)

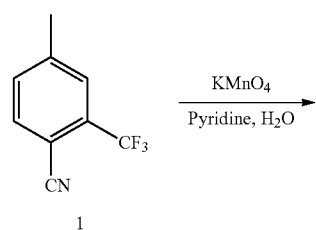

-continued

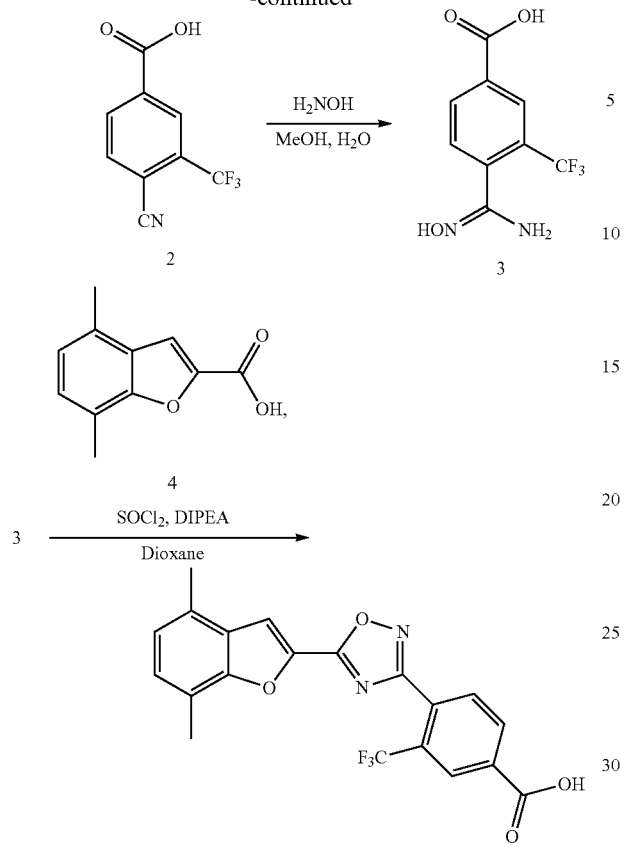

Step (i): 4-Cyano-3-(trifluoromethyl)benzoic acid (2)

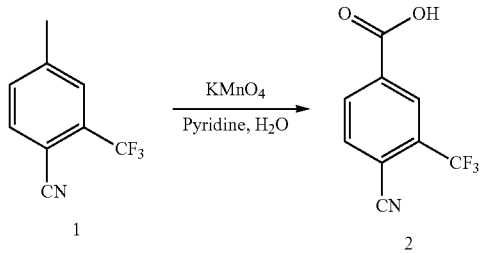

Potassium permanganate (0.67 g, 4.3 mmol) was added to a solution of 4-methyl-2-(trifluoromethyl)benzonitrile (1) (0.79 g, 4.3 mmol) in pyridine (8 mL) and H₂O (2 mL) and the mixture was stirred at 100° C. in a sealed vessel. The progress of the reaction was monitored and three further portions of potassium permanganate (0.67 g, 4.3 mmol) were charged until the reaction reached ~85% completion. The hot reaction mixture was filtered through a plug of celite, washing through with EtOAc and the filtrate was concentrated in vacuo. The residue was partitioned between DCM (150 mL) and 1 M aq. HCl (100 mL), the organic solution was dried over MgSO₄, filtered and concentrated in vacuo. The residue was purified by silica gel chromatography (40 g, 0-5% MeOH in DCM) to afford 4-cyano-3-(trifluoromethyl)benzoic acid (2) (0.51 g, 66%) as a white solid: m/z 214 [M–H]⁻ (ES⁻); ¹H NMR (400 MHz, DMSO-d₆) δ: 14.07 (1H, br s), 8.38-8.32 (3H, m).

Step (ii): 4-(N'-Hydroxycarbamimidoyl)-3-(trifluoromethyl)benzoic acid (3)

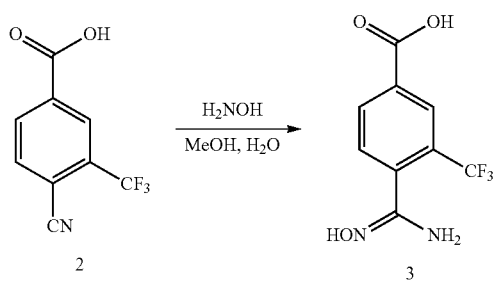

A mixture of 4-cyano-3-(trifluoromethyl)benzoic acid (2) (510 mg, 2.37 mmol) and hydroxylamine (50% solution in water) (0.44 mL, 7.1 mmol) in MeOH (3 mL) was stirred at RT for 48 h. The mixture was concentrated in vacuo and the residue was purified by capture and release on SCX (15 g) to afford 4-(N'-hydroxycarbamimidoyl)-3-(trifluoromethyl)benzoic acid (3) (300 mg, 43%) as a colourless solid: m/z 249 [M+H]⁺ (ES⁺), 247 [M–H]⁻ (ES⁻).

Step (iii): 4-(5-(4,7-Dimethylbenzofuran-2-yl)-1,2,4-oxadiazol-3-yl)-3-(trifluoromethyl)benzoic acid (BHBA-004)

A mixture of 4,7-dimethylbenzofuran-2-carboxylic acid (4) (300 mg, 1.58 mmol) and SOCl₂ (345 μL, 4.73 mmol) in toluene (5 mL) was heated at reflux for 3 h. The mixture was cooled to RT, concentrated in vacuo and co-evaporated with toluene. The residue was dissolved in anhydrous dioxane (5 mL) and added to a stirring suspension of 4-(N'-hydroxycarbamimidoyl)-3-(trifluoromethyl)benzoic acid (3) (327 mg, 1.318 mmol) in anhydrous dioxane (5 mL). The mixture was stirred at RT for 1 h, then at reflux for 16 h. The mixture was cooled to RT, concentrated in vacuo and the residue was triturated with MeOH (2 mL) to give the title compound (230 mg, 43%) as a white solid: m/z 403 [M+H]+(ES+), 401 [M−H]− (ES−); $^1$H NMR (400 MHz, DMSO-d$_6$) δ: 13.85 (1H, br s), 8.43-8.42 (2H, m), 8.27 (1H, s), 8.16 (1H, d), 7.30 (1H, d), 7.13 (1H, d), 2.56 (3H, s), 2.52 (3H, s).

Synthesis 8

4-(5-(3,4,7-Trimethylbenzofuran-2-yl)-1,2,4-oxadiazol-3-yl)benzoic acid (BHBA-008)

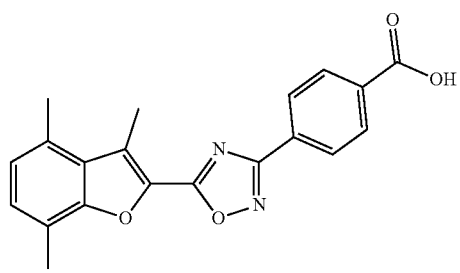 [SMILES: Cc1ccc(C)c2c(C)c(-c3nc(-c4ccc(C(=O)O)cc4)no3)oc12]

The title compound (237 mg, 93% for final step) was prepared in essentially the same manner as in steps (iii) and (v) for (BHBA-005) except 3,4,7-trimethylbenzofuran-2-carboxylic acid was used instead of 4,7-dimethylbenzofuran-2-carboxylic acid and methyl 4-(N'-hydroxycarbamimidoyl) benzoate was used instead of methyl 4-(N'-hydroxycarbamimidoyl)-3-nitrobenzoate in step (iii): m/z 349 [M+H]+ (ES+), 347 [M−H]− (ES−); $^1$H NMR (400 MHz, DMSO-d$_6$) δ: 13.30 (1H, br. s), 8.20 (2H, d) 8.13 (2H, d), 7.21 (1H, d), 7.01 (1H, d), 2.89 (3H, s), 2.66 (3H, s), 2.48 (3H, s).

Synthesis 9

3-Chloro-4-(5-(3,4,7-trimethylbenzofuran-2-yl)-1,2,4-oxadiazol-3-yl)benzoic acid (BHBA-009)

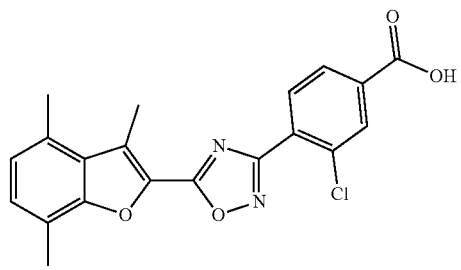 [SMILES: Cc1ccc(C)c2c(C)c(-c3nc(-c4ccc(C(=O)O)cc4Cl)no3)oc12]

The title compound (55 mg, 93% for final step) was prepared in essentially the same manner as in steps (iii) and (v) for (BHBA-005) except 3,4,7-trimethylbenzofuran-2-carboxylic acid was used instead of 4,7-dimethylbenzofuran-2-carboxylic acid and methyl 3-chloro-4-(N'-hydroxycarbamimidoyl)benzoate was used instead of methyl 4-(N-hydroxycarbamimidoyl)-3-nitrobenzoate in step (iii): m/z 383 [M+H]+ (ES+), 381 [M−H]− (ES−); $^1$H NMR (400 MHz, DMSO-d$_6$) δ: 8.11-7.97 (3H, m), 7.24 (1H, d), 7.04 (1H, d), 2.89 (3H, s), 2.67 (3H, s), 2.49 (3H, s).

Synthesis 10

4-(5-(4-Isopropyl-7-methylbenzofuran-2-yl)-1,2,4-oxadiazol-3-yl)benzoic acid (BHBA-010)

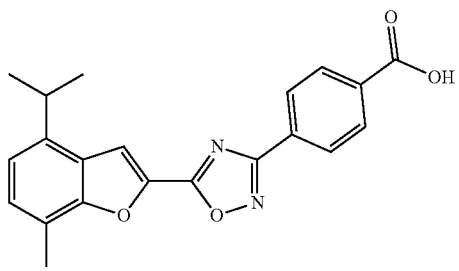 [SMILES: Cc1ccc(C(C)C)c2cc(-c3nc(-c4ccc(C(=O)O)cc4)no3)oc12]

The title compound (95 mg, 48% for final step) was prepared in essentially the same manner as (BHBA-001) except 5-isopropyl-2-methylphenol was used instead of 2,5-dimethylphenol in step (i): m/z 361 [M−H]− (ES−); $^1$H NMR (400 MHz, DMSO-d$_6$) δ: 13.31 (1H, s), 8.31 (1H, s), 8.25 (2H, d), 8.17 (2H, d), 7.34 (1H, dd), 7.19 (1H, d), 3.41 (1H, m), 2.54 (3H, s), 1.33 (6H, d).

Synthesis 11

4-(5-(7-Chloro-4-methylbenzofuran-2-yl)-1,2,4-oxadiazol-3-yl)benzoic acid (BHBA-015)

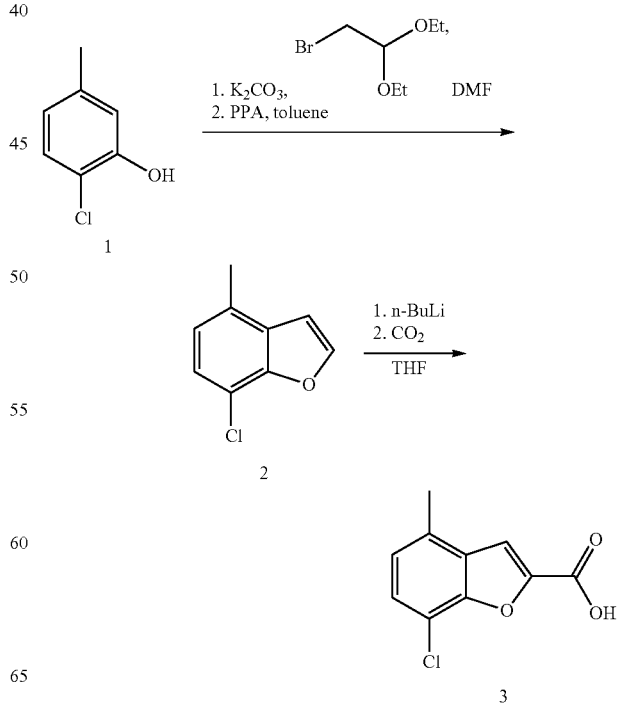

-continued

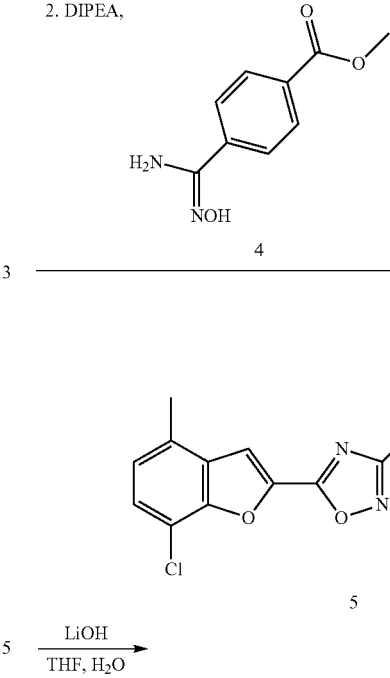

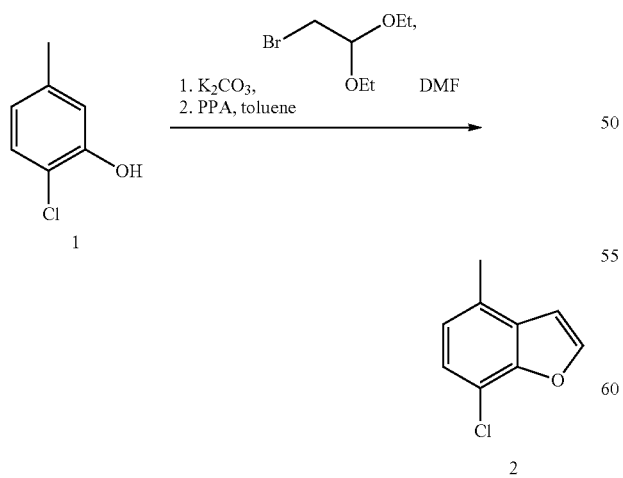

Step (i): 7-Chloro-4-methylbenzofuran (2)

The title compound (2) (4.1 g, 69%) was prepared from 2-chloro-5-methylphenol (1) using a procedure essentially the same as in step (i) for (BHBA-011): $^1$H NMR (400 MHz, CDCl$_3$) δ: 7.67 (1H, s), 7.19 (1H, d), 6.96 (1H, d), 6.82 (1H, s), 2.49 (3H, s).

Step (ii): 7-Chloro-4-methylbenzofuran-2-carboxylic acid (3)

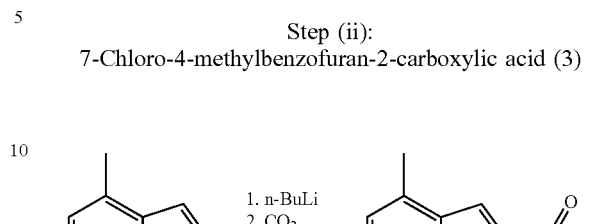

The title compound (3) (1.3 g, 100%) was prepared from 7-chloro-4-methylbenzofuran (2) using a procedure essentially the same as in step (ii) for (BHBA-011): m/z 209 [M−H]$^−$ (ES$^−$); $^1$H NMR (400 MHz, DMSO-d$_6$) δ: 13.77 (1H, br. s), 7.86 (1H, s), 7.49 (1H, d), 7.16 (1H, d), 2.52 (3H, d).

Step (iii): Methyl 4-(5-(7-chloro-4-methylbenzo-furan-2-yl)-1,2,4-oxadiazol-3-yl)benzoate (5)

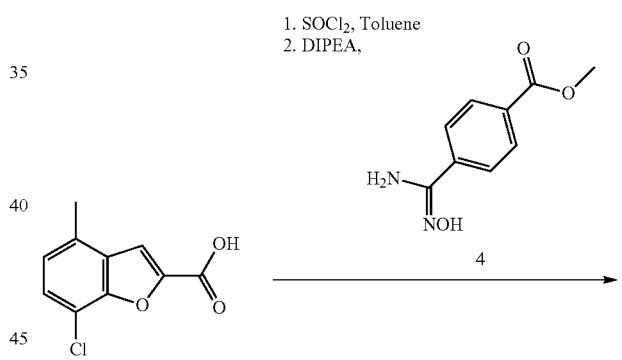

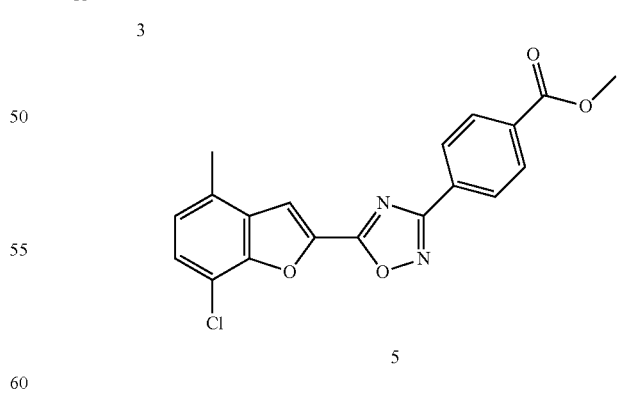

The title compound (5) (123 mg, 70%) was prepared from 7-chloro-4-methylbenzofuran-2-carboxylic acid (3) using a procedure essentially the same as in step (iii) for (BHBA-005): m/z 369 [M+H]$^+$ (ES$^+$); $^1$H NMR (400 MHz, CDCl$_3$) δ: 8.29 (2H, d), 8.20 (2H, d), 7.81 (1H, s), 7.39 (1H, d), 7.10 (1H, dd), 3.97 (3H, s), 2.59 (3H, s).

Step (iv): 4-(5-(7-Chloro-4-methylbenzofuran-2-yl)-1,2,4-oxadiazol-3-yl)benzoic acid (BHBA-015)

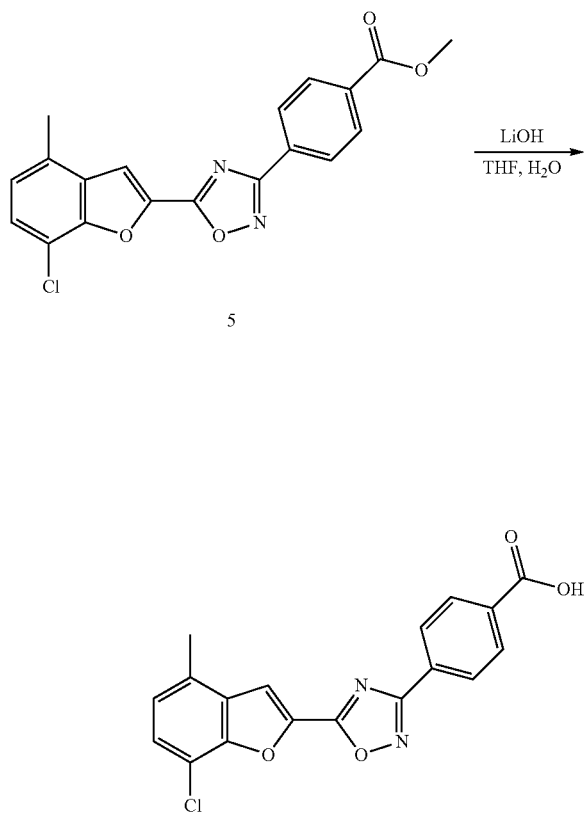

5

The title compound (104 mg, 88%) was prepared from methyl 4-(5-(7-chloro-4-methylbenzofuran-2-yl)-1,2,4-oxadiazol-3-yl)benzoate (5) using a procedure essentially the same as in step (v) for (BHBA-001): m/z 353 [M−H]⁻ (ES⁻); ¹H NMR (400 MHz, DMSO-d$_6$) δ: 13.35 (1H, br. s), 8.37 (1H, s), 8.24 (2H, d), 8.16 (2H, d), 7.58 (1H, d), 7.24 (1H, d), 2.59 (3H, s).

Synthesis 12

3-Chloro-4-(5-(7-chloro-4-methylbenzofuran-2-yl)-1,2,4-oxadiazol-3-yl)benzoic acid (BHBA-017)

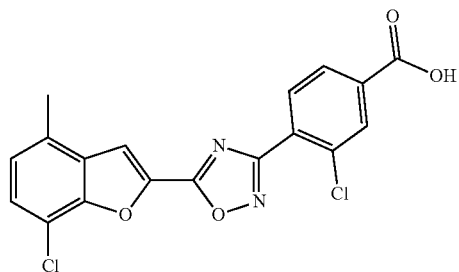 [SMILES: Cc1ccc(Cl)c2oc(-c3nc(-c4ccc(C(=O)O)cc4Cl)no3)cc12]

The title compound (59 mg, 76% for final step) was prepared in essentially the same manner as (BHBA-015) except methyl 3-chloro-4-(N'-hydroxycarbamimidoyl)benzoate was used instead of methyl 4-(N'-hydroxycarbamimidoyl)benzoate in step (iii): m/z 387/389 [M−H]⁻ (ES⁻); ¹H NMR (400 MHz, DMSO-d$_6$) δ: 13.67 (1H, br. s), 8.39 (1H, s), 8.28-8.03 (3H, m), 7.58 (1H, d), 7.24 (1H, d), 2.59 (3H, s).

Synthesis 13

4-(5-(4-Chloro-7-methylbenzofuran-2-yl)-1,2,4-oxadiazol-3-yl)benzoic acid (BHBA-016)

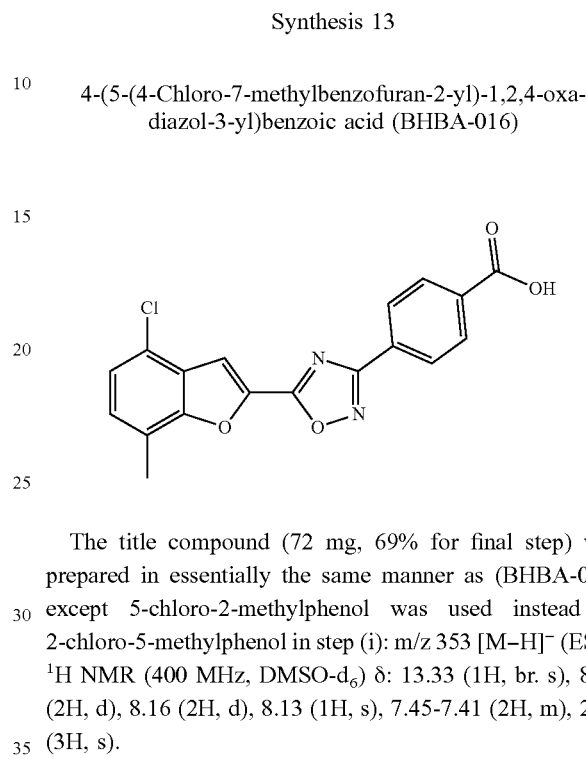

The title compound (72 mg, 69% for final step) was prepared in essentially the same manner as (BHBA-015) except 5-chloro-2-methylphenol was used instead of 2-chloro-5-methylphenol in step (i): m/z 353 [M−H]⁻ (ES⁻); ¹H NMR (400 MHz, DMSO-d$_6$) δ: 13.33 (1H, br. s), 8.24 (2H, d), 8.16 (2H, d), 8.13 (1H, s), 7.45-7.41 (2H, m), 2.57 (3H, s).

Synthesis 14

3-Chloro-4-(5-(4-chloro-7-methylbenzofuran-2-yl)-1,2,4-oxadiazol-3-yl)benzoic acid (BHBA-018)

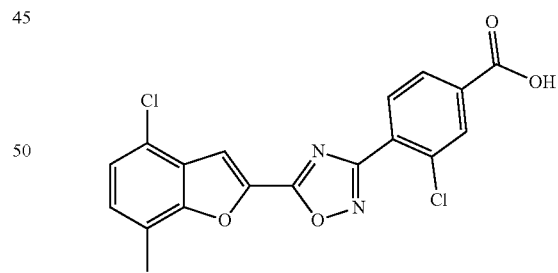

The title compound (42 mg, 76% for final step) was prepared in essentially the same manner as (BHBA-015) except 5-chloro-2-methylphenol was used instead of 2-chloro-5-methylphenol in step (i) and methyl 3-chloro-4-(N'-hydroxycarbamimidoyl)benzoate was used instead of methyl 4-(N'-hydroxycarbamimidoyl)benzoate in step (iii): m/z 387/389 [M−H]⁻ (ES⁻); ¹H NMR (400 MHz, DMSO-d$_6$) δ: 13.71 (1H, br. s), 8.20 (1H, d), 8.15 (1H, s), 8.14 (1H, d), 8.12-8.07 (1H, m), 7.49-7.39 (2H, m), 2.56 (3H, s).

Synthesis 15

4-(5-(4,7-Dichlorobenzofuran-2-yl)-1,2,4-oxadiazol-3-yl)benzoic acid (BHBA-011)

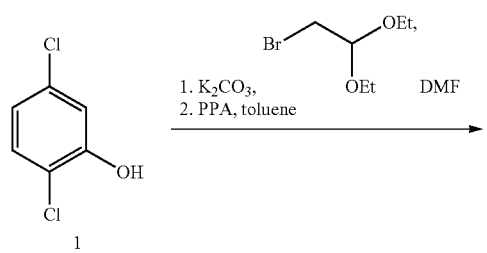

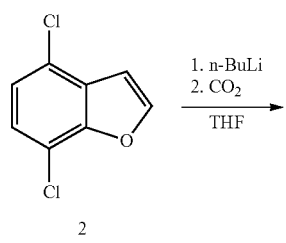

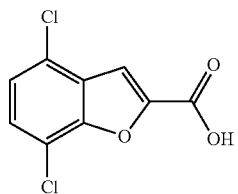

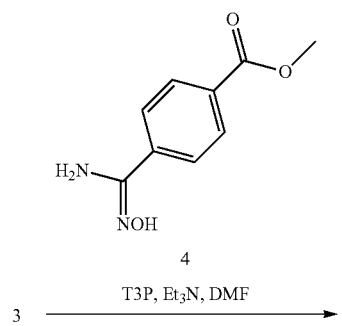

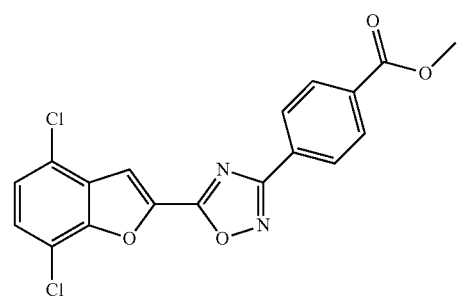

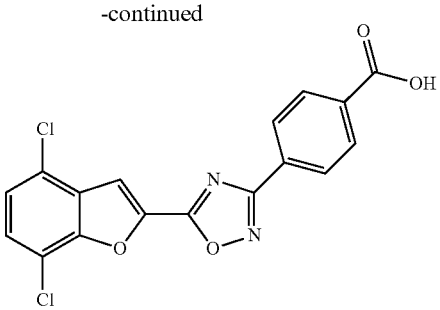

Step (i): 4,7-Dichlorobenzofuran (2)

Bromoacetaldehyde diethyl acetal (15 mL, 98 mmol) was added dropwise to a stirring suspension of 2,5-dichlorophenol (1) (10 g, 61 mmol) and K$_2$CO$_3$ (22.6 g, 164 mmol) in anhydrous DMF (100 mL). The reaction mixture was stirred at 140° C. under N$_2$ for 2 h, then cooled to RT. The mixture was partitioned between EtOAc (100 mL) and H$_2$O (100 mL) and the aq. phase was further extracted with EtOAc (300 mL). The combined organic extracts were sequentially washed with water (300 mL) and brine (200 mL), dried over MgSO$_4$ and filtered. The solution was concentrated in vacuo and the product was partially purified by silica gel chromatography (330 g, 0-5% EtOAc in isohexane) to afford the 1,4-dichloro-2-(2,2-diethoxyethoxy)benzene intermediate (20.5 g at 70% purity) as colourless oil. The intermediate was dissolved in toluene (100 mL) and treated with polyphosphoric acid (50.0 g, 194 mmol). The mixture was heated at reflux, under N$_2$, for 2 h. On cooling to RT the mixture was poured into iced water (200 mL) and the product was extracted with EtOAc (600 mL). The organic solution was washed with brine (500 mL), dried over MgSO$_4$, filtered and concentrated in vacuo. The product was purified by silica gel chromatography (330 g, isohexane) to afford the title compound (2) (5.7 g, 50%) as a white solid: $^1$H NMR (400 MHz, CDCl$_3$) δ: 7.70 (1H, d), 7.22 (1H, d), 7.16 (1H, d), 6.89 (1H, d).

Step (ii): 4,7-Dichlorobenzofuran-2-carboxylic acid (3)

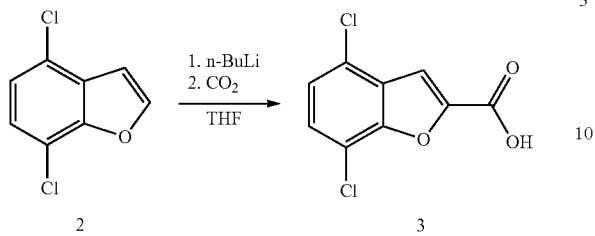

A solution of 4,7-dichlorobenzofuran (2) (4.03 g, 21.5 mmol) in anhydrous THF (50 mL) was cooled to −20° C. and treated with n-butyllithium (1.6 M in hexanes) (17.5 mL, 28.0 mmol). The mixture continued to stir at −20° C. for 1 h, and then anhydrous $CO_2$ was passed through the reaction mixture as the mixture was warmed to RT. After a further 4 h, the mixture was acidified with 1 M HCl and the product was extracted with EtOAc (150 mL). The organic solution was washed with brine (500 mL), dried over $MgSO_4$, filtered and concentrated in vacuo. The residue was purified by silica gel chromatography (120 g, 0-100% EtOAc in isohexane), followed by trituration with $Et_2O$ to afford the title compound (3) (2.8 g, 56%) as a yellow solid: m/z 229/231 [M−H]⁻ (ES⁻); ¹H NMR (400 MHz, DMSO-$d_6$) δ: 14.07 (1H, br. s), 7.73 (1H, s), 7.67 (1H, d), 7.50 (1H, d).

Step (iii): Methyl 4-(5-(4,7-dichlorobenzofuran-2-yl)-1,2,4-oxadiazol-3-yl)benzoate (5)

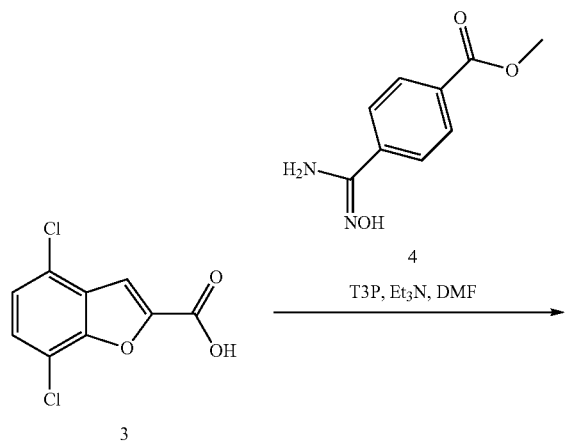

The title compound (5) (172 mg, 43%) was prepared from 4,7-dichlorobenzofuran-2-carboxylic acid (3) using a procedure essentially the same as in step (iv) for (BHBA-001): ¹H NMR (400 MHz, CDCl₃) δ: 8.27 (2H, d), 8.18 (2H, d), 7.85 (1H, s), 7.43 (1H, d), 7.31 (1H, d), 3.96 (3H, s).

Step (iv): 4-(5-(4,7-Dichlorobenzofuran-2-yl)-1,2,4-oxadiazol-3-yl)benzoic acid (BHBA-011)

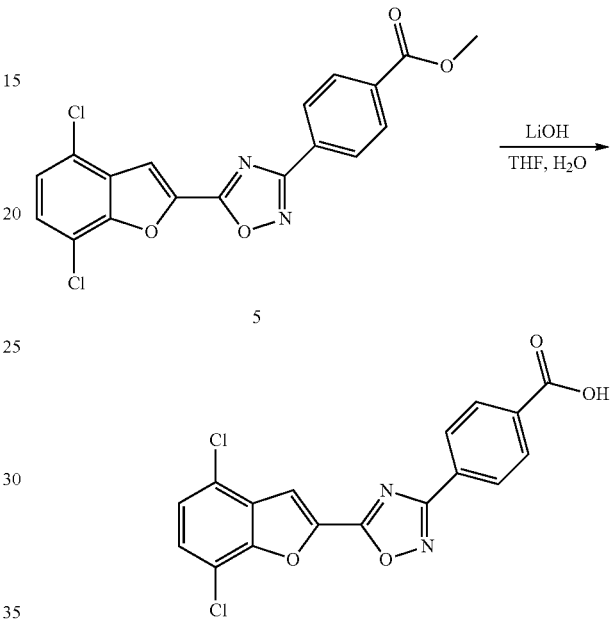

The title compound (120 mg, 69%) was prepared from methyl 4-(5-(4,7-dichlorobenzofuran-2-yl)-1,2,4-oxadiazol-3-yl)benzoate (5) using a procedure essentially the same as in step (v) for (BHBA-001): m/z 373/375 [M−H]⁻ (ES⁻); ¹H NMR (400 MHz, DMSO-$d_6$) δ: 13.33 (1H, br. s), 8.29 (1H, s), 8.25 (2H, d), 8.16 (2H, d), 7.74 (1H, d), 7.57 (1H, d).

Synthesis 16

2-Fluoro-4-(5-(4,7-dichlorobenzofuran-2-yl)-1,2,4-oxadiazol-3-yl)benzoic acid (BHBA-014)

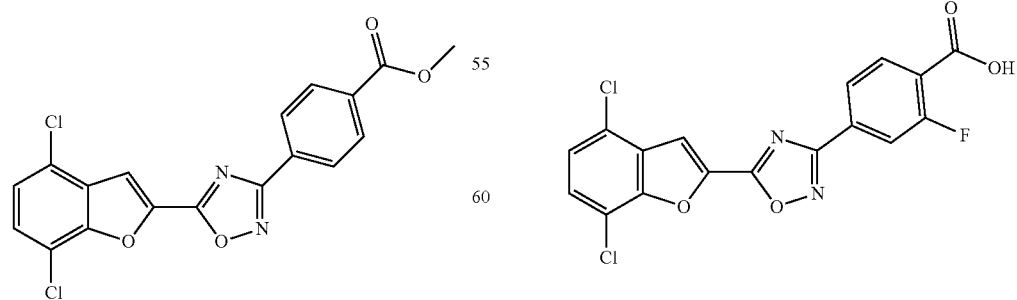

The title compound (22 mg, 63% for final step) was prepared in essentially the same manner as (BHBA-011) except methyl 2-fluoro-4-(N'-hydroxycarbamimidoyl)benzoate was used instead of methyl 4-(N'-hydroxycarbamimidoyl)benzoate in step (iv): m/z 391/393 [M−H]⁻ (ES⁻); ¹H NMR (400 MHz, DMSO-d₆) δ: 13.61 (1H, br. s), 8.30 (1H, s), 8.10-8.03 (2H, m), 7.96 (1H, dd), 7.75 (1H, d), 7.57 (1H, d).

Synthesis 17

2-Methyl-4-(5-(4,7-dichlorobenzofuran-2-yl)-1,2,4-oxadiazol-3-yl)benzoic acid (BHBA-013)

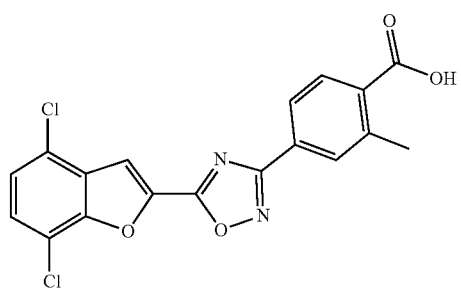 [SMILES: Cc1cc(-c2noc(-c3cc4c(Cl)ccc(Cl)c4o3)n2)ccc1C(=O)O]

The title compound (15 mg, 45% for final step) was prepared in essentially the same manner as (BHBA-011) except methyl 4-(N'-hydroxycarbamimidoyl)-2-methylbenzoate was used instead of methyl 4-(N'-hydroxycarbamimidoyl)benzoate in step (iv): m/z 387 [M−H]⁻ (ES⁻); ¹H NMR (400 MHz, DMSO-d₆) δ: 13.20 (1H, br. s), 8.29 (1H, s), 8.05-8.02 (3H, m), 7.75 (1H, d), 7.58 (1H, d), 2.64 (3H, s).

Synthesis 18

3-Chloro-4-(5-(4,7-dichlorobenzofuran-2-yl)-1,2,4-oxadiazol-3-yl)benzoic acid (BHBA-012)

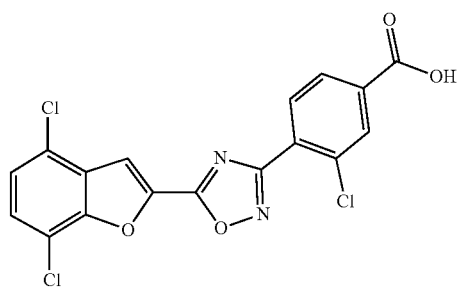 [SMILES: O=C(O)c1ccc(-c2noc(-c3cc4c(Cl)ccc(Cl)c4o3)n2)c(Cl)c1]

The title compound (4 mg, 18% for final step) was prepared in essentially the same manner as (BHBA-011) except methyl 3-chloro-4-(N'-hydroxycarbamimidoyl)benzoate was used instead of methyl 4-(N'-hydroxycarbamimidoyl)benzoate in step (iv): m/z 407/409 [M−H]⁻ (ES⁻); ¹H NMR (400 MHz, DMSO-d₆) δ: 13.68 (1H, s), 8.32 (1H, s), 8.19 (1H, d), 8.14 (1H, d), 8.09 (1H, dd), 7.76 (1H, d), 7.59 (1H, d).

Synthesis 19

4-(5-(7-Fluoro-4-(trifluoromethyl)benzofuran-2-yl)-1,2,4-oxadiazol-3-yl)benzoic acid (BHBA-019)

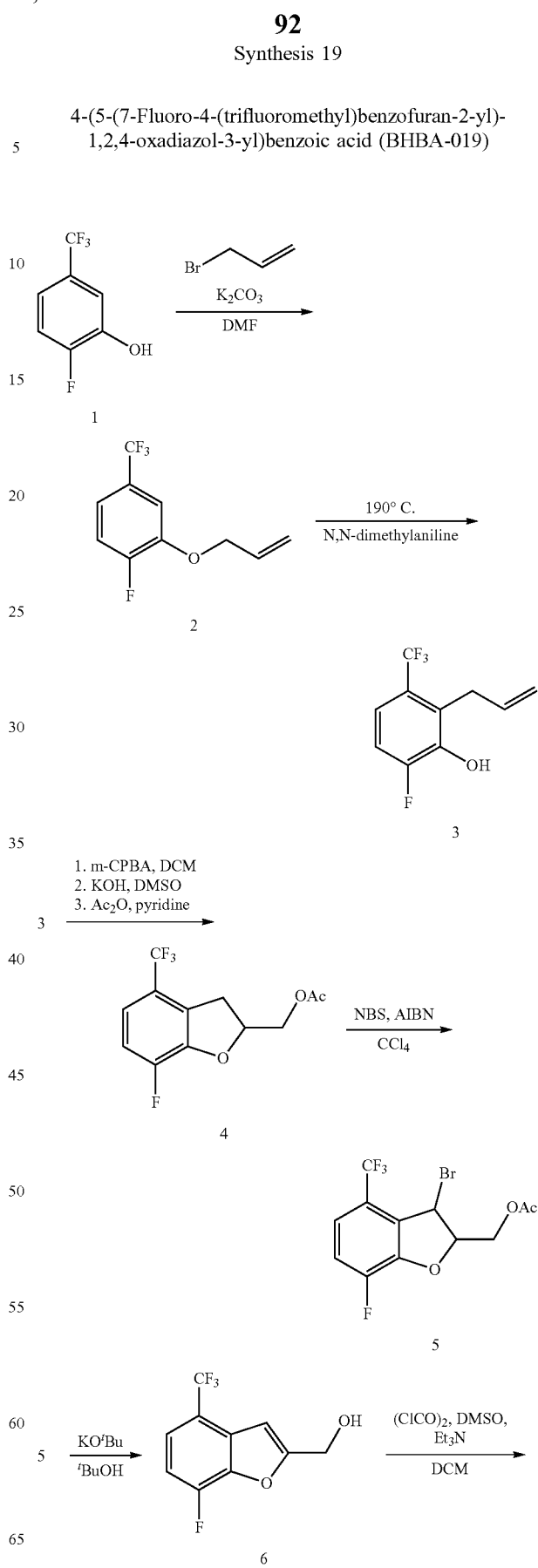

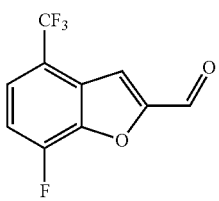

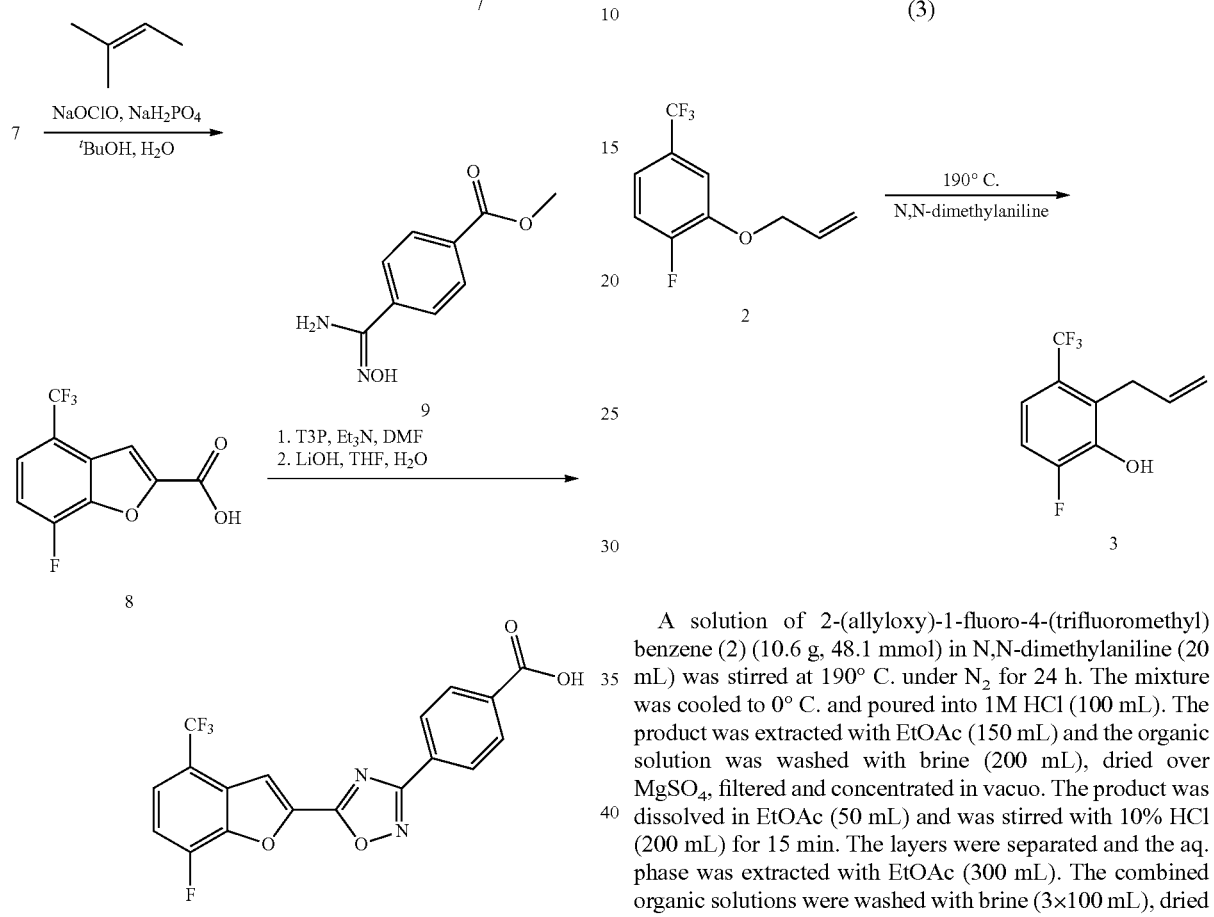

dried over MgSO₄, filtered and concentrated in vacuo. The product was purified by silica gel chromatography (120 g, 0-10% EtOAc in isohexane) to afford the title compound (2) (10.6 g, 87%) as a pale yellow oil: $^1$H NMR (400 MHz, CDCl₃) δ: 7.25-7.12 (3H, m), 6.15-5.99 (1H, m), 5.51-5.42 (1H, m), 5.38-5.32 (1H, m), 4.70-4.57 (2H, m).

Step (ii): 2-Allyl-6-fluoro-3-(trifluoromethyl)phenol (3)

A solution of 2-(allyloxy)-1-fluoro-4-(trifluoromethyl)benzene (2) (10.6 g, 48.1 mmol) in N,N-dimethylaniline (20 mL) was stirred at 190° C. under N₂ for 24 h. The mixture was cooled to 0° C. and poured into 1M HCl (100 mL). The product was extracted with EtOAc (150 mL) and the organic solution was washed with brine (200 mL), dried over MgSO₄, filtered and concentrated in vacuo. The product was dissolved in EtOAc (50 mL) and was stirred with 10% HCl (200 mL) for 15 min. The layers were separated and the aq. phase was extracted with EtOAc (300 mL). The combined organic solutions were washed with brine (3×100 mL), dried over MgSO₄, filtered and concentrated in vacuo. The product was purified by silica gel chromatography (120 g, 0-5% EtOAc in isohexane) to afford the title compound (3) (8.7 g, 82%) as a red oil: m/z 219 [M−H]⁻ (ES⁻); $^1$H NMR (400 MHz, CDCl₃) δ: 7.24-7.17 (1H, m), 7.08-7.00 (1H, m), 6.06-5.89 (1H, m), 5.53 (1H, s), 5.11-5.01 (2H, m), 3.63-3.51 (2H, m).

Step (iii): (7-Fluoro-4-(trifluoromethyl)-2,3-dihydrobenzofuran-2-yl)methyl acetate (4)

Step (i): 2-(Allyloxy)-1-fluoro-4-(trifluoromethyl)benzene (2)

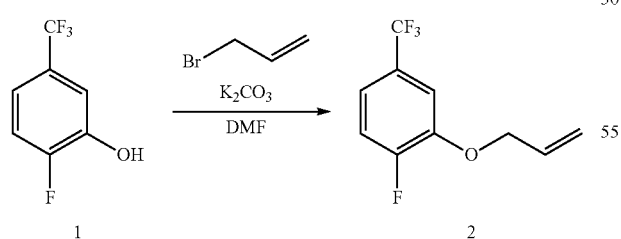

Allyl bromide (12.0 mL, 139 mmol) was added to a stirring mixture of 2-fluoro-5-(trifluoromethyl)phenol (1) (7.0 mL, 56 mmol) and K₂CO₃ (23 g, 170 mmol) in DMF (60 mL). The mixture was stirred at 80° C. under N₂ for 2 h, and then cooled to RT. The mixture was diluted with brine (100 mL) and the product was extracted with EtOAc (300 mL). The organic solution was washed with brine (100 mL),

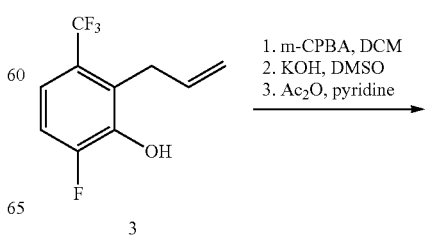

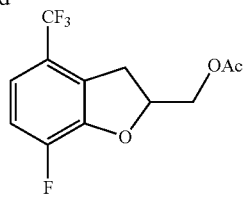

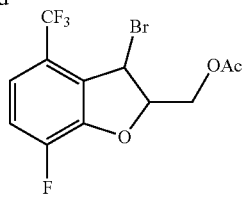

3-Chloroperoxybenzoic acid (13.3 g, 59.4 mmol) was added to a solution of 2-allyl-6-fluoro-3-(trifluoromethyl)phenol (3) (8.7 g, 40 mmol) in DCM and the mixture was stirred at RT under N₂ for 18 h. The mixture was diluted with EtOAc (100 mL) and washed with sat. aq. NaHCO₃ (150 mL). The aq. layer was further extracted with EtOAc (100 mL) and the combined organic extracts were sequentially washed with 10% Na₂S₂CO₃ (400 mL) and brine (200 mL). The organic solution was dried over MgSO₄, filtered and concentrated in vacuo to give intermediate 6-fluoro-2-(oxiran-2-ylmethyl)-3-(trifluoromethyl)phenol (7.6 g).

The intermediate was dissolved in DMSO (60 mL) and treated with a solution of potassium hydroxide (2.2 g, 38 mmol) in H₂O (5 mL). The mixture was then stirred at RT for 72 h. The mixture was diluted with H₂O (100 mL) and the product was extracted with EtOAc (450 mL). The organic solution was washed with brine (600 mL), dried over MgSO₄, filtered and concentrated in vacuo to give intermediate (7-fluoro-4-(trifluoromethyl)-2,3-dihydrobenzofuran-2-yl)methanol (7.1 g).

This intermediate was dissolved in pyridine (30 mL), treated with acetic anhydride (3.7 mL, 39 mmol) and the mixture was stirred at RT under N₂ for 4 h. The mixture was slowly poured into 10% aq. HCl (200 mL) and then the product was extracted with EtOAc (300 mL). The organic solution was sequentially washed with 10% aq. HCl (300 mL) and brine (200 mL), dried over MgSO₄, filtered and concentrated in vacuo. The product was purified by silica gel chromatography (80 g, 0-10% EtOAc in isohexane) to afford the title compound (4) (2.5 g, 29%) as a pale yellow solid: ¹H NMR (400 MHz, CDCl₃) δ: 7.08-7.05 (1H, m), 7.02-6.97 (1H, m), 5.19-5.12 (1H, m), 4.36-4.26 (2H, m), 3.50 (1H, dd), 3.18 (1H, dd), 2.07 (3H, s).

Step (iv): (3-Bromo-7-fluoro-4-(trifluoromethyl)-2,3-dihydrobenzofuran-2-yl)methyl acetate (5)

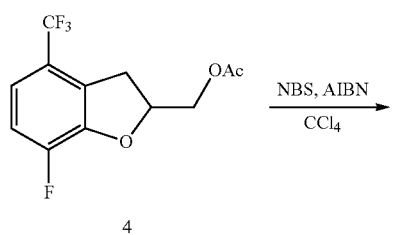

NBS (1.6 g, 8.8 mmol) and AIBN (19 mg, 0.12 mmol) were added to a solution of (7-fluoro-4-(trifluoromethyl)-2,3-dihydrobenzofuran-2-yl)methyl acetate (4) (2.5 g, 8.8 mmol) in CCl₄ (20 mL) and the mixture was stirred at 60° C. under N₂ for 2 h, then at reflux for 3 h. The mixture was cooled to RT, then partitioned between aq. 10% Na₂S₂CO₃ (50 mL) and DCM (50 mL). The organic solution was washed with brine (100 mL), dried over MgSO₄, filtered and concentrated in vacuo. The product was purified by silica gel chromatography (120 g, 0-10% EtOAc in isohexane) to afford (3-bromo-7-fluoro-4-(trifluoromethyl)-2,3-dihydrobenzofuran-2-yl)methyl acetate (5) (2.4 g, 75%) as a pale yellow oil: ¹H NMR (400 MHz, CDCl₃) δ: 7.24-7.13 (2H, m), 5.57-5.52 (1H, m), 5.41-5.31 (1H, m), 4.33-4.21 (1H, m), 4.16-4.04 (1H, m), 2.07 (3H, s).

Step (v): (7-Fluoro-4-(trifluoromethyl)benzofuran-2-yl)methanol (6)

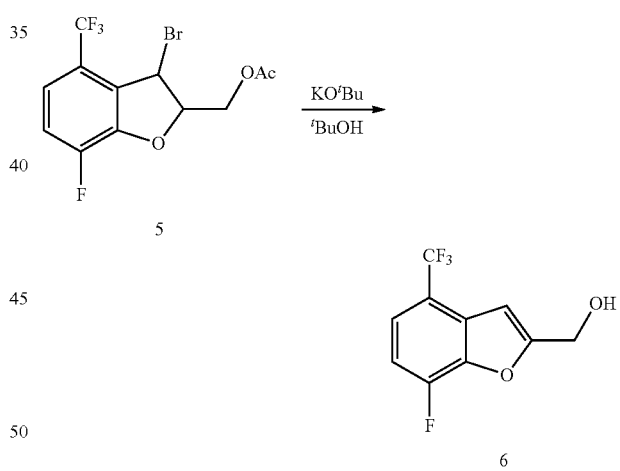

A solution of potassium tert-butoxide (1 M in t-BuOH) (10 mL, 10 mmol) was added to a solution of (3-bromo-7-fluoro-4-(trifluoromethyl)-2,3-dihydrobenzofuran-2-yl)methyl acetate (5) (3.3 g, 9.2 mmol) in t-BuOH (20 mL) and the mixture was stirred at 60° C. under N₂ for 1.5 h, then at reflux for 18 h. The mixture was cooled to RT, then poured into iced water (100 mL) and the product was extracted with EtOAc (300 mL). The organic solution was washed with brine (500 mL), dried over MgSO₄, filtered and concentrated in vacuo. The product was purified by silica gel chromatography (80 g, 0-10% EtOAc in isohexane) to afford the title compound (6) (0.9 g, 43%) as a pale yellow oil: ¹H NMR (400 MHz, CDCl₃) δ: 7.47-7.43 (1H, m), 7.10-7.05 (1H, m), 6.90-6.89 (1H, m), 4.83 (2H, d), 2.02 (1H, br. t).

Step (vi): 7-Fluoro-4-(trifluoromethyl)benzofuran-2-carbaldehyde (7)

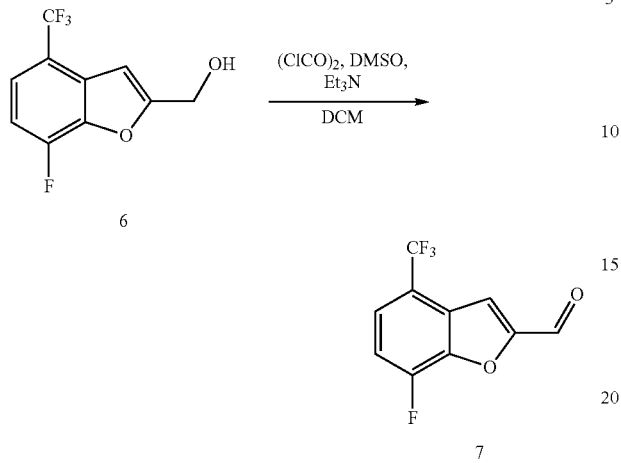

A solution of oxalyl chloride (0.55 mL, 6.3 mmol) in DCM (20 mL) was stirred at −78° C. under N$_2$, and treated with DMSO (0.893 mL, 12.6 mmol). After 1 h, a solution of (7 fluoro-4-(trifluoromethyl)benzofuran-2-yl)methanol (6) (0.74 g, 3.2 mmol) in DCM (10 mL) was added and the mixture continued to stir at −78° C. After a further 45 min, Et$_3$N (2.65 mL, 18.9 mmol) was added and the mixture was allowed to warm to RT. The mixture was partitioned between EtOAc (150 mL) and water (50 mL), and the organic solution was washed with brine (200 mL), dried over MgSO$_4$, filtered and concentrated in vacuo. The product was purified by silica gel chromatography (80 g, 0-5% EtOAc in isohexane) to afford the title compound (7) (0.66 g, 91%) as a yellow solid: $^1$H NMR (400 MHz, CDCl$_3$) δ: 9.98 (1H, s), 7.77-7.71 (1H, m), 7.68-7.57 (1H, m), 7.39-7.30 (1H, m).

Step (vii): 7-Fluoro-4-(trifluoromethyl)benzofuran-2-carboxylic acid (8)

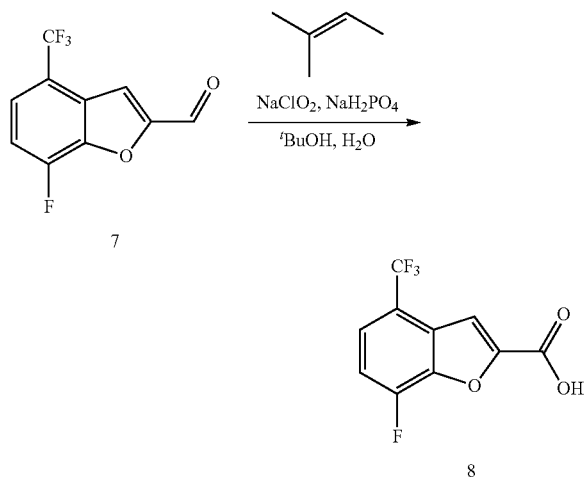

A mixture of NaClO$_2$ (1.3 g, 14 mmol) and NaH$_2$PO$_4$ (1.3 g, 11 mmol) in H$_2$O (5 mL) was added to a stirred mixture of 7-fluoro-4-(trifluoromethyl)benzofuran-2-carbaldehyde (7) (0.36 g, 1.6 mmol) and 2-methylbut-2-ene (15 mL, 140 mmol) in t-BuOH (20 mL) and the resulting mixture was stirred at RT for 1 h. The reaction was quenched by the addition of aq. Na$_2$SO$_3$ (20 mL), followed by brine (20 mL). The product was extracted with EtOAc (150 mL), and the organic solution was washed with brine (100 mL), dried over MgSO$_4$, filtered and concentrated in vacuo. The product was purified by capture and release on SAX (10 g), eluting with 5% acetic acid in MeOH to provide the title compound (8) (0.39 g, 100%): m/z 247 [M−H]$^-$ (ES); $^1$H NMR (400 MHz, DMSO-d$_6$) δ: 7.69-7.66 (1H, m), 7.49-7.44 (1H, m), 7.24 (1H, br. s), acid proton not observed.

Step (viii): 4-(5-(7-Fluoro-4-(trifluoromethyl)benzofuran-2-yl)-1,2,4-oxadiazol-3-yl)benzoic acid (BHBA-019)

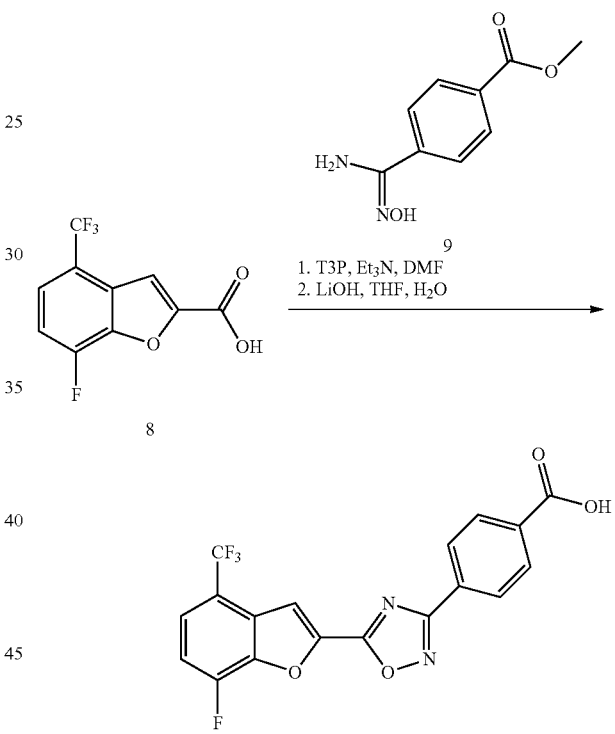

A mixture of 7-fluoro-4-(trifluoromethyl)benzofuran-2-carboxylic acid (8) (100 mg, 0.403 mmol), DIPEA (350 μL, 2.02 mmol), methyl 4-(N'-hydroxycarbamimidoyl)benzoate (9) (117 mg, 0.605 mmol) and T3P (50% solution in EtOAc) (590 μL, 1.01 mmol) in DMF (10 mL) was stirred at RT for 30 min, and then at 90° C. for 18 h. The mixture was cooled to RT, treated with further methyl 4-(N'-hydroxycarbamimidoyl)benzoate (9) (117 mg, 0.605 mmol) and T3P (50% solution in EtOAc) (255 μL, 0.436 mmol) and heated at 90° C. for 48 h. The mixture was cooled to RT and poured onto ice/water. The resulting precipitate was collected by filtration. The solid was suspended in a mixture of THF (2.5 mL) and water (2.5 mL), LiOH (5 mg, 0.2 mmol) was added and the mixture was stirred at 40° C. for 18 h. The mixture was cooled to RT and acidified by the addition of 1 M HCl. The precipitate was collected by filtration. The filtrate was extracted with EtOAc (75 mL) and the organic solution was dried over MgSO$_4$ and filtered. The solvent was removed in vacuo and the residue was combined with the solid obtained previously and purified by capture and release on SAX (2 g). The material was further purified by reverse-phase HPLC to afford the title compound (2 mg, 2%) as a white solid: m/z 391 [M−H]⁻ (ES⁻); ¹H NMR (400 MHz, DMSO-d$_6$) δ: 13.33 (1H, br. s), 8.30-8.29 (1H, m), 8.22-8.13 (4H, m), 7.93-7.90 (1H, m), 7.78-7.73 (1H, m).

Synthesis 20

3-Chloro-4-(5-(7-fluoro-4-(trifluoromethyl)benzofuran-2-yl)-1,2,4-oxadiazol-3-yl)benzoic acid (BHBA-020)

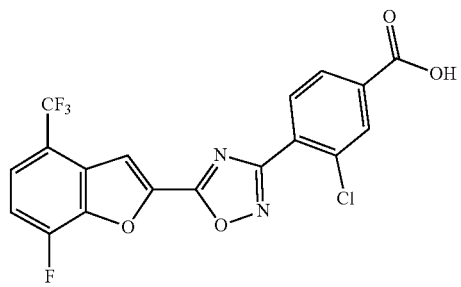 [SMILES: O=C(O)c1ccc(-c2noc(-c3cc4c(C(F)(F)F)ccc(F)c4o3)n2)c(Cl)c1]

The title compound (35 mg, 91% for final step) was prepared in essentially the same manner as (BHBA-019) except methyl 3-chloro-4-(N'-hydroxycarbamimidoyl)benzoate was used instead of methyl 4-(N'-hydroxycarbamimidoyl)benzoate in step (viii): m/z 425 [M−H]⁻ (ES⁻); ¹H NMR (400 MHz, DMSO-d$_6$) δ: 13.67 (1H, br. s), 8.32-8.31 (1H, m), 8.23 (1H, d), 8.16 (1H, d), 8.11 (1H, dd), 7.91 (1H, dd), 7.75 (1H, t).

Synthesis 21

4-(5-(4,7-Dimethylbenzo[b]thiophen-2-yl)-1,2,4-oxadiazol-3-yl)benzoic acid (BHBA-021)

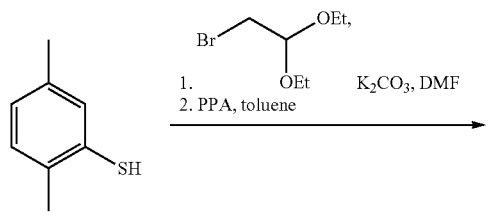

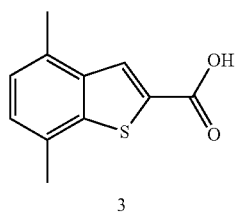

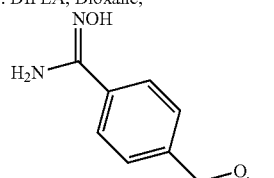

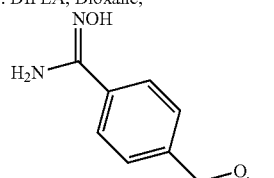

Step (i): 4,7-Dimethylbenzo[b]thiophene (2)

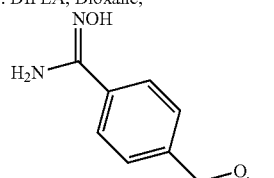

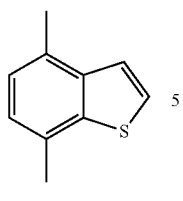

A mixture of 2,5-dimethylbenzenethiol (1) (5.0 g, 36 mmol), 2-bromo-1,1-diethoxyethane (9.0 mL, 58 mmol) and K$_2$CO$_3$ (12.5 g, 90.0 mmol) in anhydrous DMF (30 mL) was stirred at 65° C. for 2 h. The mixture was allowed to cool to RT, and then partitioned between EtOAc (50 mL) and water (100 mL). The organic solution was washed with brine (50 mL), dried over MgSO$_4$, filtered and concentrated in vacuo. The residue was dissolved in anhydrous toluene (80 mL), treated with pyrophosphoric acid (18.1 g, 102 mmol) and the mixture was stirred at 100° C. for 1 h. The mixture was cooled to RT, and then poured into water (200 mL) and the product was extracted with EtOAc (100 mL). The organic solution was dried over MgSO$_4$, filtered and then concentrated in vacuo. The material was purified by silica gel chromatography (120 g, 0-5% EtOAc in isohexane) to afford the title compound (2) (3.7 g, 63%) as an orange oil: $^1$H NMR (400 MHz, DMSO-d$_6$) δ: 7.74 (1H, d), 7.52 (1H, d), 7.13-7.05 (2H, m), 2.54 (3H, s), 2.47 (3H, s).

Step (ii): 4,7-Dimethylbenzo[b]thiophene-2-carboxylic acid (3)

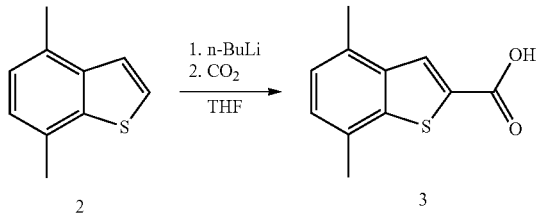

A solution of 4,7-dimethylbenzo[b]thiophene (2) (1.0 g, 6.2 mmol) in anhydrous THF (20 mL) was stirred at −78° C., under nitrogen, before n-butyllithium (2.5 M in hexanes) (3.0 mL, 7.4 mmol) was added slowly, dropwise such that the temperature was maintained below −60° C. After the addition the mixture continued to stir at −78° C. for 45 min before it was poured onto crushed solid carbon dioxide (15.0 g, 341 mmol) and warmed to RT with stirring. The mixture was partitioned between EtOAc (50 mL) and 2M NaOH (50 mL). The aqueous phase was made acidic by the addition of conc. HCl and the product was extracted with EtOAc (50 mL). The organic solution was dried over MgSO$_4$, filtered and concentrated in vacuo to afford 4,7-dimethylbenzo[b]thiophene-2-carboxylic acid (3) (570 mg, 42%) as a cream coloured solid: m/z 207 [M+H]$^+$ (ES$^+$), 205 [M−H]$^−$ (ES$^−$);
$^1$H NMR (400 MHz, DMSO-d$_6$) δ: 13.44 (1H, br. s), 8.15 (1H, s), 7.24 (1H, d), 7.18 (1H, d), 2.58 (3H, s), 2.47 (3H, s).

Step (iii): Methyl 4-(5-(4,7-dimethylbenzo[b]thiophen-2-yl)-1,2,4-oxadiazol-3-yl)benzoate (5)

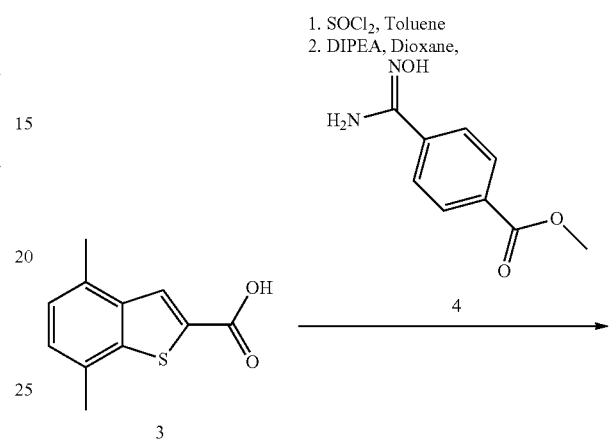

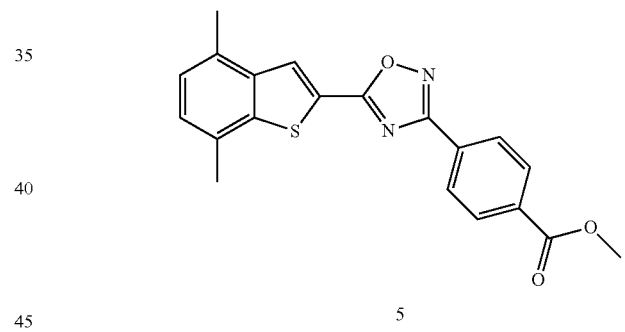

A mixture of 4,7-dimethylbenzo[b]thiophene-2-carboxylic acid (3) (100 mg, 0.5 mmol) and thionyl chloride (106 μL, 1.45 mmol) in toluene (5 mL) was stirred at 90° C. for 1 h, then 95° C. for 1 h. The mixture was cooled to RT and then the volatiles were removed in vacuo and co-evaporated with toluene (2×3 mL). The resulting yellow solid was dissolved in dioxane (3 mL) and added to a mixture of DIPEA (169 μL, 0.968 mmol) and methyl 4-(N'-hydroxycarbamimidoyl) benzoate (4) (94 mg, 0.484 mmol). The resulting mixture was stirred at RT for 17 h, then at 90° C. for 5 h. The mixture was allowed to cool to RT and then diluted with MeOH (5 mL) and stirred for 30 min. The precipitate was collected, washed with MeOH (5 mL) and dried in air to afford the title compound (5) (128 mg, 73%) as a white solid: m/z 365 [M+H]$^+$ (ES$^+$); $^1$H NMR (400 MHz, DMSO-d$_6$) δ: 8.53 (1H, s), 8.21 (2H, d), 8.15 (2H, d), 7.30 (1H, d), 7.25 (1H, d), 3.90 (3H, s), 2.64 (3H, s), 2.53 (3H, s).

Step (iv): 4-(5-(4,7-Dimethylbenzo[b]thiophen-2-yl)-1,2,4-oxadiazol-3-yl)benzoic acid (BHBA-021)

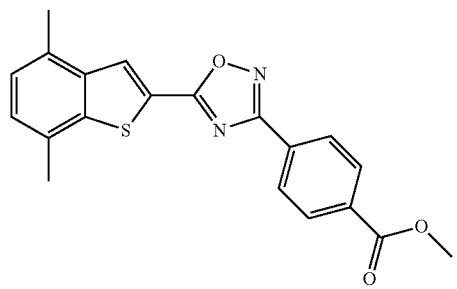

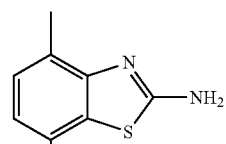

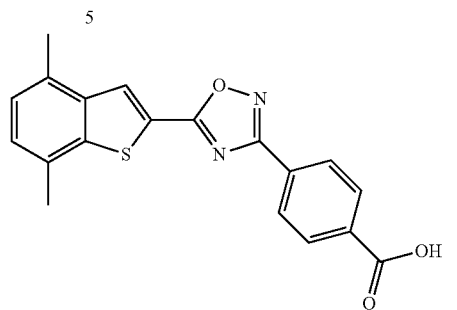

The title compound (109 mg, 90%) was prepared from methyl 4-(5-(4,7-dimethylbenzo[b]thiophen-2-yl)-1,2,4-oxadiazol-3-yl)benzoate (5) using a procedure essentially the same as in step (v) for (BHBA-001): m/z 351 [M+H]$^+$ (ES$^+$), 349 [M−H]$^-$ (ES$^-$); $^1$H NMR (400 MHz, DMSO-d$_6$) δ: 13.32 (1H, s), 8.57 (1H, s), 8.22 (2H, d), 8.15 (2H, d), 7.32 (1H, d), 7.27 (1H, d), 2.66 (3H, s), 2.54 (3H, s).

Synthesis 22

3-Chloro-4-(5-(4,7-dimethylbenzo[b]thiophen-2-yl)-1,2,4-oxadiazol-3-yl)benzoic acid (BHBA-022)

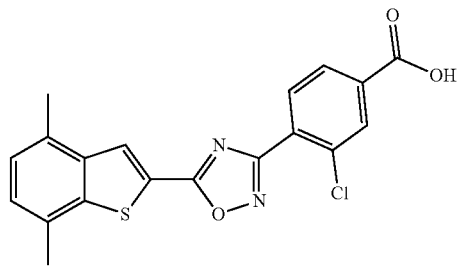 [SMILES: Cc1ccc(C)c2sc(-c3nc(-c4ccc(C(=O)O)cc4Cl)no3)cc12]

The title compound (73 mg, 81% for final step) was prepared in essentially the same manner as (BHBA-021) except methyl 3-chloro-4-(N'-hydroxycarbamimidoyl)benzoate was used instead of methyl 4-(N'-hydroxycarbamimidoyl)benzoate in step (iii): m/z 385 [M+H]$^+$ (ES$^+$), 383 [M−H]$^-$ (ES$^-$); $^1$H NMR (400 MHz, DMSO-d$_6$) δ: 13.67 (1H, br. s), 8.59 (1H, s), 8.18 (1H, d), 8.14 (1H, d), 8.11-8.06 (1H, m), 7.33 (1H, d), 7.27 (1H, d), 2.66 (3H, s), 2.54 (3H, s).

Synthesis 23

4-(5-(4,7-Dimethylbenzo[d]thiazol-2-yl)-1,2,4-oxadiazol-3-yl)benzoic acid (BHBA-027)

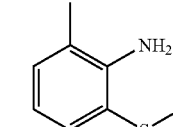

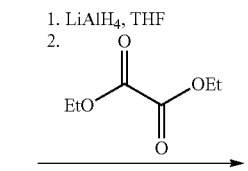

1. LiAlH$_4$, THF
2. 
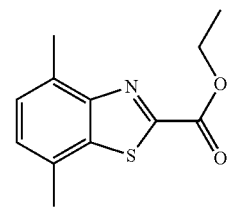

1. LiOH, THF, H$_2$O
2. T3P, DIPEA, DMF,

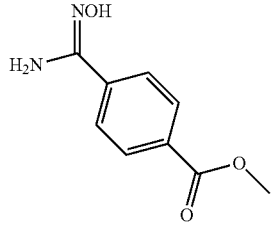

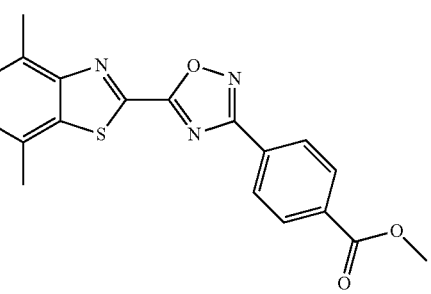

LiOH
THF, H$_2$O

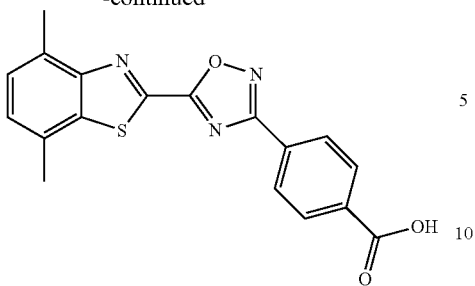

Step (i): 6,6'-Disulfanediylbis(2,5-dimethylaniline) (2)

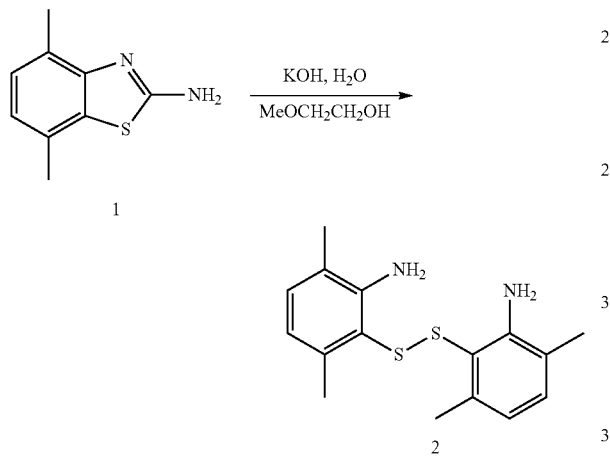

A mixture of 4,7-dimethylbenzo[d]thiazol-2-amine (1) (1.0 g, 5.6 mmol) and KOH (6.0 g, 110 mmol) in a mixture of H$_2$O (6.0 mL) and 2-methoxyethanol (6 mL) was refluxed under nitrogen for 5 days. The reaction mixture was cooled to RT, and the suspension was decanted. The gelatinous residue was washed with water (100 mL) and EtOAc (100 mL). The extracts were neutralised with acetic acid (3 mL), and the organic phase separated. The organic solution was dried over MgSO$_4$, filtered and concentrated in vacuo. The residue was purified by silica gel chromatography (120 g, 0-100% DCM in EtOAc) to give 6,6'-disulfanediylbis(2,5-dimethylaniline) (2) (0.55 g, 64%) as a yellow solid: m/z 305 [M+H]$^+$ (ES$^+$); $^1$H NMR (400 MHz, CDCl$_3$) δ: 6.91 (2H, d), 6.47 (2H, d), 4.32 (4H, s), 2.12 (6H, s), 2.09 (6H, s).

Step (ii): Ethyl 4,7-dimethylbenzo[d]thiazole-2-carboxylate (3)

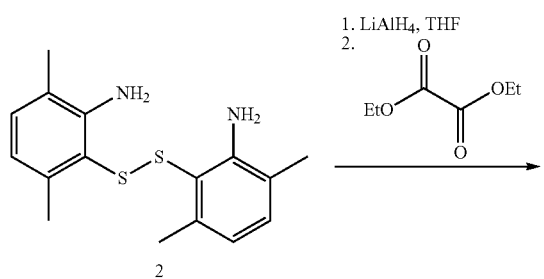

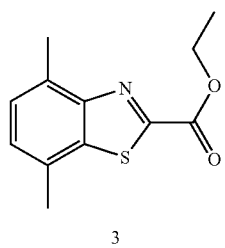

LiAlH$_4$ (1 M in THF) (0.86 mL, 0.86 mmol) was added dropwise to a solution of 2-((2,5-dimethylphenyl)disulfanyl)-3,6-dimethylaniline (2) (0.5 g, 1.7 mmol) in anhydrous THF (10 mL, 120 mmol) at RT under nitrogen. The reaction mixture was stirred at RT for 3 h, after which a further portion of LiAlH$_4$ (0.86 mL, 0.86 mmol) was added. After a further 18 h the mixture was again charged with LiAlH$_4$ (0.86 mL, 0.86 mmol) and stirred for an additional 1 h. The reaction was quenched by the cautious addition of water, followed by saturated ammonium chloride solution (30 mL). The product was extracted with EtOAc (150 mL), and the organic solution was dried over MgSO$_4$, filtered and concentrated in vacuo. The residue was combined with diethyl oxalate (5.0 mL, 1.1 mmol) and the mixture was stirred at 170° C. under nitrogen for 24 h. The majority (80-90%) of the diethyl oxalate was removed by Kugelrohr distillation under reduced pressure. The product was purified by silica gel chromatography (40 g, 0-100% DCM-isohexane) to give ethyl 4,7-dimethylbenzo[d]thiazole-2-carboxylate (3) (0.1 g, 34%) as a brown oil: m/z 236 [M+H]$^+$ (ES$^+$); $^1$H NMR (400 MHz, DMSO-d$_6$) δ: 7.43-7.30 (2H, m), 4.45 (2H, q), 2.67 (3H, s), 2.53 (3H, s), 1.38 (3H, t).

Step (iii): Methyl 4-(5-(4,7-dimethylbenzo[d]thiazol-2-yl)-1,2,4-oxadiazol-3-yl)benzoate (5)

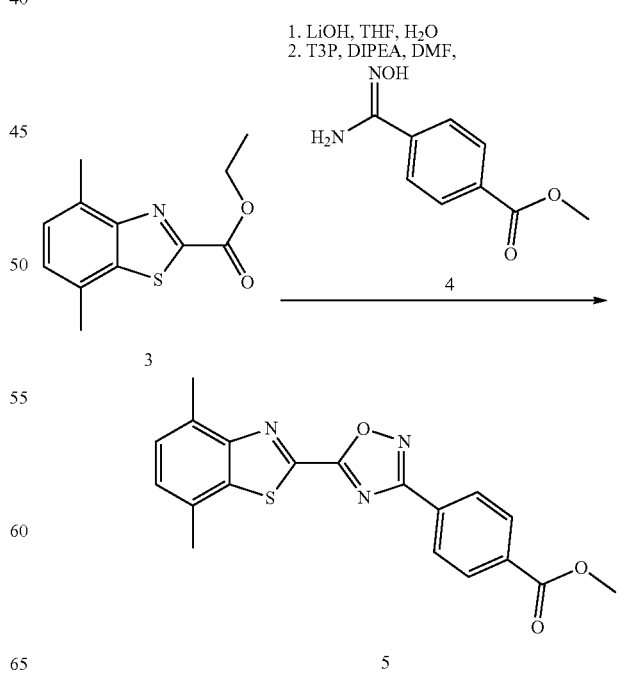

A mixture of ethyl 4,7-dimethylbenzo[d]thiazole-2-carboxylate (5) (85 mg, 0.36 mmol) and LiOH (2 M in H₂O) (180 µl, 0.36 mmol) in THF (1 mL) was stirred at RT for 20 h and then concentrated in vacuo. The residue was dissolved in anhydrous DMF (1 mL) and treated with T3P (50% in EtOAc) (459 µL, 0.722 mmol), methyl 4-(N'-hydroxycarbamimidoyl)benzoate (4) (140 mg, 0.722 mmol) and DIPEA (189 µl, 1.08 mmol). The mixture was stirred at RT for 10 min, then heated to 90° C. for 1 h. The mixture was cooled to RT and diluted with MeOH (20 mL) and water (5 mL). The resultant solid was collected, washed with MeOH (5 mL) and dried in air to afford the title compound (5) (23 mg, 17% yield) as a beige solid: m/z 366 [M+H]⁺ (ES⁺); ¹H NMR (400 MHz, DMSO-d₆) δ: 8.27 (2H, d), 8.19 (2H, d), 7.46 (1H, d), 7.42 (1H, d), 3.92 (3H, s), 2.75 (3H, s), 2.60 (3H, s).

Step (iv): 4-(5-(4,7-Dimethylbenzo[d]thiazol-2-yl)-1,2,4-oxadiazol-3-yl)benzoic acid (BHBA-027)

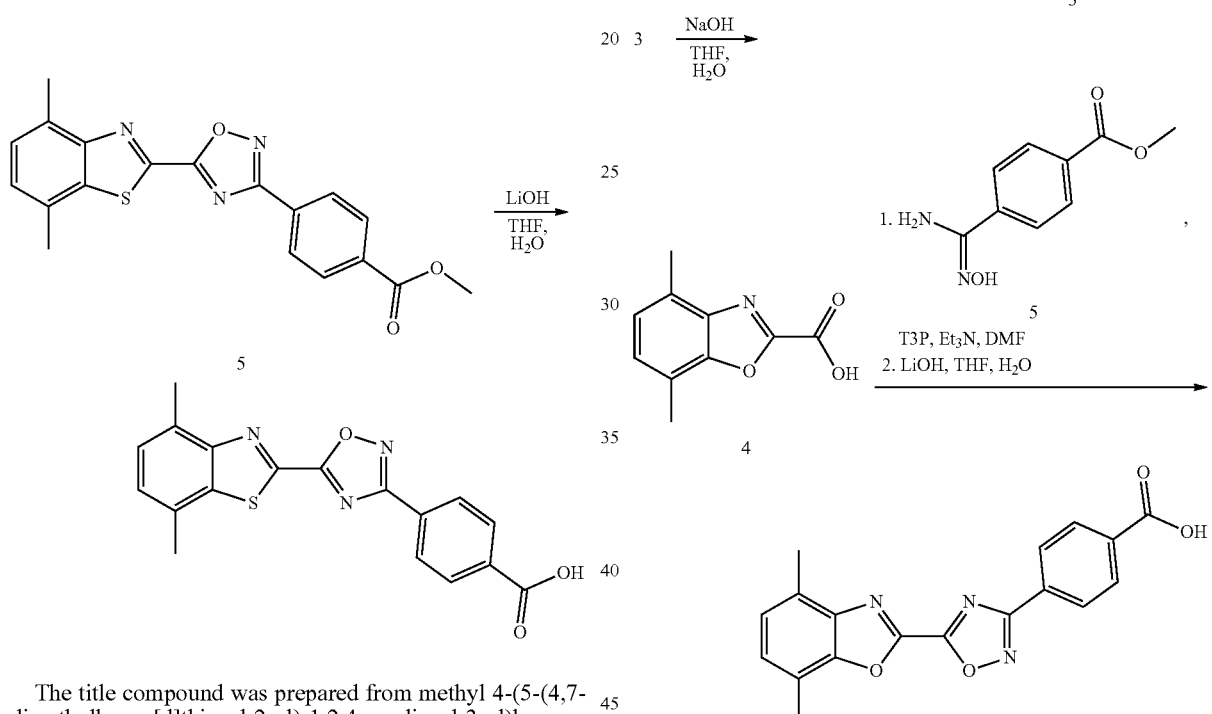

The title compound was prepared from methyl 4-(5-(4,7-dimethylbenzo[d]thiazol-2-yl)-1,2,4-oxadiazol-3-yl)benzoate (5) using a procedure essentially the same as in step (v) for (BHBA-001): m/z 352 [M+H]⁺ (ES⁺), 350 [M−H]⁻ (ES⁻); ¹H NMR (400 MHz, DMSO-d₆) δ: 13.35 (1H, br. s), 8.25 (2H, d), 8.17 (2H, d), 7.47 (1h, d), 7.42 (1H, d), 2.75 (3H, s), 2.60 (3H, s).

Synthesis 24

4-(5-(4,7-Dimethylbenzo[d]oxazol-2-yl)-1,2,4-oxadiazol-3-yl)benzoic acid (BHBA-023)

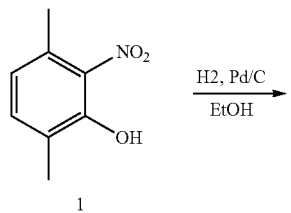

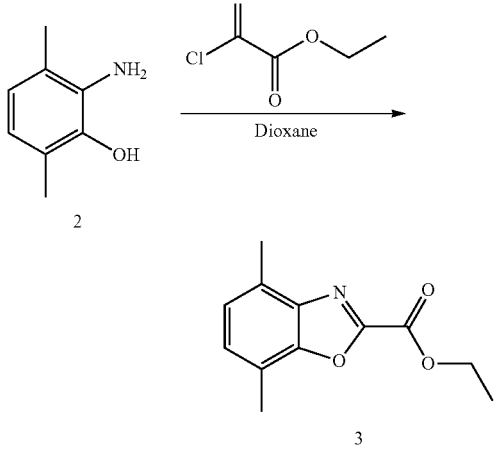

Step (i): 2-Amino-3,6-dimethylphenol (2)

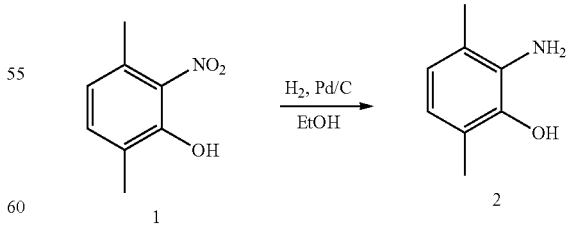

3,6-Dimethyl-2-nitrophenol (1) (2.75 g, 16.5 mmol) was dissolved in ethanol (165 mL) and passed through a Thales 'H-cube' cartridge (10% Pd/C) at a flow rate of 1 mL/min at 40° C. under full H₂ mode. The solution was then concentrated in vacuo to provide the title compound (2) (2.35 g, 94%): m/z 138 [M+H]⁺ (ES⁺); ¹H NMR (400 MHz, CDCl₃) δ: 6.66-6.58 (1H, m), 6.58-6.49 (1H, m), 4.70 (1H, br. s), 3.58 (2H, br. s), 2.19 (3H, s), 2.16 (3H, s).

Step (ii): Ethyl 4,7-dimethylbenzo[d]oxazole-2-carboxylate (3)

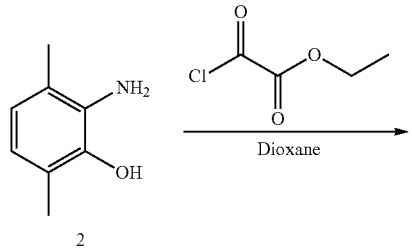

A mixture of 2-amino-3,6-dimethylphenol (2) (1.8 g, 13 mmol) was dissolved in dioxane (5 mL), treated with ethyl 2-chloro-2-oxoacetate (1.5 mL, 13 mmol) and the mixture was heated to 190° C. in the microwave for 20 min. The reaction mixture was diluted with EtOAc, washed with sodium hydrogen carbonate then dried over MgSO₄ and filtered. The organic solution was concentrated in vacuo onto silica and purified by silica gel chromatography (80 g, 0-10% EtOAc in isohexane) to afford the title compound (3) (1.75 g, 61%) as a pale cream solid: m/z 220 [M+H]⁺ (ES⁺); ¹H NMR (400 MHz, DMSO-d₆) δ: 7.30 (1H, d), 7.21 (1H, d), 4.45 (2H, q), 2.53 (3H, s), 2.48 (3H, s), 1.38 (3H, t).

Step (iii): 4,7-Dimethylbenzo[d]oxazole-2-carboxylic acid (4)

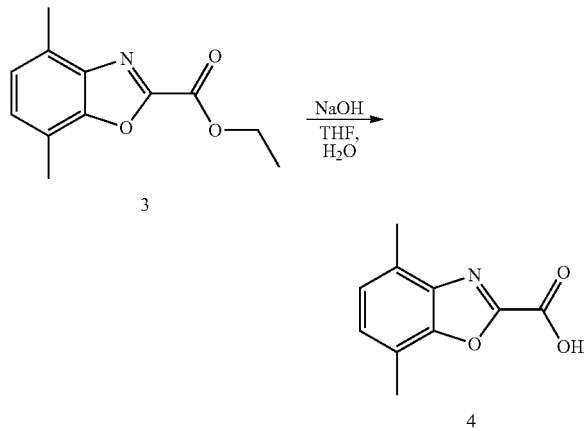

Ethyl 4,7-dimethylbenzo[d]oxazole-2-carboxylate (3) (1.75 g, 7.98 mmol) was dissolved in THF (20 mL) and treated with NaOH (2 M in MeOH) (4.79 mL, 9.58 mmol). The mixture was stirred at RT for 1 h, then diluted with water and acidified by the addition of 1 M HCl. The product was extracted with EtOAc (3×70 mL), the combined organic extracts were dried over Na₂SO₄, filtered and concentrated in vacuo to give the title compound (4) (1.3 g, 87%) as an off white solid: m/z 192 [M+H]⁺ (ES⁺); ¹H NMR (400 MHz, DMSO-d₆) δ: 8.67 (1H, s), 7.15-7.07 (2H, m), 2.50 (3H, s), 2.46 (3H, s).

Step (iv): Methyl 4-(5-(4,7-dimethylbenzo[d]oxazol-2-yl)-1,2,4-oxadiazol-3-yl)benzoate (BHBA-023)

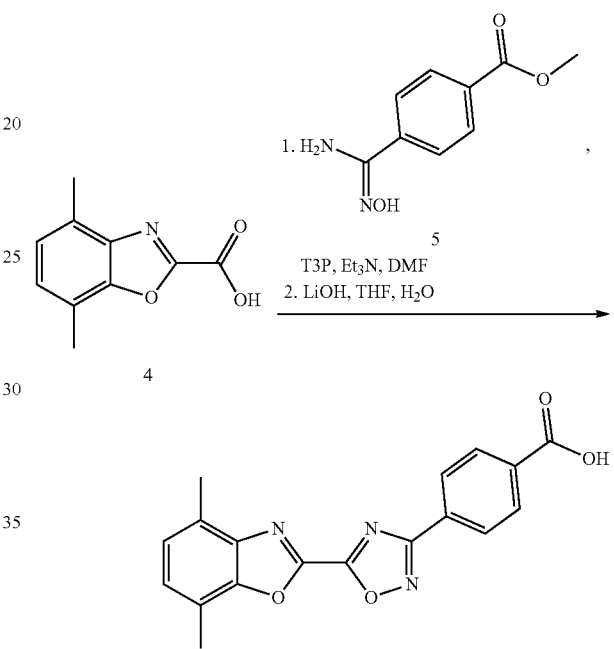

A mixture of 4,7-dimethylbenzo[d]oxazole-2-carboxylic acid (4) (500 mg, 2.62 mmol), DIPEA (914 μL, 5.23 mmol), methyl 4-(N'-hydroxycarbamimidoyl)benzoate (5) (508 mg, 2.62 mmol) and T3P (50% solution in EtOAc) (3.1 mL, 5.2 mmol) in DMF (1.5 mL) was stirred at RT for 90 min, then at 90° C. for 18 h and at 105° C. for 6 h. The mixture was cooled to RT and diluted with EtOAc (30 mL). The organic solution was sequentially washed with 1 M HCl (60 mL), satd. NaHCO₃ (30 mL) and brine (30 mL), then dried over Na₂SO₄ and filtered. The solution was concentrated in vacuo and the residue partially purified by silica gel chromatography (20 g, 0-100% EtOAc in isohexane). The residue was suspended in THF (4 mL), treated with aq. 2 M LiOH (753 μL, 1.51 mmol) and the mixture was stirred at RT for 18 h. The mixture was acidified by the addition of 1 M HCl and the resulting solid was collected by filtration and washed with MeOH (10 mL) and Et₂O (10 mL). The solid was recrystallised from a mixture of toluene and MeCN then further purified by reverse-phase HPLC to afford the title compound (90 mg, 10%): m/z 391 [M–H]⁻ (ES⁻); ¹H NMR (400 MHz, DMSO-d₆) δ: 13.36 (1H, br. s), 8.28 (2H, d), 8.18 (2H, d), 7.38 (1H, d), 7.30 (1H, d), 2.61 (3H, s), 2.57 (3H, s).

Synthesis 25

4-(5-(4,7-Dimethylbenzo[d]oxazol-2-yl)-1,2,4-oxadiazol-3-yl)-2-fluorobenzoic acid (BHBA-026)

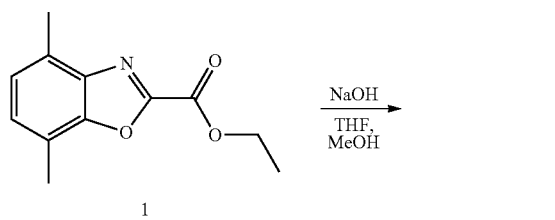

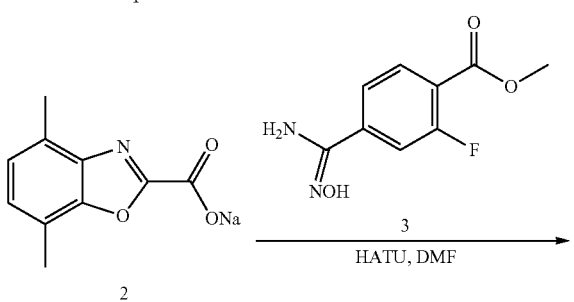

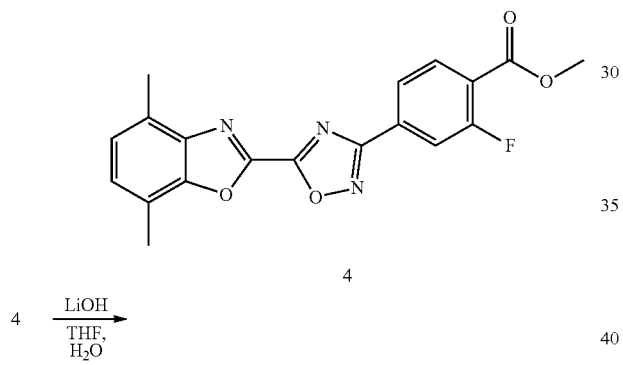

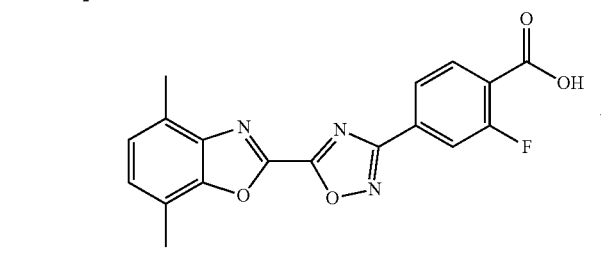

Step (i): Sodium 4,7-dimethylbenzo[d]oxazole-2-carboxylate (2)

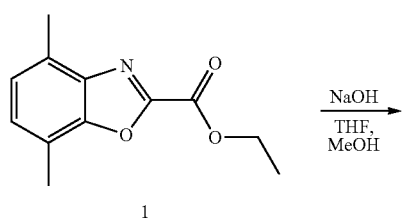

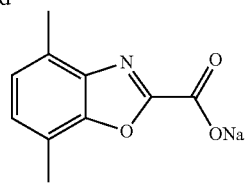

Ethyl 4,7-dimethylbenzo[d]oxazole-2-carboxylate (1) (1.1 g, 3.0 mmol) was dissolved in THF (3 mL), treated with 2 M NaOH in MeOH (3.0 mL, 6.0 mmol) and the resultant mixture was stirred at RT for 3 h. The mixture was diluted with water (20 mL) and washed with Et$_2$O (75 mL). The aqueous phase was concentrated in vacuo and the residue was triturated with a 3:1 mixture of Et$_2$O:H$_2$O (20 mL) to give the title compound (2) (515 mg, 76%) as a brown solid: m/z 192 [M−Na+2H]$^+$ (ES$^+$); $^1$H NMR (400 MHz, DMSO-d$_6$) δ: 7.07 (1H, d), 7.02 (1H, d), 2.48 (3H, s), 2.43 (3H, s).

Step (ii): Methyl 4-(5-(4,7-dimethylbenzo[d]oxazol-2-yl)-1,2,4-oxadiazol-3-yl)-2-fluorobenzoate (4)

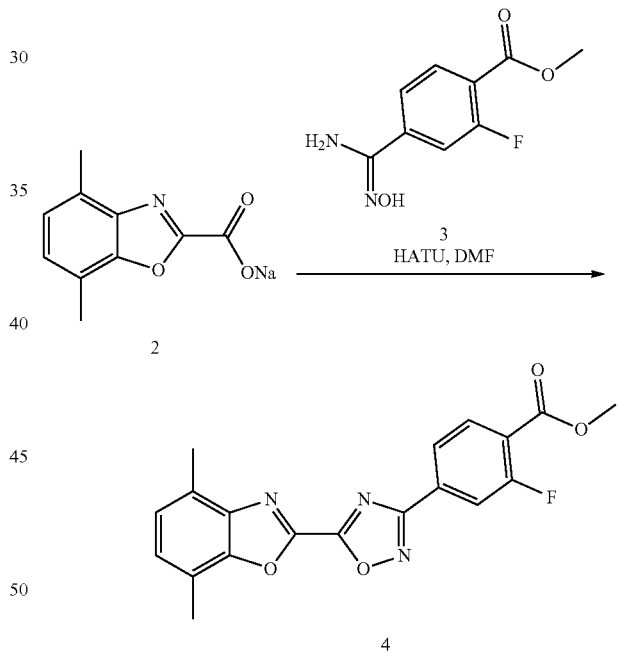

A mixture of sodium 4,7-dimethylbenzo[d]oxazole-2-carboxylate (2) (130 mg, 0.579 mmol) and HATU (242 mg, 0.637 mmol) in DMF (2 mL) was stirred at RT and methyl 2-fluoro-4-(N'-hydroxycarbamimidoyl)benzoate (3) (141 mg, 0.579 mmol) was added. The mixture was stirred at RT for 30 min then at 100° C. for 1 h. The mixture was cooled to RT, diluted with MeOH (5 mL) and water (20 mL) and the product was extracted with EtOAc (30 mL). The organic solution was washed with brine (20 mL), dried over MgSO$_4$ and filtered. The solution was concentrated in vacuo and the residue was purified by silica gel chromatography, eluting with 10% EtOAc in isohexane to yield the title compound (4) (25 mg, 11%): m/z 368 [M+H]$^+$ (ES$^+$); $^1$H NMR (400

MHz, CDCl₃) δ: 8.10-8.09 (2H, m), 8.04 (1H, d), 7.24 (1H, d), 7.18 (1H, d), 3.97 (3H, s), 2.68 (3H, s), 2.60 (3H, s).

Step (iii): 4-(5-(4,7-Dimethylbenzo[d]oxazol-2-yl)-1,2,4-oxadiazol-3-yl)-2-fluorobenzoic acid (BHBA-026)

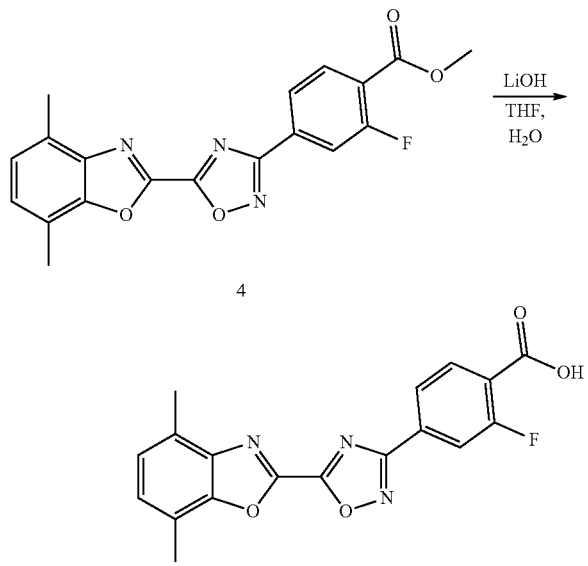

A mixture of methyl 4-(5-(4,7-dimethylbenzo[d]oxazol-2-yl)-1,2,4-oxadiazol-3-yl)-2-fluorobenzoate (4) (22 mg, 0.06 mmol) and 2 M LiOH (35 µL, 0.07 mmol) in THF (3 mL) was stirred at room temperature for 18 h. 1 M aq. HCl (75 uL) was added followed by water (2 mL) and the resulting precipitate was collected by filtration and washed with water (2 mL). The solid was then slurried in DCM: isohexane (9:1, 2 mL), collected by filtration and dried in vacuo to yield the title compound (9 mg, 44%): m/z 354 [M+H]⁺ (ES⁺), 352 [M−H]⁻ (ES⁻); ¹H NMR (400 MHz, DMSO-d₆) δ: 13.64 (1H, br. s), 8.15-8.04 (2H, m), 8.00 (1H, d), 7.39 (1H, d), 7.31 (1H, d), 2.61 (3H, s), 2.56 (3H, s).

Synthesis 26

3-Chloro-4-(5-(4,7-dimethylbenzo[d]oxazol-2-yl)-1,2,4-oxadiazol-3-yl)benzoic acid (BHBA-024)

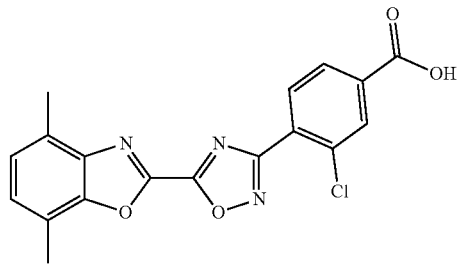 [SMILES: Cc1ccc(C)c2oc(-c3nc(-c4ccc(C(=O)O)cc4Cl)no3)nc12]

The title compound (26 mg, 42% for final step) was prepared in essentially the same manner as (BHBA-026) except methyl 3-chloro-4-(N'-hydroxycarbamimidoyl)benzoate was used instead of methyl 2-fluoro-4-(N'-hydroxycarbamimidoyl)benzoate in step (iii): m/z 370 [M+H]⁺ (ES⁺), 368 [M−H]⁻ (ES⁻); ¹H NMR (400 MHz, DMSO-d₆) δ: 13.71 (1H, br. s), 8.26 (1H, d), 8.16 (1H, d), 8.15-8.09 (1H, m), 7.39 (1H, d), 7.31 (1H, d), 2.61 (3H, s), 2.56 (3H, s).

Synthesis 27

4-(5-(4,7-Dimethylbenzo[d]oxazol-2-yl)-1,2,4-oxadiazol-3-yl)-2-methylbenzoic acid (BHBA-025)

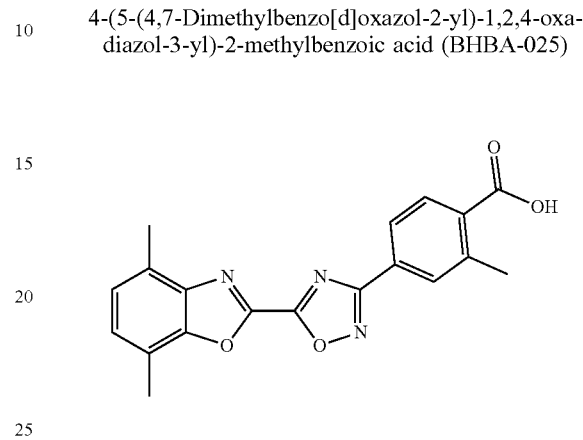

The title compound (7 mg, 19% for final step) was prepared in essentially the same manner as (BHBA-026) except methyl 2-methyl-4-(N'-hydroxycarbamimidoyl)benzoate was used instead of methyl 2-fluoro-4-(N'-hydroxycarbamimidoyl)benzoate in step (iii): m/z 350 [M+H]⁺ (ES⁺), 348 [M−H]⁻ (ES⁻); ¹H NMR (400 MHz, DMSO-d₆) δ: 13.23 (1H, br. s), 8.13-7.97 (3H, m), 7.39 (1H, d), 7.30 (1H, d), 2.65 (3H, s), 2.61 (3H, s), 2.56(3H, s).

Synthesis 28

4-(3-(4,7-Dimethylbenzofuran-2-yl)-1,2,4-oxadiazol-5-yl)benzoic acid (BHBA-028)

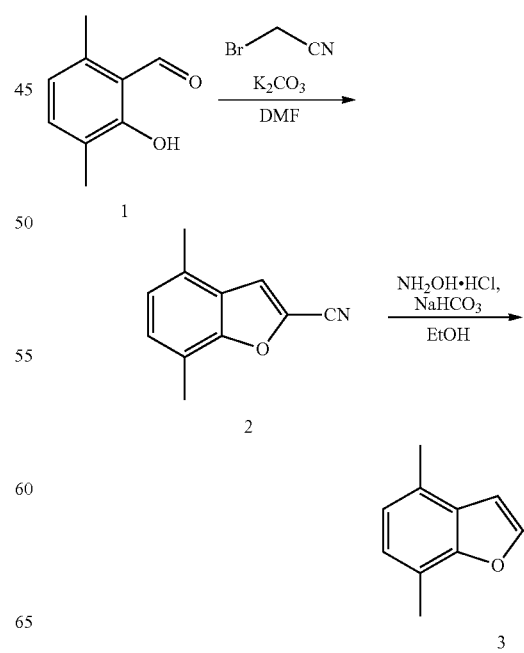

Step (ii): N'-Hydroxy-4,7-dimethylbenzofuran-2-carboximidamide (3)

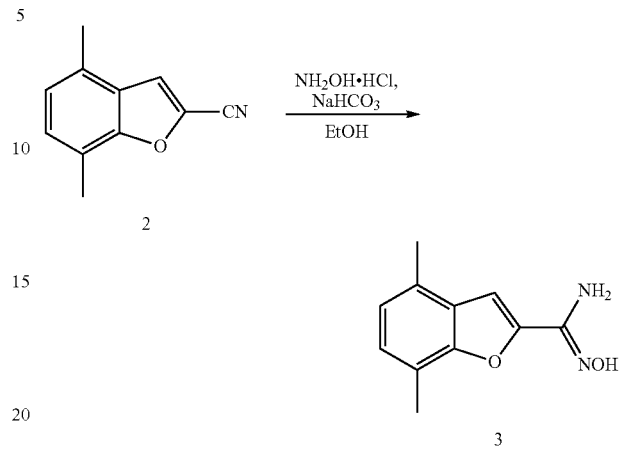

A mixture of 4,7-dimethylbenzofuran-2-carbonitrile (2) (2.0 g, 12 mmol), hydroxylamine hydrochloride (1.22 g, 17.5 mmol) and NaHCO₃ (2.9 g, 35 mmol) in EtOH (20 mL) was heated under reflux for 1 h. The mixture was then cooled to RT and the inorganic solid was removed by filtration. The filtrate was concentrated in vacuo, the residue was dissolved in EtOAc (100 mL) and washed with satd. NaHCO₃ (30 mL) and water (30 mL). The organic solution was dried over MgSO₄, filtered and concentrated in vacuo to give N'-hydroxy-4,7-dimethylbenzofuran-2-carboximidamide (3) (1.6 g, 50%) as a brown sticky solid: m/z 205 [M+H]⁺ (ES⁺).

Step (iii): Methyl 4-(3-(4,7-dimethylbenzofuran-2-yl)-1,2,4-oxadiazol-5-yl)benzoate (5)

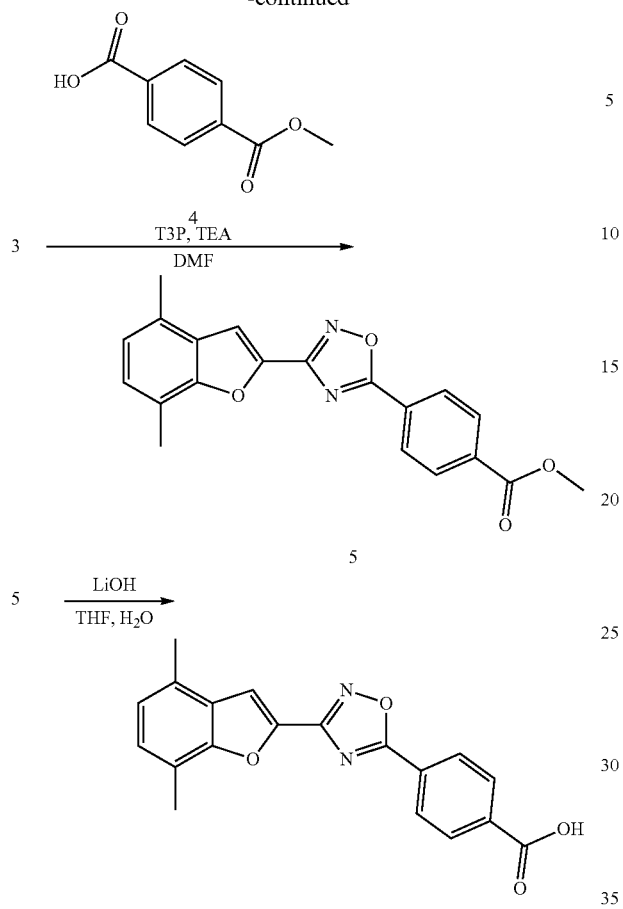

Step (i): 4,7-Dimethylbenzofuran-2-carbonitrile (2)

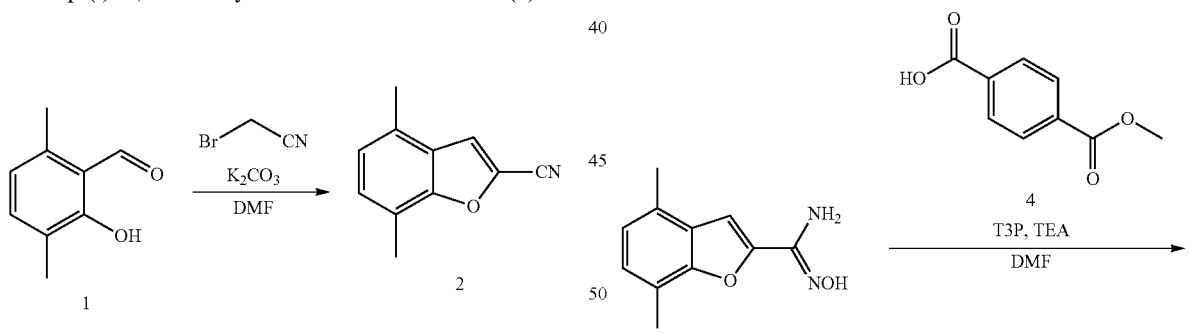

2-Bromoacetonitrile (2.0 g, 17 mmol) was added dropwise to a stirring mixture of 2-hydroxy-3,6-dimethylbenzaldehyde (1) (2.0 g, 13 mmol) and K₂CO₃ (3.7 g, 27 mmol) in anhydrous DMF (30 mL) and the reaction mixture was stirred at 150° C. for 75 min. The mixture was cooled to RT, poured over crushed ice and then extracted with Et₂O (120 mL). The organic solution was dried over MgSO₄, filtered and concentrated in vacuo. The residue was triturated with isohexane to give 4,7-dimethylbenzofuran-2-carbonitrile (2) (1.7 g, 67%) as a dark brown solid: ¹H NMR (400 MHz, CDCl₃) δ: 7.46 (1H, s), 7.18 (1H, d), 7.04 (1H, d), 2.54-2.43 (6H, m).

A mixture of N'-hydroxy-4,7-dimethylbenzofuran-2-carboximidamide (3) (300 mg, 1.47 mmol), 4-(methoxycarbonyl)benzoic acid (4) (265 mg, 1.47 mmol), T3P (50% in EtOAc) (2.16 mL, 3.67 mmol) and Et₃N (1.02 mL, 7.34 mmol) in DMF (5 mL) was stirred at RT for 90 min, then at 90° C. for 18 h. The mixture was cooled to RT and water (15 mL) was added. The resultant solid was collected by filtration and triturated with Et₂O and then methanol to afford the title compound (5) (200 mg, 39%) as a brown solid: ¹H NMR (400 MHz, DMSO-d₆) δ: 8.35 (2H, d), 8.22 (2H, d), 7.89 (1H, s), 7.20 (1H, d), 7.07 (1H, d), 3.93 (3H, s), 2.54 (3H, s). The protons from one of the benzofuran methyl groups are obscured by the residual DMSO peak.

Step (iv): 4-(3-(4,7-Dimethylbenzofuran-2-yl)-1,2,4-oxadiazol-5-yl)benzoic acid (BHBA-028)

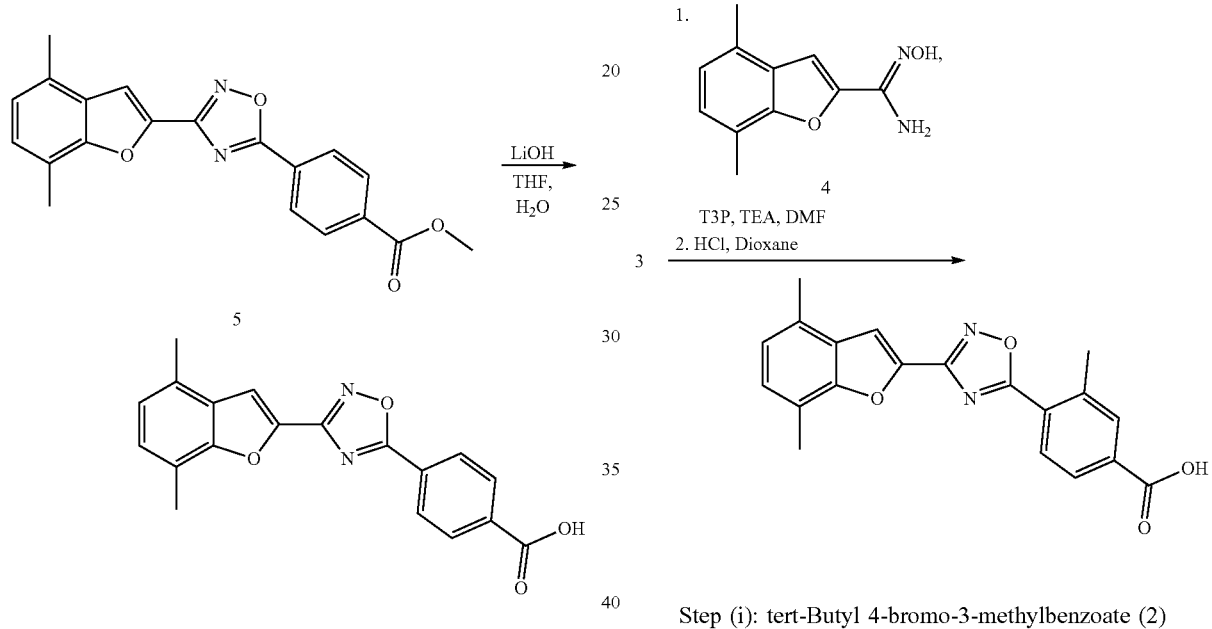

The title compound (95 mg, 49%) was prepared from methyl 4-(3-(4,7-dimethylbenzofuran-2-yl)-1,2,4-oxadiazol-5-yl)benzoate (5) using a procedure essentially the same as in step (v) for (BHBA-001): m/z 333 [M–H]⁻ (ES⁻); ¹H NMR (400 MHz, DMSO-d₆) δ: 13.47 (1H, br. s), 8.32 (2H, d), 8.20 (2H, d), 7.90 (1H, s), 7.20 (1H, d), 7.07 (1H, d), 2.54 (3H, s). The protons from one of the benzofuran methyl groups are obscured by the residual DMSO peak.

Synthesis 29

4-(3-(4,7-Dimethylbenzofuran-2-yl)-1,2,4-oxadiazol-5-yl)-3-methylbenzoic acid (BHBA-029)

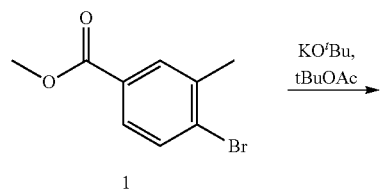

Step (i): tert-Butyl 4-bromo-3-methylbenzoate (2)

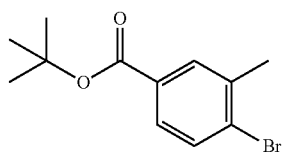

A mixture of methyl 4-bromo-3-methylbenzoate (1) (5.0 g, 22 mmol), KOtBu (4.9 g, 44 mmol) and tert-butyl acetate (51 g, 440 mmol) was stirred at RT under N₂ for 18 h. The mixture was partitioned between EtOAc (100 mL) and water (100 mL). The organic solution was washed sequentially with satd. NaHCO₃ and brine, dried over Na₂SO₄ and filtered. The solution was concentrated in vacuo and the residue was purified by silica gel chromatography (80 g, 0-10% EtOAc in isohexane) to afford the title compound (2) (4.5 g, 76%) as a colourless oil: ¹H NMR (400 MHz, CDCl₃) δ: 7.83 (1H, d), 7.64 (1H, dd), 7.57-7.55 (1H, m), 2.43 (3H, s), 1.59 (9H, s).

Step (ii): 4-(tert-Butoxycarbonyl)-2-methylbenzoic acid (3)

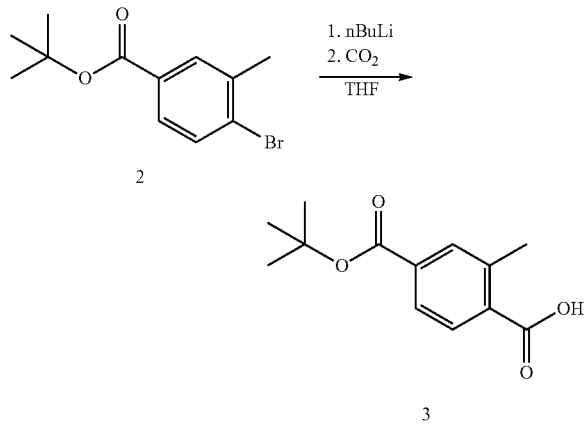

A stirred solution of tert-butyl 4-bromo-3-methylbenzoate (2) (3.6 g, 13 mmol) in anhydrous THF (60 mL) was cooled to −78° C. under N₂ and treated dropwise with n-butyl-lithium (1.6 M in hexanes) (10.4 mL, 16.6 mmol) over 30 min. The mixture was stirred at −78° C. for 2 h, then warmed to −30° C. while bubbling CO₂ gas (sublimed from dry ice and bubbled through conc. H₂SO₄) through. After 30 min the mixture was warmed to RT, then quenched by the addition of satd. aq. NH₄Cl solution (20 mL). The mixture was acidified by the addition of 1 M HCl and extracted with Et₂O (200 mL). The organic solution was dried over MgSO₄, filtered and concentrated in vacuo. The residue was purified by silica gel chromatography (80 g, 0-50% (0.15% AcOH in EtOAc) in isohexane) to afford the title compound (3) (0.5 g, 16%) as a white solid: m/z 235 [M−H]⁻ (ES⁻); ¹H NMR (400 MHz, CDCl₃) δ: 8.08 (1H, d), 7.88-7.85 (2H, m), 2.69 (3H, s), 1.61 (9H, s). The carboxylic acid proton was not observed.

Step (iii): 4-(3-(4,7-Dimethylbenzofuran-2-yl)-1,2,4-oxadiazol-5-yl)-3-methylbenzoic acid (BHBA-029)

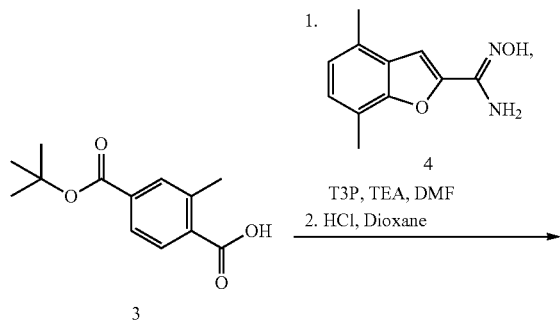

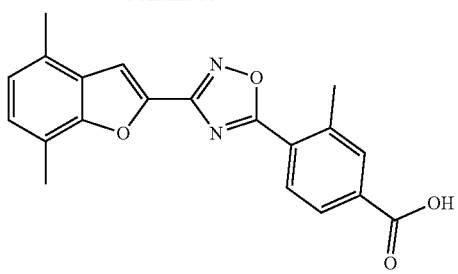

A mixture of 4-(tert-butoxycarbonyl)-2-methylbenzoic acid (3) (100 mg, 0.423 mmol), T3P (50% in EtOAc) (0.623 mL, 1.06 mmol), N'-hydroxy-4,7-dimethylbenzofuran-2-carboximidamide (4) (86 mg, 0.42 mmol) and TEA (0.295 mL, 2.12 mmol) in DMF (5 mL) was stirred at RT for 90 min, then at 90° C. for 18 h. Further portions of N'-hydroxy-4,7-dimethylbenzofuran-2-carboximidamide (4) (86 mg, 0.423 mmol), TEA (0.295 mL, 2.12 mmol) and T3P 50% in EtOAc (0.623 mL, 1.058 mmol) were added and the mixture was stirred at 90° C. for a further 18 h. The mixture was cooled to RT and partitioned between EtOAc (90 mL) and water (15 mL). The organic solution was washed sequentially with 1 M HCl and brine, then dried over Na₂SO₄, filtered and concentrated in vacuo. The residue was purified by silica gel chromatography (20 g, 0-30% EtOAc in isohexane) to afford the partially purified intermediate. The material was suspended in 4M HCl in dioxane (2.5 mL, 9.9 mmol) and the mixture was stirred at RT under N₂ for 18 h, then at 40° C. for 1 h. The mixture was concentrated in vacuo and the residue was triturated with MeCN to give 4-(3-(4,7-dimethylbenzofuran-2-yl)-1,2,4-oxadiazol-5-yl)-3-methylbenzoic acid (18 mg, 12%) as a white solid: m/z 349 [M+H]⁺ (ES⁺), 347 [M−H]⁻ (ES⁻); ¹H NMR (400 MHz, DMSO-d₆) δ: 13.42 (1H, br. s), 8.25 (1H, d), 8.04 (1H, s), 7.99 (1H, d), 7.88 (1H, s), 7.20 (1H, d), 7.07 (1H, d), 2.79 (3H, s), 2.53 (3H, s). The protons from one of the benzofuran methyl groups are obscured by the residual DMSO peak.

Synthesis 30

4-(3-(4,7-Dimethylbenzofuran-2-yl)-1,2,4-oxadiazol-5-yl)-2-fluorobenzoic acid (BHBA-033)

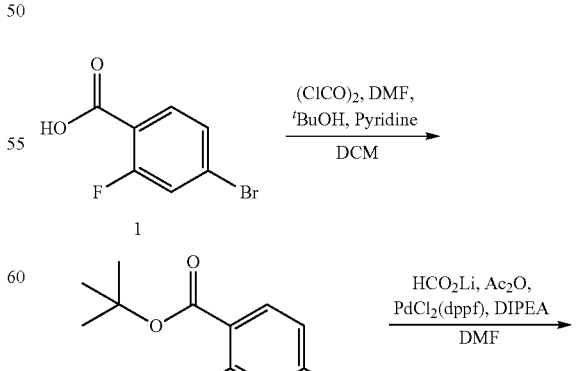

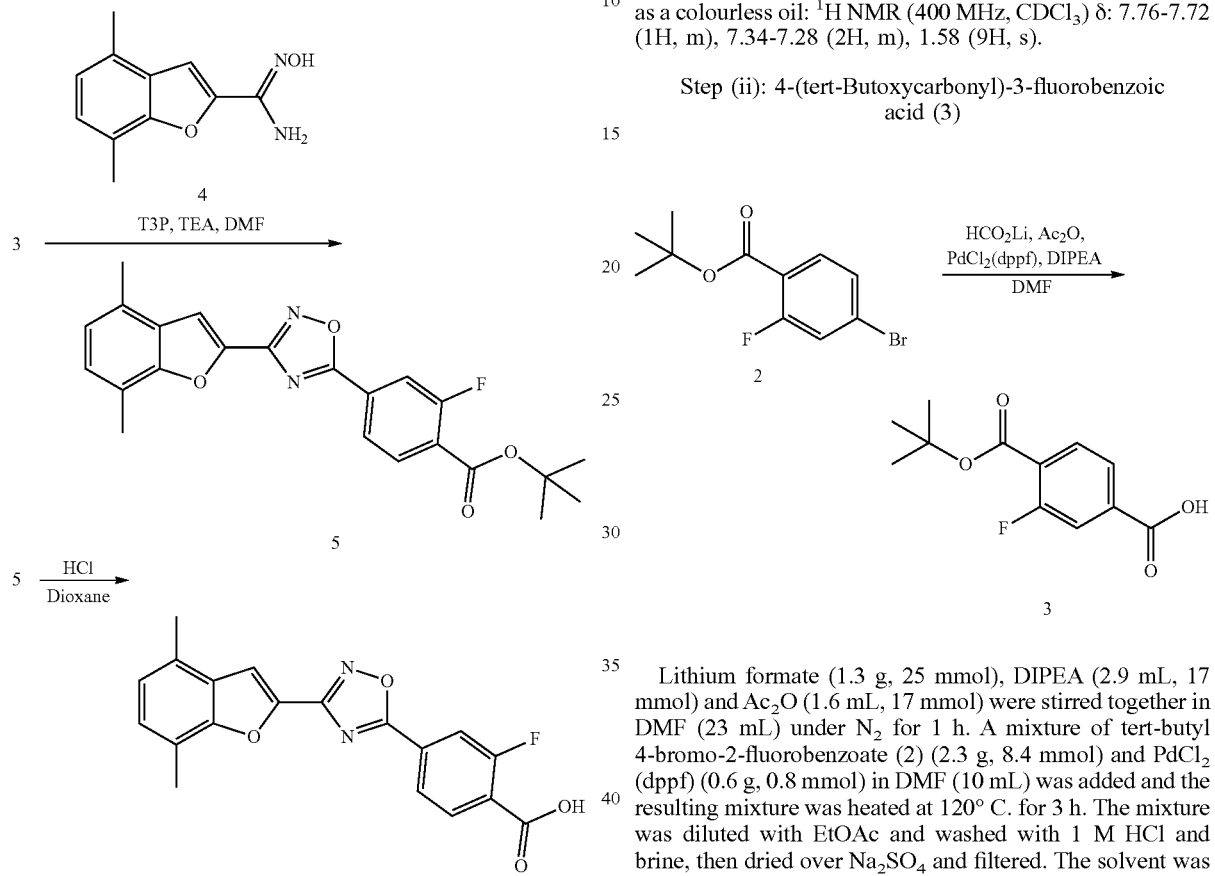

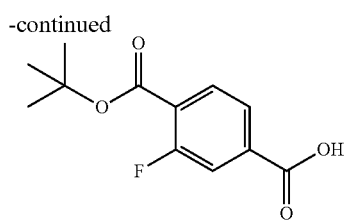

Step (i): tert-Butyl 4-bromo-2-fluorobenzoate (2)

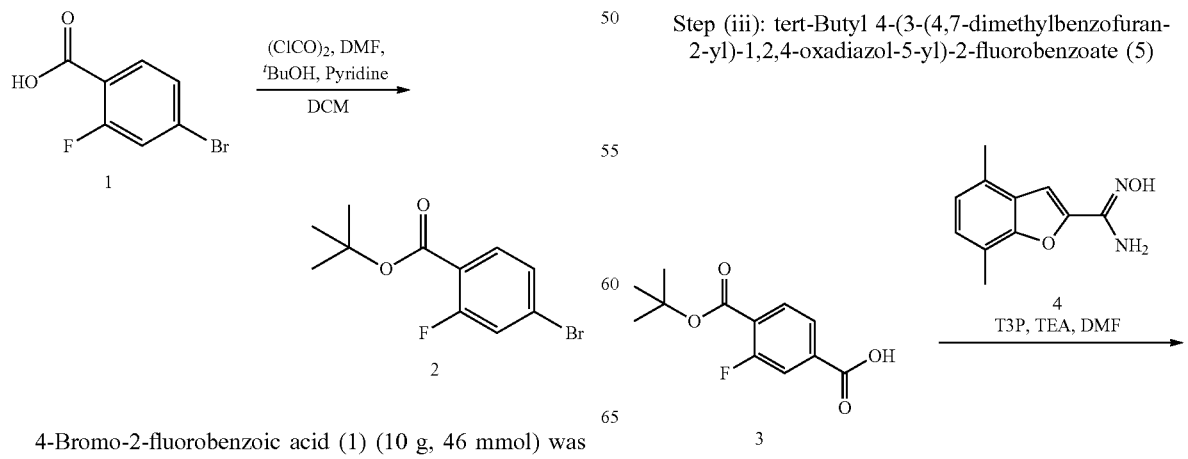

4-Bromo-2-fluorobenzoic acid (1) (10 g, 46 mmol) was suspended in DCM (100 mL), treated with oxalyl chloride (12.0 mL, 137 mmol) followed by DMF (36 μL, 0.46 mmol) and the mixture was stirred at RT for 5 h. The mixture was concentrated in vacuo to give a yellow oil which was redissolved in THF and added dropwise to a mixture of pyridine (5.5 mL, 68 mmol) and ᵗBuOH (8.7 mL, 91 mmol) in THF (100 mL) at 0° C. The mixture was then warmed to RT, stirred at RT for 18 h, then at 50° C. for 5 h. The mixture was cooled to RT, concentrated in vacuo and the residue was purified by silica gel chromatography (220 g, 0-10% EtOAc in isohexane) to afford the title compound (2) (9.3 g, 74%) as a colourless oil: $^1$H NMR (400 MHz, CDCl$_3$) δ: 7.76-7.72 (1H, m), 7.34-7.28 (2H, m), 1.58 (9H, s).

Step (ii): 4-(tert-Butoxycarbonyl)-3-fluorobenzoic acid (3)

Lithium formate (1.3 g, 25 mmol), DIPEA (2.9 mL, 17 mmol) and Ac$_2$O (1.6 mL, 17 mmol) were stirred together in DMF (23 mL) under N$_2$ for 1 h. A mixture of tert-butyl 4-bromo-2-fluorobenzoate (2) (2.3 g, 8.4 mmol) and PdCl$_2$(dppf) (0.6 g, 0.8 mmol) in DMF (10 mL) was added and the resulting mixture was heated at 120° C. for 3 h. The mixture was diluted with EtOAc and washed with 1 M HCl and brine, then dried over Na$_2$SO$_4$ and filtered. The solvent was removed in vacuo and the residue was purified by silica gel chromatography (40 g, 0-50% EtOAc in isohexane) to afford the title compound (3) (500 mg, 23%) as a pale green solid: m/z 239 [M−H]$^-$ (ES$^-$); $^1$H NMR (400 MHz, CDCl$_3$) δ: 7.97-7.89 (2H, m), 7.84-7.81 (1H, m), 1.61 (9H, s). The carboxylic acid proton was not observed.

Step (iii): tert-Butyl 4-(3-(4,7-dimethylbenzofuran-2-yl)-1,2,4-oxadiazol-5-yl)-2-fluorobenzoate (5)

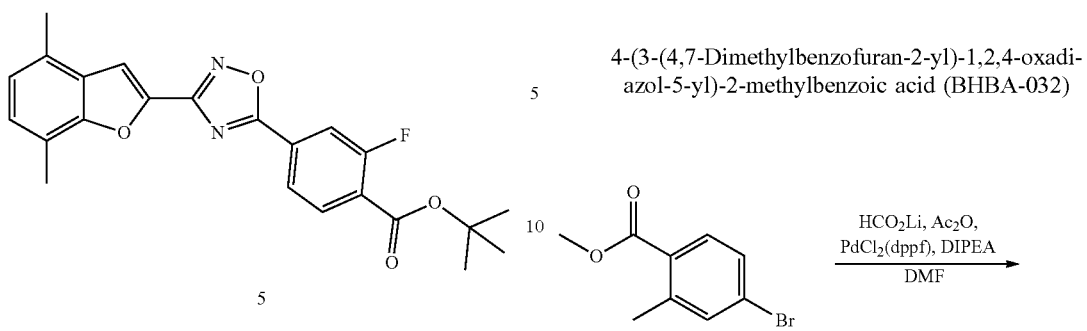

tert-Butyl 4-(3-(4,7-dimethylbenzofuran-2-yl)-1,2,4-oxadiazol-5-yl)-2-fluorobenzoate (5) (80 mg, 26%) was prepared from 4-(tert-butoxycarbonyl)-3-fluorobenzoic acid (3) and N'-hydroxy-4,7-dimethylbenzofuran-2-carboximidamide (4) using a procedure essentially the same as in step (iv) for (BHBA-001): ¹H NMR (400 MHz, DMSO-d₆) δ: 8.13-8.06 (3H, m), 7.91 (1H, s), 7.21 (1H, d), 7.07 (1H, d), 2.53 (3H, s), 1.58 (9H, s). The protons from one of the benzofuran methyl groups are obscured by the residual DMSO peak.

Step (iv): 4-(3-(4,7-Dimethylbenzofuran-2-yl)-1,2,4-oxadiazol-5-yl)-2-fluorobenzoic acid (BHBA-033)

tert-Butyl 4-(3-(4,7-dimethylbenzofuran-2-yl)-1,2,4-oxadiazol-5-yl)-2-fluorobenzoate (5) (80 mg, 0.20 mmol) was treated with 4 M HCl in Dioxane (5.0 mL, 20 mmol) and the mixture was stirred at RT under N₂ for 18 h. The mixture was concentrated in vacuo and the residue was purified by silica gel chromatography (20 g, 0-100% [EtOAc 0.1% AcOH] in isohexane) to afford the title compound (40 mg, 57%) as a white solid: m/z 353 [M+H]⁺(ES⁺), 351 [M−H]⁻ (ES⁻); ¹H NMR (400 MHz, DMSO-d₆) δ: 13.78 (1H, br. s), 8.15-8.06 (3H, m), 7.89 (1H, s), 7.20 (1H, d), 7.06 (1H, d), 2.53 (3H, s). The protons from one of the benzofuran methyl groups are obscured by the residual DMSO peak.

Synthesis 31

4-(3-(4,7-Dimethylbenzofuran-2-yl)-1,2,4-oxadiazol-5-yl)-2-methylbenzoic acid (BHBA-032)

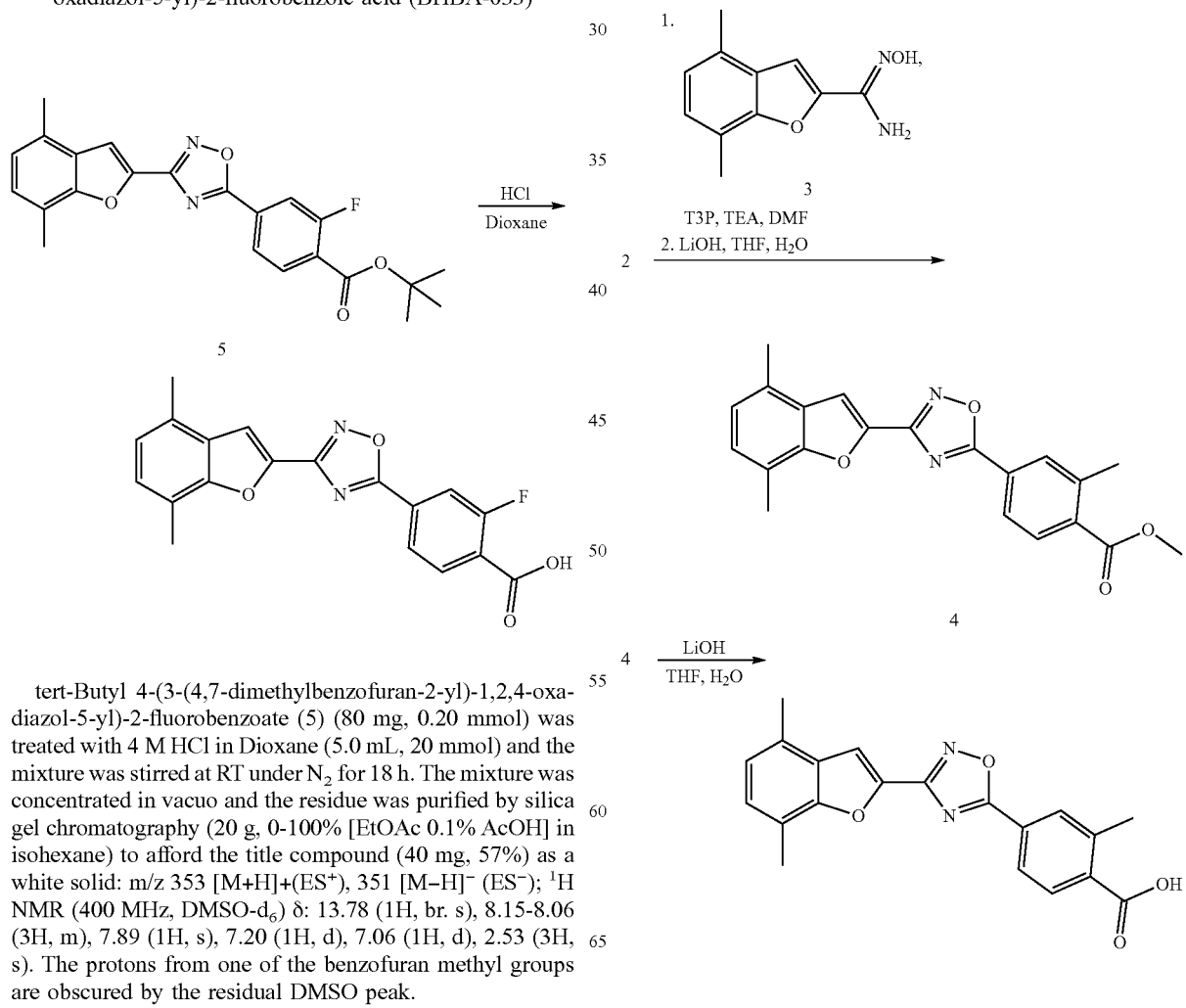

Step (i): 4-(Methoxycarbonyl)-3-methylbenzoic acid (2)

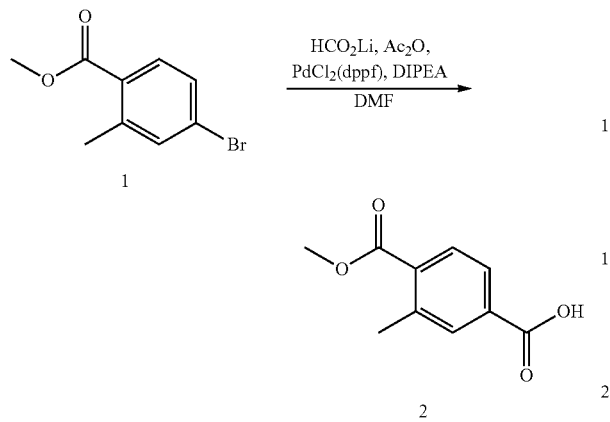

The title compound (2) (2 g, 47%) was prepared from methyl 4-bromo-2-methylbenzoate (1) using a procedure essentially the same as in step (ii) for (BHBA-033): m/z 195 [M+H]+(ES+), 193 [M−H]− (ES−); 1H NMR (400 MHz, CDCl3) δ: 7.98-7.95 (3H, m), 3.91 (3H, s), 2.63 (3H, s).

Step (ii): 4-(3-(4,7-Dimethylbenzofuran-2-yl)-1,2,4-oxadiazol-5-yl)-2-methylbenzoic acid (BHBA-032)

A mixture of 4-(methoxycarbonyl)-3-methylbenzoic acid (2) (314 mg, 1.62 mmol), N'-hydroxy-4,7-dimethylbenzofuran-2-carboximidamide (3) (300 mg, 1.47 mmol), and DIPEA (513 μL, 2.94 mmol) in DMF (20 mL) was treated with T3P (50% in EtOAc) (1.7 mL, 2.9 mmol) and the resultant mixture was stirred at RT for 16 h. The mixture was partitioned between EtOAc (50 mL) and 1 M HCl (50 mL) and the phases were separated. The organic solution was sequentially washed with 1 M HCl (50 mL), satd. Na2CO3 solution (100 mL) and brine (50 mL), then dried over MgSO4 and filtered. The solution was concentrated in vacuo and the residue was dissolved in THF (1 mL) and treated with 2 M LiOH (1 mL, 2 mmol). The mixture was stirred at RT for 18 h, then acidified by the addition of 1 M HCl. The resulting solid was collected by filtration, washed with MeOH, then dried in vacuo to afford the title compound (50 mg, 10%) as a white solid: m/z 349 [M+H]+ (ES+), 347 [M−H]− (ES−); 1H NMR (400 MHz, DMSO-d6) δ: 13.35 (1H, br. s), 8.14 (1H, s), 8.11-8.09 (1H, m), 8.05-8.03 (1H, m), 7.88 (1H, s), 7.20 (1H, d), 7.07 (1H, d), 2.64 (3H, s), 2.53 (3H, s). The protons from one of the benzofuran methyl groups are obscured by the residual DMSO peak.

Synthesis 32

3-Chloro-4-(3-(4,7-dimethylbenzofuran-2-yl)-1,2,4-oxadiazol-5-yl)benzoic acid (BHBA-031)

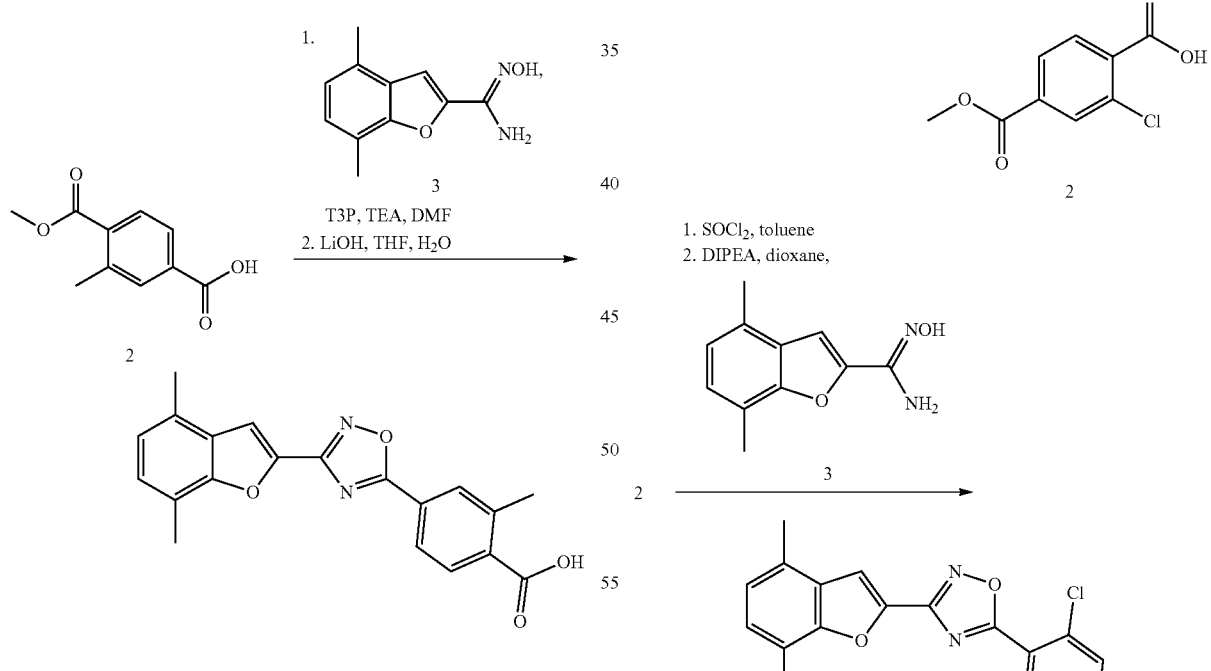

127

-continued

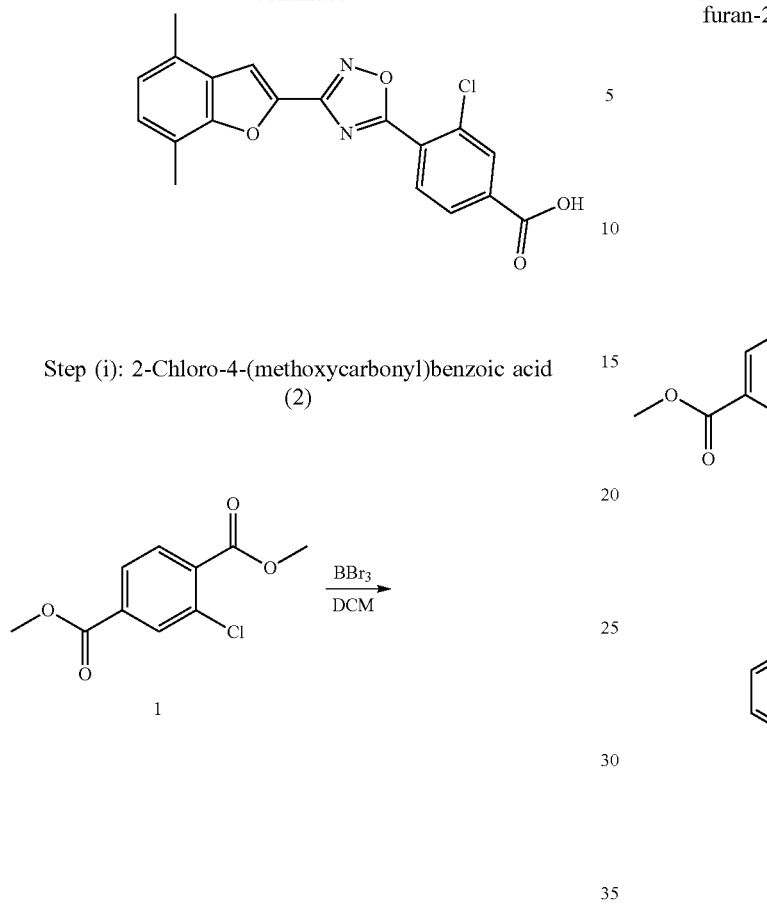

Step (i): 2-Chloro-4-(methoxycarbonyl)benzoic acid (2)

A solution of dimethyl 2-chloroterephthalate (2.5 g, 11 mmol) in DCM (20 mL) was cooled to −5° C. and treated with BBr$_3$ (1 M in DCM) (11 mL, 11 mmol) dropwise over 30 min. The mixture was then warmed to RT and stirred for 18 h. The mixture was poured into ice, warmed to RT and the pH was adjusted to 8 by the addition of solid NaHCO$_3$. The aq. solution was washed with EtOAc (50 mL), acidified by the addition of 1 M HCl and extracted with EtOAc (160 mL). The organic solution was washed with brine (80 mL), dried over MgSO$_4$, filtered and concentrated in vacuo. The residue was purified by silica gel chromatography (120 g, 0-10% [MeOH 5% AcOH] in DCM) to afford the title compound (2) (1.5 g, 62%) as white solid: m/z 215 [M+H]$^+$ (ES$^+$), 213 [M−H]$^-$ (ES$^-$); $^1$H NMR (400 MHz, DMSO-d$_6$) δ: 13.79 (1H, br. s), 8.00-7.95 (2H, m), 7.90-7.88 (1H, m), 3.89 (3H, s).

128

Step (ii): Methyl 3-chloro-4-(3-(4,7-dimethylbenzofuran-2-yl)-1,2,4-oxadiazol-5-yl)benzoate (4)

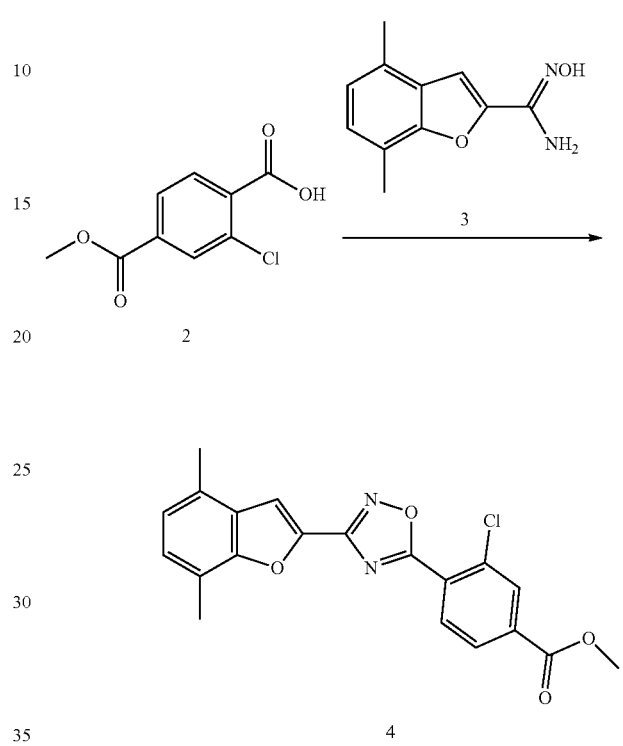

Methyl 3-chloro-4-(3-(4,7-dimethylbenzofuran-2-yl)-1,2,4-oxadiazol-5-yl)benzoate (4) (174 mg, 49%) was prepared from 2-chloro-4-(methoxycarbonyl)benzoic acid (2) and N'-hydroxy-4,7-dimethylbenzofuran-2-carboximidamide (3) using a procedure essentially the same as in step (iii) for (BHBA-005): m/z 383 [M+H]$^+$ (ES$^+$); $^1$H NMR (400 MHz, CDCl$_3$) δ: 8.28-8.26 (2H, m), 8.10 (1H, dd), 7.65 (1H, s), 7.13 (1H, d), 7.02 (1H, d), 4.00 (3H, s), 2.59 (3H, s), 2.55 (3H, s).

Step (iii): 3-Chloro-4-(3-(4,7-dimethylbenzofuran-2-yl)-1,2,4-oxadiazol-5-yl)benzoic acid (BHBA-031)

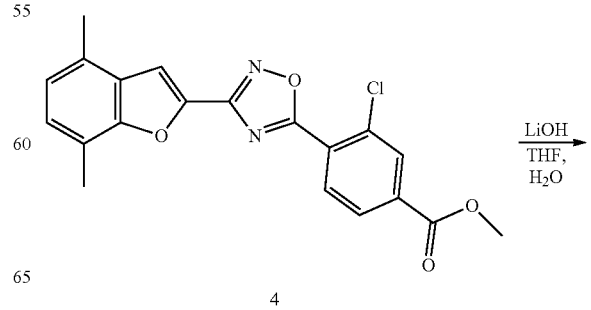

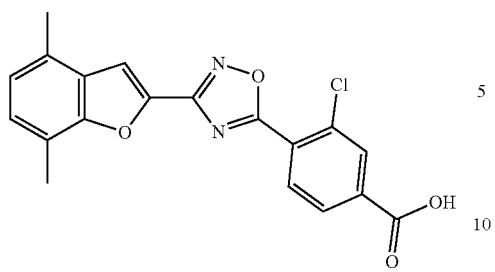

The title compound (155 mg, 92%) was prepared from methyl 3-chloro-4-(3-(4,7-dimethylbenzofuran-2-yl)-1,2,4-oxadiazol-5-yl)benzoate (4) using a procedure essentially the same as in step (v) for (BHBA-001): m/z 367 [M−H]⁻ (ES⁻); $^1$H NMR (400 MHz, DMSO-$d_6$) δ: 13.80 (1H, br. s), 8.35 (1H, d), 8.18 (1H, d), 8.13 (1H, dd), 7.91 (1H, s), 7.21 (1H, d), 7.08 (1H, d), 2.54 (3H, s). The protons from one of the benzofuran methyl groups are obscured by the residual DMSO peak.

Synthesis 33

4-(3-(4,7-Dimethylbenzofuran-2-yl)-1,2,4-oxadiazol-5-yl)-3-fluorobenzoic acid (BHBA-030)

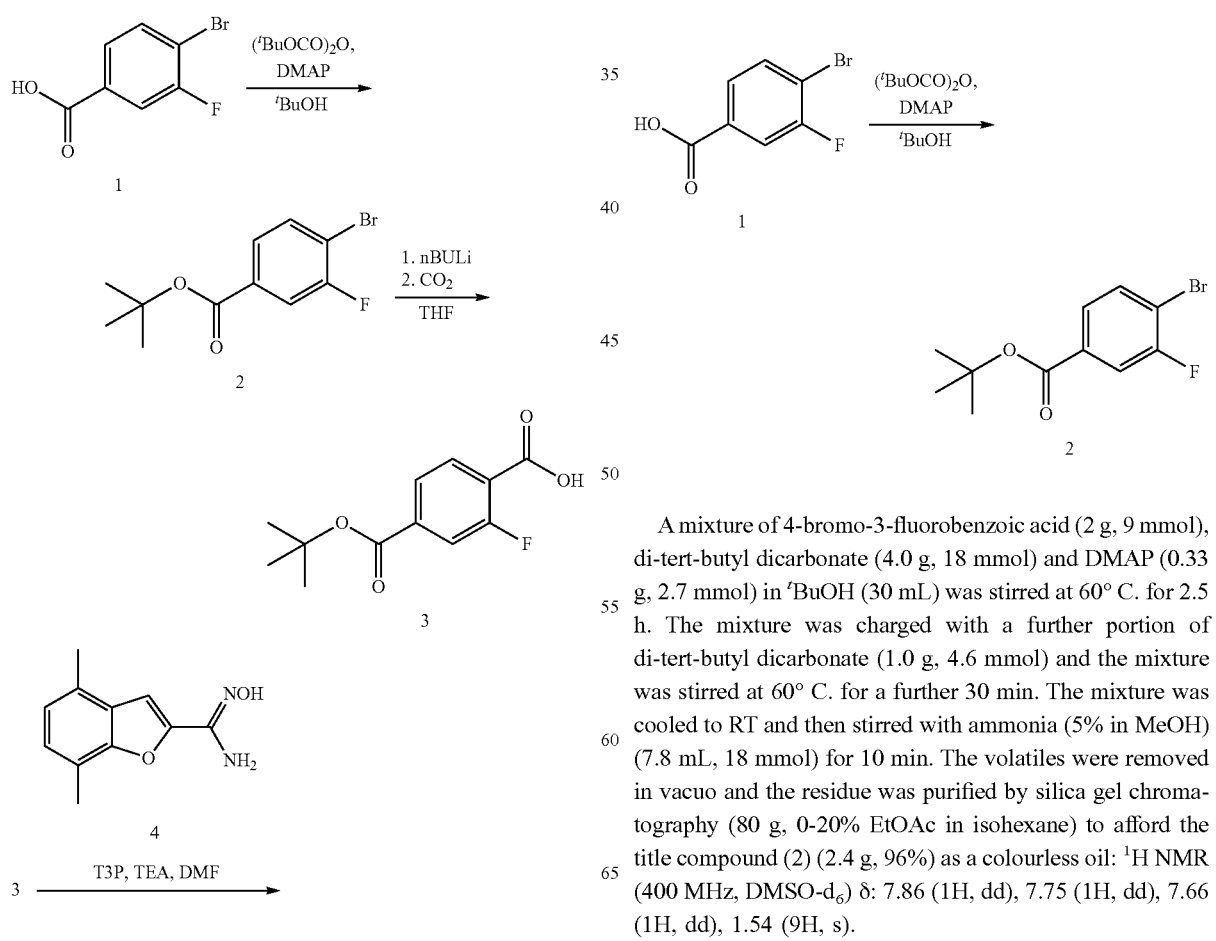

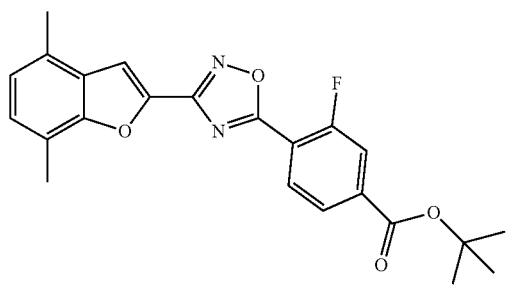

Step (i): tert-Butyl 4-bromo-3-fluorobenzoate (2)

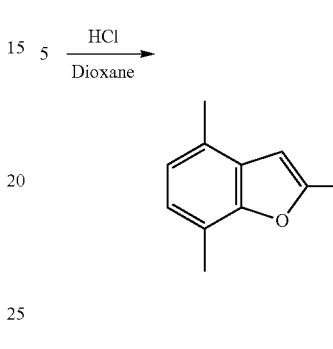

A mixture of 4-bromo-3-fluorobenzoic acid (2 g, 9 mmol), di-tert-butyl dicarbonate (4.0 g, 18 mmol) and DMAP (0.33 g, 2.7 mmol) in $^t$BuOH (30 mL) was stirred at 60° C. for 2.5 h. The mixture was charged with a further portion of di-tert-butyl dicarbonate (1.0 g, 4.6 mmol) and the mixture was stirred at 60° C. for a further 30 min. The mixture was cooled to RT and then stirred with ammonia (5% in MeOH) (7.8 mL, 18 mmol) for 10 min. The volatiles were removed in vacuo and the residue was purified by silica gel chromatography (80 g, 0-20% EtOAc in isohexane) to afford the title compound (2) (2.4 g, 96%) as a colourless oil: $^1$H NMR (400 MHz, DMSO-$d_6$) δ: 7.86 (1H, dd), 7.75 (1H, dd), 7.66 (1H, dd), 1.54 (9H, s).

Step (ii): 4-(tert-Butoxycarbonyl)-2-fluorobenzoic acid (3)

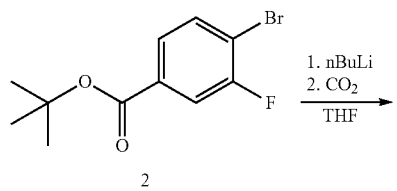

n-Butyllithium (1.6 M in hexanes) (1.5 mL, 2.4 mmol) was added dropwise to a solution of tert-butyl 4-bromo-3-fluorobenzoate (2) (0.50 g, 1.8 mmol) in anhydrous THF (5 mL) under $N_2$ at −78° C. The mixture was stirred at this temperature for 45 min, then poured onto crushed solid $CO_2$ (3.2 g, 73 mmol) and then warmed slowly to RT with stirring. The mixture was partitioned between EtOAc (40 mL) and 5% $Na_2CO_3$ solution (30 mL). The aqueous was acidified by the addition of 1 M HCl and the product was extracted with EtOAc (50 mL). The organic solution was dried over $MgSO_4$, filtered and concentrated in vacuo to afford the title compound (3) (168 mg, 31% yield) as a yellow solid: m/z 239 [M−H]⁻ (ES⁻); ¹H NMR (400 MHz, DMSO-d₆) δ: 13.59 (1H, br. s), 7.97 (1H, t), 7.78 (1H, dd), 7.70 (1H, dd), 1.55 (9H, s).

Step (iii): tert-Butyl 4-(3-(4,7-dimethylbenzofuran-2-yl)-1,2,4-oxadiazol-5-yl)-3-fluorobenzoate (5)

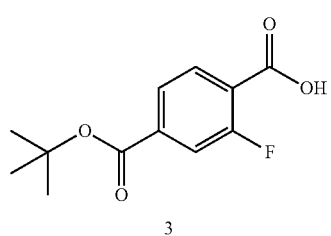

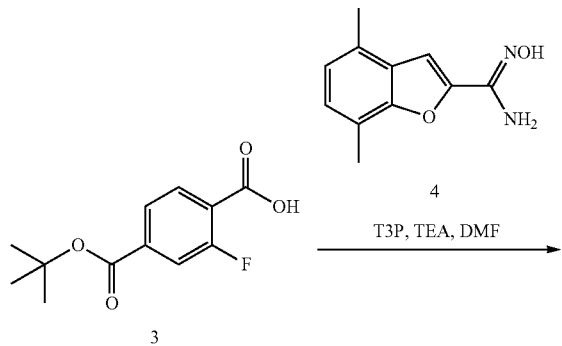

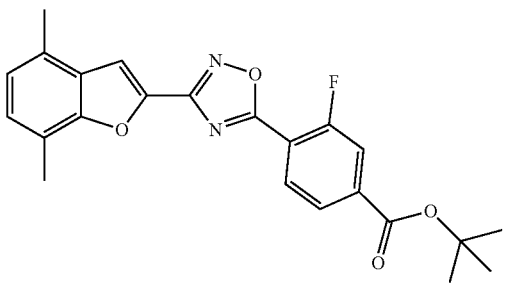

tert-Butyl 4-(3-(4,7-dimethylbenzofuran-2-yl)-1,2,4-oxadiazol-5-yl)-3-fluorobenzoate (5) (90 mg, 32%) was prepared from 4-(tert-butoxycarbonyl)-2-fluorobenzoic acid (3) and N'-hydroxy-4,7-dimethylbenzofuran-2-carboximidamide (4) using a procedure essentially the same as in step (iv) for (BHBA-001): m/z 409 [M+H]⁺ (ES⁺); ¹H NMR (400 MHz, DMSO-d₆) δ: 8.35 (1H, t), 7.96 (1H, dd), 7.92 (1H, dd), 7.89 (1H, s), 7.20 (1H, d), 7.06 (1H, d), 2.53 (3H, s), 1.59 (9H, s). The protons from one of the benzofuran methyl groups are obscured by the residual DMSO peak.

Step (iv): 4-(3-(4,7-Dimethylbenzofuran-2-yl)-1,2,4-oxadiazol-5-yl)-3-fluorobenzoic acid (BHBA-030)

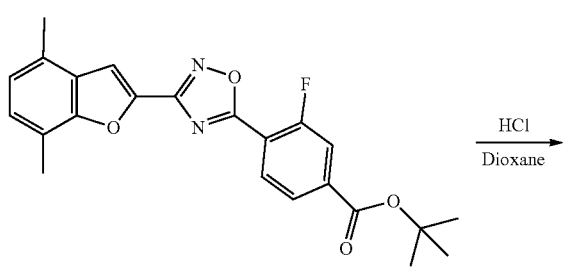

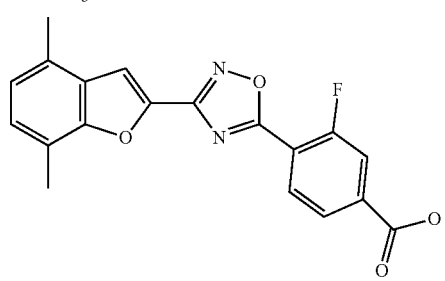

The title compound (51 mg, 66%) was prepared from tert-butyl 4-(3-(4,7-dimethylbenzofuran-2-yl)-1,2,4-oxadiazol-5-yl)-3-fluorobenzoate (5) using a procedure essentially the same as in step (iv) for (BHBA-033): m/z 353 [M+H]⁺ (ES⁺), 351 [M−H]⁻ (ES); ¹H NMR (400 MHz, DMSO-d₆) δ: 13.78 (1H, br. s), 8.36 (1H, t), 8.01 (1H, d), 7.95 (1H, dd), 7.89 (1H, s), 7.20 (1H, d), 7.07 (1H, d), 2.53 (3H, s). The protons from one of the benzofuran methyl groups are obscured by the residual DMSO peak.

Synthesis 34

4-(5-(4,7-Dimethylbenzofuran-2-yl)-1,3,4-oxadiazol-2-yl)benzoic acid (BHBA-034)

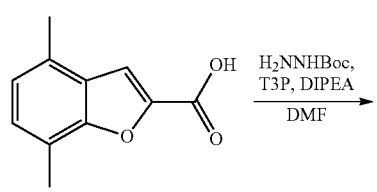

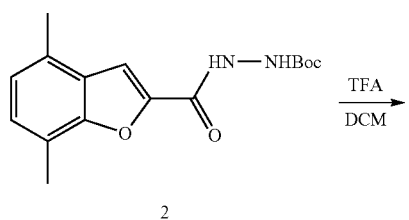

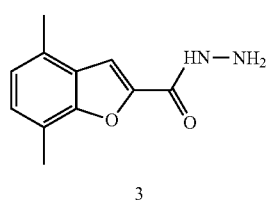

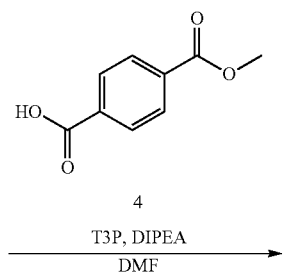

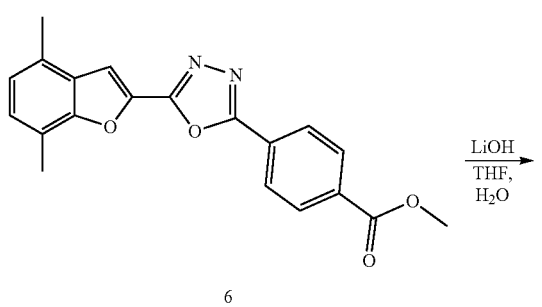

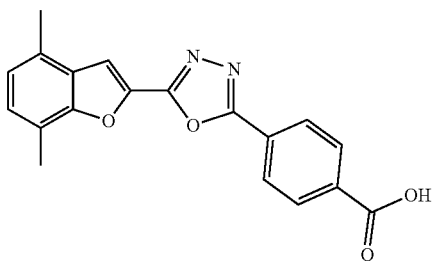

Step (i): tert-Butyl 2-(4,7-dimethylbenzofuran-2-carbonyl)hydrazinecarboxylate (2)

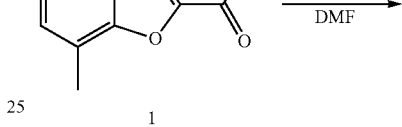

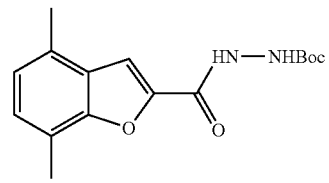

A mixture of 4,7-dimethylbenzofuran-2-carboxylic acid (1) (1.0 g, 5.3 mmol), tert-butyl hydrazinecarboxylate (0.76 g, 5.8 mmol) and DIPEA (1.84 mL, 10.5 mmol) in DMF (20 mL) was treated with T3P (50% in EtOAc) (6.20 mL, 10.5 mmol) and the resultant mixture was stirred at RT for 3 h. The mixture was partitioned between EtOAc (100 mL) and 1 M HCl (100 mL) and the phases were separated. The organic solution was sequentially washed with 1 M HCl (100 mL), satd. Na$_2$CO$_3$ solution (200 mL) and brine (100 mL), then dried over MgSO$_4$, filtered and concentrated in vacuo to afford the title compound (2) (1.3 g, 77%) as a white solid: m/z 303 [M−H]$^-$ (ES$^-$); $^1$H NMR (400 MHz, CDCl$_3$) δ: 8.56 (1H, br. s), 7.47 (1H, s), 7.11 (1H, d), 6.96 (1H, d), 6.66 (1H, br. s), 2.47-2.44 (6H, m), 1.52 (9H, s).

Step (ii): 4,7-Dimethylbenzofuran-2-carbohydrazide (3)

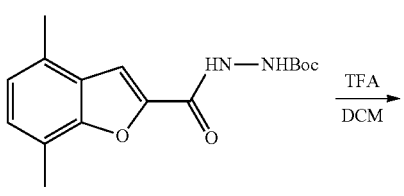

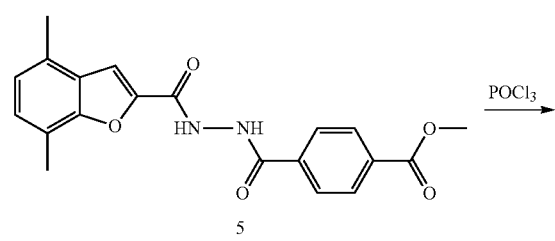

-continued

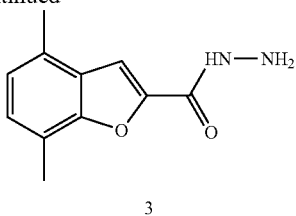

3 tert-Butyl 2-(4,7-dimethylbenzofuran-2-carbonyl)hydrazinecarboxylate (2) (1.3 g, 4.3 mmol) was dissolved in DCM (10 mL), treated with TFA (2.6 mL, 34 mmol) and stirred at RT for 2 h. The mixture was concentrated in vacuo and the residue was purified by capture and release on SCX (20 g), eluting with 1% $NH_3$ in MeOH to provide 4,7-dimethylbenzofuran-2-carbohydrazide (3) (700 mg, 80%) as a white solid: m/z 205 [M+H]+(ES$^+$); $^1$H NMR (400 MHz, DMSO-$d_6$) δ: 9.95 (1H, br. s), 7.54 (1H, s), 7.13 (1H, d), 7.00 (1H, d), 4.56 (2H, br. s), 2.46 (6H, s).

Step (iii): Methyl 4-(2-(4,7-dimethylbenzofuran-2-carbonyl)hydrazinecarbonyl)benzoate

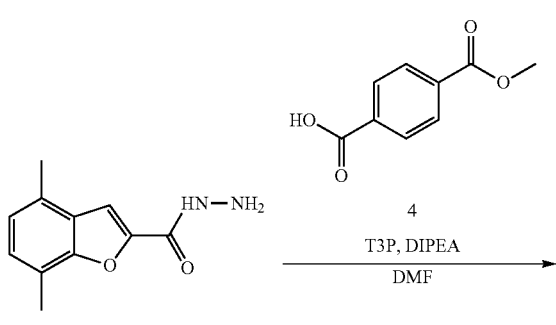

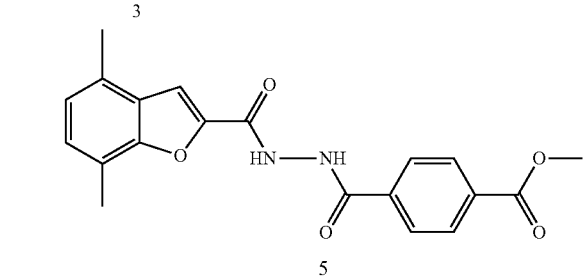

A mixture of 4,7-dimethylbenzofuran-2-carbohydrazide (3) (240 mg, 1.18 mmol), 4-(methoxycarbonyl)benzoic acid (4) (233 mg, 1.29 mmol) and DIPEA (410 μL, 2.35 mmol) in DMF (20 mL) was treated with T3P (50% in EtOAc) (690 μL, 2.35 mmol) and then stirred at RT for 3 h. The mixture was diluted with EtOAc (100 mL) and washed sequentially with 1 M HCl (200 mL), satd. $Na_2CO_3$ solution (200 mL) and brine (100 mL). The organic solution was dried over $MgSO_4$, filtered and concentrated in vacuo to afford the title compound (5): m/z 367 [M+H]$^+$ (ES$^+$), 365 [M−H]$^-$ (ES$^-$); $^1$H NMR (400 MHz, DMSO-$d_6$) δ: 10.79 (2H, s), 8.11 (2H, d), 8.05 (2H, d), 7.76 (1H, s), 7.20 (1H, d), 7.05 (1H, d), 3.90 (3H, s). The protons from the benzofuran methyl groups are obscured by the residual DMSO peak.

Step (iii): Methyl 4-(5-(4,7-dimethylbenzofuran-2-yl)-1,3,4-oxadiazol-2-yl)benzoate (6)

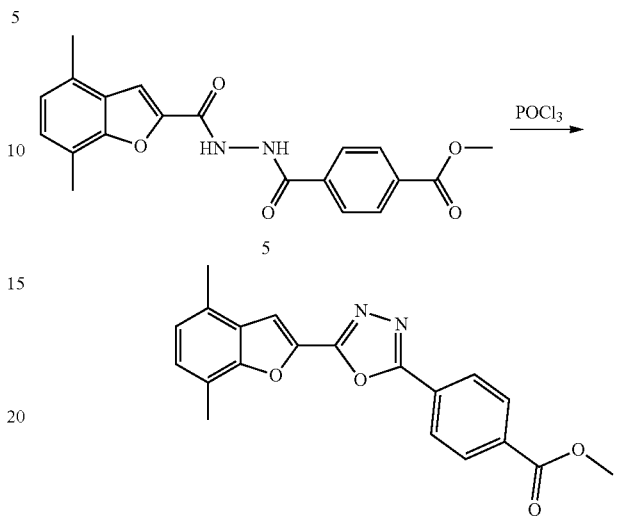

A mixture of methyl 4-(2-(4,7-dimethylbenzofuran-2-carbonyl)hydrazinecarbonyl)benzoate (5) (0.4 g, 1.1 mmol) and $POCl_3$ (3.0 mL, 32 mmol) was heated at 95° C. for 2 h, then concentrated in vacuo. The residue was treated with a mixture of ice (60 g) and 25% aq. NaOH (20 mL) and the resulting precipitate was collected by filtration, washed with water and dried in vacuo. The solid was triturated with MeOH and dried in vacuo to give the title compound (6) (200 mg, 53%) as a cream solid: m/z 349 [M+H]$^+$ (ES$^+$); $^1$H NMR (400 MHz, DMSO-$d_6$) δ: 8.28 (2H, d), 8.21 (2H, d), 8.06 (1H, s), 7.24 (1H, d), 7.11 (1H, d), 3.93 (3H, s), 2.55 (3H, s), 2.53 (3H, s).

Step (iv): 4-(5-(4,7-Dimethylbenzofuran-2-yl)-1,3,4-oxadiazol-2-yl)benzoic acid (BHBA-034)

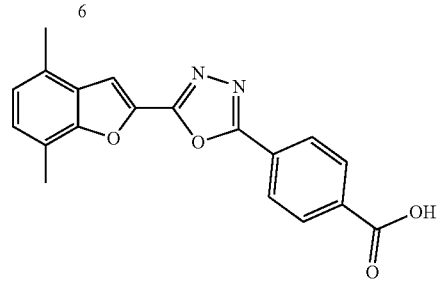

The title compound (180 mg, 94%) was prepared from methyl 4-(5-(4,7-dimethylbenzofuran-2-yl)-1,3,4-oxadiazol-2-yl)benzoate (6) using a procedure essentially the same as in step (v) for (BHBA-001): m/z 335 [M+H]$^+$ (ES$^+$), 333 [M−H]$^−$ (ES$^−$); $^1$H NMR (400 MHz, DMSO-d$_6$) δ: 13.42 (1H, s), 8.24 (2H, d), 8.18 (2H, d), 8.04 (1H, s), 7.23 (1H, d), 7.09 (1H, d), 2.54 (3H, s), 2.52 (3H, s).

Synthesis 35

4-(5-(4,7-Dimethylbenzofuran-2-yl)-1,3,4-oxadiazol-2-yl)-3-methylbenzoic acid (BHBA-035)

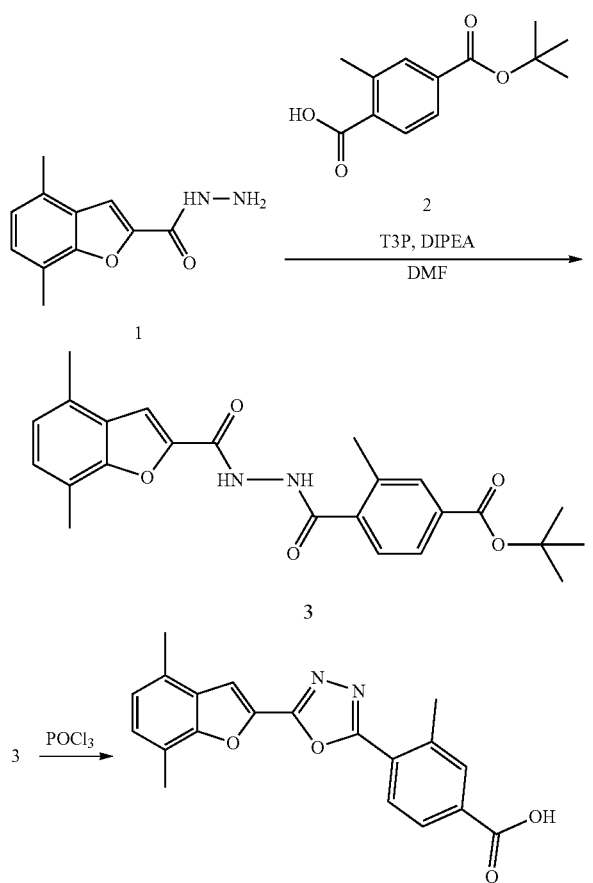

Step (i): Methyl tert-butyl 4-(2-(4,7-dimethylbenzofuran-2-carbonyl)hydrazinecarbonyl)-3-methylbenzoate (3)

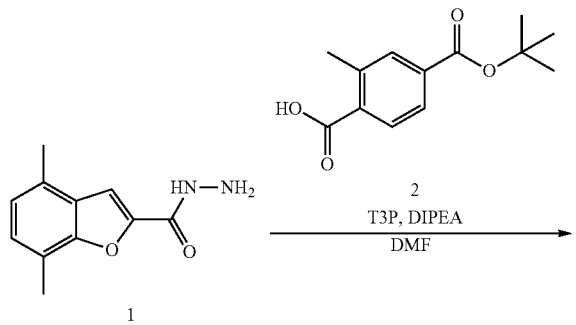

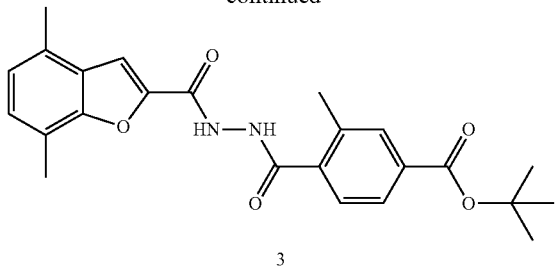

The title compound (3) (350 mg, 97%) was prepared from 4,7-dimethylbenzofuran-2-carbohydrazide (1) and 4-(tert-butoxycarbonyl)-2-methylbenzoic acid (2) using a procedure essentially the same as in step (iii) for (BHBA-034): m/z 423 [M+H]$^+$ (ES$^+$), 421 [M−H]$^−$ (ES$^−$); $^1$H NMR (400 MHz, CDCl$_3$) δ 9.40 (1H, d), 8.59 (1H, d), 7.90-7.86 (2H, m), 7.59 (1H, d), 7.55 (1H, s), 7.14 (1H, d), 7.00 (1H, d), 2.57 (3H, s), 2.52-2.49 (6H, m), 1.61 (9H, s).

Step (iv): 4-(5-(4,7-Dimethylbenzofuran-2-yl)-1,3,4-oxadiazol-2-yl)-3-methylbenzoic acid (BHBA-035)

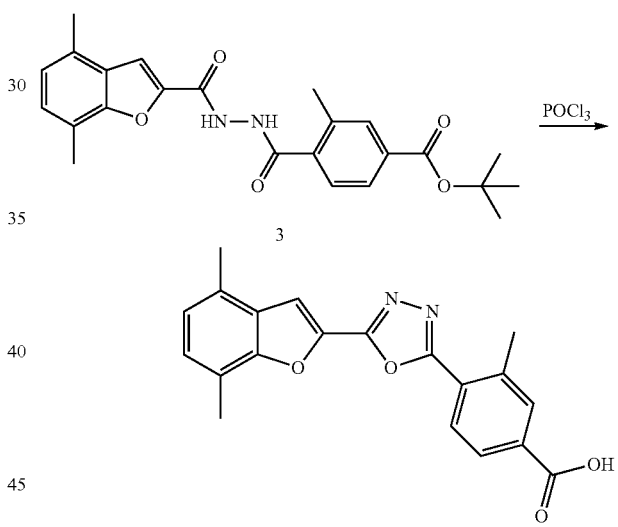

A mixture of tert-butyl 4-(2-(4,7-dimethylbenzofuran-2-carbonyl)hydrazinecarbonyl)-3-methylbenzoate (3) (340 mg, 0.805 mmol) and POCl$_3$ (3.0 mL, 32 mmol) was heated at 90° C. for 2 h, then cooled to RT and concentrated in vacuo. The residue was treated with ice-cold 25% NaOH (4 mL) and stirred for 10 min, then THF (10 mL) was added and the mixture was stirred for 1 h. The mixture was diluted with EtOAc and acidified with conc. HCl. The organic solution was washed with brine, dried over Na$_2$SO$_4$, filtered and concentrated in vacuo. The residue was purified by silica gel chromatography (12 g cartridge, 0-5% [1% AcOH in MeOH] in DCM). The residue was then triturated with MeOH and Et$_2$O and then recrystalised from 2:1 toluene/MeCN and then purified by reverse-phase HPLC to give the title compound (10 mg, 4%) as a white solid: m/z 349 [M+H]$^+$ (ES$^+$), 347 [M−H]$^−$ (ES$^−$); $^1$H NMR (400 MHz, DMSO-d$_6$) δ: 13.36 (1H, br. s), 8.20 (1H, d), 8.06-8.04 (2H, m), 7.99 (1H, d), 7.24 (1H, d), 7.10 (1H, d), 2.79 (3H, s), 2.55 (3H, s), 2.52 (3H, s).

Synthesis 36

4-(5-(4,7-Dimethylbenzofuran-2-yl)-1,3,4-oxadiazol-2-yl)-2-fluorobenzoic acid (BHBA-037)

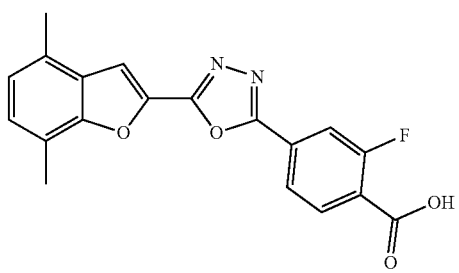 [SMILES: Cc1ccc(C)c2oc(-c3nnc(-c4ccc(C(=O)O)c(F)c4)o3)cc12]

The title compound (43 mg, 15% for the final step) was prepared in essentially the same manner as (BHBA-035) except 4-(tert-butoxycarbonyl)-3-fluorobenzoic acid was used instead of 4-(tert-butoxycarbonyl)-2-methylbenzoic acid in step (i): m/z 353 [M+H]+ (ES+), 351 [M−H]− (ES−); $^1$H NMR (400 MHz, DMSO-$d_6$) δ: 13.69 (1H, br. s), 8.14-8.09 (2H, m), 8.06-8.02 (2H, m), 7.24 (1H, d), 7.10 (1H, d), 2.54 (3H, s), 2.52 (3H, s).

Synthesis 37

3-Chloro-4-(5-(4,7-dimethylbenzofuran-2-yl)-1,3,4-oxadiazol-2-yl)benzoic acid (BHBA-036)

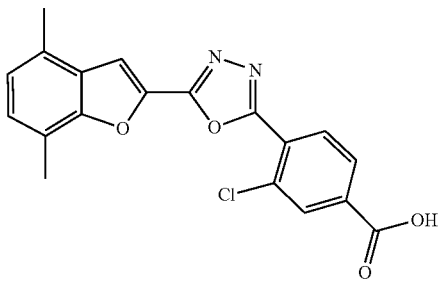 [SMILES: Cc1ccc(C)c2oc(-c3nnc(-c4ccc(C(=O)O)cc4Cl)o3)cc12]

The title compound (11 mg, 30% for the final step) was prepared in essentially the same manner as (BHBA-034) except 4-(tert-butoxycarbonyl)-2-chlorobenzoic acid was used instead of 4-(methoxycarbonyl)benzoic acid in step (iii): m/z 367 [M−H]− (ES−); $^1$H NMR (400 MHz, DMSO-$d_6$) δ: 13.77 (1H, br. s), 8.29 (1H, d), 8.16 (1H, d), 8.12-8.10 (1H, m), 8.06 (1H, s), 7.25 (1H, d), 7.10 (1H, d), 2.55 (3H, s), 2.52 (3H, s).

Synthesis 38

4-(5-(4,7-Dimethylbenzofuran-2-yl)-1,2,4-thiadiazol-3-yl)benzoic acid (BHBA-038)

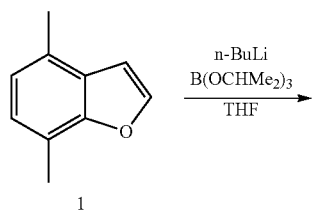

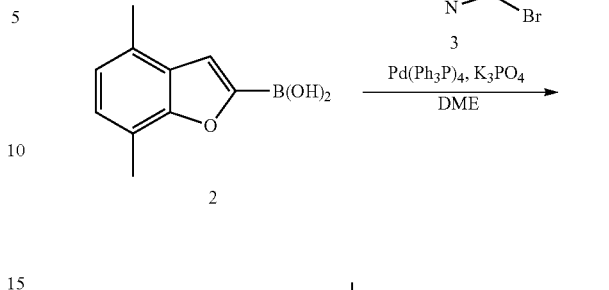

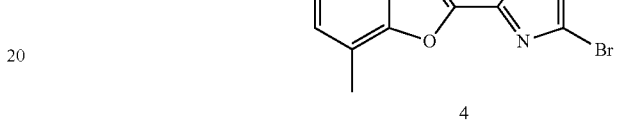

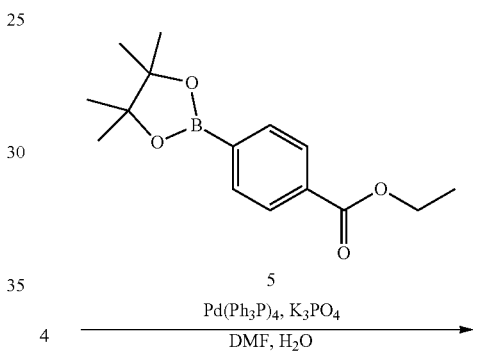

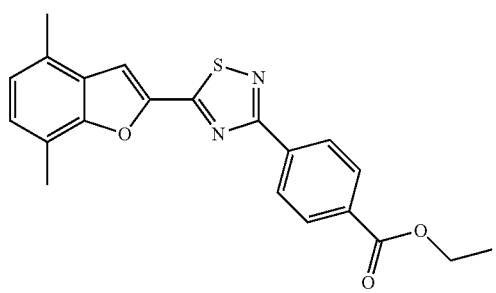

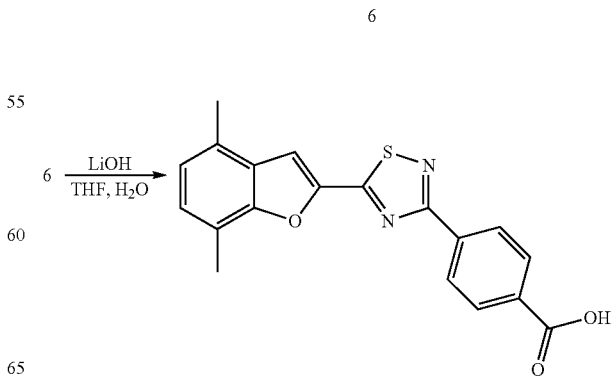

Step (i): (4,7-Dimethylbenzofuran-2-yl)boronic acid (2)

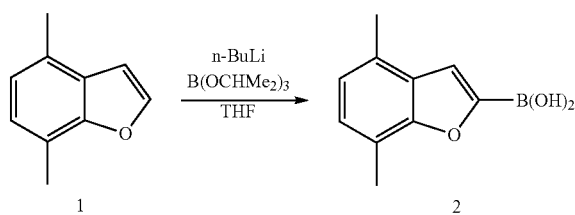

A solution of 4,7-dimethylbenzofuran (1) (2.70 g, 18.5 mmol) was dissolved in anhydrous THF (50 mL) and cooled to −78° C. The solution was treated with n-butyllithium (1.6 M in hexanes (12.7 mL, 20.3 mmol) and stirred at −78° C. for 60 min. Triisopropyl borate (4.7 mL, 20 mmol) was added and the mixture was stirred at −78° C. for 20 min before the addition of 2 M HCl (20 mL). The mixture was warmed to RT and then extracted with Et$_2$O (100 mL). The organic solution was dried over Na$_2$SO$_4$, filtered and concentrated in vacuo. The residue was triturated with isohexane (30 mL) to give the title compound (2) (2.5 g, 71%) as a white solid: m/z 191 [M+H]$^+$ (ES$^+$); $^1$H NMR (400 MHz, DMSO-d$_6$) δ: 8.45 (2H, br. s), 7.48 (1H, s), 7.02 (1H, d), 6.91 (1H, d), 2.44 (6H, d).

Step (ii): 3-Bromo-5-(4,7-dimethylbenzofuran-2-yl)-1,2,4-thiadiazole (4)

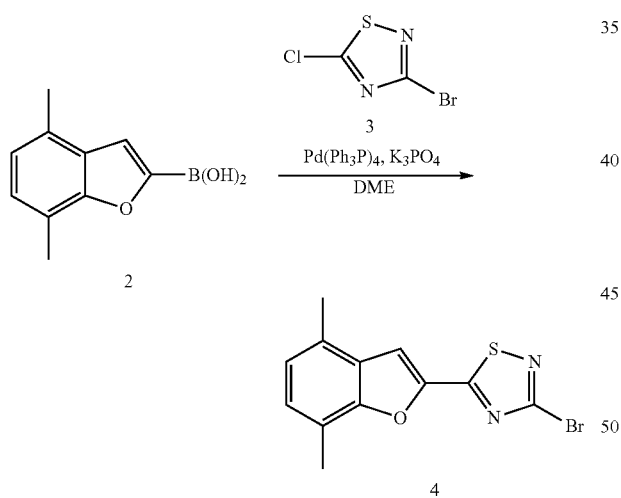

A mixture of 4,7-dimethylbenzofuran-2-ylboronic acid (2) (0.5 g, 2.6 mmol), 3-bromo-5-chloro-1,2,4-thiadiazole (3) (0.525 g, 2.63 mmol), K$_3$PO$_4$ (1.12 g, 5.26 mmol) and Pd(Ph$_3$P)$_4$ (0.304 g, 0.263 mmol) in DME (7 mL) and water (1 mL) in a sealed tube was heated in a microwave reactor at 120° C. for 15 min. The mixture was diluted with EtOAc (30 mL) and washed with water (20 mL) and brine (20 mL). The organic solution was dried over MgSO$_4$, filtered and concentrated in vacuo. The residue was purified by silica gel chromatography (12 g, 0-10% EtOAc in isohexane) to afford the title compound (4) (372 mg, 46%) as a white solid: $^1$H NMR (400 MHz, CDCl$_3$) δ: 7.66 (1H, s), 7.15 (1H, d), 7.02 (1H, d), 2.53 (6H, s).

Step (iii): Ethyl 4-(5-(4,7-dimethylbenzofuran-2-yl)-1,2,4-thiadiazol-3-yl)benzoate (6)

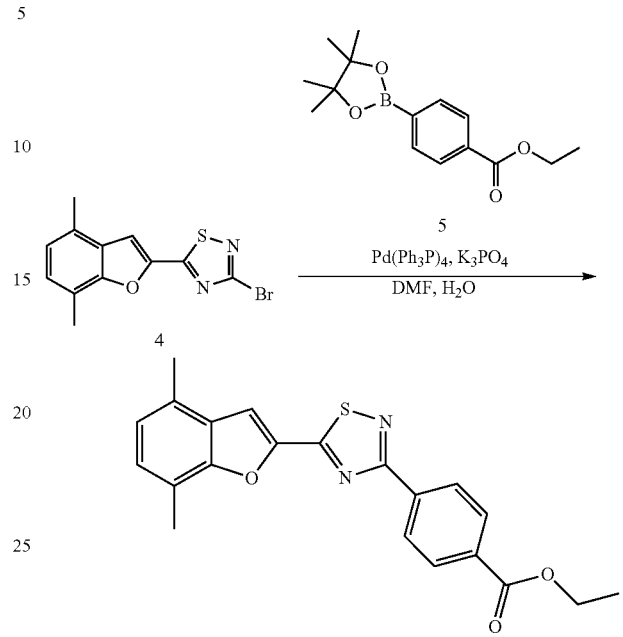

A mixture of 3-bromo-5-(4,7-dimethylbenzofuran-2-yl)-1,2,4-thiadiazole (4) (100 mg, 0.323 mmol), ethyl 4-(4,4,5,5-tetramethyl-1,3,2-dioxaborolan-2-yl)benzoate (5) (107 mg, 0.388 mmol), K$_3$PO$_4$.H$_2$O (149 mg, 0.647 mmol) and Pd(Ph$_3$P)$_4$ (37 mg, 0.03 mmol) in DMF (2 mL) and H$_2$O (0.5 mL) in a sealed tube was heated in a microwave reactor at 130° C. for 15 min. The mixture was cooled to RT and partitioned between DCM (10 mL) and H$_2$O (3 mL). The organic solution was washed with water (3 mL), passed through a phase separation cartridge and concentrated in vacuo. The residue was purified by silica gel chromatography (12 g, 0-10% EtOAc in isohexane) to afford the title compound (6) (80 mg, 56%) as a white solid: $^1$H NMR (400 MHz, DMSO-d$_6$) δ: 8.45 (2H, d), 8.17 (2H, d), 8.09 (1H, s), 7.25 (1H, d), 7.10 (1H, d), 4.36 (2H, q), 2.55 (3H, s), 2.52 (3H, s), 1.36 (3H, t).

Step (iv): 4-(5-(4,7-Dimethylbenzofuran-2-yl)-1,2,4-thiadiazol-3-yl)benzoic acid (BHBA-038)

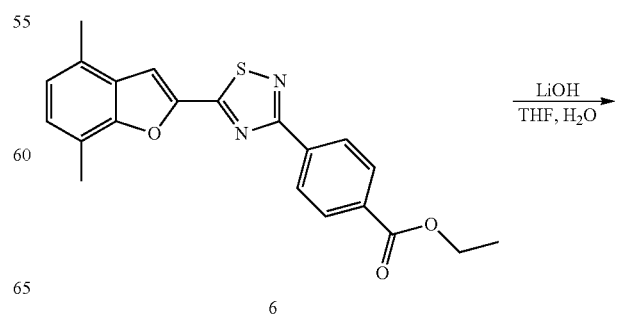

-continued

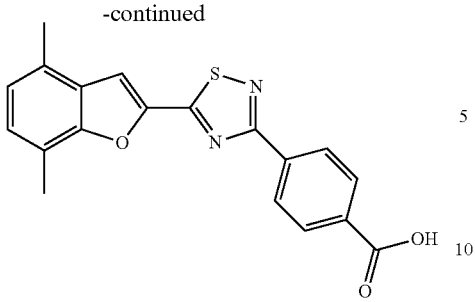

The title compound (18 mg, 19%) was prepared from ethyl 4-(5-(4,7-dimethylbenzofuran-2-yl)-1,2,4-thiadiazol-3-yl)benzoate (6) using a procedure essentially the same as in step (v) for (BHBA-001): m/z 351 [M+H]+ (ES+), 349 [M−H]− (ES−); 1H NMR (400 MHz, DMSO-d6) δ: 13.22 (1H, br. s), 8.42 (2H, d), 8.15 (2H, d), 8.08 (1H, s), 7.24 (1H, d), 7.10 (1H, d), 2.55 (3H, s), 2.52 (3H, s).

Synthesis 39

4-(5-(4,7-Dimethylbenzofuran-2-yl)-1,2,4-thiadiazol-3-yl)-2-fluorobenzoic acid (BHBA-041)

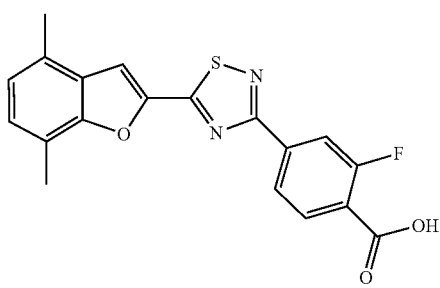

The title compound (10 mg, 11% for the final step) was prepared in essentially the same manner as (BHBA-038) except that ethyl 2-fluoro-4-(4,4,5,5-tetramethyl-1,3,2-dioxaborolan-2-yl)benzoate was used instead of ethyl 4-(4,5,5-tetramethyl-1,3,2-dioxaborolan-2-yl)benzoate in step (iii): m/z 369 [M+H]+ (ES+), 367 [M−H]− (ES−); 1H NMR (400 MHz, DMSO-d6) δ: 13.52 (1H, br. s), 8.21 (1H, dd), 8.13-8.07 (3H, m), 7.25 (1H, d), 7.10 (1H, d), 2.55 (3H, s), 2.52 (3H, s).

Synthesis 40

4-(5-(4,7-Dimethylbenzofuran-2-yl)-1,2,4-thiadiazol-3-yl)-2-methylbenzoic acid (BHBA-040)

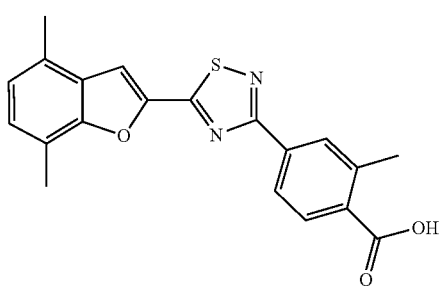 [SMILES: Cc1cc(-c2nsc(-c3cc4c(C)ccc(C)c4o3)n2)ccc1C(=O)O]

The title compound (10 mg, 10% for the final step) was prepared in essentially the same manner as (BHBA-038) except that methyl 2-methyl-4-(4,4,5,5-tetramethyl-1,3,2-dioxaborolan-2-yl)benzoate was used instead of ethyl 4-(4,4,5,5-tetramethyl-1,3,2-dioxaborolan-2-yl)benzoate in step (iii): m/z 365 [M+H]+ (ES+), 363 [M−H]− (ES−); 1H NMR (400 MHz, DMSO-d6) δ: 13.08 (1H, br. s), 8.23 (1H, s), 8.19 (1H, d), 8.08 (1H, s), 7.99 (1H, d), 7.24 (1H, d), 7.10 (1H, d), 2.64 (3H, s), 2.55 (3H, s), 2.52 (3H, s).

Synthesis 41

3-Chloro-4-(5-(4,7-dimethylbenzofuran-2-yl)-1,2,4-thiadiazol-3-yl)benzoic acid (BHBA-039)

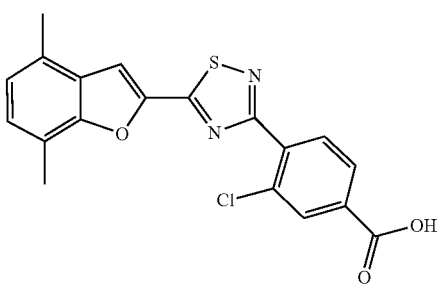 [SMILES: Cc1ccc(C)c2oc(-c3nc(-c4ccc(C(=O)O)cc4Cl)ns3)cc12]

The title compound (22 mg, 38% for the final step) was prepared in essentially the same manner as (BHBA-038) except that (2-chloro-4-(methoxycarbonyl)phenyl)boronic acid was used instead of ethyl 4-(4,4,5,5-tetramethyl-1,3,2-dioxaborolan-2-yl)benzoate in step (iii): m/z 383 [M−H]− (ES−); 1H NMR (400 MHz, DMSO-d6) δ: 13.59 (1H, br. s), 8.18-8.16 (1H, m), 8.11 (1H, d), 8.08-8.05 (2H, m), 7.24 (1H, d), 7.09 (1H, d), 2.54 (3H, s), 2.51 (3H, s).

Synthesis 42

4-(3-(4,7-Dimethylbenzofuran-2-yl)-1,2,4-thiadiazol-5-yl)benzoic acid (BHBA-042)

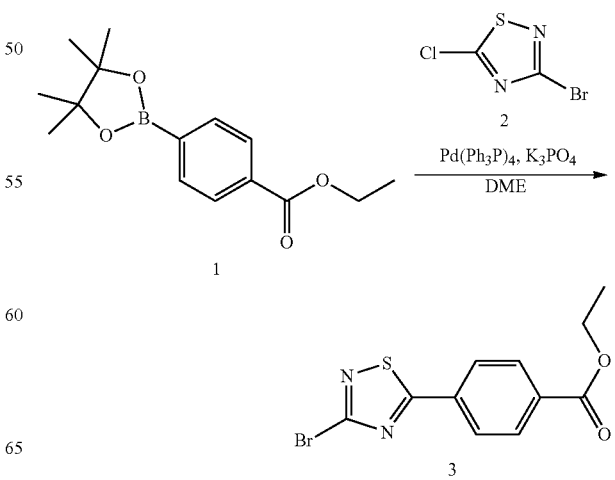

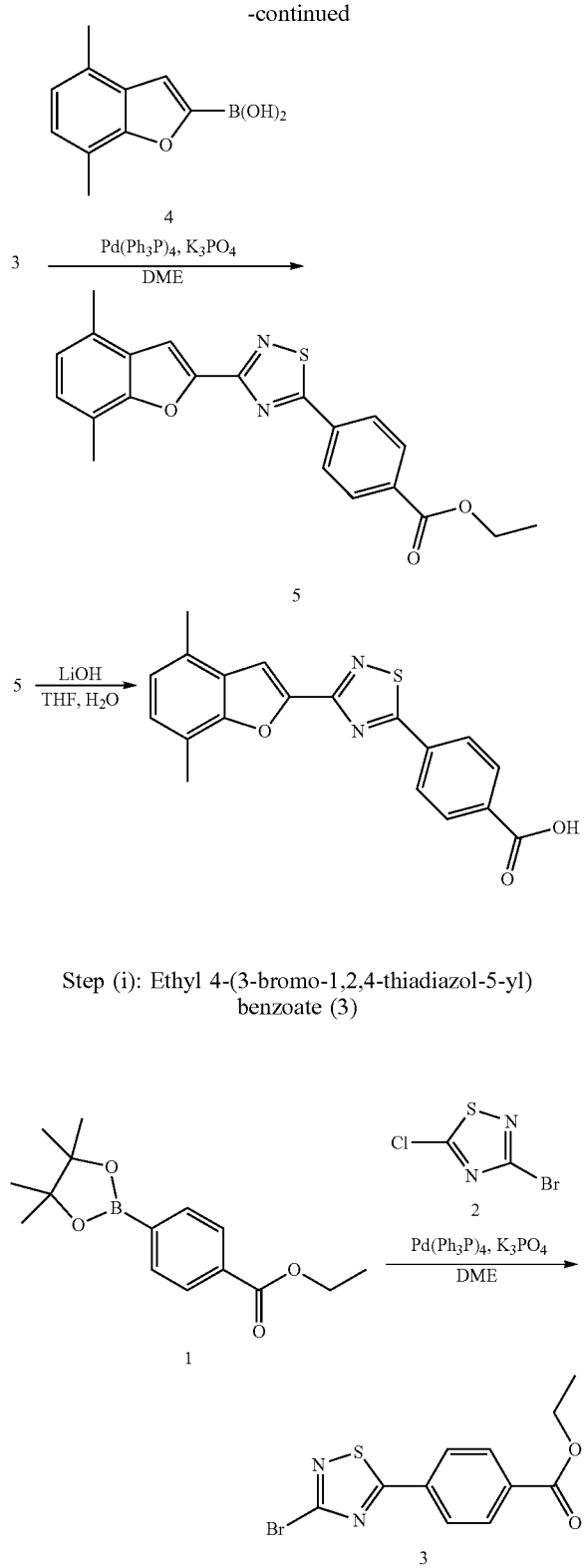

Step (i): Ethyl 4-(3-bromo-1,2,4-thiadiazol-5-yl)benzoate (3)

A mixture of ethyl 4-(4,4,5,5-tetramethyl-1,3,2-dioxaborolan-2-yl)benzoate (1) (330 mg, 1.19 mmol), 3-bromo-5-chloro-1,2,4-thiadiazole (2) (238 mg, 1.19 mmol), $K_3PO_4$ (507 mg, 2.39 mmol) and $Pd(Ph_3P)_4$ (138 mg, 0.120 mmol) in DME (4 mL) and water (1 mL) in a sealed tube was heated in a microwave reactor at 120° C. for 15 min. The mixture was diluted with EtOAc (30 mL) and washed sequentially with water (20 mL) and brine (30 mL). The organic solution was dried over $MgSO_4$, filtered and concentrated in vacuo. The residue was purified by silica gel chromatography (12 g, 0-10% EtOAc in isohexane) to afford ethyl 4-(3-bromo-1,2,4-thiadiazol-5-yl)benzoate (220 mg, 55%) as an off white solid: m/z 313/315 $[M+H]^+$ ($ES^+$); $^1H$ NMR (400 MHz, $CDCl_3$) δ: 8.18 (2H, d), 8.02 (2H, d), 4.44 (2H, q), 1.43 (3H, t).

Step (ii): Ethyl 4-(3-(4,7-dimethylbenzofuran-2-yl)-1,2,4-thiadiazol-5-yl)benzoate (5)

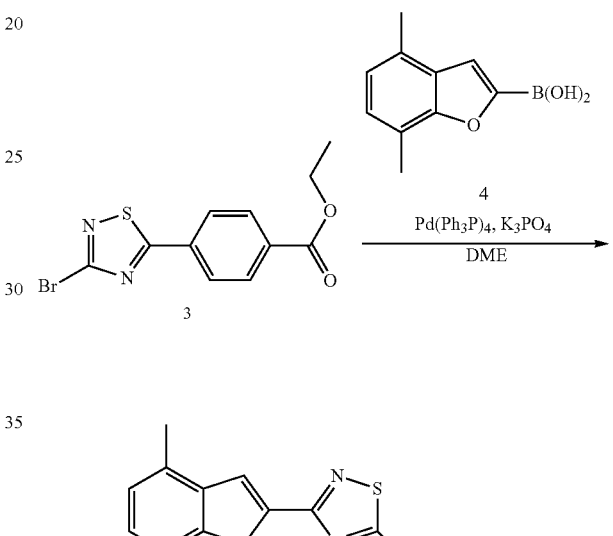

A mixture of 4,7-dimethylbenzofuran-2-ylboronic acid (4) (0.12 g, 0.64 mmol), ethyl 4-(3-bromo-1,2,4-thiadiazol-5-yl)benzoate (3) (0.20 g, 0.64 mmol), $K_3PO_4$ (0.27 g, 1.3 mmol) and $Pd(Ph_3P)_4$ (0.074 g, 0.064 mmol) in DMF (4 mL) and water (1 mL) in a sealed tube was heated at 130° C. for 15 min. The mixture was diluted with EtOAc (30 mL) and washed sequentially with water (20 mL) and brine (20 mL). The organic layer was dried over $MgSO_4$, filtered and concentrated in vacuo. The residue was purified by silica gel chromatography (12 g, 0-10% EtOAc in isohexane) to afford ethyl 4-(3-(4,7-dimethylbenzofuran-2-yl)-1,2,4-thiadiazol-5-yl)benzoate (5) (110 mg, 45%) as a white solid: m/z 379 $[M+H]^+$ ($ES^+$); $^1H$ NMR (400 MHz, $CDCl_3$) δ: 8.21 (2H, d), 8.13 (2H, d), 7.70 (1H, s), 7.11 (1H, d), 7.00 (1H, d), 4.45 (2H, q), 2.62 (3H, s), 2.57 (3H, s), 1.44 (3H, t).

147

Step (iii): 4-(3-(4,7-Dimethylbenzofuran-2-yl)-1,2,4-thiadiazol-5-yl)benzoic acid (BHBA-0421)

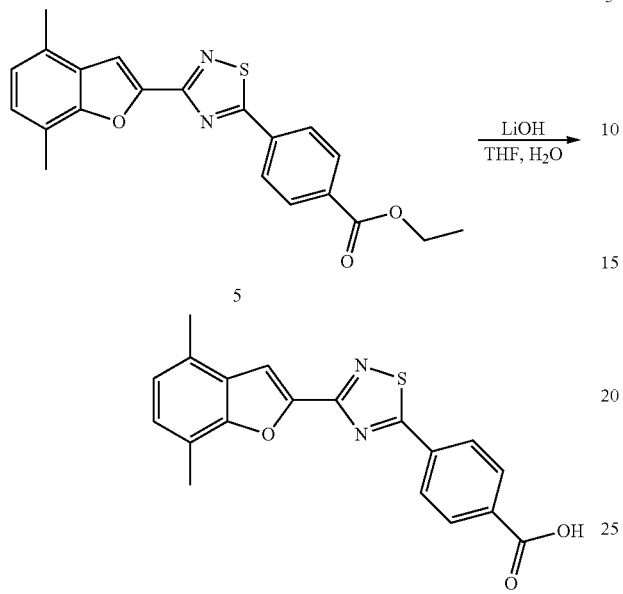

The title compound (10 mg, 11%) was prepared from ethyl 4-(3-(4,7-dimethylbenzofuran-2-yl)-1,2,4-thiadiazol-5-yl)benzoate (5) using a procedure essentially the same as in step (v) for (BHBA-001): m/z 351 [M+H]$^+$ (ES$^+$), 349 [M−H]$^-$ (ES$^-$); $^1$H NMR (400 MHz, DMSO-d$_6$) δ: 8.27 (2H, d), 8.16 (2H, d), 7.86 (1H, s), 7.18 (1H, d), 7.06 (1H, d), 2.54 (3H, s), 2.52 (3H, s). The carboxylic acid proton was not observed.

Synthesis 43

4-(3-(4,7-Dimethylbenzofuran-2-yl)-1,2,4-thiadiazol-5-yl)-2-methylbenzoic acid (BHBA-043)

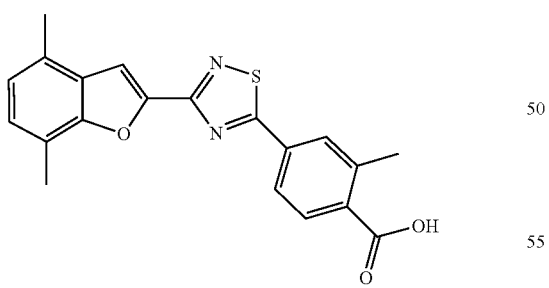

The title compound (110 mg, 71% for the final step) was prepared in essentially the same manner as (BHBA-042) except that ethyl 2-methyl-4-(4,4,5,5-tetramethyl-1,3,2-dioxaborolan-2-yl)benzoate was used instead of ethyl 4-(4,4,5,5-tetramethyl-1,3,2-dioxaborolan-2-yl)benzoate in step (i): m/z 365 [M+H]$^+$ (ES$^+$), 363 [M−H]$^-$ (ES$^-$); $^1$H NMR (400 MHz, DMSO-d$_6$) δ: 13.24 (1H, br. s), 8.09-8.00 (3H, m), 7.85 (1H, s), 7.17 (1H, d), 7.05 (1H, d), 2.65 (3H, s), 2.54 (3H, s), 2.52 (3H, s).

148

Synthesis 44

4-(3-(4,7-Dimethylbenzofuran-2-yl)-1,2,4-thiadiazol-5-yl)-2-fluorobenzoic acid (BHBA-044)

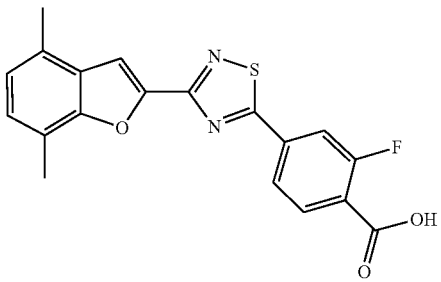 [SMILES: Cc1ccc(C)c2oc(-c3nsc(-c4ccc(C(=O)O)c(F)c4)n3)cc12]

The title compound (82 mg, 67% for the final step) was prepared in essentially the same manner as (BHBA-042) except that ethyl 2-fluoro-4-(4,4,5,5-tetramethyl-1,3,2-dioxaborolan-2-yl)benzoate was used instead of ethyl 4-(4,4,5,5-tetramethyl-1,3,2-dioxaborolan-2-yl)benzoate in step (i): m/z 369 [M+H]$^+$ (ES$^+$), 367 [M−H]$^-$ (ES$^-$); $^1$H NMR (400 MHz, DMSO-d$_6$) δ: 13.65 (1H, br. s), 8.11-8.04 (3H, m), 7.85 (1H, s), 7.17 (1H, d), 7.04 (1H, d), 2.53 (3H, s), 2.51 (3H, s).

Synthesis 45

4-(5-(5-Chloro-4,7-dimethylbenzofuran-2-yl)-1,2,4-oxadiazol-3-yl)benzoic acid (BHBA-045)

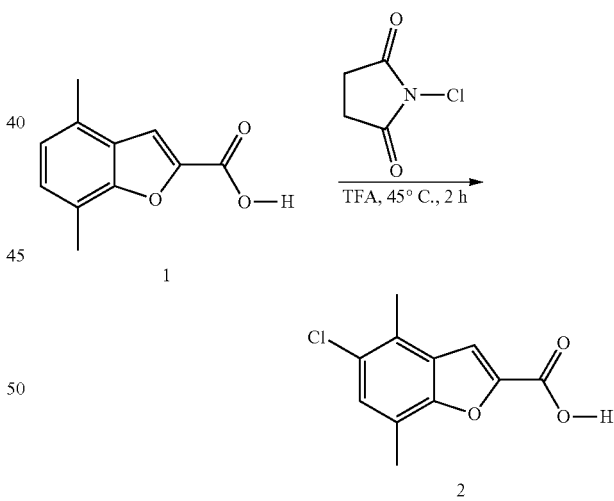

1. SOCl$_2$, toluene
2. Dioxane, reflux

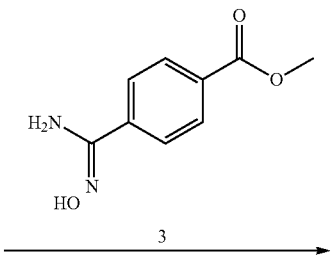

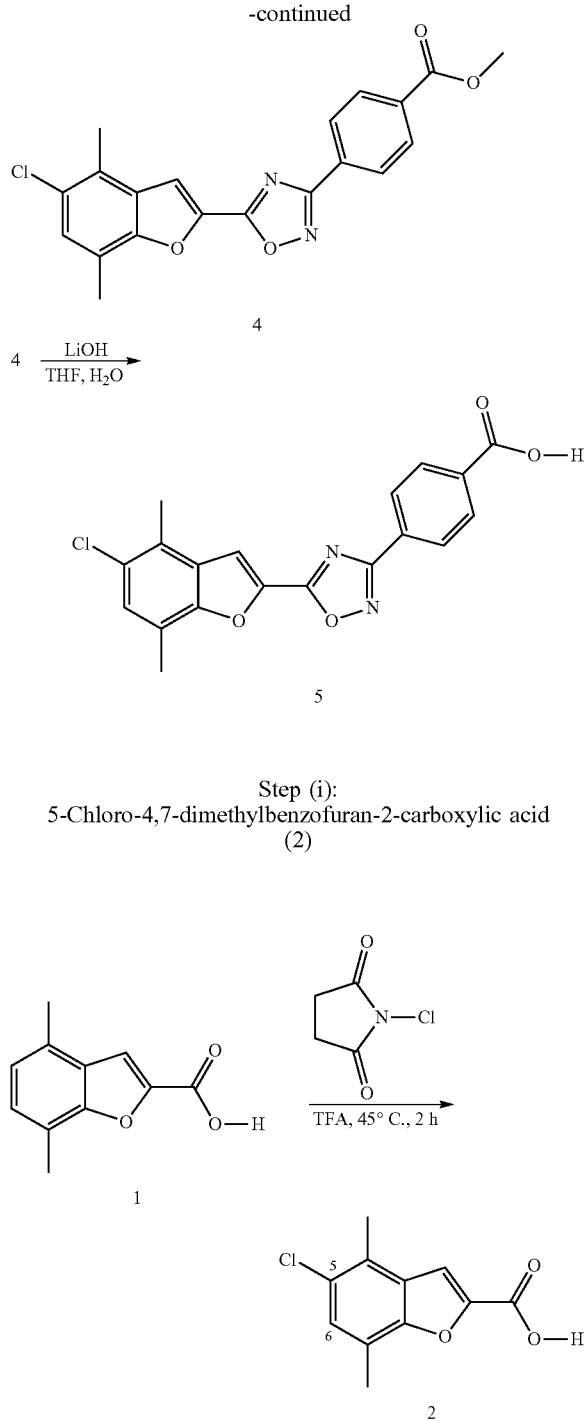

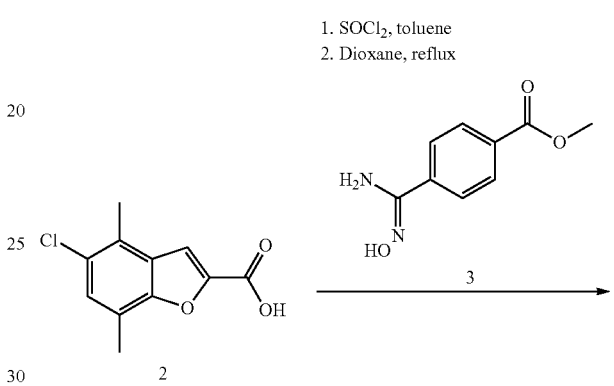

Step (i):
5-Chloro-4,7-dimethylbenzofuran-2-carboxylic acid (2)

4,7-Dimethylbenzofuran-2-carboxylic acid (1) (320 mg, 1.682 mmol) was suspended in TFA (5 mL) and treated with 1-chloropyrrolidine-2,5-dione (449 mg, 3.36 mmol) and stirred at 45° C. for 2 hours. The reaction mixture was concentrated in vacuo and partitioned between EtOAc (30 mL) and water (20 mL), further washing with water (20 mL) and brine (20 mL). The organic layer was dried using magnesium sulfate, absorbed onto silica and purified by chromatography on the Companion (12 g column, 0-40% EtOAc in iHex); this gave no separation of the SM and products. The solid was re-dissolved in DMSO and purified by PREP HPLC 30-80% (MeCN containing 0.1% formic acid) in 0.1% formic acid (aq.) to give 5-chloro-4,7-dimethylbenzofuran-2-carboxylic acid (2) (330 mg, 87% yield) as a white solid: m/z 225 (M+H)+(ES+). $^1$H NMR (400 MHz, DMSO-$d_6$) δ: 13.7 (1H, s), 7.78 (1H, s), 7.35 (1H, s), 2.47 (3H, s), 2.42 (3H, s). The NMR data indicate that the chlorine is located at the 5- or 6-position.

Step (ii): Methyl 4-(5-(5-chloro-4,7-di methylbenzofuran-2-yl)-1,2,4-oxadiazol-3-yl)benzoate (4)

5-Chloro-4,7-dimethylbenzofuran-2-carboxylic acid (2) (200 mg, 0.890 mmol) was suspended in toluene (5 mL), treated with SOCl$_2$ (195 μL, 2.67 mmol) and heated to reflux for 3 hours. The reaction mixture was cooled to room temperature and concentrated in vacuo, azeotroping with toluene to give 5-chloro-4,7-dimethylbenzofuran-2-carbonyl chloride which was then dissolved in dioxane (5 mL) and added to a stirring suspension of methyl 4-(N-hydroxycarbamimidoyl)benzoate (3) (176 mg, 0.905 mmol) in dioxane (5 mL) at room temperature and the mixture was stirred for 1 hour before heating to reflux overnight. The reaction was cooled to room temperature, concentrated in vacuo, triturated with MeOH (2 mL), and filtered and washed with MeOH (2 mL). The compound was dried in a vacuum oven overnight to give methyl 4-(5-(5-chloro-4,7-dimethylbenzofuran-2-yl)-1,2,4-oxadiazol-3-yl)benzoate (5) (230 mg, 0.601 mmol, 73.0% yield) as a pale pink solid. This material was too insoluble to obtain NMR data and the mixture was used without further purification.

Step 4-(5-(5-Chloro-4,7-dimethylbenzofuran-2-yl)-1,2,4-oxadiazol-3-yl)benzoic acid (BHBA-045)

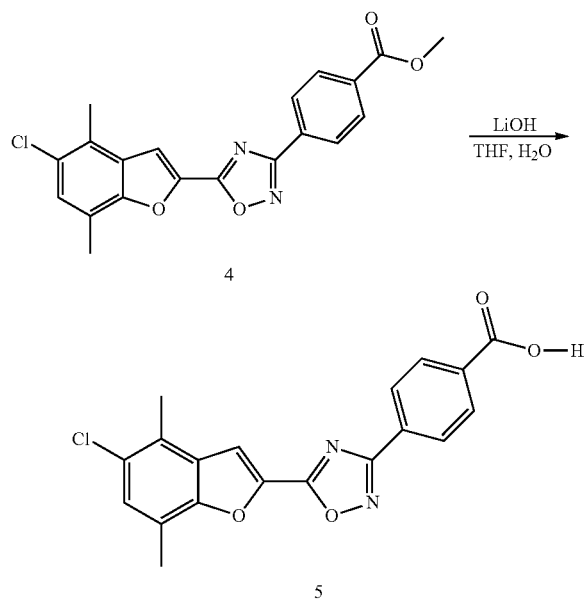

Methyl 4-(5-(5-chloro-4,7-dimethylbenzofuran-2-yl)-1,2,4-oxadiazol-3-yl)benzoate (4) (140 mg, 0.366 mmol) was dissolved in THF (2 mL) and treated with a 2 M lithium hydroxide solution (914 μL, 1.829 mmol) and stirred at 40° C. for two days. The reaction mixture was acidified using 2 N HCl, and the solid collected by filtration, washed with MeOH, and dried to give 4-(5-(5-chloro-4,7-dimethylbenzofuran-2-yl)-1,2,4-oxadiazol-3-yl)benzoic acid (5) (138 mg, 95% yield) as a white solid: m/z 366.9 (M−H)⁻ (ES⁻). $^{1}$H NMR (400 MHz, DMSO-$d_6$) δ: 13.34 (1H, br. s), 8.36 (1H, s), 8.23 (2H, d), 8.17 (2H, d), 7.48 (1H, s), 2.58 (3H, s), 2.55 (3H, s).

Biological Modelling of RARβ Agonists for Treatment of Nerve Injury—1

A simple approach to upregulate RARβ2 expression in vivo is to use an RARβ agonist, since the gene for this receptor contains an RARE, resulting in auto-regulation (see, e.g., Leid et al., 1992). Also, this is a much more practical solution than gene therapy to the treatment of CNS injuries, since retinoids are small lipophilic molecules which can potentially reach all the injured neurons, and the dose can be readily controlled.

The corticospinal tract (CST) of rats was crushed at the C4 level in rats and the RAR agonist (CD2019, 6-(4-methoxy-3-(1-methylcyclohexyl)phenyl)-2-naphthalenecarboxylic acid, a selective RARβ agonist) was applied to the lateral ventricle in vivo for 2 weeks. The results demonstrate that CD2019 leads to an upregulation of RARβ2 in the CST neuronal cell bodies. After 5 weeks, BDA labelling of CST axons showed that in lesioned control animals, no labelled axons cross the lesion site but agonist treated rats showed a significant number of axons crossing and extending several millimeters beyond the lesion site. Specifically, in vehicle treated animals, axons (white) did not grow across a SCI, but in CD2019 treated animals, many axons were observed crossing the injury site.

In behavioural tests after 5 weeks, the CD2019 treated rats performed as well as non-lesioned animals.

Figure 1B:
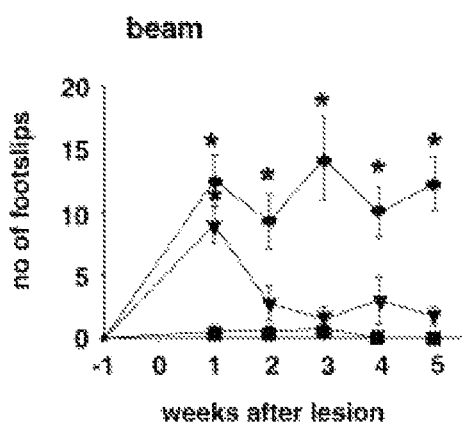

FIGS. 1A and 1B show two graphs of the number of rat footslips as a function of the number of weeks after lesion, for grid task (FIG. 1A) and beam task (FIG. 1B). The data in FIGS. 1A and 1B demonstrate that CD2019 induces functional recovery of the forelimb in lesioned animals. Rats were treated at the time of lesion by i.c.v. with CD2019 at 180 ng/kg/day for 14 days. CD2019 treated lesioned rats showed functional recovery 4 weeks post lesion in a grid task (FIG. 1A), and 2 weeks post lesion in a beam task (FIG. 1B), whereas there was no significant recovery in the vehicle treated lesioned animals. Error bar shows SEM. Asterisks denote significant difference between the lesioned treated (CD2019 or vehicle) and non-lesioned vehicle treated group. *$P<0.05$, students t test, n=6 rats for each treatment group.

When pieces of cortex from these RARβ agonist treated animals were cultured, neurite outgrowth was observed, in contrast to cortex from control lesioned animals. Specifically, axons did not grow from adult vehicle treated cortex, but did grow from adult CD2019 treated cortex.

Biological Modelling of RARβ Agonists for Treatment of Nerve Injury—2

In another example of nerve injury, the four sensory roots from each of four DRG at the level of the left forelimb were severed and re-implanted into the spinal cord. Rats were treated with a number of different retinoids with different selectivity profiles (as shown in the following table; all human data) as well as RARβ agonists (CD2019 and BHBA-001).

TABLE 1

| Retinoid | RARβ potency $EC_{50}$ (nM) | Selectivity over RARα | Selectivity over RARγ |
|---|---|---|---|
| 9-cis-RA | 0.74 | 7.3-fold | 1.5-fold |
| AM80 (Tamibarotene) | 7.53 | 4-fold | 6-fold |
| ATRA (Tretinoin) | 0.16 | 0.1-fold | 0.7-fold |
| 13-cis-RA (Isotretinoin) | 0.25 | 0.2-fold | 1.7-fold |
| Acitretin | 3.56 | 0.4-fold | 0.9-fold |
| CD2019 | 0.83 | 11-fold | 1.9-fold |

In behavioural tests after 5 weeks, only the CD2019 (a known RARβ agonist) and the BHBA-001 treated rats performed as well as non-lesioned animals.

Figure 2A:
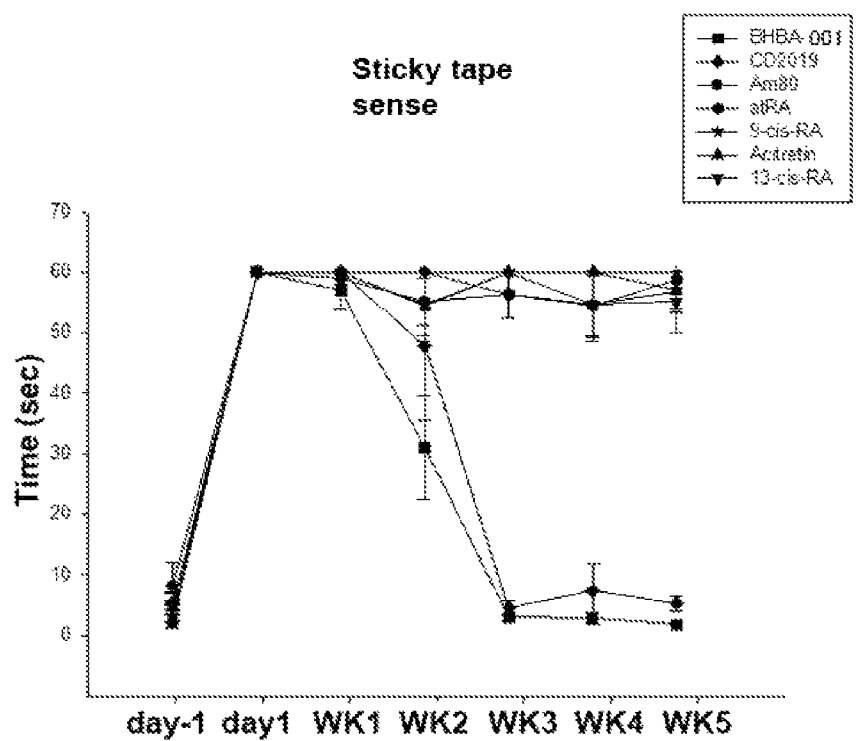
FIGS. 2A and 2B show two graphs of the time taken for rats to sense sticky tape (FIG. 2A) and to remove sticky tape (FIG. 2B) that is placed on its injured forepaw, as a function of the number of weeks after injury, as described in the biological modeling study below.
Figure 2B:
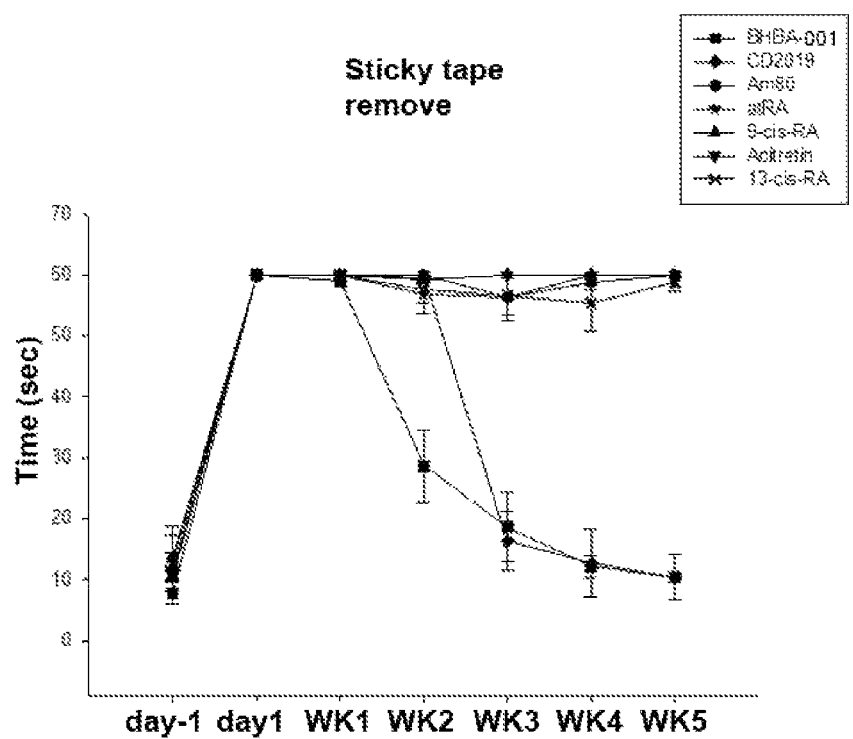

FIGS. 2A and 2B show two graphs of the time taken for rats to sense sticky tape (FIG. 2A) and to remove sticky tape (FIG. 2B) that is placed on its injured forepaw, as a function of the number of weeks after injury. Rats were treated with 1 mg/kg of the test compound or vehicle two days after lesion, and then three times a week for the period of the experiment. Error bars show SEM. ***$P<0.001$, students t test, n=3-4 rats for each treatment group. At weeks 3, 4, and 5, there was significant difference between the rats treated with RARβ agonist as compared to rats treated with other retinoid agonists and vehicle.

The data in FIGS. 2A and 2B further demonstrate that RARβ selectivity is required for functional recovery of the forelimb. The lesioned rats treated with RARβ agonist showed functional recovery, as indicated by sticky tape sensing (FIG. 2A) and sticky tape removal (FIG. 2B); there was no recovery in lesioned rats treated with any of the other retinoid agonists or vehicle.

Interaction of RARβ2 Signalling with Other Pathways Involved in Neurite Outgrowth:

The importance of the RARβ signalling pathway in axonal/neurite outgrowth was also demonstrated by illustrating its interaction with other pathways than are known to be involved in this process.

Phosphoinositide 3-Kinase Pathway:

Pathways that are known to stimulate neurite outgrowth include cyclic AMP (cAMP)-dependent protein kinase A (PKA) and phosphoinositide 3-kinase (PI3K), and these are able to overcome myelin inhibition (see, e.g., Williams et al., 2005). The inventors examined how the RARβ signalling pathway might be linked to either of these pathways.

In cultures of cerebellar neurons grown in the presence of myelin, it was demonstrated that the RARβ agonist CD2019 causes the outgrowth of neurites and that in the presence of a PKA inhibitor which prevents cAMP signalling (KT5720), there was little or no effect on RARβ agonist mediated neurite outgrowth.

However, when the cerebellar neurons were cultured in the presence of the RAR agonist (CD2019) and a PI3K inhibitor (LY295002), neurite outgrowth was severely impeded. Specifically, the PI3K inhibitor (LY295002) prevents RARβ agonist (CD2019) mediated neurite outgrowth in the presence of MAG, whereas the cAMP inhibitor (KT5720) does not affect RARβ agonist (CD2019) mediated outgrowth. Furthermore, Western blots of cerebellar cultures treated with 1 µM RARβ agonist CD2019 showed a significant 4-fold increase in neuronal phospho-Akt, but not total Akt, a target of PI3K, as compared to control cultures. This suggests that the RARβ agonist acts via the PI3K pathway in stimulating neurite outgrowth by increasing the phosphorylation of AKT but not the total pool of AKT. In vivo, the inventors have also demonstrated that phosphor AKT is induced in the injured CST neurons by CD2019, suggesting that the agonist acts through the same mechanism as in vitro (see, e.g., Agudo et al., 2010).

While there is interest in the PI3K pathway as a target for CNS regeneration, it is difficult to prepare specific targets to the kinase itself, whereas specific RARβ agonists can be prepared which can modulate this pathway.

Material and Methods:

Animal Surgery:

All animal experiments were carried out under UK home office regulations. Dorsal column lesions were performed on adult male rats as previously described (see, e.g., Bradbury et al., 2002). Mini-osmotic pumps with a flow rate of 0.5 µL/hour for 14 days (Alzet™) were filled with 10 µM RARβ agonist (CD2019, obtained from CIRD Galderma, Sophia-Antipolis, France), or vehicle (10% DMSO in PBS). CD2019 is 5 fold selective RARβ over RARα and 12 fold selective RARβ over RARγ (see, e.g., Bernard et al., 1992; Delescluse et al., 1991). The pumps were placed subcutaneously and connected to a brain infusion catheter (Alzet™), which was inserted into the lateral ventricle (Bregma coordinates: rostrocaudal: −0.8 mm, mediolateral: −1.5 mm and dorsoventral: −4.5 mm). This gave a dose of CD2019 of 180 ng/kg/day. The dose was based previous in vivo studies on activation of RARα and RARβ signalling in the adult rat brain (see, e.g., Goncalves et al., 2009). Animals which underwent behavioural studies and subsequent tracing (n=6 per treatment) were kept for six weeks before being sacrificed with a lethal injection of pentobarbital and transcardially perfused with 4% PFA. Dissected tissue (cervical and lumbar spinal cord) was processed for immunofluoresence.

Western Blotting:

Protein was extracted from the cortex of adult rats 14 days post surgery (n=3 per group). The amount of protein was determined using a bicinchoninic acid (BCA) protein assay kit (Pierce). Protein (10 µg) was loaded on 10% or 6% SDS-PAGE gel. Semi-dry blotting was performed, and the blots were probed with rabbit anti-RARβ (Santa Cruz, dilution of 1:500), rabbit anti-phospho-Akt, rabbit anti-Akt (both from Cell Signalling Technology, dilution of 1:1000), and mouse anti-GFAP (Sigma, dilution 1:1000). The membranes were then incubated with HRP-conjugated secondary antibodies (anti-mouse IgM+A 1:5000 from Abcam, and anti-mouse and anti-rabbit from Amersham Pharmacia Biotech 1:5000) and HRP activity was visualized by applying chemiluminescent substrate (ECL; Amersham Pharmacia Biotech) followed by exposure of the membrane to X-ray film. For a loading control, the blots were probed with mouse anti-βIII tubulin (Promega, dilution of 1:1000) and developed as above. The exposed films were analyzed by Gene Tools™ program (Syngene). Signal density was calculated as the ratio of signal intensity to β-III tubulin.

RT-PCR:

RNA was isolated and cDNA synthesis was carried out as previously described (see, e.g., Corcoran et al., 2000). For PCR of rat RARβ2 (Accession no AJ002942), the following primers were used: forward (ttcgtggactttctgtgc) and reverse (tgtagaaatccaggatctgcc); which yields a product of 134 bp. These primers are rat RARβ2 specific and cannot therefore detect other RAR/RXR isoforms. Thirty cycles were carried out using the following conditions, 94° C. for 30 seconds, 56° C. for 30 seconds, and 72° C. for 30 seconds.

Neurite Outgrowth Assays:

Cerebellar neurons isolated from post-natal day 3 rat pups were cultured over monolayers of parental 3T3 cells in control media, or media supplemented with a recombinant MAG-Fc chimera (R&D Systems) used at a final concentration of 20 µg/mL MAG-Fc. The monolayers were established for 24 hours prior to addition of the neurons and the co-cultures were maintained for approximately 21 hours. Following careful fixation with 4% paraformaldehyde, the neurons were immuno-stained with a GAP-43 antibody (from Graham Wilkin, Imperial College), dilution of 1:500, and the mean length of the longest neurite per cell was measured for approximately 120-150 neurons as previously described (see, e.g., Williams et al., 2005). DRG and cortical explants were obtained from adult rats, they were cultured in cellogen as previously described (see, e.g., Corcoran and Maden, 1999). Three explants per treatment were used. Neurite outgrowth was assessed 3 days later by immunohistochemistry with NF200 (Sigma, dilution of 1:200). The average lengths of the neurites were measured using image pro plus software. Media consisted of DMEM-F12 (Invitrogen) containing N2 (Invitrogen) supplemented with glucose (33 mM) and glutamine (2 mM).

Labelling of CST Neurons/Tract and Immunohistochemistry:

Descendent corticospinal tract axons were anterogradely traced after the dorsal column crush was performed by injected BDA (10% in PBS, Mw10K from Molecular Probes) into the motor cortex as previously described (see, e.g., Yip et al., 2006). Six injections were done in the right cortex (0.5 µL of BDA/injection point). Animals (n=6 per treatment) were perfused and the spinal cord was transferred to PBS (plus 0.1% sodium azide) and embedded in gelatin (10%, 300 bloom; Sigma, Poole, UK). Gelatin blocks were hardened in 4% paraformaldehyde, and 40 µm free-floating serial transverse sections were cut on a vibratome (Leica, Nussloch, Germany) and collected in 24-well plates containing PBS (plus 0.1% sodium azide).

BDA was detected using the tyramide amplification kit (Perkin-Elmer) coupled with extra-avidin-FITC (Amersham Pharmacia Biotech, UK, 1:500). All BDA-labelled fibres observed within a 1-mm square grid were counted at measured intervals from 5 mm above to 5 mm below the lesion site by an experimenter, blinded to treatment. BDA positive axons were counted in every third section (5 sections per animal at each point analysed, and a total of 40 sections per animal) at the same medio-lateral distance from the midpoint (as seen by the central canal).

CST neurons were labelled by retrograde tracing injecting 2 µL of 5% Fluorogold (FG, Molecular Probes) 2 mm deep into the cervical spinal cord (C3-C4) at a rate of 0.5 µL/minute (n=3 rats per group). In sham animals, FG was injected 0.5 mm bilateral to the medial line of spinal cord (1 µL per side), and in lesioned animals FG (2 µL) was injected into the injury. After 14 days, the cortices were fixed for 2 hours in 4% paraformaldehyde (PFA), embedded in OCT compound and stored frozen. Sagittal sections (12 µm) were cut and 4 sequential slides containing 2 sections from lateral 3.4-3.9 mm were taken for analysis (see, e.g., Paxinos and Watson, 2002).

Immunohistochemistry was carried out using anti-rabbit phospho-Akt (Cell Signalling technology, dilution of 1:100). Secondary antibody used was anti-rabbit Cy3 conjugated (Jackson, used at 1:1000). Images were captured at 100× magnification using a Roperscientific digital camera.

Behavioural Testing:

The behavioural tests were carried out as previously described (see, e.g., Bradbury et al., 2002). Rats (n=6 per treatment group) were first trained for two weeks before surgery to perform grid walk and beam walk; they were then tested by an observer blinded to the experimental treatment once a week for five weeks after lesion.

Graphs and Statistics:

Graphs were plotted using Sigma plot. Data is expressed as mean±S.E.M and statistical analysis carried out using Student's t test using Sigma Stat software (SPSS Software Ltd, Birmingham UK). Means, SEM, SD and P-values are provided as summary statistics.

Biological Methods

Transactivation Assays for RARα, RARβ, and RARγ Receptors

Transcriptional transactivation assays were performed with gal4 fusion receptor constructs, created using each of the RARβ ligand binding domains of either mouse or human, co-transfected with the pFR-luc (Stratagene) reporter construct in COS-7 cells. Thus, transfected cells will constitutively express the gal4-RARβ fusion protein which in turn may be transactivated by all trans retinoic acid (atRA) to induce the expression of the luciferase that is driven by a gal4UAS.

Briefly, on day 1, 96 well plates were seeded with 8000 cells per well then left to recover overnight. On day 2, the cells were co-transfected with 100 ng of reporter plasmid and 10 ng of the appropriate receptor plasmid per well using lipofectamine (Invitrogen). On day 3, the lipofectamine containing media was replaced by a DMEM without phenol red, followed by the addition of test compound dissolved in 1 µL of DMSO to each well's 100 µL total volume. Finally, on day 4, the cells were lysed and their luciferase substrate was provided by the BrightGlo™ reagent (Promega), the plates were then read on the MicroBeta TriLux™ (Perkin Elmer).

On each plate, an 8 point dose-response curve of atRA was run in duplicate and dose-response curves of test compounds were also generated in duplicate.

$EC_{50}$ data both for test compounds and atRA was generated by fitting dose-response curves using GraphPad Prism™. Data for test compounds are quoted as $EC_{50}$ values. Where replicate data has been generated, the data are quoted as the mean $EC_{50}$ from the separate experiments.

Biological Data

The following compounds were examined using the transactivation assays for RARα, RARβ, and RARγ, as described above:

BHBA-001, BHBA-002, BHBA-003, BHBA-004, BHBA-005, BHBA-006, BHBA-007, BHBA-008, BHBA-009, BHBA-010, BHBA-011, BHBA-012, BHBA-013, BHBA-014, BHBA-015, BHBA-016, BHBA-017, BHBA-018, BHBA-019, BHBA-020, BHBA-021, BHBA-022, BHBA-023, BHBA-024, BHBA-025, BHBA-026, BHBA-027, BHBA-028, BHBA-029, BHBA-030, BHBA-031, BHBA-032, BHBA-033, BHBA-034, BHBA-035, BHBA-036, BHBA-037, BHBA-038, BHBA-039, BHBA-040, BHBA-041, BHBA-042, BHBA-043, BHBA-044, BHBA-045.

The data are summarised in the following table. $EC_{50}$'s values are reported as mean values of three or more determinations.

TABLE 2

| Code No. | RARβ $EC_{50}$ (nM) | RARα $EC_{50}$ (nM) | RARγ $EC_{50}$ (nM) | RARα/RARβ ratio (*) | RARγ/RARβ ratio (**) |
|---|---|---|---|---|---|
| atRA | 1.88 | 1.2 | 0.9 | 0.6 | 0.5 |
| BHBA-001 | 1.94 | 26 | 11 | 13.4 | 5.6 |
| BHBA-002 | 11.4 | 136 | 29 | 12 | 2.5 |
| BHBA-003 | 16 | 160 | 36 | 10 | 2 |
| BHBA-004 | 10 | inactive | inactive | large | large |
| BHBA-005 | 23 | 130 | 55 | 5 | 2 |
| BHBA-006 | 14 | 89 | 25 | 6 | 2 |
| BHBA-007 | 2.2 | 16 | 8.4 | 7 | 4 |
| BHBA-008 | 1.9 | 17 | 6.8 | 9 | 3.5 |
| BHBA-009 | 4.2 | 32 | 11 | 7.6 | 2.6 |
| BHBA-010 | 2.9 | 25 | 0.53 | 8 | 0.18 |
| BHBA-011 | 4.3 | 26 | 14 | 6 | 3 |
| BHBA-012 | 17 | 67 | 17 | 4 | 1 |
| BHBA-013 | 16 | 140 | 110 | 9 | 7 |
| BHBA-014 | 2.0 | 12 | 11 | 6 | 6 |
| BHBA-015 | 2.9 | 23 | 12 | 8 | 4 |
| BHBA-016 | 2.7 | 18 | 6 | 7 | 2 |
| BHBA-017 | 7.4 | 56 | 18 | 8 | 2.4 |
| BHBA-018 | 41 | 150 | 140 | 3.5 | 3.4 |
| BHBA-019 | 2.5 | 19 | 5.3 | 7.6 | 2 |
| BHBA-020 | 8 | 60 | 23 | 7.5 | 3 |
| BHBA-021 | 3.4 | 30 | 6.3 | 9 | 2 |
| BHBA-022 | 16 | 77 | 18 | 5 | 1.1 |
| BHBA-023 | 11 | 114 | 83 | 10 | 7.5 |
| BHBA-024 | 24 | 180 | 47 | 7.5 | 2 |
| BHBA-025 | 41 | 150 | 140 | 3.6 | 3.4 |
| BHBA-026 | 13 | 47 | 77 | 3.6 | 6 |
| BHBA-027 | 9 | 61 | 25 | 6.7 | 2.7 |
| BHBA-028 | 8.2 | 26 | 8.3 | 3 | 1 |
| BHBA-029 | 14 | 210 | 19 | 15 | 1.3 |
| BHBA-030 | 10 | 58 | 18 | 5.8 | 1.8 |
| BHBA-031 | 17 | 150 | 42 | 8.8 | 2.5 |
| BHBA-032 | 8.1 | 150 | 22 | 18.5 | 2.7 |
| BHBA-033 | 13 | 45 | 23 | 3.5 | 1.8 |
| BHBA-034 | 20 | 92 | 58 | 4.6 | 2.9 |
| BHBA-035 | 67 | 91 | 83 | 1.3 | 1.2 |
| BHBA-036 | 28 | 225 | 58 | 8 | 2.1 |
| BHBA-037 | 45 | 91 | 60 | 2 | 1.3 |
| BHBA-038 | 5.1 | 19 | 6.1 | 3.7 | 1.2 |
| BHBA-039 | 3.6 | 65 | 13 | 18 | 3.6 |
| BHBA-040 | 11 | 72 | 130 | 6.5 | 11.8 |
| BHBA-041 | 4.3 | 20 | 4.7 | 4.6 | 1.0 |
| BHBA-042 | 3.1 | 9.4 | 2.3 | 3 | 0.74 |
| BHBA-043 | 5.2 | 44 | 25 | 8.5 | 4.8 |
| BHBA-044 | 2 | 26 | 3.4 | 13 | 1.7 |
| BHBA-045 | 4 | 91 | 40 | 22.7 | 10 |

(*) The ratio of the "RARα activity" to the "RARβ activity" is referred to as "RARα/RARβ ratio" and reflects the fold-selectivitity for RARβ over RARα. A value greater than 1 indicates selectivity for RARβ.
(**) The ratio of the "RARγ activity" to the "RARβ activity" is referred to as "RARγ/RARβ ratio" and reflects the fold-selectivitity for RARβ over RARγ. A value greater than 1 indicates selectivity for RARβ.

(In the above table, "inactive" means that no agonist action was seen at the highest concentration tested.)

All of the above BHBA compounds were found to be agonists of RARβ. Most of the BHBA compounds have a RARβ activity of less than about 30 nM. Many of the BHBA compounds have a RARβ activity of less than about 20 nM. Many of the BHBA compounds have a RARβ activity of less than about 10 nM. Many of the BHBA compounds have a RARβ activity of less than about 5 nM. Many of the BHBA compounds have a RARβ activity of less than about 3 nM.

In addition, most of above BHBA compounds were found to be selective for RARβ as compared to RARα. For most of the BHBA compounds, the selectivity for RARβ as compared to RARα is by a factor or at least about 1.5 (e.g., the ratio of the RARβ activity to the RARα activity is at least about 1.5). For many of the BHBA compounds, the selectivity for RARβ as compared to RARα is by a factor of at least about 2. For many of the BHBA compounds, the selectivity for RARβ as compared to RARα is by a factor of at least about 3. For many of the BHBA compounds, the selectivity for RARβ as compared to RARα is by a factor of at least about 4. For many of the BHBA compounds, the selectivity for RARβ as compared to RARα is by a factor of at least about 5. For several of the BHBA compounds, the selectivity for RARβ as compared to RARα is by a factor of at least about 10.

In addition, most of above BHBA compounds were found to be selective for RARβ as compared to RARγ. For most of the BHBA compounds, the selectivity for RARβ as compared to RARγ is by a factor or at least about 2 (e.g., the ratio of the RARβ activity to the RARγ activity is at least about 2). For many of the BHBA compounds, the selectivity for RARβ as compared to RARγ is by a factor of at least about 3. For several of the BHBA compounds, the selectivity for RARβ as compared to RARγ is by a factor of at least about 5.

Indeed, many of the BHBA compounds have both selectivity for RARβ as compared to RARα by a factor of at least 3 and selectivity for RARβ as compared to RARγ by a factor of at least 3:

BHBA-001, BHBA-004, BHBA-007, BHBA-008, BHBA-011, BHBA-013, BHBA-014, BHBA-015, BHBA-018, BHBA-020, BHBA-023, BHBA-025, BHBA-026, BHBA-039, BHBA-040, BHBA-043, and BHBA-045.

Additional mouse and human data for two preferred compounds is summarised below.

TABLE 3

| Mammal | Compound | BHBA-001 | BHBA-002 |
|---|---|---|---|
| Mouse | RARβ potency-EC$_{50\ (nm)}$ | 1.94 | 11.46 |
| | Selectivity over RARα | 14-fold | 12-fold |
| | Selectivity over RARγ | 6-fold | 3-fold |
| Human | RARβ potency-EC$_{50\ (nm)}$ | 2.05 | 21.45 |
| | Selectivity over RARα | 23-fold | 12-fold |
| | Selectivity over RARγ | 5-fold | 2-fold |

For comparison, Yoshimura et al., 2000, describes the synthesis and testing of a number of benzofuran and benzothiophene derivatives having a central pyrrole ring. See, e.g., Table 1 on page 2931 therein, from which selected examples and the corresponding data are shown below. All of the compounds are reported to be RARα agonists and furthermore to be highly selective for RARα. However, the compounds had little or no RARβ agonist activity.

TABLE 4

Compounds from Yoshimura et al., 2000

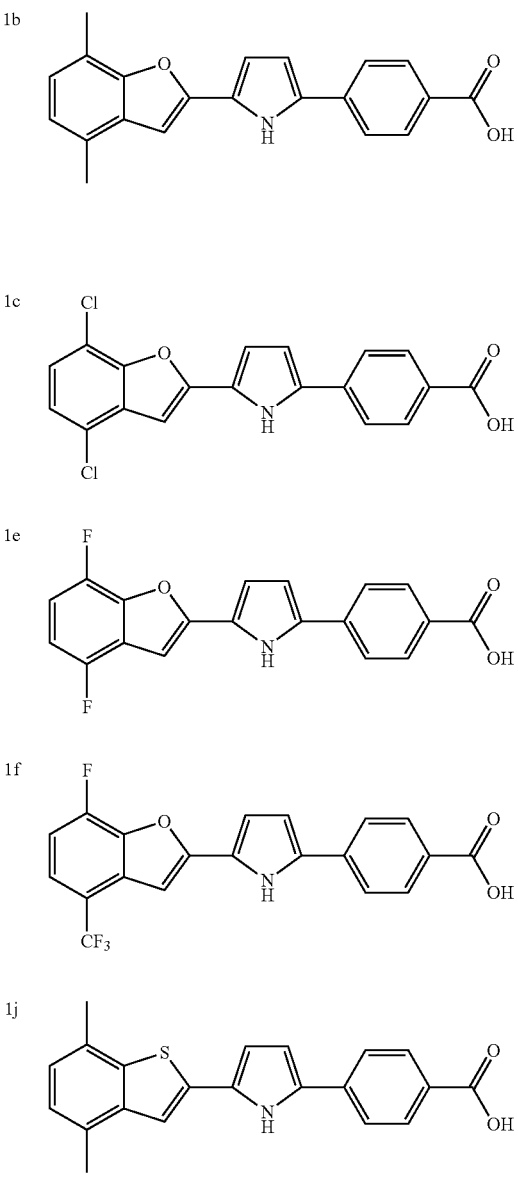

TABLE 5

Binding Affinity from Yoshimura et al, 2000

| Example No. | RARα relative IC$_{50}$ | RARβ relative IC$_{50}$ | RARγ relative IC$_{50}$ | RARα/ RARβ ratio | RARγ/ RARβ ratio |
|---|---|---|---|---|---|
| atRA | 1 | 1 | 1 | 1 | 1 |
| 1b | 1.4 ± 0.3 | 490 ± 60 | >1000 | 0.0029 | n/a |
| 1c | 1.5 ± 0.3 | 690 ± 300 | >1000 | 0.0022 | n/a |
| 1e | 2.5 ± 0.3 | >1000 | >1000 | n/a | n/a |
| 1f | 1.9 ± 0.4 | 500 ± 50 | >1000 | 0.0038 | n/a |
| 1j | 6.1 ± 0.4 | >1000 | >1000 | n/a | n/a |

TABLE 6

| | Subtype-Specific Transactivation from Yoshimura et al., 2000 | | | | |
|---|---|---|---|---|---|
| Example No. | RARα relative IC$_{30}$ | RARβ relative IC$_{30}$ | RARγ relative IC$_{30}$ | RARα/ RARβ ratio | RARγ/ RARβ ratio |
| atRA | 1 | 1 | 1 | 1 | 1 |
| 1b | 0.37 ± 0.02 | 25 ± 12 | 240 ± 30 | 0.148 | 9.60 |
| 1c | 0.70 ± 0.15 | 110 ± 30 | 820 ± 290 | 0.006 | 7.45 |
| 1e | 0.80 ± 0.17 | 210 ± 40 | 1750 ± 750 | 0.0038 | 8.33 |
| 1f | 0.29 ± 0.04 | 8.5 ± 0.4 | 110 ± 20 | 0.034 | 12.9 |
| 1j | 1.3 ± 0.6 | 130 ± 60 | 840 ± 360 | 0.010 | 6.46 |

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited herein in order to more fully describe and disclose the invention and the state of the art to which the invention pertains. Full citations for these references are provided below.

Each of these references is incorporated herein by reference in its entirety into the present disclosure, to the same extent as if each individual reference was specifically and individually indicated to be incorporated by reference.

Agudo M, Yip P, Davies M, Bradbury E, Doherty P, McMahon S, Maden M, Corcoran J P (2010) A retinoic acid receptor beta agonist (CD2019) overcomes inhibition of axonal outgrowth via phosphoinositide 3-kinase signalling in the injured adult spinal cord. Neurobiol Dis 37:147-155.

Arora et al., 2004, "Compounds", US patent publication number US 2004/0152699 A1 published 5 Aug. 2004.

Barrow et al., 2009, "Novel Substituted Pyrazoles, 1,2,4-Oxadiazoles, and 1,3,4-Oxadiazoles", international patent (PCT) publication number WO 2009/146343 A1, published 3 Dec. 2009.

Barrow et al., 2011, "Novel Substituted Pyrazoles, 1,2,4-Oxadiazoles, and 1,3,4-Oxadiazoles", US patent publication number US 2011/0081297 A1, published 7 Apr. 2011.

Barth et al., "Methods for treating methylmalonic academia", international patent (PCT) publication number WO 2011/072281 A1, published 16 Jun. 2011.

Bastien J, Rochette-Egly C (2004) Nuclear retinoid receptors and the transcription of retinoid-target genes. Gene 328:1-16.

Bernard et al., 1992, "Identification of synthetic retinoids with selectivity for human nuclear retinoic acid receptor gamma", Biochem. Biophys. Res. Commun., Vol. 186, pp. 977-983.

Bradbury E J, Moon L D, Popat R J, King V R, Bennett G S, Patel P N, Fawcett J W, McMahon S B (2002) Chondroitinase ABC promotes functional recovery after spinal cord injury. Nature 416:636-640.

Cai et al., 2003, "Substituted 3-aryl-5-aryl-[1,2,4]-oxadiazoles and analogs as activators of caspases and inducers of apoptosis and the use thereof", US Patent Publication No. 2003/0045546 A1 published 6 Mar. 2003.

Cai et al., 2005, "Substituted 3-aryl-5-aryl-[1,2,4]-oxadiazoles and analogs as activators of caspases and inducers of apoptosis and the use thereof", US Patent Publication No. 2005/0154012 A1 published 14 Jul. 2005.

Cho et al., 2010, "The palladium-catalyzed trifluoromethylation of aryl chlorides", Science, Vol. 328, No. 5986, pp. 1679-1681.

Corcoran J, Maden M (1999) Nerve growth factor acts via retinoic acid synthesis to stimulate neurite outgrowth [letter]. Nat Neurosci 2:307-308.

Corcoran J, Shroot B, Pizzey J, Maden M (2000) The role of retinoic acid receptors in neurite outgrowth from different populations of embryonic mouse dorsal root ganglia [In Process Citation]. J Cell Sci 113 (Pt 14):2567-2574.

Corcoran J, So P L, Barber R D, Vincent K J, Mazarakis N D, Mitrophanous K A, Kingsman S M, Maden M (2002) Retinoic acid receptor beta2 and neurite outgrowth in the adult mouse spinal cord in vitro. J Cell Sci 115:3779-3786.

Delescluse et al., 1991, "Selective high affinity retinoic acid receptor alpha or beta-gamma ligands," Mol. Pharmacol., Vol. 40, pp. 556-562.

Goncalves et al., 2009, "Sequential RARbeta and alpha signalling in vivo can induce adult forebrain neural progenitor cells to differentiate into neurons through Shh and FGF signalling pathways", Dev. Biol., Vol. 326, pp. 305-313.

He Z, Koprivica V (2004) The nogo signaling pathway for regeneration block. Annu Rev Neurosci 27:341-368.

Imazaki et al., 2012, "Ruthenium-Catalyzed Transformation of Aryl and Alkenyl Triflates to Halides", Journal of the American Chemical Society, Vol. 134, No. 36, pp. 14760-14763.

Karp et al., 2004, "1,2,4-Oxadiazole benzoic acid compounds and their use for nonsense suppression and the treatment of disease", US patent publication number US 2004/0204461 A1, published 14 Oct. 2004.

Kikuchi et al., 2000, "Synthesis and structure-activity relationships of 5,6,7,8-tetrahydro-5,5,8,8-tetramethyl-2-quinoxaline derivatives with retinoic acid receptor α activity", J. Med. Chem., Vol. 43, pp. 409-419.

Kikuchi et al., 2001, "Heterocycle-containing carboxylic acid derivative and drug containing the same", U.S. Pat. No. 6,329,402 granted 11 Dec. 2001.

Kimura et al., 2003, "Function regulator for retinoid relative receptor", Japanese patent publication number J P 2003-81832, published 19 Mar. 2003.

Kwon B K, Tetzlaff W (2001) Spinal cord regeneration: from gene to transplants. Spine 26:S13-S22.

Lehmann et al., 2005, "New Treatment of GERD II", international patent (PCT) publication number WO 2005/077373 A2, published 25 Aug. 2005.

Leid M, Kastner P, Chambon P (1992) Multiplicity generates diversity in the retinoic acid signalling pathways. Trends Biochem Sci 17:427-433.

Lu P, Yang H, Jones L L, Filbin M T, Tuszynski M H (2004) Combinatorial therapy with neurotrophins and cAMP promotes axonal regeneration beyond sites of spinal cord injury. J Neurosci 24:6402-6409.

Lund et al., 2005, "Discovery of a potent, orally available, and isoform-selected retinoica acid β2 receptor agonist", J. Med. Chem., Vol. 48, pp. 7517-7519.

Maden and Corcoran, 2000, "Factor", international patent (PCT) publication number WO 00/57900 A2, published 5 Oct. 2000.

Maden et al., 1996, "Vitamin A-deficient quail embryos have half a hindbrain and other neural defects", Curr. Biol., Vol. 6, pp. 417-426.

McOmie et al., 1968, "Demethylation of aryl methyl ethers by boron tribromide", Tetrahedron, Vol. 24, No. 5, pp. 2289-2292.

Olsson et al., 2009, "Compounds with activity at retinoic acid receptors", US Patent Publication No. 2009/0176837 A1 published 9 Jul. 2009.

Pan et al., 2011, "An Improved Palladium-Catalyzed Conversion of Aryl and Vinyl Triflates to Bromides and Chlorides", Organic Letters, Vol. 13, No. 18, pp. 4974-4976.

Paxinos and Watson, 2002, "The Rat Brain in Stereotaxic Coordinates", 2nd edition, Academic Press, London.

Quinn S D, De Boni U (1991) Enhanced neuronal regeneration by retinoic acid of murine dorsal root ganglia and of fetal murine and human spinal cord in vitro. In Vitro Cell Dev Biol 27:55-62.

Ritter, 1993, "Synthetic transformations of vinyl and aryl triflates", Synthesis, Vol. 8, pp. 735-762.

Schnell L, Schneider R, Kolbeck R, Barde Y A, Schwab M E (1994) Neurotrophin-3 enhances sprouting of corticospinal tract during development and after adult spinal cord lesion [see comments]. Nature 367:170-173.

Seino et al., 2004, "Prevention of acute and chronic allograft rejection by a novel retinoic acid receiptor-α-selective agonist", Inter. Immunology, Vol. 16, No. 5, pp. 665-673.

So P L, Yip P K, Bunting S, Wong L F, Mazarakis N D, Hall S, McMahon S, Maden M, Corcoran J P (2006) Interactions between retinoic acid, nerve growth factor and sonic hedgehog signalling pathways in neurite outgrowth. Dev Biol 298:167-175.

Tagami et al., 1997, "Fused-ring carboxylic acid derivatives", European patent publication number EP 0889032 A1, published 7 Jan. 1999.

Tagami et al., 2000a, "Fused-ring carboxylic acid derivatives", U.S. Pat. No. 6,121,309 granted 19 Sep. 2000.

Tagami et al., 2000b, "Carboxylic acid derivatives having fused rings", U.S. Pat. No. 6,110,959 granted 29 Aug. 2000.

Tagami et al., 2002, "Carboxylic acid derivatives having fused rings," U.S. Pat. No. 6,358,995 granted 19 Mar. 2002.

Tsuda et al., 1999, "Pyrrole deriviatives and medicinal composition", U.S. Pat. No. 5,998,459 granted 7 Dec. 1999.

Watson et al., 2009, "Formation of ArF from LPdAr(F): Catalytic conversion of aryl triflates to aryl fluorides", Science, Vol. 325, pp. 1661-1664.

White et al., 1998, "Defects in embryonic hindbrain development and fetal resorption resulting from vitamin A deficiency in the rat are prevented by feeding pharmacological levels of all-trans-retinoic acid", Proc. Natl. Acad. Sci. USA, Vol. 95, pp. 13459-12364.

Williams G, Eickholt B J, Maison P, Prinjha R, Walsh F S, Doherty P (2005) A complementary peptide approach applied to the design of novel semaphorin/neuropilin antagonists. J Neurochem 92:1180-1190.

Wong L F, Yip P K, Battaglia A, Grist J, Corcoran J, Maden M, Azzouz M, Kingsman S M, Kingsman A J, Mazarakis N D, McMahon S B (2006) Retinoic acid receptor beta2 promotes functional regeneration of sensory axons in the spinal cord. Nat Neurosci 9:243-250.

Yamauchi et al., 2001, "Methods for preventing, inhibiting, or treating graft rejection reactions in graft-versus-host disease (GVHD) and organ transplantation", U.S. Pat. No. 6,258,811 B1, granted 10 Jul. 2001.

Yamauchi et al., 2000, "Retinoic acid agonists as preventive and therapeutic agents for nephritis", European patent publication number EP 1025857 A1, published 9 Aug. 2000.

Yamauchi et al., 1997, "Methods for preventing, inhibiting, or treating graft rejection reactions in graft-versus-host disease (GVHD) and organ transplantation", European patent publication number EP 0930075 A1, published 21 Jul. 1999.

Yip P K, Wong L F, Pattinson D, Battaglia A, Grist J, Bradbury E J, Maden M, McMahon S B, Mazarakis N D (2006) Lentiviral vector expressing retinoic acid receptor beta2 promotes recovery of function after corticospinal tract injury in the adult rat spinal cord. Hum Mol Genet 15:3107-3118.

Yoshimura et al., 2000, "Discovery of novel and potent retinoic acid receptor α agonists: synthesis and evaluation of benzofuranyl-pyrrole and benzothiophenyl-pyrrole derivatives", J. Med. Chem., Vol. 43, pp. 2929-2937.

The invention claimed is:

1. A method of treatment of a condition or disorder that is mediated by activating retinoic acid receptor β (RARβ) in a subject having said condition or disorder;
   wherein the condition is:
      paralysis;
   wherein the treatment is effected by activating retinoic acid receptor β (RARβ);
   the method comprising administering to said subject a therapeutically-effective amount of a compound;
   wherein the compound is selected from compounds of the following formula and pharmaceutically acceptable salts thereof:

$$\text{structure with } R^{Q1}, R^{Q3}, R^{Q4}, R^{Q2}, Y^1, Y^2, X^1, X^2, X^3, R^{P1}, R^{P2}, R^4$$

wherein:
one of $X^1$, $X^2$, and $X^3$ is independently O or S;
each of the other two of $X^1$, $X^2$, and $X^3$ is N;
$Y^1$ is independently O or S;
$Y^2$ is independently CH, $CR^Y$ or N;
—$R^Y$ is saturated linear or branched $C_{1-3}$alkyl;
—$R^{Q1}$ is independently —$R^{Q1A}$, —$R^{Q1B}$, or —$R_{Q1C}$;
—$R^{Q1A}$ is saturated linear or branched $C_{1-3}$alkyl;
—$R^{Q1B}$ is —F, —Cl, —Br, or —I;
—$R^{Q1C}$ is —$CF_3$;
—$R^{Q2}$ is independently —$R^{Q2A}$, —$R^{Q2B}$, or —$R^{Q2C}$;
—$R^{Q2A}$ is saturated linear or branched $C_{1-3}$alkyl;
—$R^{Q2B}$ is independently —F, —Cl, —Br, or —I;
—$R^{Q2C}$ is —$CF_3$;
—$R^{Q3}$ is independently —H or —$R^{Q3X}$;
—$R^{Q3X}$ is independently —$R^{Q3A}$, —$R^{Q3B}$, —$R^{Q3C}$, or —$R^{Q3D}$;
—$R^{Q3A}$ is saturated linear or branched $C_{1-3}$alkyl;
—$R^{Q3B}$ is saturated linear or branched $C_{1-3}$alkoxy;
—$R^{Q3C}$ is independently —F, —Cl, —Br, or —I;
—$R^{Q3D}$ is —$CF_3$;
—$R^{Q4}$ is independently —H or —$R^{Q4X}$;

—$R^{Q4X}$ is independently —$R^{Q4A}$, —$R^{Q4B}$, —$R^{Q4C}$, or —$R^{Q4D}$;
—$R^{Q4A}$ is saturated linear or branched $C_{1-3}$alkyl;
—$R^{Q4B}$ is saturated linear or branched $C_{1-3}$alkoxy;
—$R^{Q4C}$ is independently —F, —Cl, —Br, or —I;
—$R^{Q4D}$ is —$CF_3$;
one of —$R^{P1}$ and —$R^{P2}$ is —H or —$R^P$;
the other of —$R^{P1}$ and —$R^{P2}$ is —H;
—$R^P$ is independently —$R^{PA}$, —$R^{PB}$, —$R^{PC}$, or —$R^{PD}$;
—$R^{PA}$ is saturated linear or branched $C_{1-3}$alkyl;
—$R^{PB}$ is independently —F, —Cl, —Br, or —I;
—$R^{PC}$ is —$CF_3$;
—$R^{PD}$ is independently —$NH_2$ or —$NHR^{PDD}$;
—$R^{PDD}$ is saturated linear or branched $C_{1-3}$alkyl;
—$R^A$ is independently —H or —$R^{AA}$; and
—$R^{AA}$ is independently saturated linear or branched $C_{1-4}$alkyl, phenyl, or benzyl.

2. The method according to claim 1, wherein the compound is a compound of the following formula, or a pharmaceutically acceptable salt thereof:

(BHBA-001)

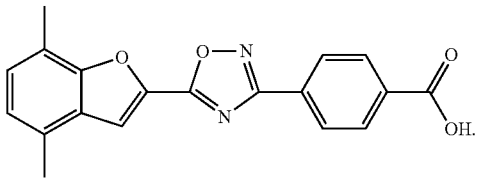

3. The method according to claim 2, wherein the paralysis is:
localised paralysis;
monoplegia;
quadriplegia;
paraplegia; or
Bell's palsy.

4. The method according to claim 1, wherein the paralysis is:
localised paralysis;
monoplegia;
quadriplegia;
paraplegia; or
Bell's palsy.

5. A method of treatment of a condition or disorder that is mediated by activating retinoic acid receptor β (RARβ) in a subject having said condition or disorder;
wherein the condition is:
a neurodegenerative disorder;
wherein the treatment is effected by activating retinoic acid receptor β (RARβ);
the method comprising administering to said subject a therapeutically-effective amount of a compound;
wherein the compound is selected from compounds of the following formula and pharmaceutically acceptable salts thereof:

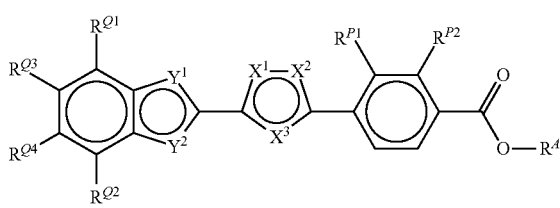

wherein:
one of $X^1$, $X^2$, and $X^3$ is independently O or S;
each of the other two of $X^1$, $X^2$, and $X^3$ is N;
$Y^1$ is independently O or S;
$Y^2$ is independently CH, $CR^Y$ or N;
—$R^Y$ is saturated linear or branched $C_{1-3}$alkyl;
—$R^{Q1}$ is independently —$R^{Q1A}$, —$R^{Q1B}$, or —$R^{Q1C}$;
—$R^{Q1A}$ is saturated linear or branched $C_{1-3}$alkyl;
—$R^{Q1B}$ is —F, —Cl, —Br, or —I;
—$R^{Q1C}$ is —$CF_3$;
—$R^{Q2}$ is independently —$R^{Q2A}$, —$R^{Q2B}$, or —$R^{Q2C}$;
—$R^{Q2A}$ is saturated linear or branched $C_{1-3}$alkyl;
—$R^{Q2B}$ is independently —F, —Cl, —Br, or —I;
—$R^{Q2C}$ is —$CF_3$;
—$R^{Q3}$ is independently —H or —$R^{Q3X}$;
—$R^{Q3X}$ is independently —$R^{Q3A}$, —$R^{Q3B}$, —$R^{Q3C}$, or —$R^{Q3D}$;
—$R^{Q3A}$ is saturated linear or branched $C_{1-3}$alkyl;
—$R^{Q3B}$ is saturated linear or branched $C_{1-3}$alkoxy;
—$R^{Q3C}$ is independently —F, —Cl, —Br, or —I;
—$R^{Q3D}$ is —$CF_3$;
—$R^{Q4}$ is independently —H or —$R^{Q4X}$;
—$R^{Q4X}$ is independently —$R^{Q4A}$, —$R^{Q4B}$, —$R^{Q4C}$, or —$R^{Q4D}$;
—$R^{Q4A}$ is saturated linear or branched $C_{1-3}$alkyl;
—$R^{Q4B}$ is saturated linear or branched $C_{1-3}$alkoxy;
—$R^{Q4C}$ is independently —F, —Cl, —Br, or —I;
—$R^{Q4D}$ is —$CF_3$;
one of —$R^{P1}$ and —$R^{P2}$ is —H or —$R^P$;
the other of —$R^{P1}$ and —$R^{P2}$ is —H;
—$R^P$ is independently —$R^{PA}$, —$R^{PB}$, —$R^{PC}$, or —$R^{PD}$;
—$R^{PA}$ is saturated linear or branched $C_{1-3}$alkyl;
—$R^{PB}$ is independently —F, —Cl, —Br, or —I;
—$R^{PC}$ is —$CF_3$;
—$R^{PD}$ is independently —$NH_2$ or —$NHR^{PDD}$;
—$R^{PDD}$ is saturated linear or branched $C_{1-3}$alkyl;
—$R^A$ is independently —H or —$R^{AA}$; and
—$R^{AA}$ is independently saturated linear or branched $C_{1-4}$alkyl, phenyl, or benzyl.

6. The method according to claim 5, wherein the compound is a compound of the following formula, or a pharmaceutically acceptable salt thereof:

(BHBA-001)

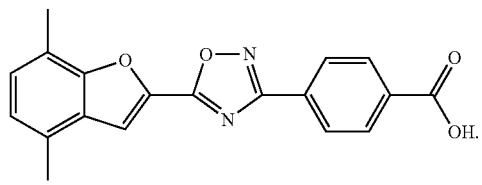

7. The method according to claim 6, wherein the neurodegenerative disorder is:
senile dementia;
Huntington's disease;
Parkinson's disease; or
motor neurone disease.

8. The method according to claim 6, wherein the neurodegenerative disorder is:
Alzheimer's disease.

9. The method according to claim 8, wherein the Alzheimer's disease is:
early stage Alzheimer's disease;
intermediate stage Alzheimer's disease; or
late stage Alzheimer's disease.

10. The method according to claim 6, wherein the neurodegenerative disorder is:
a cognitive disorder.

11. The method according to claim 6, wherein the neurodegenerative disorder is:
cognitive impairment.

12. The method according to claim 6, wherein the neurodegenerative disorder is:
mild cognitive impairment.

13. The method according to claim 6, wherein the neurodegenerative disorder is:
memory impairment.

14. The method according to claim 6, wherein the neurodegenerative disorder is:
memory deficit.

15. The method according to claim 5, wherein the neurodegenerative disorder is:
senile dementia;
Huntington's disease;
Parkinson's disease; or
motor neurone disease.

16. The method according to claim 5, wherein the neurodegenerative disorder is:
Alzheimer's disease.

17. The method according to claim 16, wherein the Alzheimer's disease is:
early stage Alzheimer's disease;
intermediate stage Alzheimer's disease; or
late stage Alzheimer's disease.

18. The method according to claim 5, wherein the neurodegenerative disorder is:
a cognitive disorder.

19. The method according to claim 5, wherein the neurodegenerative disorder is:
cognitive impairment.

20. The method according to claim 5, wherein the neurodegenerative disorder is:
mild cognitive impairment.

21. The method according to claim 5, wherein the neurodegenerative disorder is:
memory impairment.

22. The method according to claim 5, wherein the neurodegenerative disorder is:
memory deficit.

23. A method of treatment of a condition or disorder that is mediated by activating retinoic acid receptor β (RARβ) in a subject having said condition or disorder;
wherein the condition is:
neurally-based impotence;
wherein the treatment is effected by activating retinoic acid receptor β (RARβ);
the method comprising administering to said subject a therapeutically-effective amount of a compound;
wherein the compound is selected from compounds of the following formula and pharmaceutically acceptable salts thereof:

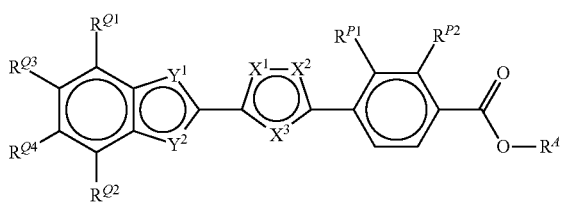

wherein:
one of $X^1$, $X^2$, and $X^3$ is independently O or S;
each of the other two of $X^1$, $X^2$, and $X^3$ is N;
$Y^1$ is independently O or S;
$Y^2$ is independently CH, $CR^Y$ or N;
—$R^Y$ is saturated linear or branched $C_{1-3}$alkyl;
—$R^{Q1}$ is independently —$R^{Q1A}$, —$R^{Q1B}$, or —$R^{Q1C}$;
—$R^{Q1A}$ is saturated linear or branched $C_{1-3}$alkyl;
—$R^{Q1B}$ is —F, —Cl, —Br, or —I;
—$R^{Q1C}$ is —$CF_3$;
—$R^{Q2}$ is independently —$R^{Q2A}$, —$R^{Q2B}$, or —$R^{Q2C}$;
—$R^{Q2A}$ is saturated linear or branched $C_{1-3}$alkyl;
—$R^{Q2B}$ is independently —F, —Cl, —Br, or —I;
—$R^{Q2C}$ is —$CF_3$;
—$R^{Q3}$ is independently —H or —$R^{Q3X}$;
—$R^{Q3X}$ is independently —$R^{Q3A}$, $R^{Q3B}$, —$R^{Q3C}$, or —$R^{Q3D}$;
—$R^{Q3A}$ is saturated linear or branched $C_{1-3}$alkyl;
—$R^{Q3B}$ is saturated linear or branched $C_{1-3}$alkoxy;
—$R^{Q3C}$ is independently —F, —Cl, —Br, or —I;
—$R^{Q3D}$ is —$CF_3$;
—$R^{Q4}$ is independently —H or —$R^{Q4X}$;
—$R^{Q4X}$ is independently —$R^{Q4A}$, $R^{Q4B}$, —$R^{Q4C}$, or —$R^{Q4D}$;
—$R^{Q4A}$ is saturated linear or branched $C_{1-3}$alkyl;
—$R^{Q4B}$ is saturated linear or branched $C_{1-3}$alkoxy;
—$R^{Q4C}$ is independently —F, —Cl, —Br, or —I;
—$R^{Q4D}$ is —$CF_3$;
one of —$R^{P1}$ and —$R^{P2}$ is —H or —$R^P$;
the other of —$R^{P1}$ and —$R^{P2}$ is —H;
—$R^P$ is independently —$R^{PA}$, —$R^{PB}$, —$R^{PC}$, or —$R^{PD}$;
—$R^{PA}$ is saturated linear or branched $C_{1-3}$alkyl;
—$R^{PB}$ is independently —F, —Cl, —Br, or —I;
—$R^{PC}$ is —$CF_3$;
—$R^{PD}$ is independently —$NH_2$ or —$NHR^{PDD}$;
—$R^{PDD}$ is saturated linear or branched $C_{1-3}$alkyl;
—$R^A$ is independently —H or —$R^{AA}$; and
—$R^{AA}$ is independently saturated linear or branched $C_{1-4}$alkyl, phenyl, or benzyl.

24. The method according to claim 23, wherein the compound is a compound of the following formula, or a pharmaceutically acceptable salt thereof:

(BHBA-001)

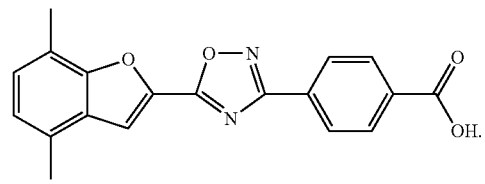

25. A method of treatment of a condition or disorder that is mediated by activating retinoic acid receptor β (RARβ) in a subject having said condition or disorder;
wherein the condition is:
a neurological disorder caused by a neurological injury; or
a neurological disorder caused by a neuropathy;
wherein the treatment is effected by activating retinoic acid receptor β (RARβ);
the method comprising administering to said subject a therapeutically-effective amount of a compound;

wherein the compound is selected from compounds of the following formula and pharmaceutically acceptable salts thereof:

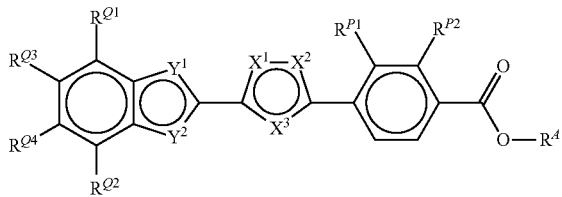

wherein:
one of $X^1$, $X^2$, and $X^3$ is independently O or S;
each of the other two of $X^1$, $X^2$, and $X^3$ is N;
$Y^1$ is independently O or S;
$Y^2$ is independently CH, $CR^Y$ or N;
—$R^Y$ is saturated linear or branched $C_{1-3}$alkyl;
—$R^{Q1}$ is independently —$R^{Q1A}$, —$R^{Q1B}$, or —$R^{Q1C}$;
—$R^{Q1A}$ is saturated linear or branched $C_{1-3}$alkyl;
—$R^{Q1B}$ is —F, —Cl, —Br, or —I;
—$R^{Q1C}$ is —$CF_3$;
—$R^{Q2}$ is independently —$R^{Q2A}$, —$R^{Q2B}$, or —$R^{Q2C}$;
—$R^{Q2A}$ is saturated linear or branched $C_{1-3}$alkyl;
—$R^{Q2B}$ is independently —F, —Cl, —Br, or —I;
—$R^{Q2C}$ is —$CF_3$;
—$R^{Q3}$ is independently —H or —$R^{Q3X}$;
—$R^{Q3X}$ is independently —$R^{Q3A}$, $R^{Q3B}$, —$R^{Q3C}$, or —$R^{Q3D}$;
—$R^{Q3A}$ is saturated linear or branched $C_{1-3}$alkyl;
—$R^{Q3B}$ is saturated linear or branched $C_{1-3}$alkoxy;
—$R^{Q3C}$ is independently —F, —Cl, —Br, or —I;
—$R^{Q3D}$ is —$CF_3$;
—$R^{Q4}$ is independently —H or —$R^{Q4X}$;
—$R^{Q4X}$ is independently —$R^{Q4A}$, $R^{Q4B}$, —$R^{Q4C}$, or —$R^{Q4D}$;
—$R^{Q4A}$ is saturated linear or branched $C_{1-3}$alkyl;
—$R^{Q4B}$ is saturated linear or branched $C_{1-3}$alkoxy;
—$R^{Q4C}$ is independently —F, —Cl, —Br, or —I;
—$R^{Q4D}$ is —$CF_3$;
one of —$R^{P1}$ and —$R^{P2}$ is —H or —$R^P$;
the other of —$R^{P1}$ and —$R^{P2}$ is —H;
—$R^P$ is independently —$R^{PA}$, —$R^{PB}$, —$R^{PC}$, or —$R^{PD}$;
—$R^{PA}$ is saturated linear or branched $C_{1-3}$alkyl;
—$R^{PB}$ is independently —F, —Cl, —Br, or —I;
—$R^{PC}$ is —$CF_3$;
—$R^{PD}$ is independently —$NH_2$ or —$NHR^{PDD}$;
—$R^{PDD}$ is saturated linear or branched $C_{1-3}$alkyl;
—$R^A$ is independently —H or —$R^A$; and
—$R^{AA}$ is independently saturated linear or branched $C_{1-4}$alkyl, phenyl, or benzyl.

26. The method according to claim 25, wherein the compound is a compound of the following formula, or a pharmaceutically acceptable salt thereof:

(BHBA-001)

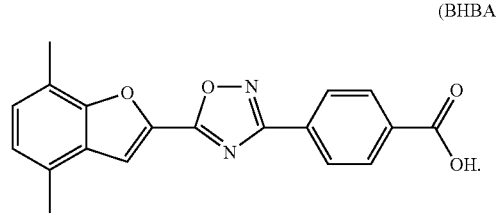

* * * * *